United States Patent
Liu et al.

(10) Patent No.: US 12,122,780 B2
(45) Date of Patent: Oct. 22, 2024

(54) PYRIMIDINYL GROUP-CONTAINING TRICYCLIC COMPOUND SERVING AS C-MET INHIBITOR

(71) Applicant: JIANGSU AOSAIKANG PHARMACEUTICAL CO., LTD., Jiangsu (CN)

(72) Inventors: Xile Liu, Shanghai (CN); Charles Z. Ding, Shanghai (CN); Shuhui Chen, Shanghai (CN); Lihong Hu, Shanghai (CN); Haiwen Wan, Shanghai (CN)

(73) Assignee: JIANGSU AOSAIKANG PHARMACEUTICAL CO., LTD., Jiangsu (CN)

( * ) Notice: Subject to any disclaimer, the term of this patent is extended or adjusted under 35 U.S.C. 154(b) by 752 days.

(21) Appl. No.: 17/427,185

(22) PCT Filed: Jan. 22, 2020

(86) PCT No.: PCT/CN2020/073842
§ 371 (c)(1),
(2) Date: Jul. 30, 2021

(87) PCT Pub. No.: WO2020/156453
PCT Pub. Date: Aug. 6, 2020

(65) Prior Publication Data
US 2023/0056559 A1    Feb. 23, 2023

(30) Foreign Application Priority Data

Feb. 1, 2019  (CN) ......................... 201910105481.5
May 31, 2019  (CN) ......................... 201910469780.7
Sep. 12, 2019  (CN) ......................... 201910865757.X
Jan. 3, 2020  (CN) ......................... 202010006610.8

(51) Int. Cl.
| C07D 487/04 | (2006.01) |
| A61P 35/00 | (2006.01) |
| C07D 401/14 | (2006.01) |
| C07D 471/14 | (2006.01) |
| C07D 491/048 | (2006.01) |
| C07D 491/052 | (2006.01) |
| C07D 495/04 | (2006.01) |

(52) U.S. Cl.
CPC ............ *C07D 487/04* (2013.01); *A61P 35/00* (2018.01); *C07D 401/14* (2013.01); *C07D 471/14* (2013.01); *C07D 491/048* (2013.01); *C07D 491/052* (2013.01); *C07D 495/04* (2013.01)

(58) Field of Classification Search
None
See application file for complete search history.

(56) References Cited

U.S. PATENT DOCUMENTS

| 2008/0214538 A1 | 9/2008 | Bourrie et al. |
| 2009/0042924 A1* | 2/2009 | Bourrie ................. A61P 35/00 514/292 |
| 2019/0248763 A1 | 8/2019 | Xu et al. |

FOREIGN PATENT DOCUMENTS

| CN | 1729190 A * | 2/2006 | ........... C07D 471/04 |
| CN | 100345850 C | 10/2007 | |
| WO | WO-2009006959 A1 | 1/2009 | |
| WO | WO-2010138661 A1 | 12/2010 | |
| WO | WO-2018077227 A1 | 5/2018 | |
| WO | WO-2022022687 A1 * | 2/2022 | |
| WO | WO-2023138492 A1 * | 7/2023 | |

OTHER PUBLICATIONS

Wang et al., J. Med. Chem. 2023, 66, 12, 7670-7697 (Year: 2023).*
International Search Report dated Apr. 26, 2020 issued in PCT application PCT/CN2020/073842.
Written Opinion of International Search Authority dated Apr. 26, 2020 issued in PCT application PCT/CN2020/073842.
First Office Action dated Aug. 30, 2022 issued in Japanese Patent Application No. 2021-544884.
Extended Search Report dated Oct. 12, 2022 issued in European Patent Application No. 20748406.4.
Nov. 2, 2023 First Office Action issued in Korean Patent Application No. 10-2021-7028054.

* cited by examiner

Primary Examiner — Jeffrey S Lundgren
Assistant Examiner — Anthony Joseph Seitz
(74) Attorney, Agent, or Firm — Harness, Dickey & Pierce, P.L.C.

(57) ABSTRACT

Disclosed are a pyrimidinyl group-containing tricyclic compound and applications thereof in preparing a cancer-treating medicament. Specifically disclosed are a compound as represented by formula (I), a pharmaceutically acceptable salt of same, or an isomer thereof.

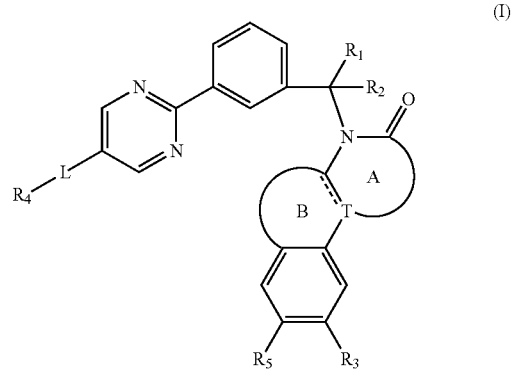

17 Claims, No Drawings

PYRIMIDINYL GROUP-CONTAINING TRICYCLIC COMPOUND SERVING AS C-MET INHIBITOR

CROSS-REFERENCE TO RELATED APPLICATIONS

This application is a U.S. National Phase Application under 35 U.S.C. 371 of International Application No. PCT/CN2020/073842, filed on Jan. 22, 2020, which claims the benefit of Chinese Patent Application No. CN201910105481.5, filed on Feb. 1, 2019, Chinese Patent Application No. CN201910469780.7, filed on May 31, 2019, Chinese Patent Application No. CN201910865757.X, filed on Sep. 12, 2019, and Chinese Patent Application No. CN202010006610.8, filed on Jan. 3, 2020. The entire disclosures of the above applications are incorporated herein by reference.

TECHNICAL FIELD

The present application relates to a class of pyrimidinyl group-containing tricyclic compounds serving as a c-Met inhibitor, and applications thereof in preparing a medicament for treating cancer. Specifically disclosed is a compound represented by formula (I), a pharmaceutically acceptable salt thereof, or an isomer thereof.

BACKGROUND

Receptor tyrosine kinase c-Met, also known as hepatocyte growth factor (HGF) receptor, is a transmembrane receptor with autonomous phosphorylation activity encoded by the MET gene, and is a unique subclass of receptor tyrosine kinase (RTKs) family, which is mainly produced in epithelial cells. HGF is the only high-affinity ligand of c-Met, which is widely present in various human tissues and organs. The binding of c-Met with HGF secreted by mesenchymal cells leads to dimerization of c-Met, which then undergoes metastatic phosphorylation at the two catalytic sites, Tyr1234 and Tyr1235, of the c-Met activation loop (A-loop), leading to the autophosphorylation of Tyr1349 and Tyr1356 in the C-terminal multifunctional docking region, thereby recruiting a variety of cellular effectors, such as GAB1, GRB2, PLC, and SRC, etc. GAB1 continues to recruit downstream effectors, such as SHP2, PI3K, CRKL, etc., to form a multi-protein signaling complex and activate a series of downstream signaling pathways, including RAS-MAPK, PI3K-AKT and STATs pathways. C-Met/HGF has a variety of biological functions, which activate the downstream signaling pathways, and plays a very important role in tumor occurrence, development, metastasis and angiogenesis.

Studies have found that c-Met is highly expressed in many tumor cells, such as hepatocellular carcinoma, gastric cancer, ovarian cancer, non-small cell lung cancer, kidney cancer and other cancer cells, and the overexpression of c-Met is closely related to the formation and prognosis of a variety of tumors. Excessive activation of the HGF/c-Met pathway will lead to the activation of downstream signaling pathways, thereby inducing cancer. In addition, the overexpression of HGF and c-Met can lead to the drug resistance of EGFR, RAS-RAF-MEK and Akt-mTOR signaling pathways to related inhibitors, which is an important mechanism of tumor cell escape. For example, in non-small cell lung cancer with EGFR activity mutation, the overexpression of HGF results in phosphorylation of c-Met, which activates the downstream PI3K-Akt pathway, leading to the drug resistance to EGFR inhibitors. Similarly, the up-regulation and secretion of HGF in the tumor microenvironment will lead to the drug resistance of cells to RAS inhibitors.

After blocking the abnormal activation of HGF/c-Met signaling pathway in tumor cells, tumor cells will have a series of changes, such as a change in morphological, a slowdown in proliferation, a decrease in tumorigenicity and a decrease in invasion ability. Therefore, the development of a highly active c-Met inhibitor can provide an effective treatment for a variety of primary abnormal c-Met signaling pathways and drug resistance c-Met abnormal expression tumors.

At present, there are mainly the following intervention therapies for c-Met pathway: (1) therapeutic antibody: binding with HGF or c-Met, inhibiting c-Met pathway by intervening the interaction between HGF and c-Met; (2) small-molecule tyrosine kinase inhibitor: inhibiting the activity of c-Met kinase or another kinase that plays an important role in cancer progression; (3) molecule similar to HS90 inhibitor: blocking the c-Met pathway by affecting the stability or expression of c-Met protein; (4) functional molecule interfering with the downstream effectors of c-Met pathway.

According to the binding mode of c-Met protein, c-Met inhibitors can be divided into two types: type I (type Ia and type IB) and type II. Type Ic-Met inhibitor is a competitive ATP inhibitor, which binds to the ATP binding pocket with U-shaped conformation around Met1211, forming hydrogen bonds with amino acid residues such as Met1160 and Asp1222, etc., in the main chain of c-Met, and forming π-π stacking interaction with Tyr1230 on A-loop. Most of the type Ic-Met inhibitor preferentially binds to kinase targets in an inactive conformation and has good selectivity. Type II c-Met inhibitor is a multi-target c-Met inhibitor, which not only occupies the ATP binding site but also enters the hydrophobic pockets formed by inactive "DFG out" conformation through Gatekeeper, so that the inhibitor can better bind to the target. When the inhibitor enters into the hydrophobic pocket of c-Met, the A-loop must make room, which requires the type IIc-Met inhibitor to have high molecular weight and strong lipophilicity.

At present, the small molecular inhibitors of c-Met in clinical research mainly include Crizotinib, Tepotinib (EMD1214063), Capmatinib, Volitinib, Cabozantinib (XL-184), and ARQ-197, etc. Although these drugs have shown good therapeutic effects in the clinic, some of them have some disadvantages, such as high clinical dosage, large clinical side effects, and low drug stability. Therefore, the development of novel c-Met inhibitors with high activity, high selectivity and good drug-like properties is still an unmet clinical need.

CONTENT OF THE PRESENT INVENTION

The present disclosure provides a compound represented by formula (I), a pharmaceutically acceptable salt thereof, or an isomer thereof, (I)

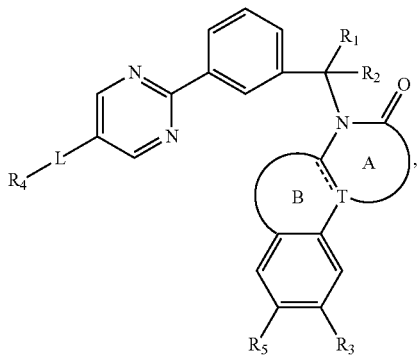

wherein, ═ is — or =;
when ═ is =, T is C;
the structural moiety or

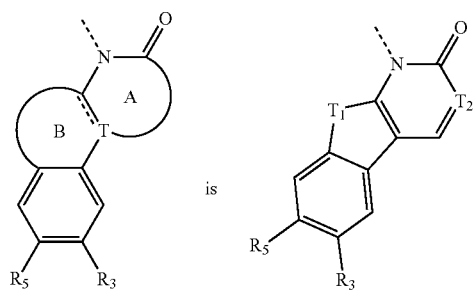

is when ═ is —, T is N;
the structural moiety

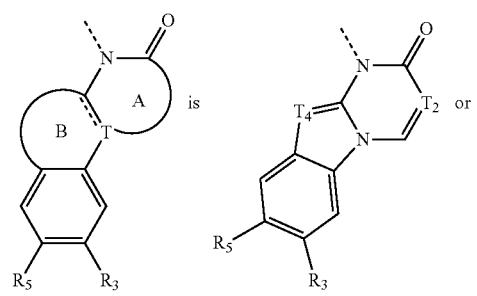

is

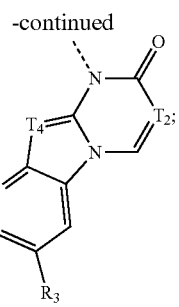

$T_1$ is

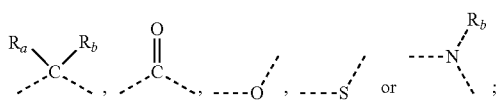

each of $R_a$ and $R_b$ is independently H, F or —CH$_3$;
each of $R_c$ is independently H or —CH$_3$;
each of $T_2$ is independently N or CR$_d$;
each of $R_d$ is independently H or F;
$T_3$ is —CH$_2$— or

each of $T_4$ is independently N or CR$_e$;
$R_e$ is H, F, Cl or —CH$_3$;
each of $R_1$ and $R_2$ is independently H, —CH$_3$, —CF$_3$, —CH$_2$CH$_3$, —CH$_2$CH$_2$CH$_3$ or —CH$_2$(CH$_3$)$_2$;
each of $R_3$ and $R_5$ is independently H, F, Cl, —CN, —OH or C$_{1-3}$ alkoxyl;
L is —O—(CH$_2$)$_n$—,

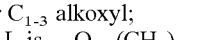

$R_f$ is H, —CH$_3$ or —CH$_2$CH$_3$,
n is 0, 1 or 2;
$R_4$ is 6-12 membered heterocycloalkyl optionally substituted by 1, 2 or 3 $R_g$, azetidinyl optionally substituted by 1, 2 or 3 $R_g$ or cyclohexyl optionally substituted by 1, 2 or 3 $R_g$;
each of $R_g$ is independently H, F, Cl, —OH, —CN, C$_{1-3}$ alkoxy, C$_{1-3}$ alkylamino, C$_{3-4}$ cycloalkyl, 4-6 membered heterocycloalkyl or C$_{1-5}$ alkyl optionally substituted by 1, 2 or 3 substituents independently selected from F, Cl, —OH, —CN,

C$_{1-3}$ alkylamino and —OCH$_3$;
the 6-12 membered heterocycloalkyl and the 4-6 membered heterocycloalkyl respectively comprise 1, 2, 3 or 4 heteroatoms independently selected from N, —O— and —S—.

The present disclosure provides a compound represented by formula (I), a pharmaceutically acceptable salt thereof, or an isomer thereof,

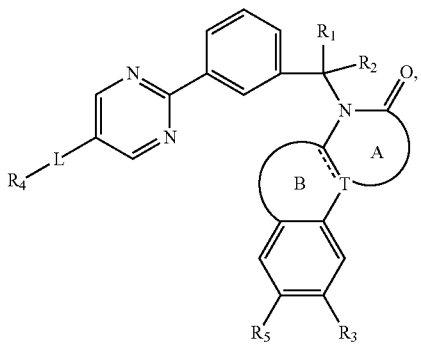
(I)

wherein, --- is — or =,
when --- is =, T is C;
the structural moiety

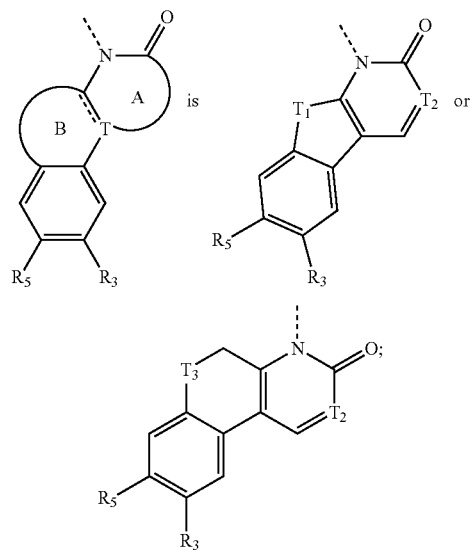

when --- is —, T is N;
the structural moiety

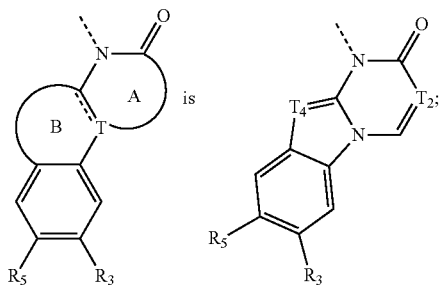

$T_1$ is

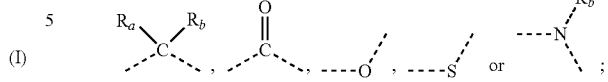

each of $R_a$ and $R_b$ is independently H, F or —CH$_3$;
each of $R_c$ is independently H or —CH$_3$;
each of $T_2$ is independently N or CR$_d$;
each of $R_d$ is independently H or F;

$T_3$ is —CH$_2$— or 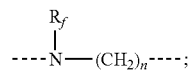;
$T_4$ is N or CR$_e$;
$R_e$ is H, F, Cl or —CH$_3$;
each of $R_1$ and $R_2$ is independently H, —CH$_3$, —CF$_3$, —CH$_2$CH$_3$, —CH$_2$CH$_2$CH$_3$ or —CH$_2$(CH$_3$)$_2$;
each of $R_3$ and $R_5$ is independently H, F, Cl, —CN, —OH or C$_{1-3}$ alkoxyl;
L is —O—(CH$_2$)$_n$— or $$----N(R_f)—(CH_2)_n----;$$

$R_f$ is H, —CH$_3$ or —CH$_2$CH$_3$;
n is 0, 1 or 2;
$R_4$ is 6-12 membered heterocycloalkyl optionally substituted by 1, 2 or 3 $R_g$;
each of $R_g$ is independently H, F, Cl, —OH, —CN, C$_{1-3}$ alkoxy or C$_{1-3}$ alkyl optionally substituted by 1, 2 or 3 substituents independently selected from F, Cl, —OH, —CN, and —OCH$_3$;
the 6-12 membered heterocycloalkyl comprises 1, 2, 3 or 4 heteroatoms independently selected from N, —O— and —S—.

The present disclosure provides a compound represented by formula (I), a pharmaceutically acceptable salt thereof, or an isomer thereof,

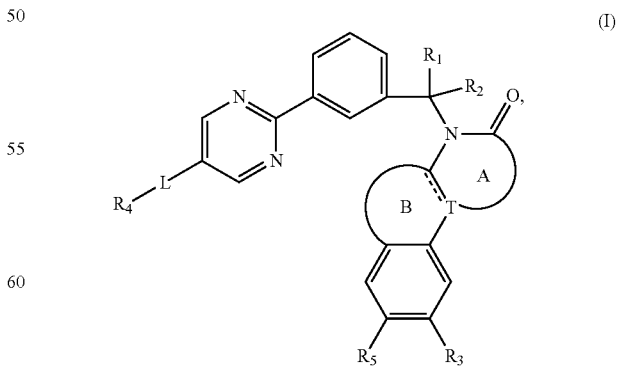
(I)

wherein, --- is — or =;
when --- is =, T is C;

the structural moiety

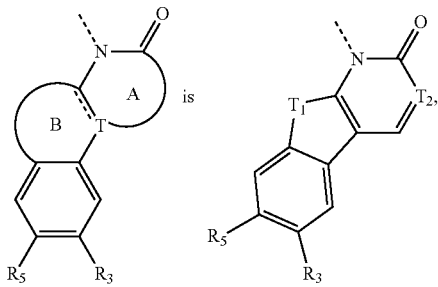

is when ╌ is —, T is N;
the structural moiety

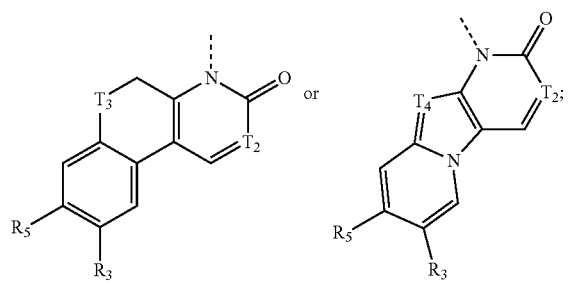

$T_1$ is

each of $R_a$ and $R_b$ is independently H, F or —CH$_3$;
each of $R_c$ is independently H or —CH$_3$;
each of $T_2$ is independently N or CR$_d$;
each of $R_d$ is independently H or F;

$T_3$ is —CH$_2$— or

$T_4$ is N or CR$_e$;
$R_e$ is H, F, Cl or —CH$_3$;
each of $R_1$ and $R_2$ is independently H, —CH$_3$, —CF$_3$, —CH$_2$CH$_3$, —CH$_2$CH$_2$CH$_3$ or —CH$_2$(CH$_3$)$_2$;
each of $R_3$ and $R_5$ is independently H, F, Cl, —CN, —OH or C$_{1-3}$ alkoxyl;
L is —O—(CH$_2$)$_n$—,

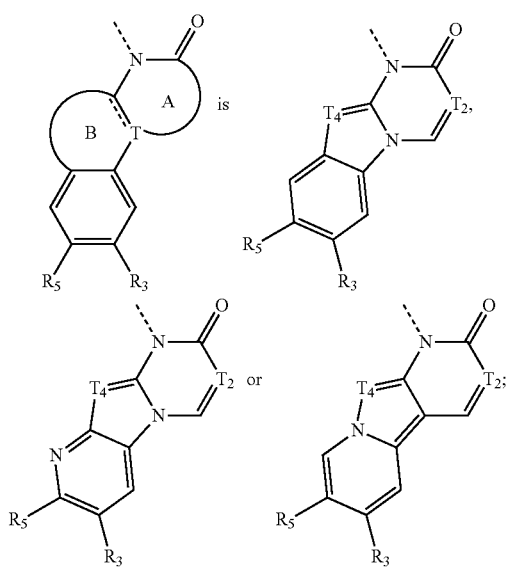

or

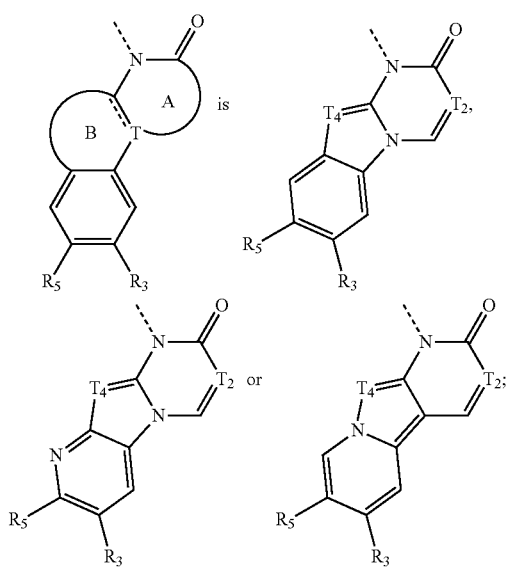;

$R_f$ is H, —CH$_3$ or —CH$_2$CH$_3$;
n is 0, 1 or 2;
$R_4$ is 6-12 membered heterocycloalkyl optionally substituted by 1, 2 or 3 $R_g$;
each of $R_g$ is independently H, F, Cl, —OH, —CN, C$_{1-3}$ alkoxy, 4-6 membered heterocycloalkyl or C$_{1-3}$ alkyl optionally substituted by 1, 2 or 3 substituents independently selected from F, Cl, —OH, —CN, C$_{1-3}$ alkylamino and —OCH$_3$;
the 6-12 membered heterocycloalkyl and the 4-6 membered heterocycloalkyl respectively comprise 1, 2, 3 or 4 heteroatoms independently selected from N, —O— and —S—.

In some embodiments of the present disclosure, the compound has the structure represented by formula (I-A) to (I-C):

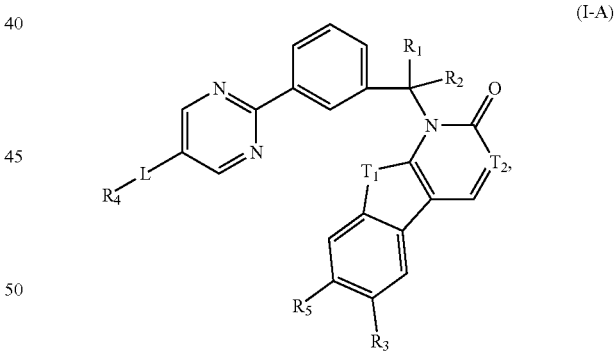

(I-A)

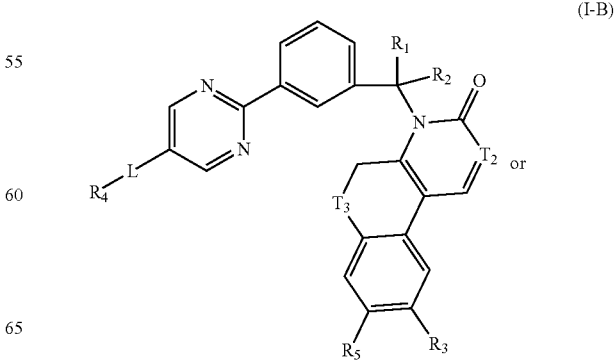

(I-B)

-continued

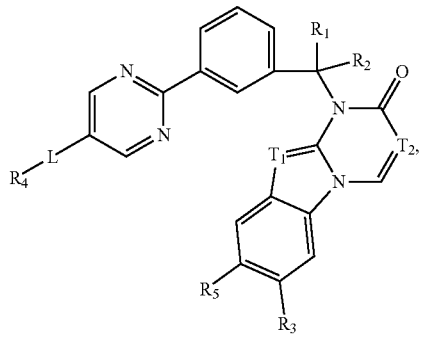
(I-C)

wherein, $T_1$, $T_2$, $T_3$, $T_4$, $R_1$, $R_2$, $R_3$, $R_4$, $R_5$ and L are as defined in the present disclosure.

In some embodiments of the present disclosure, the compound has the structure represented by formula (I-A), (I-B), (I-C) or (I-E):

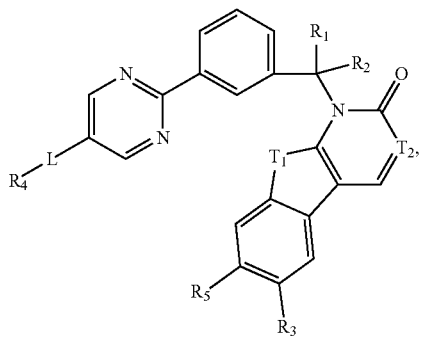
(I-A)

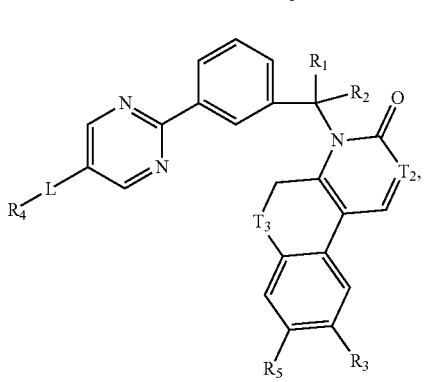
(I-B)

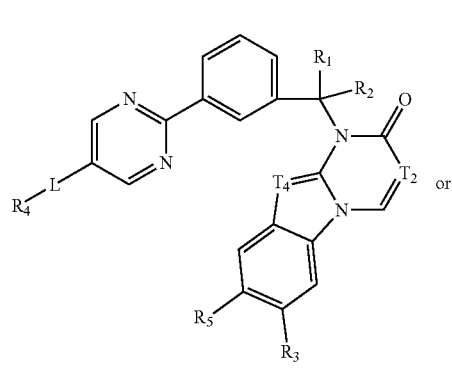
(I-C) or

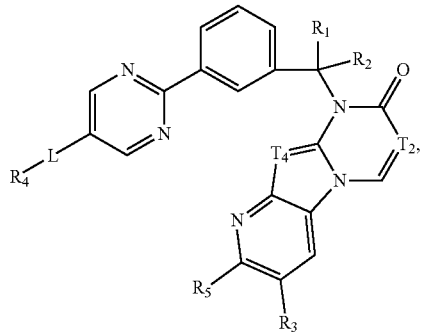
(I-E)

wherein, $T_1$, $T_2$, $T_3$, $T_4$, $R_1$, $R_2$, $R_3$, $R_4$, $R_5$ and L are as defined in the present disclosure.

In some embodiments of the present disclosure, the compound has the structure represented by formula (I-A1) to (I-A5):

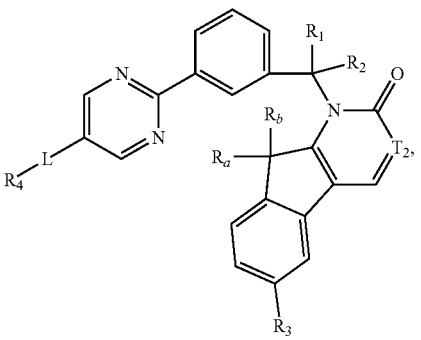
(I-A1)

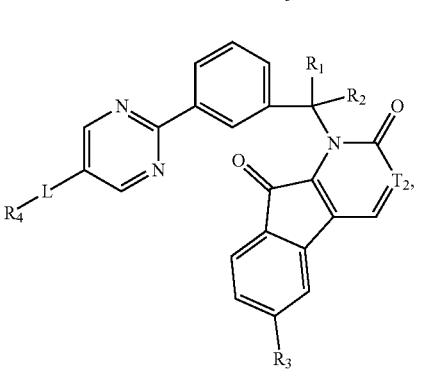
(I-A2)

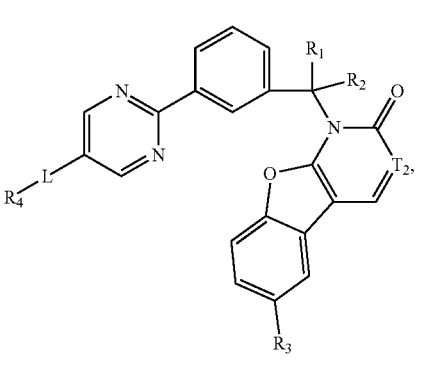
(I-A3)

-continued

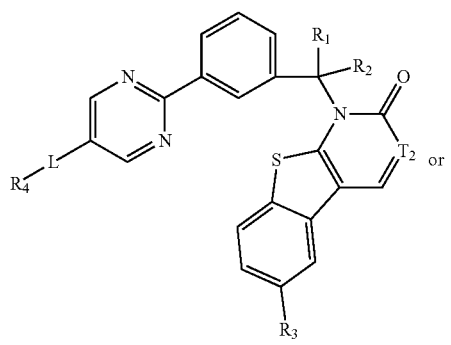
(I-A4)

(I-C1)

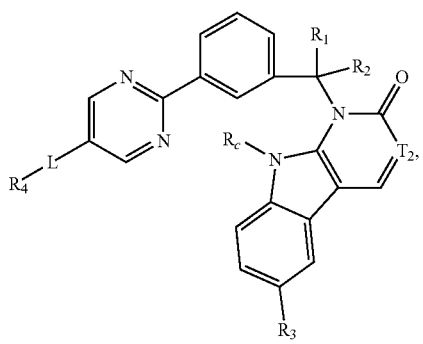
(I-A5)

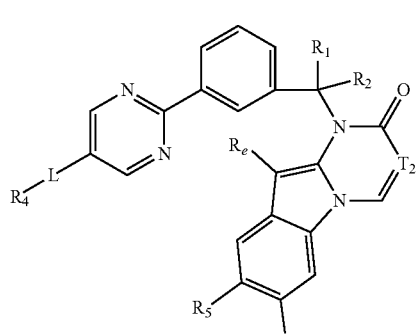
(I-C2)

wherein, $T_2$, $R_1$, $R_2$, $R_3$, $R_4$, L, $R_a$, $R_b$ and $R_c$ are as defined in the present disclosure.

In some embodiments of the present disclosure, the compound has the structure represented by formula (I-B1):

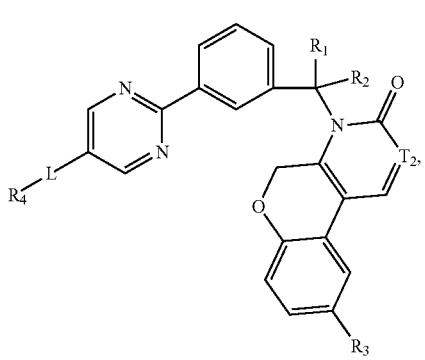
(I-B1)

wherein, $T_2$, $R_1$, $R_2$, $R_3$, $R_4$ and L are as defined in the present disclosure.

In some embodiments of the present disclosure, the compound has the structure represented by formula (I-C1) or (I-C2):

wherein, $T_2$, $R_1$, $R_2$, $R_3$, $R_4$, $R_5$, L and $R_e$ are as defined in the present disclosure.

In some embodiments of the present disclosure, the compound has the structure represented by formula (I-E1):

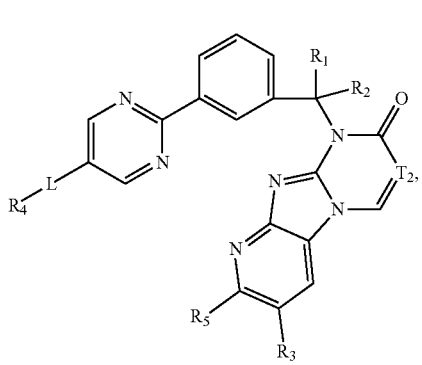
(I-E1)

wherein, $T_2$, $R_1$, $R_2$, $R_3$, $R_4$, $R_5$ and L are as defined in the present disclosure.

The present disclosure provides a compound represented by formula (I-D) or (I-F), a pharmaceutically acceptable salt thereof, or an isomer thereof,

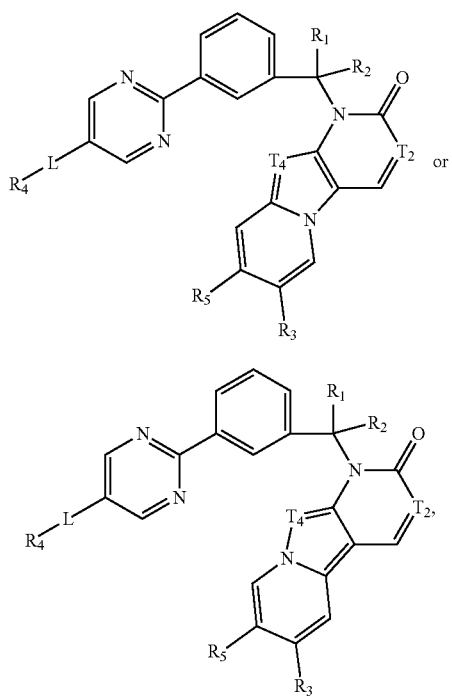

(I-D)

(I-F)

wherein, each of $T_2$ is independently N or $CR_d$;
each of $R_d$ is independently H or F;
each of $T_4$ is independently N or $CR_e$;
$R_e$ is H, F, Cl or —$CH_3$;
each of $R_1$ and $R_2$ is independently H, —$CH_3$, —$CF_3$, —$CH_2CH_3$, —$CH_2CH_2CH_3$ or —$CH_2(CH_3)_2$;
each of $R_3$ and $R_5$ is independently H, F, Cl, —CN, —OH or $C_{1-3}$ alkoxyl;

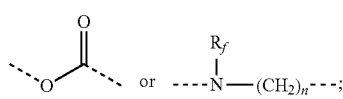

L is —$(CH_2)_n$—,
$R_f$ is H, —$CH_3$ or —$CH_2CH_3$;
n is 0, 1 or 2;
$R_4$ is 6-12 membered heterocycloalkyl optionally substituted by 1, 2 or 3 $R_g$, azetidinyl optionally substituted by 1, 2 or 3 $R_g$ or cyclohexyl optionally substituted by 1, 2 or 3 $R_g$;
each of $R_g$ is independently H, F, Cl, —OH, —CN, $C_{1-3}$ alkoxy, $C_{1-3}$ alkylamino, $C_{3-4}$ cycloalkyl, 4-6 membered heterocycloalkyl or $C_{1-5}$ alkyl optionally substituted by 1, 2 or 3 substituents independently selected from F, Cl, —OH, —CN,

$C_{1-3}$ alkylamino and —$OCH_3$;
the 6-12 membered heterocycloalkyl and the 4-6 membered heterocycloalkyl respectively comprise 1, 2, 3 or 4 heteroatoms independently selected from N, —O— and —S—.

In some embodiments of the present disclosure, the compound has the structure represented by formula (I-D1) or (I-F1):

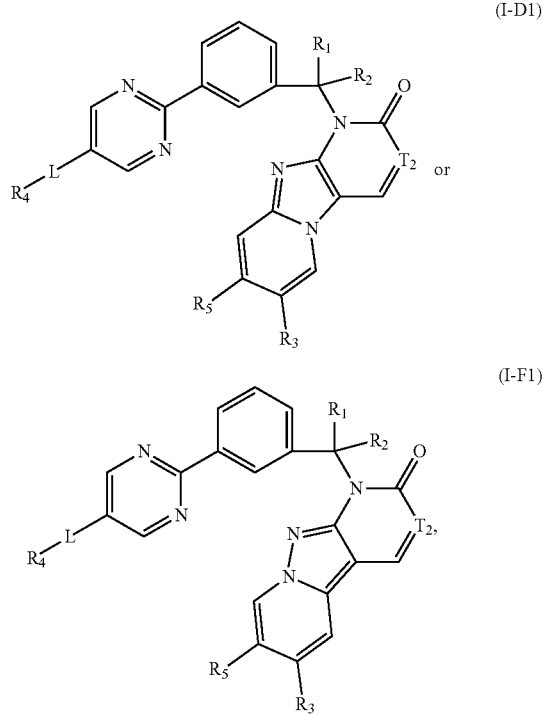

wherein, $T_2$, $R_1$, $R_2$, $R_3$, $R_5$, L and $R_4$ are as defined in the present disclosure.

In some embodiments of the present disclosure, L is —O—,

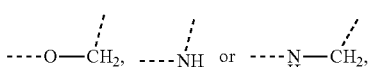

the other variants are as defined in the present disclosure.

In some embodiments of the present disclosure, L is —O—,

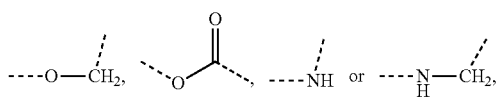

the other variants are as defined in the present disclosure.

In some embodiments of the present disclosure, $R_g$ is H, F, Cl, —OH, —CN, —$CH_3$, —$CH_2CH_3$, —$OCH_3$, —$OCH_2CH_3$, —$CF_3$, —$CH_2CF_3$, —$CH_2CH_2CF_3$, —$CH_2OH$ or —$CH_2CH_2OH$, the other variants are as defined in the present disclosure.

In some embodiments of the present disclosure, each of $R_g$ is H, F, Cl, —OH, —CN,

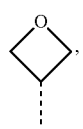

—CH$_3$, —CH$_2$CH$_3$, —CH(CH$_3$)$_2$, —OCH$_3$, —OCH$_2$CH$_3$, —CF$_3$, —CH$_2$CF$_3$, —CH$_2$CH$_2$CF$_3$, —CH$_2$OH, —CH$_2$CH$_2$OH, —CH$_2$CH$_2$OCH$_3$ or CH$_2$CH$_2$N(CH$_3$)$_2$, the other variants are as defined in the present disclosure.

In some embodiments of the present disclosure, each of R$_g$ is H, F, Cl, —OH, —CN,

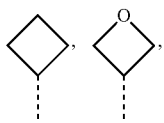

—CH$_3$, —CH$_2$CH$_3$, —CH$_2$CH$_2$CH$_3$, —CH(CH$_3$)$_2$, —CH$_2$CH(CH$_3$)$_2$, —OCH$_3$, —OCH$_2$CH$_3$, —N(CH$_3$)$_2$, —CF$_3$, —CH$_2$CF$_3$, —CH$_2$CH$_2$CF$_3$, —CH$_2$OH, —CH$_2$CH$_2$OH, —CH$_2$CH$_2$OCH$_3$, —CH$_2$CH$_2$N(CH$_3$)$_2$,

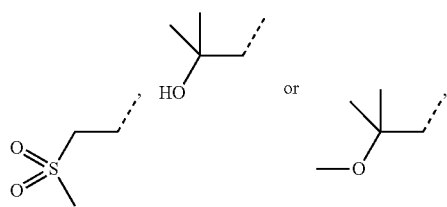

the other variants are as defined in the present disclosure.

In some embodiments of the present disclosure, R$_4$ is 6-10 membered heterocycloalkyl substituted by 1, 2 or 3 R$_g$, R$_g$ and the other variants are as defined in the present disclosure.

In some embodiments of the present disclosure, R$_4$ is 6-10 membered heterocycloalkyl optionally substituted by 1, 2 or 3 R$_g$, azetidinyl optionally substituted by 1, 2 or 3 R$_g$ or cyclohexyl optionally substituted by 1, 2 or 3 R$_g$, R$_g$ and the other variants are as defined in the present disclosure.

In some embodiments of the present disclosure, R$_4$ is

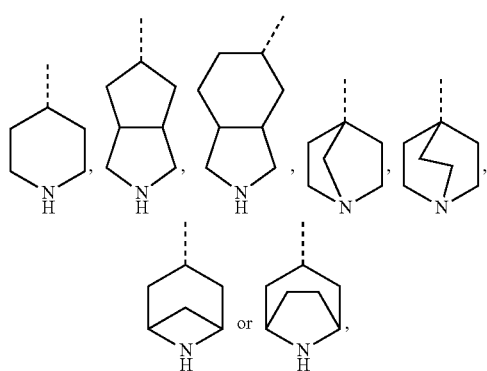

wherein

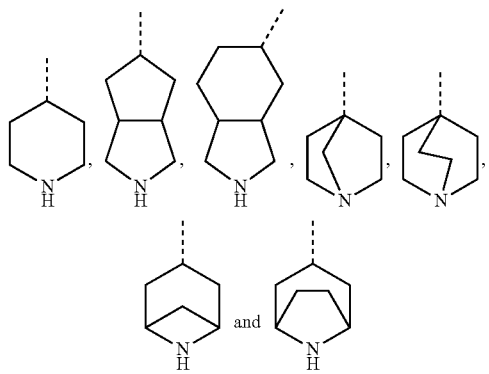

are optionally substituted by 1, 2 or 3 R$_g$, R$_g$ and the other variants are as defined in the present disclosure.

In some embodiments of the present disclosure, R$_4$ is

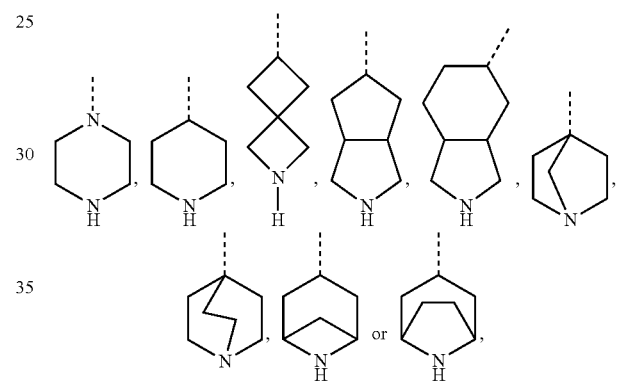

wherein

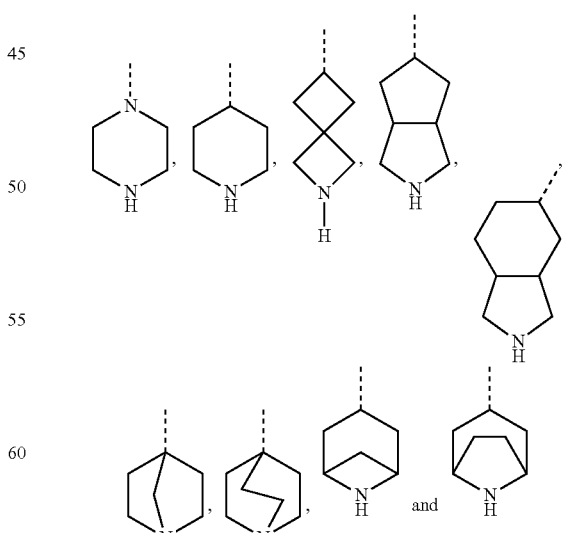

are optionally substituted by 1, 2 or 3 R$_g$, R$_g$ and the other variants are as defined in the present disclosure.

In some embodiments of the present disclosure, $R_4$ is

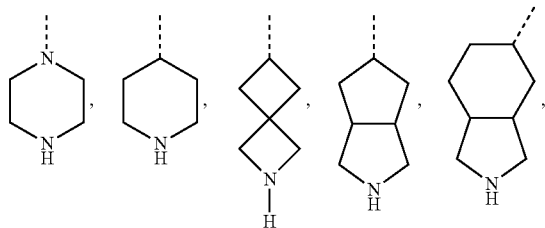

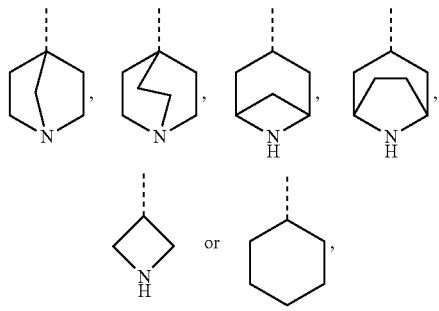

wherein

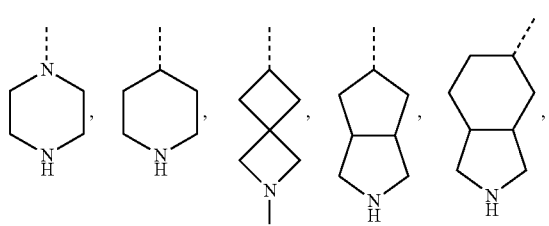

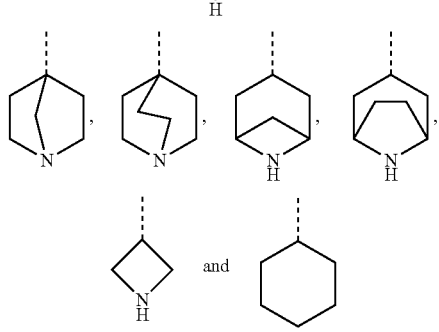

are optionally substituted by 1, 2 or 3 $R_g$, $R_g$ and the other variants are as defined in the present disclosure.

In some embodiments of the present disclosure, $R_4$ is

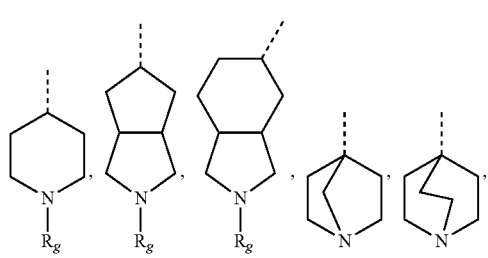

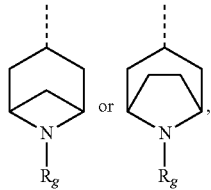

$R_g$ and the other variants are as defined in the present disclosure.

In some embodiments of the present disclosure, $R_4$ is

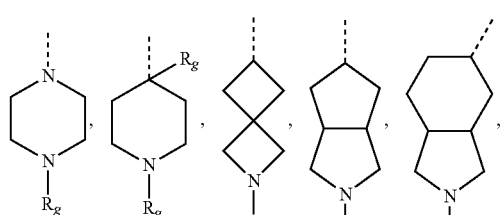

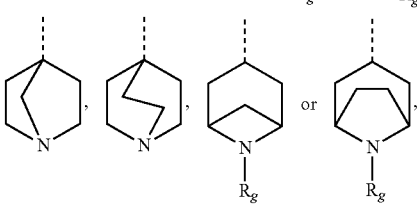

$R_g$ and the other variants are as defined in the present disclosure.

In some embodiments of the present disclosure, $R_4$ is

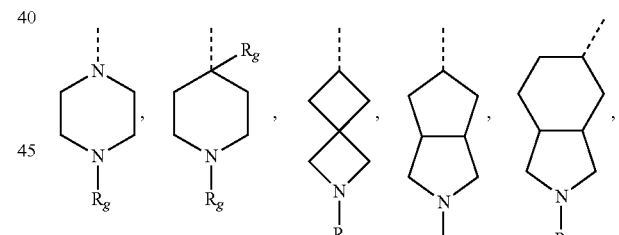

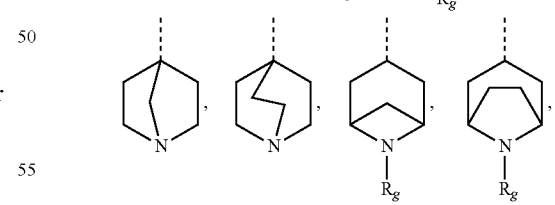

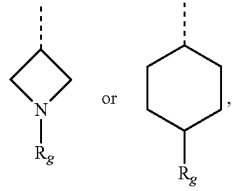

$R_g$ and the other variants are as defined in the present disclosure.

In some embodiments of the present disclosure, $R_4$ is

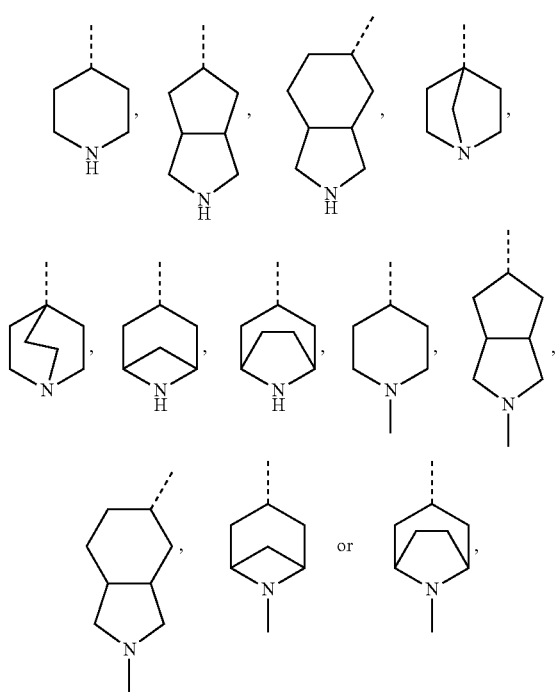

and the other variants are as defined in the present disclosure.

In some embodiments of the present disclosure, $R_4$ is

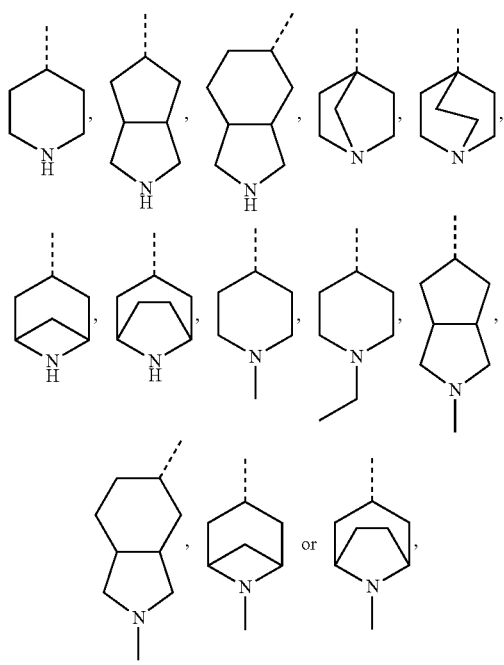

and the other variants are as defined in the present disclosure.

In some embodiments of the present disclosure, $R_4$ is

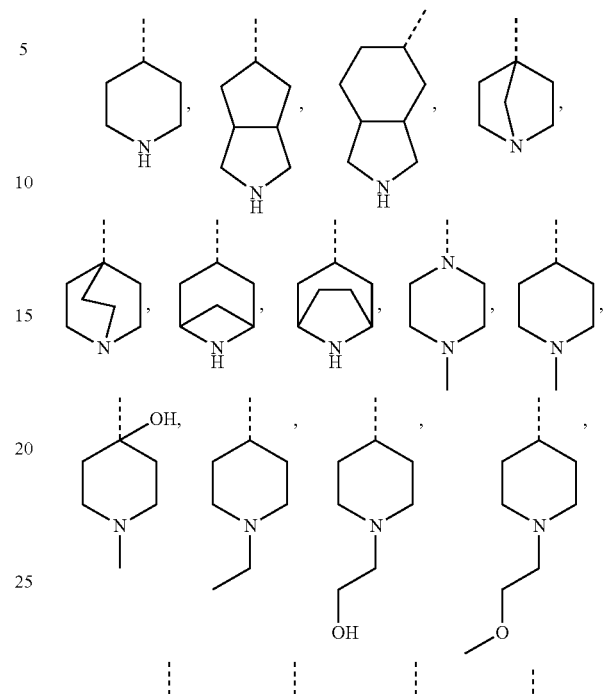

and the other variants are as defined in the present disclosure.

In some embodiments of the present disclosure, $R_4$ is

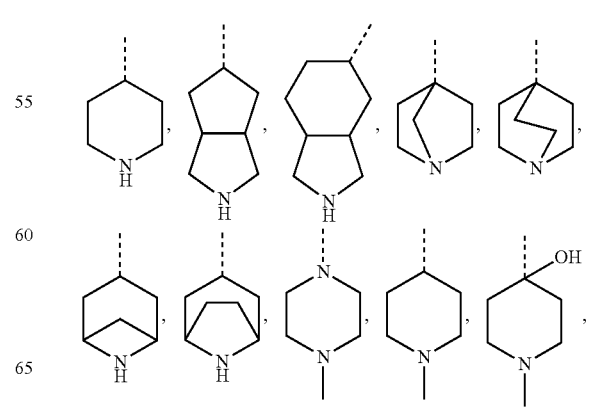

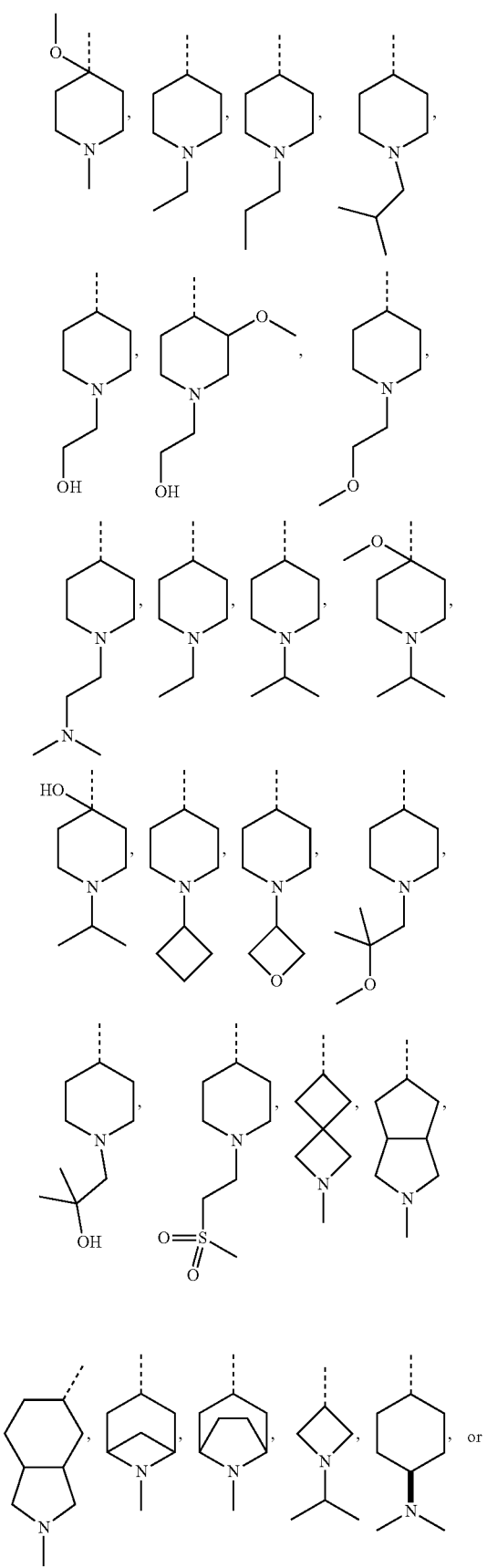
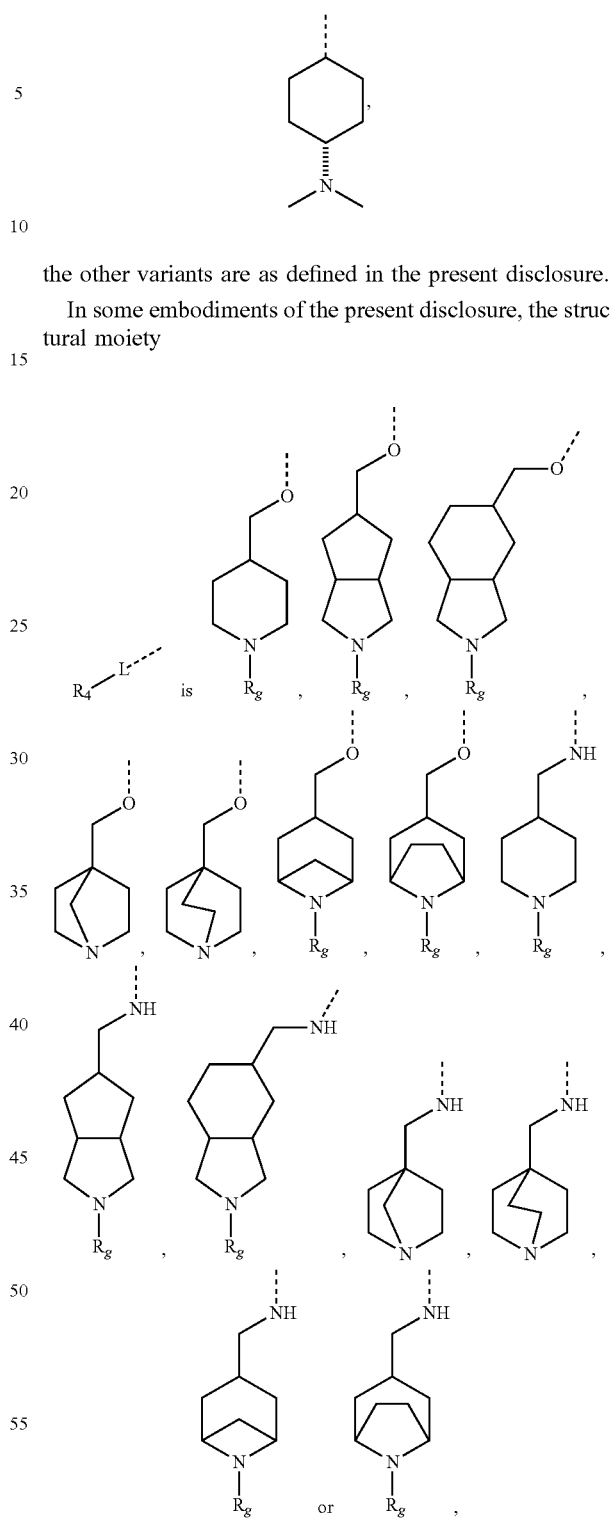
the other variants are as defined in the present disclosure.
In some embodiments of the present disclosure, the structural moiety
$R_4-L$ is
$R_g$ and the other variants are as defined in the present disclosure.
In some embodiments of the present disclosure, the structural moiety

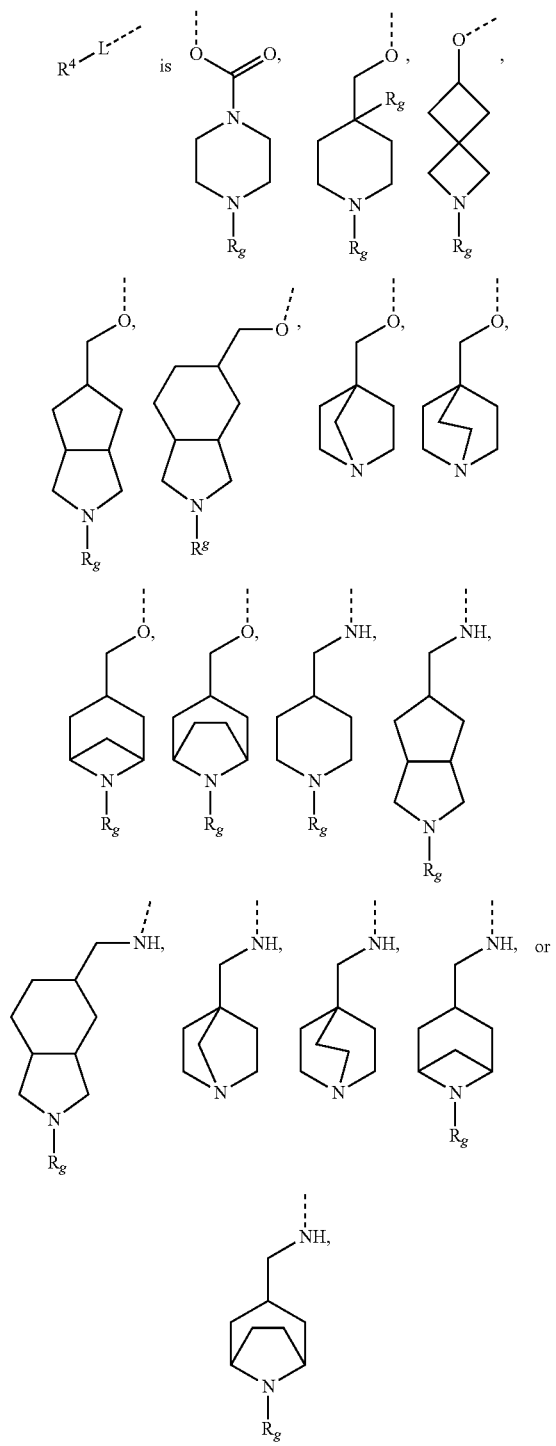
$R_g$ and the other variants are as defined in the present disclosure.
In some embodiments of the present disclosure, the structural moiety
$R_g$ and the other variants are as defined in the present disclosure.
In some embodiments of the present disclosure, the structural moiety

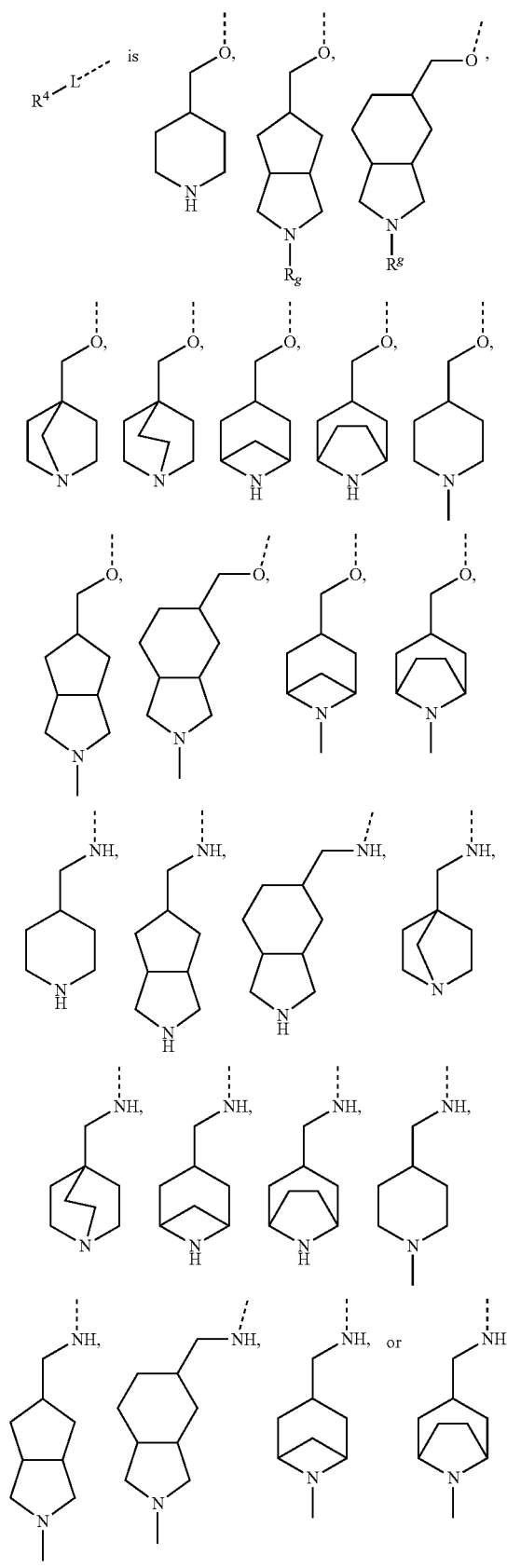
In some embodiments of the present disclosure, the structural moiety
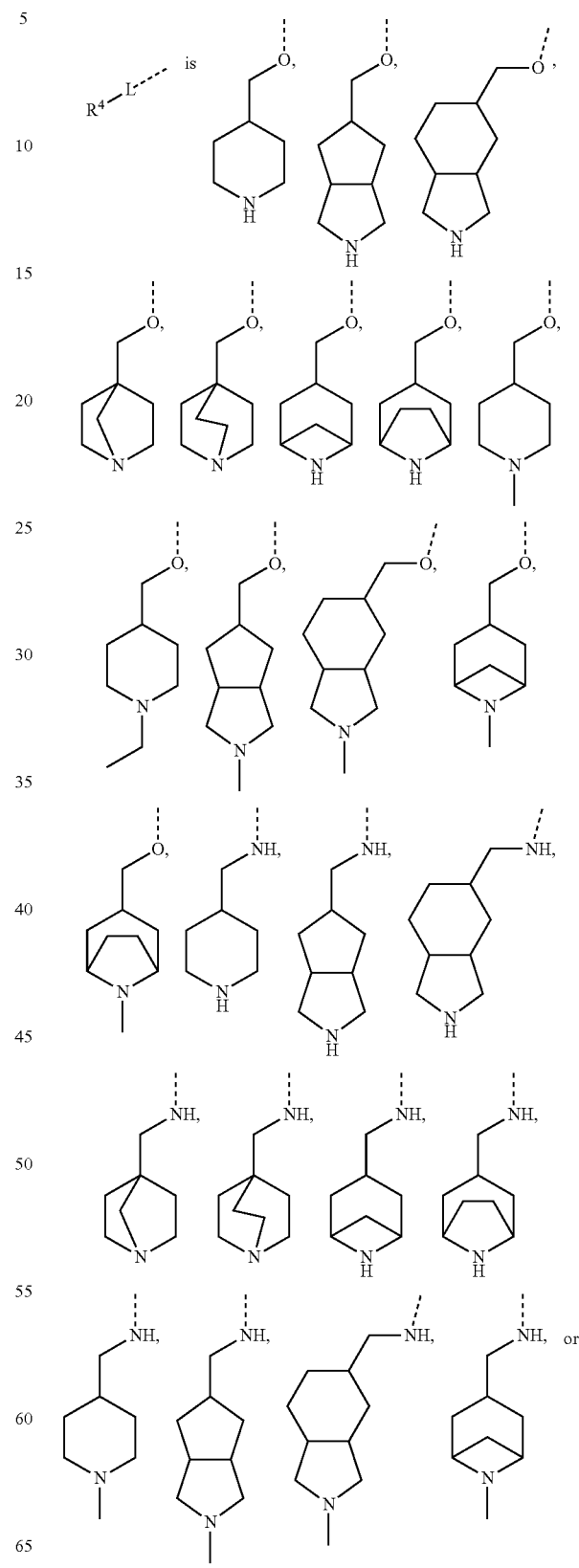
the other variants are as defined in the present disclosure.

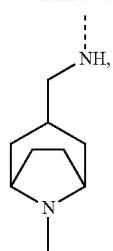
the other variants are as defined in the present disclosure.
In some embodiments of the present disclosure, the structural moiety
R₄—L is
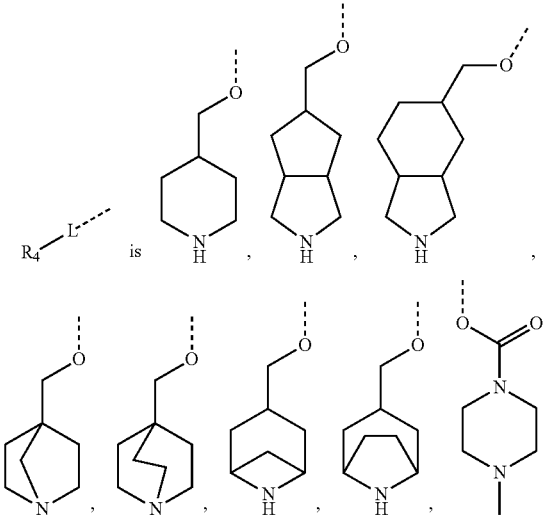
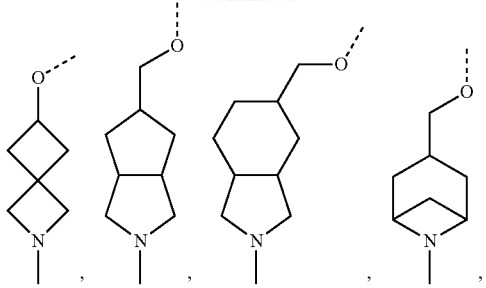
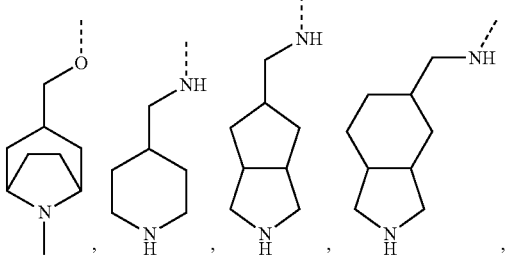
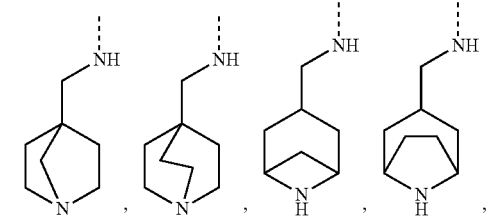
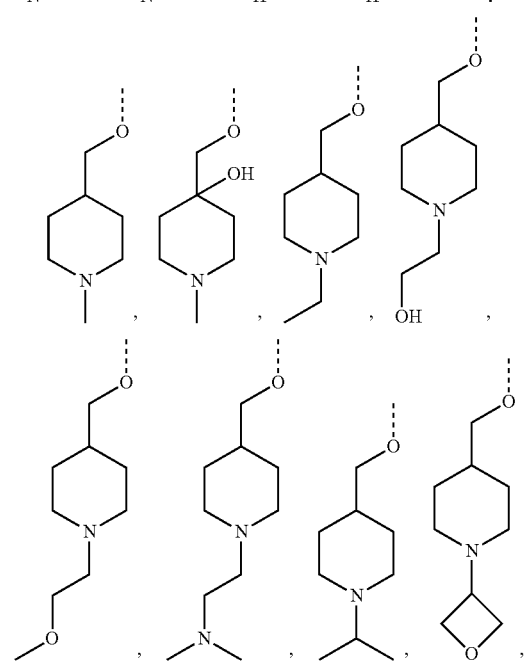
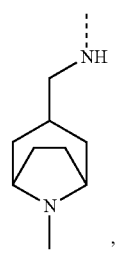
the other variants are as defined in the present disclosure.
In some embodiments of the present disclosure, the structural moiety

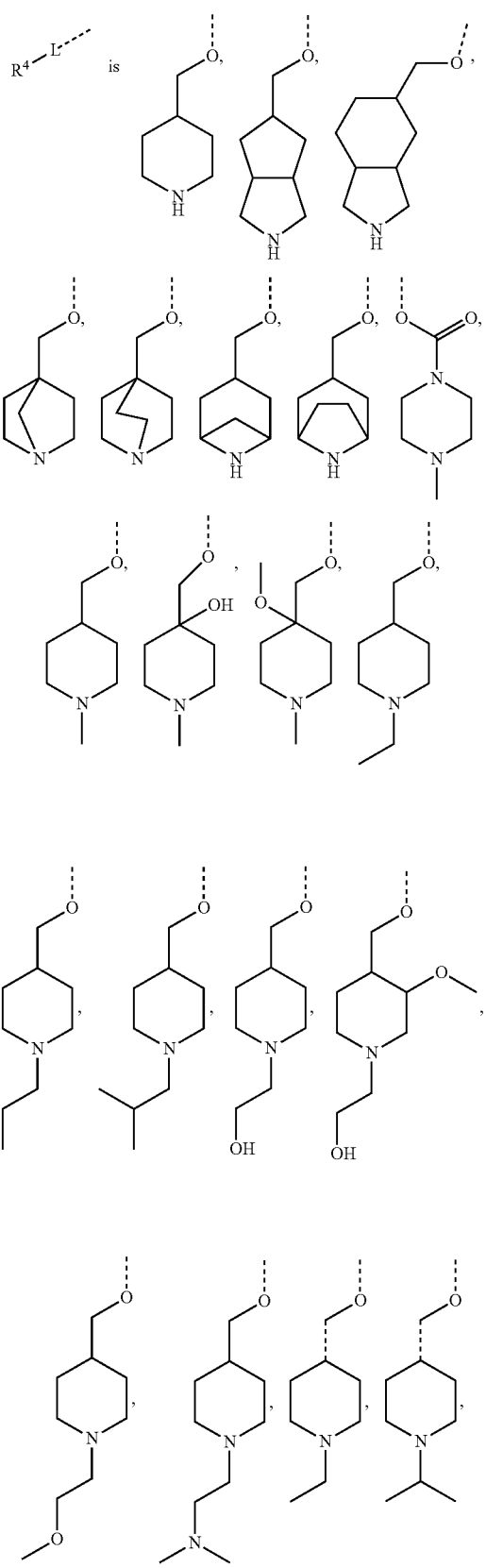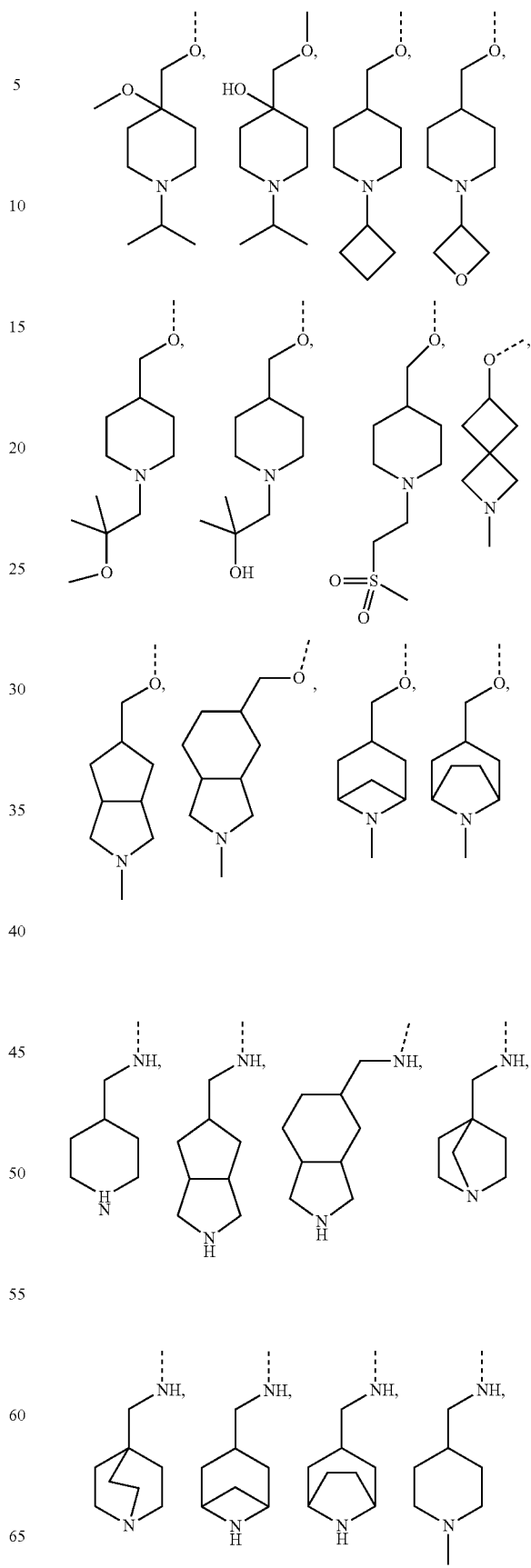

-continued

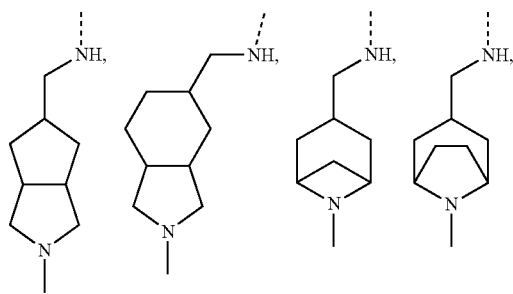

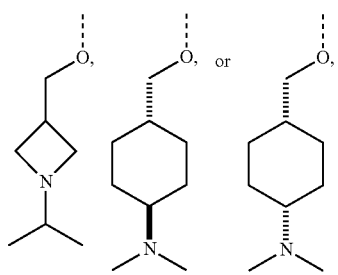

the other variants are as defined in the present disclosure.

In some embodiments of the present disclosure, the compound has the structure represented by formula (I-A6) to (I-A11):

(I-A6)

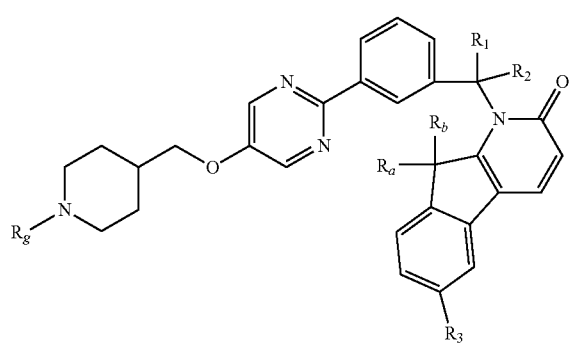

(I-A7)

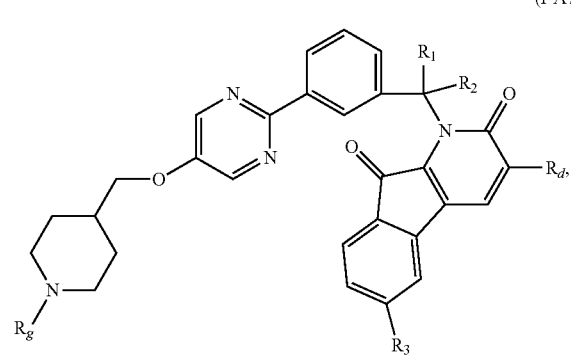

(I-A8)

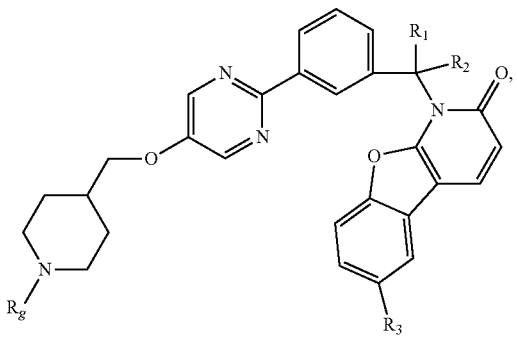

(I-A9)

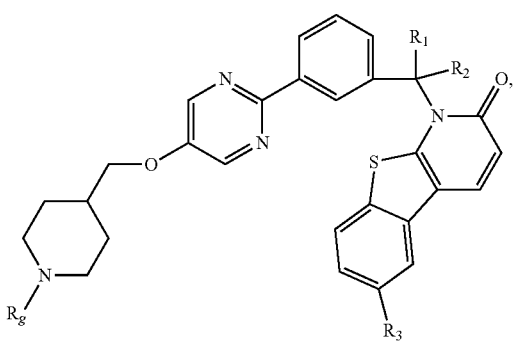

(I-A10)

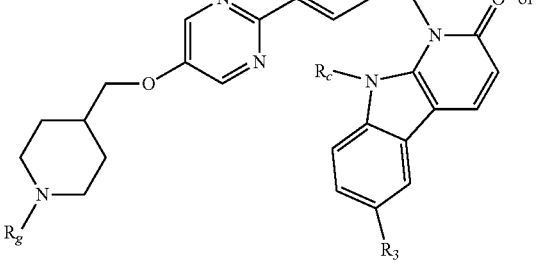

or (I-A11)

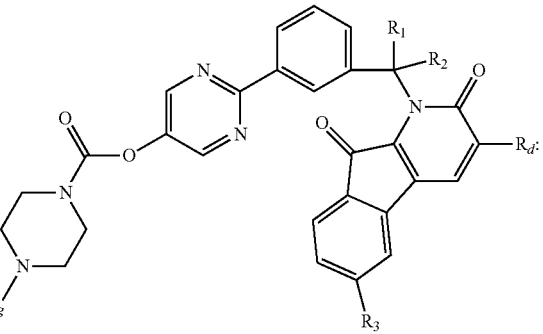

wherein, $R_2$, $R_2$, $R_3$, $R_a$, $R_b$, $R_c$, $R_d$ and $R_g$ are as defined in the present disclosure.

In some embodiments of the present disclosure, the compound has the structure represented by formula (I-B2):

(I-B2)

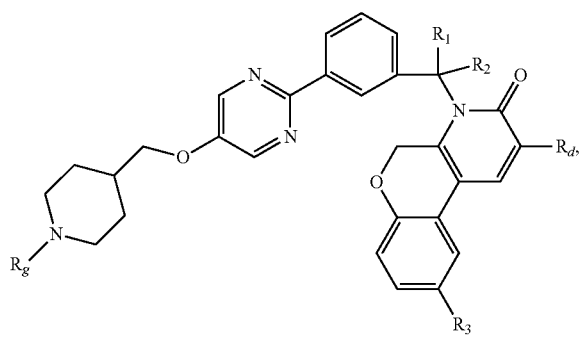

wherein, $R_1$, $R_2$, $R_3$, $R_d$ and $R_g$ are as defined in the present disclosure.

In some embodiments of the present disclosure, the compound has the structure represented by formula (I-C4) to (I-C6):

(I-C4)

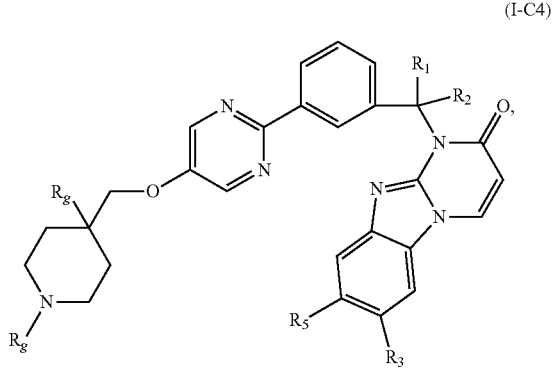

(I-C5)

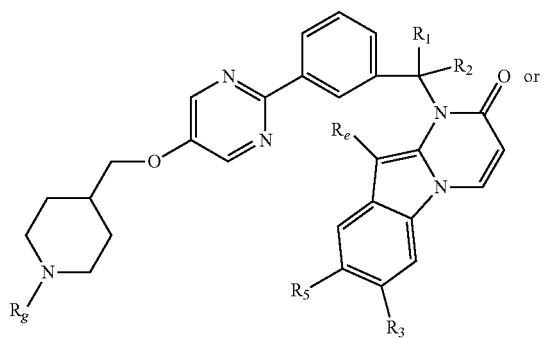

(I-C6)

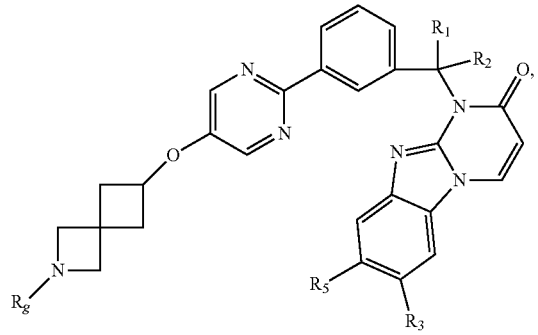

wherein, $R_1$, $R_2$, $R_3$, $R_5$, $R_e$ and $R_g$ are as defined in the present disclosure.

In some embodiments of the present disclosure, the compound has the structure represented by formula (I-E2):

(I-E2)

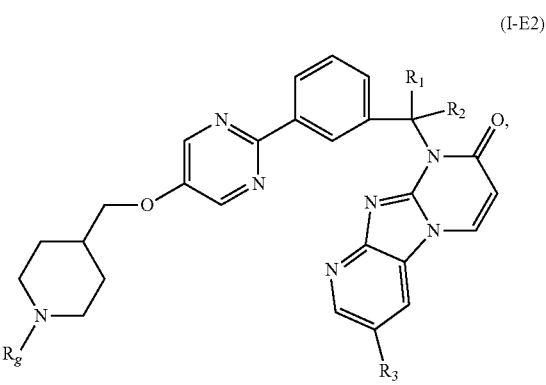

wherein, $R_1$, $R_2$, $R_3$ and $R_g$ are as defined in the present disclosure.

In some embodiments of the present disclosure, the compound has the structure represented by formula (I-D2) or (I-F2):

(I-D2)

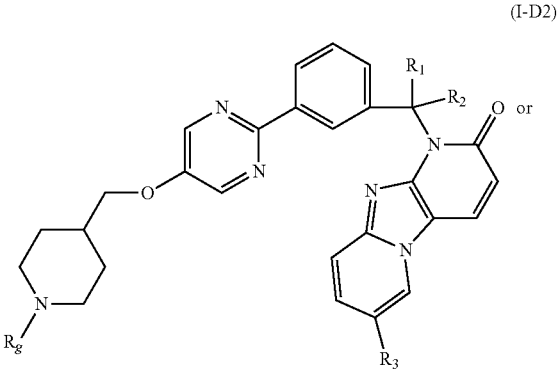

-continued
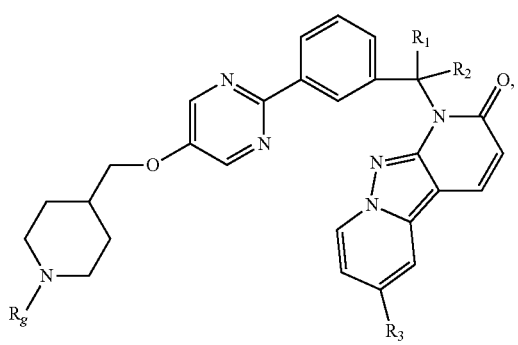
wherein, $R_1$, $R_2$, $R_3$ and $R_g$ are as defined in the present disclosure.
In some embodiments of the present disclosure, the structural moiety
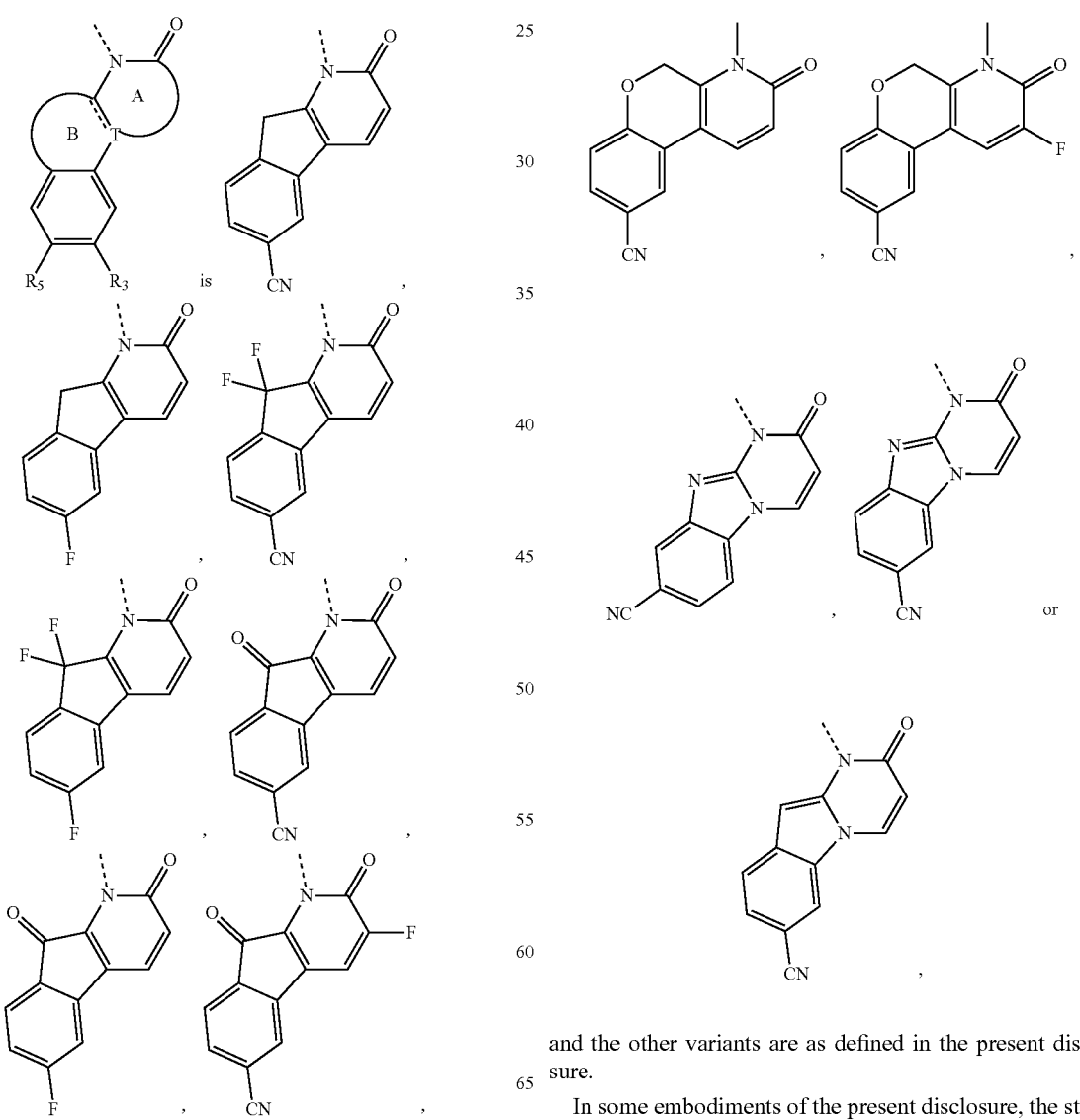
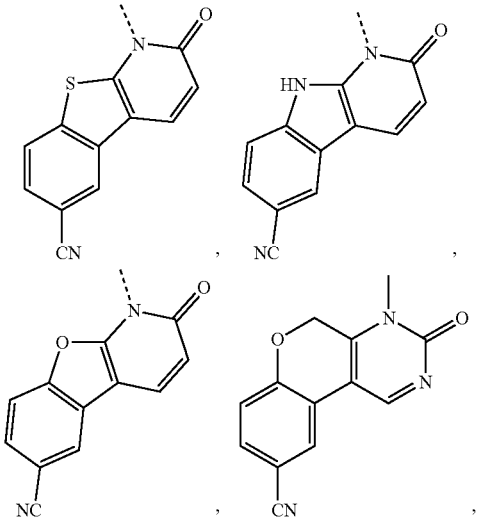
and the other variants are as defined in the present disclosure.
In some embodiments of the present disclosure, the structural moiety

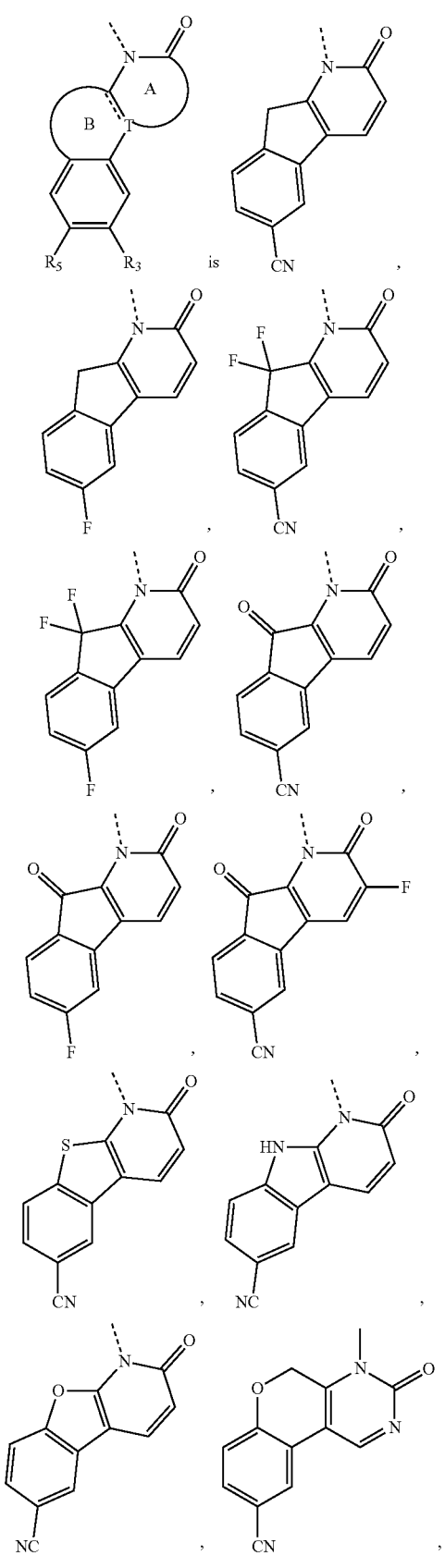
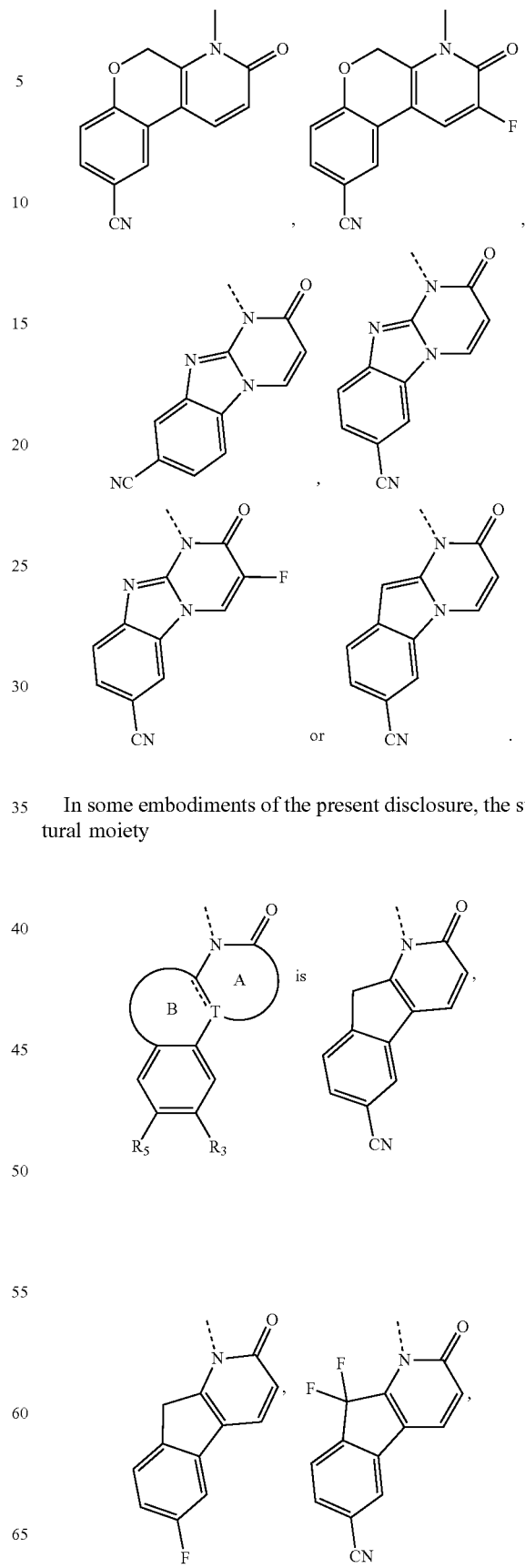
In some embodiments of the present disclosure, the structural moiety

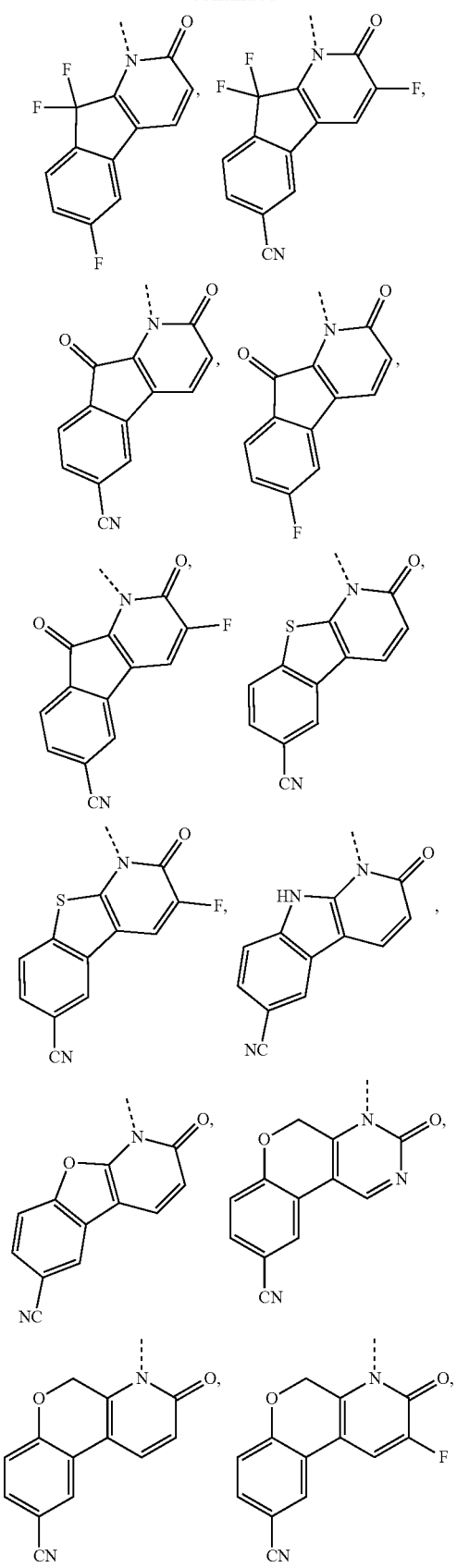
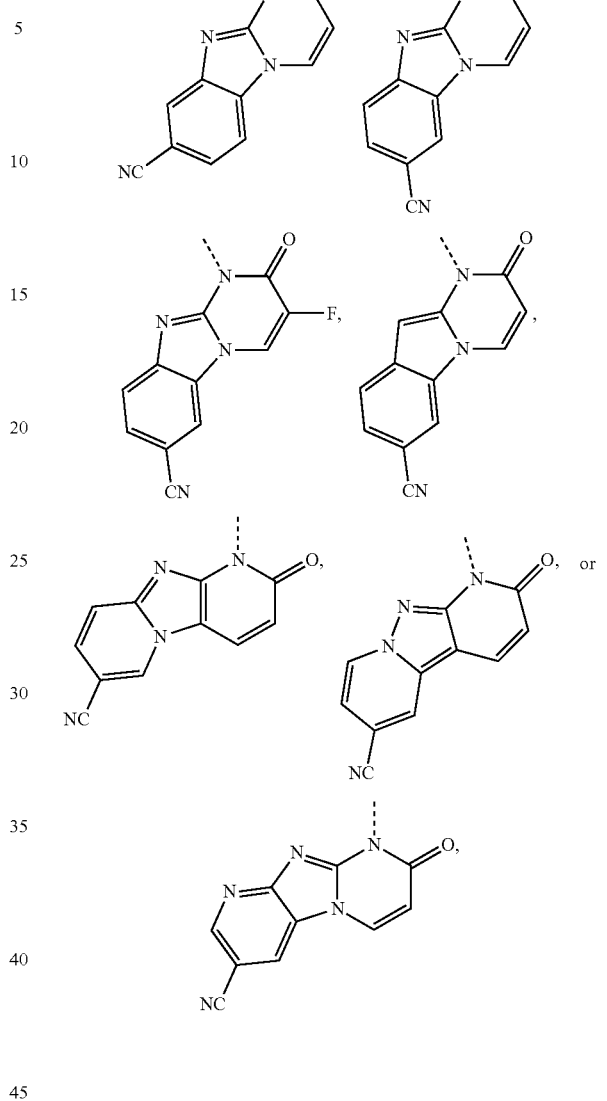
the other variants are as defined in the present disclosure.
In some embodiments of the present disclosure, the structural moiety
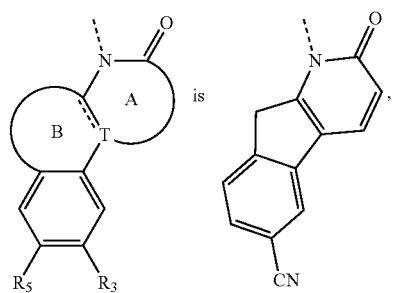

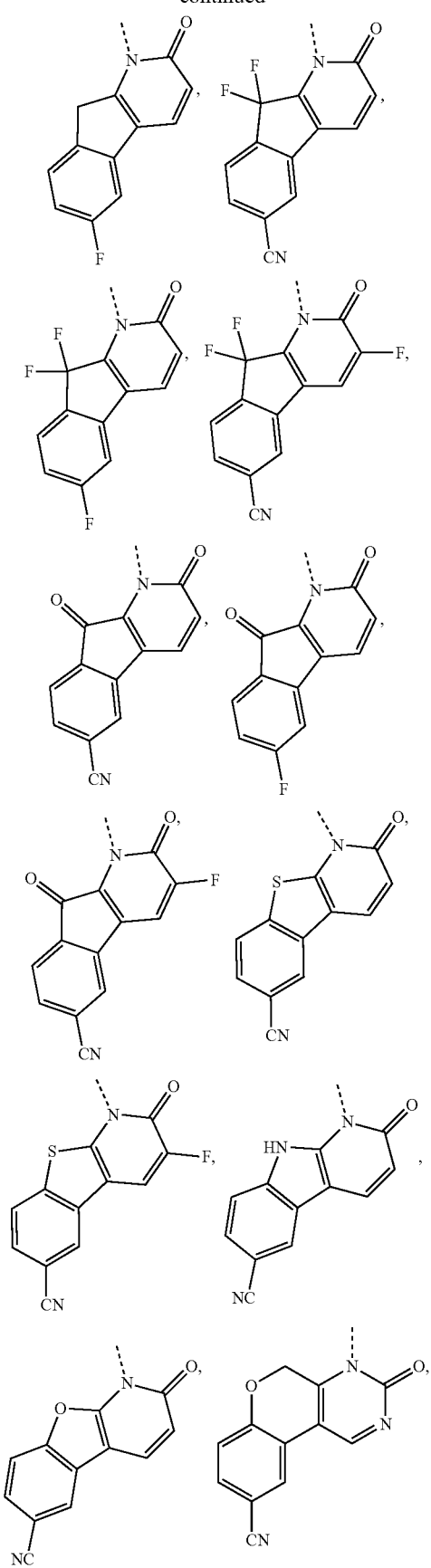
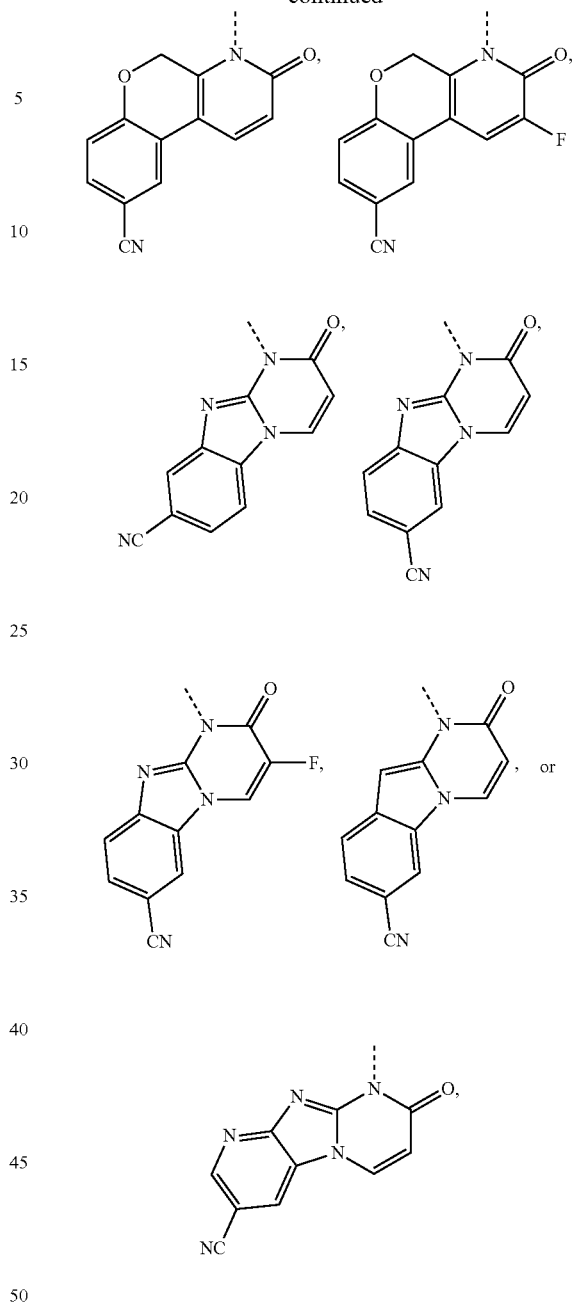

and the other variants are as defined in the present disclosure.

In some embodiments of the present disclosure, each of $R_3$ and $R_5$ is independently H, F, Cl, —CN, —OH or —OCH$_3$, the other variants are as defined in the present disclosure.

In some embodiments of the present disclosure, $R_3$ is H, F, Cl, —CN, —OH or —OCH$_3$, the other variants are as defined in the present disclosure.

In addition, some embodiments of the present disclosure are derived from arbitrary combinations of the above variables.

The present disclosure provides a compound represented by the following formula, a pharmaceutically acceptable salt thereof, or an isomer thereof,

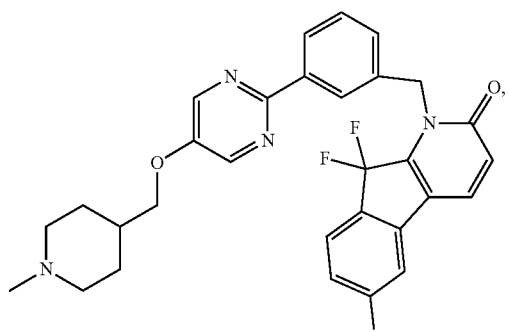
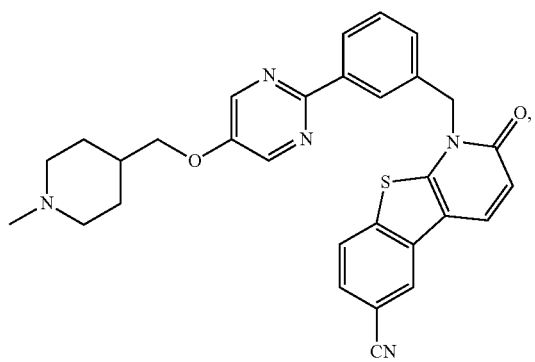
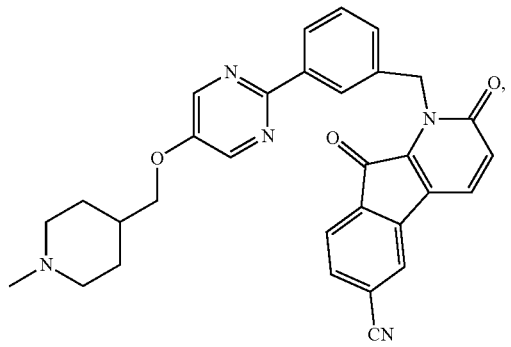
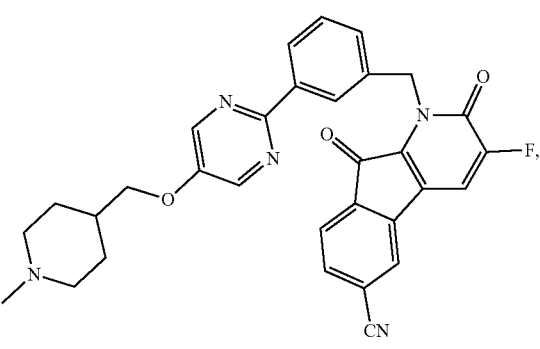
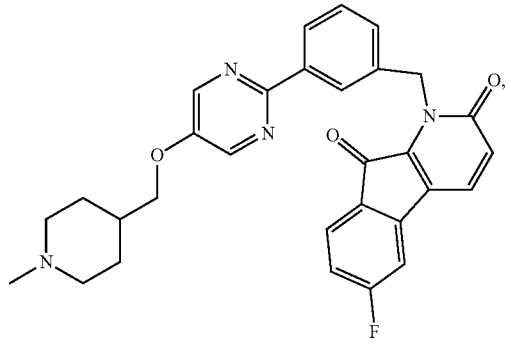
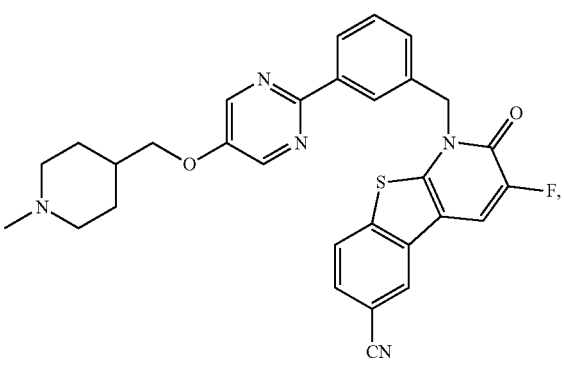
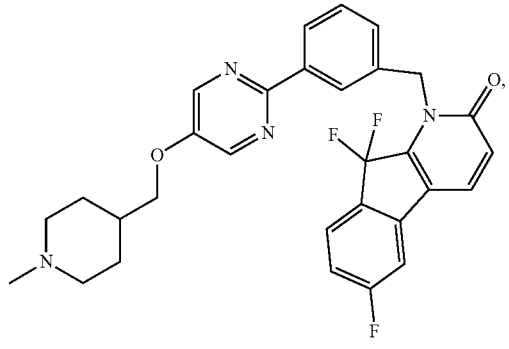
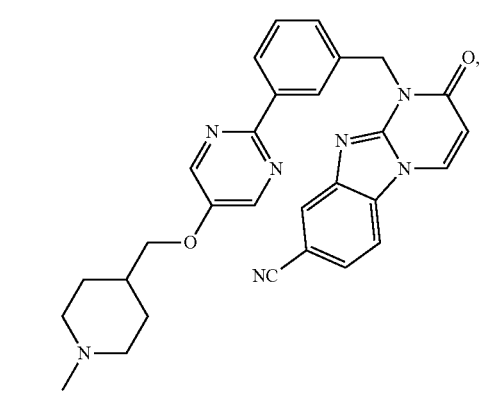
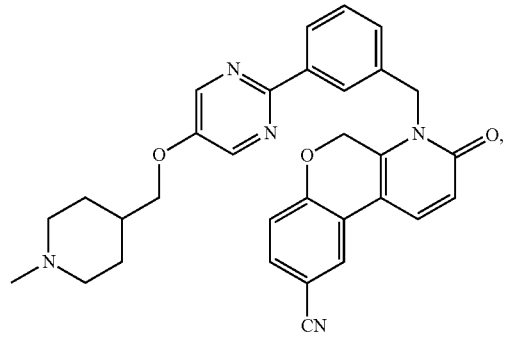

-continued
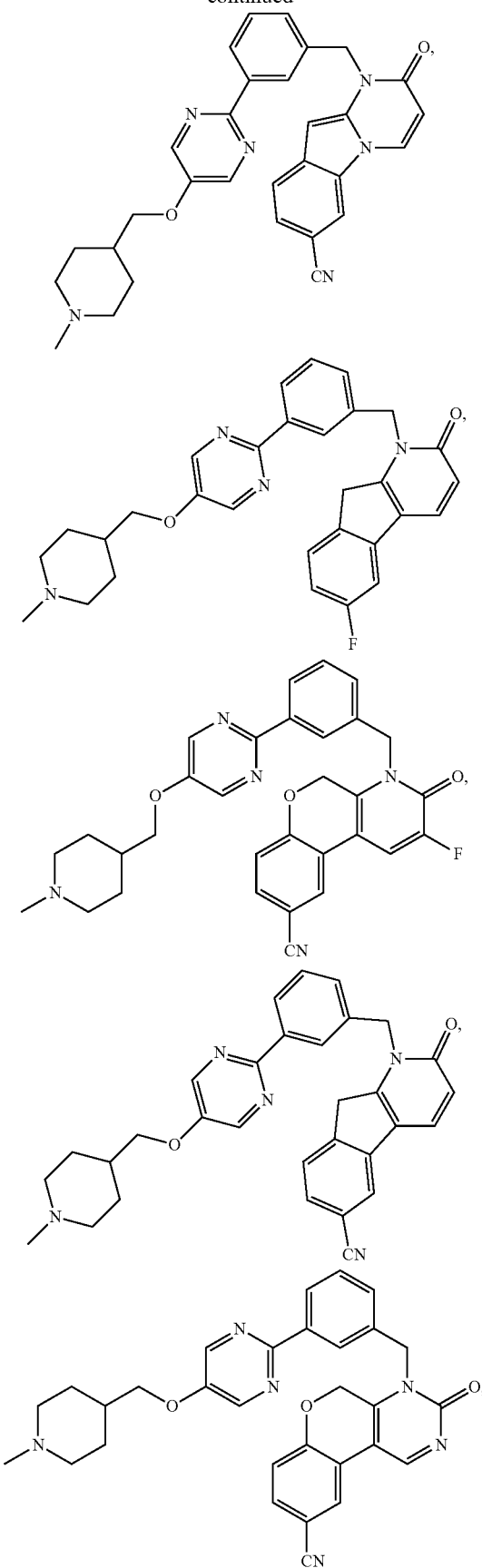
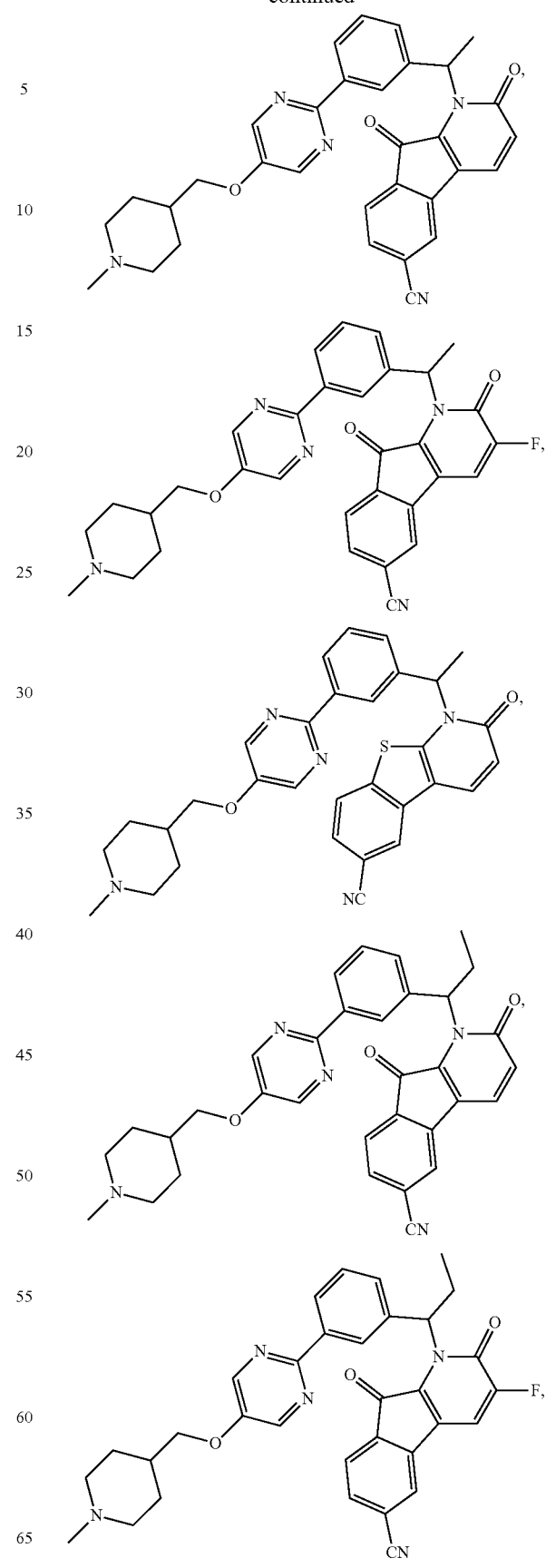

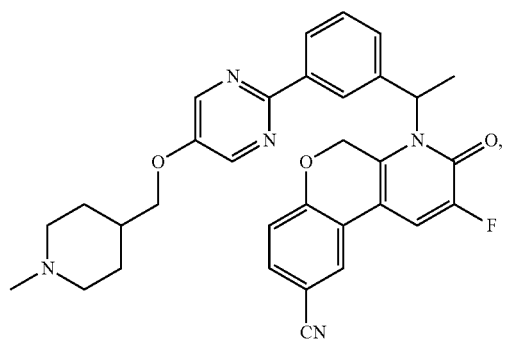
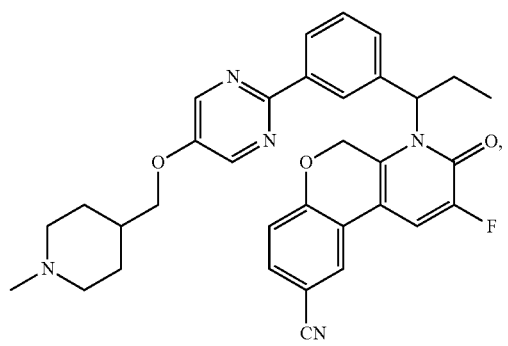
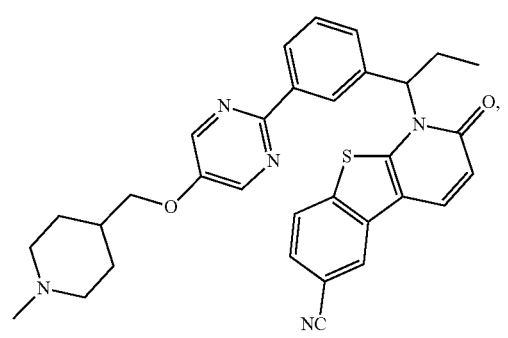
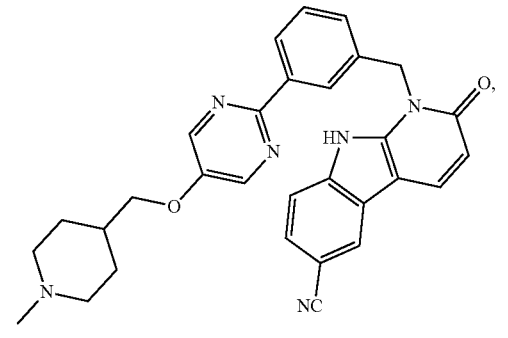
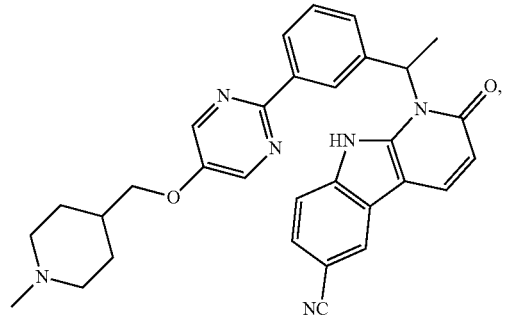
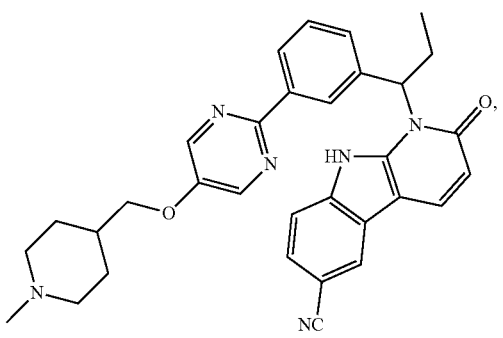
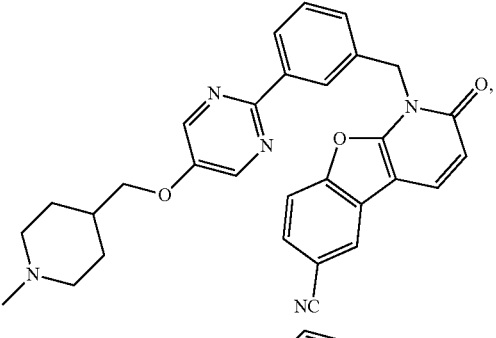
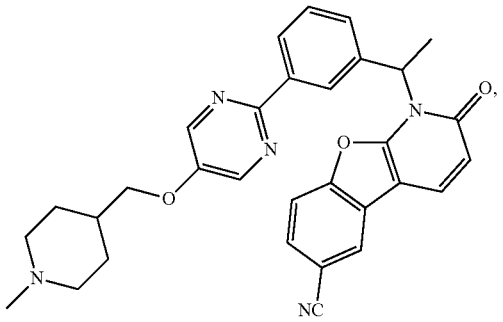
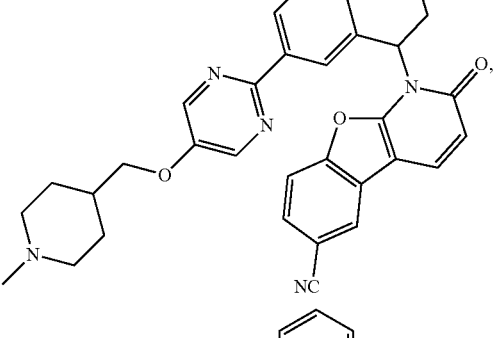
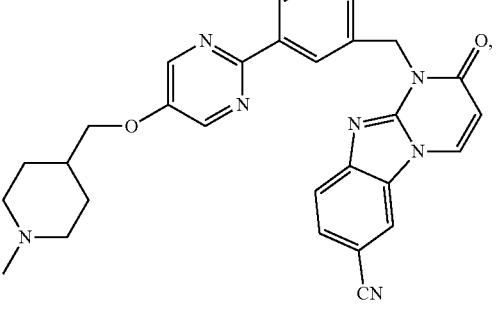

49
-continued
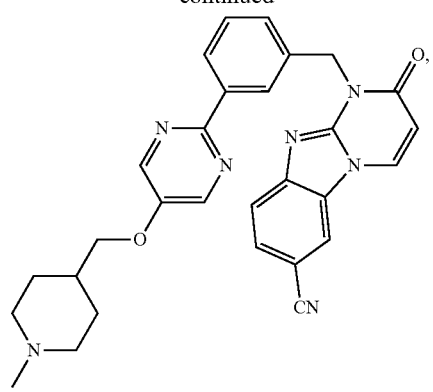
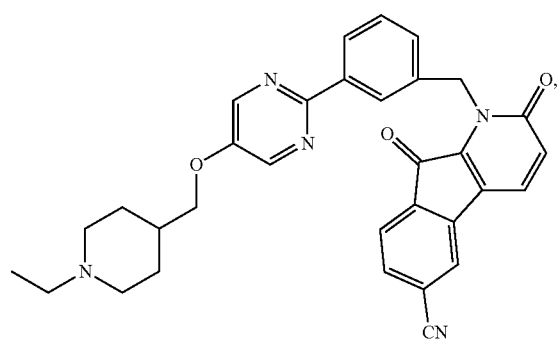
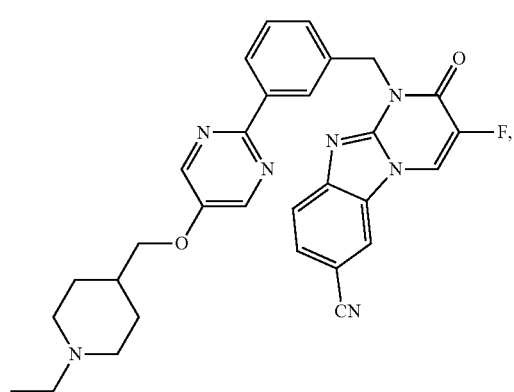
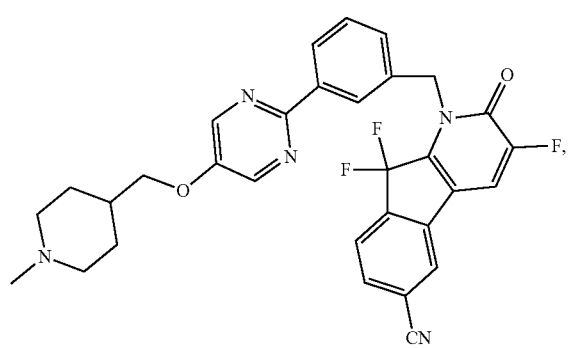
50
-continued
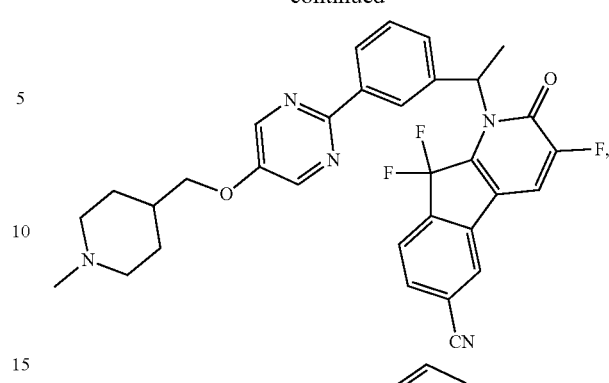
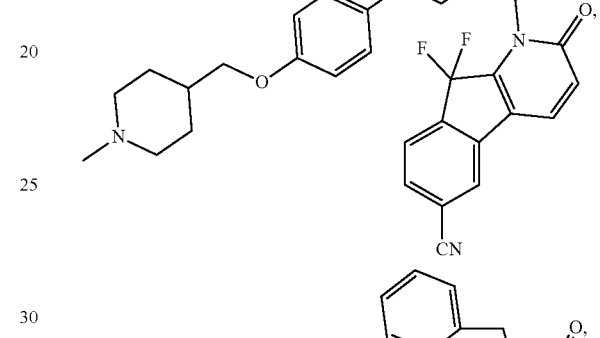
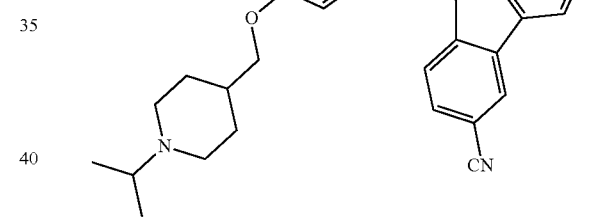
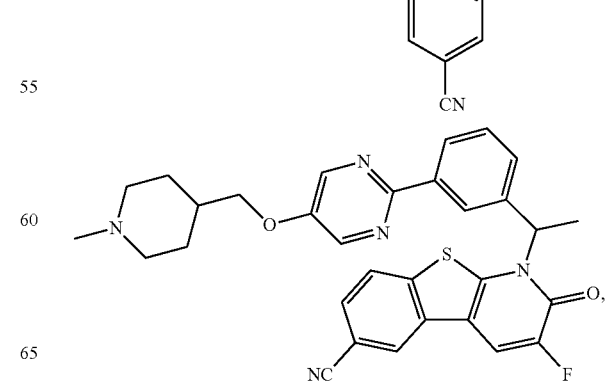

-continued
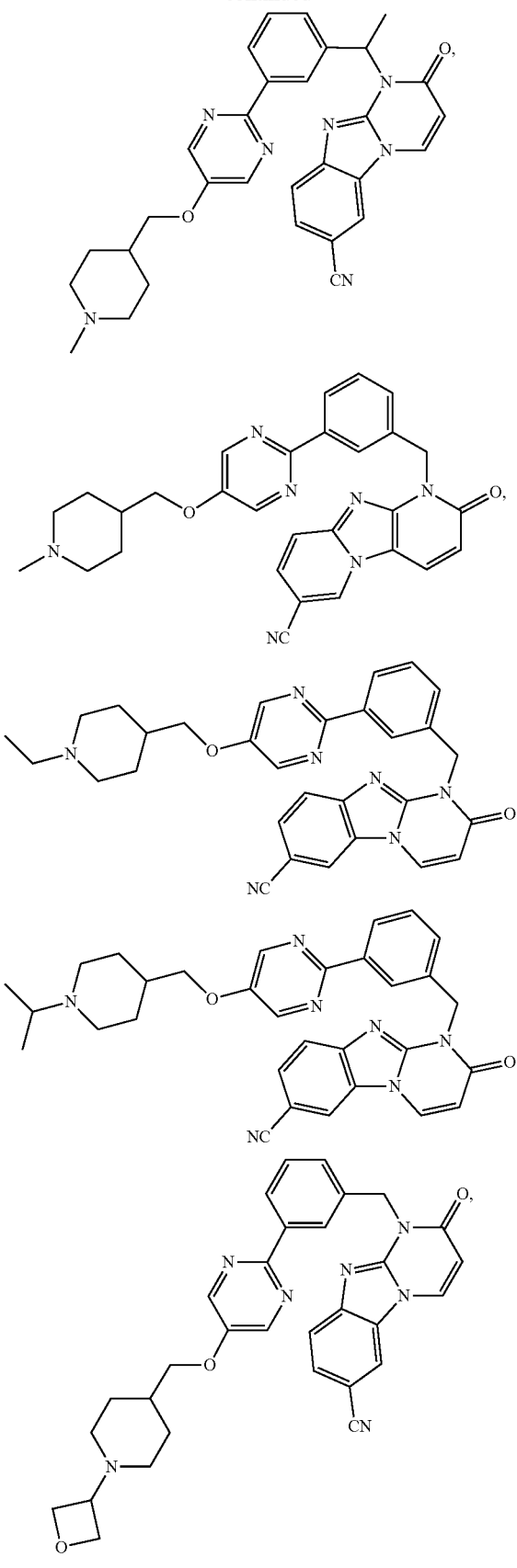
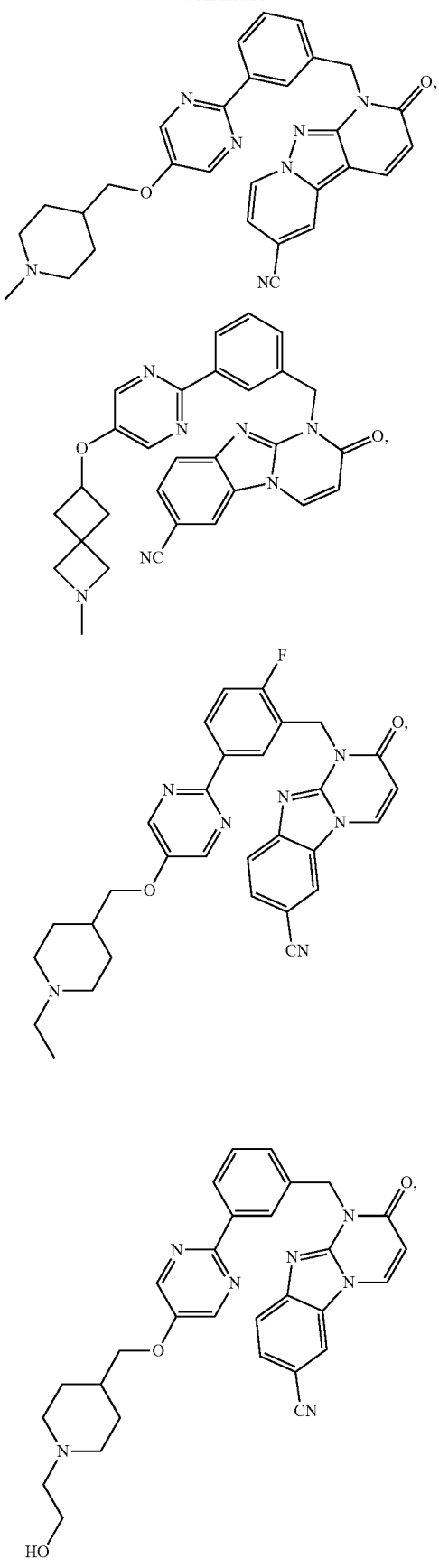

53
-continued
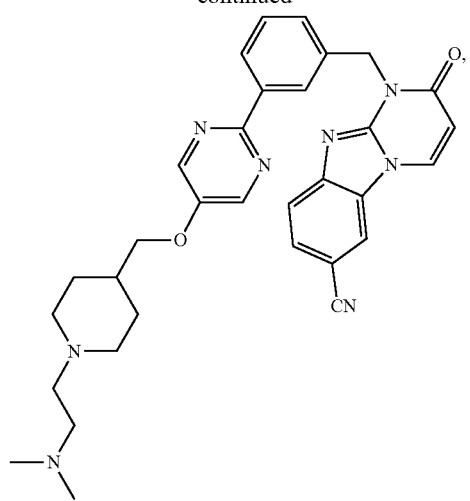
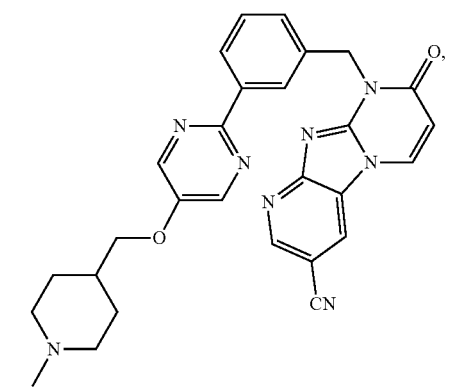
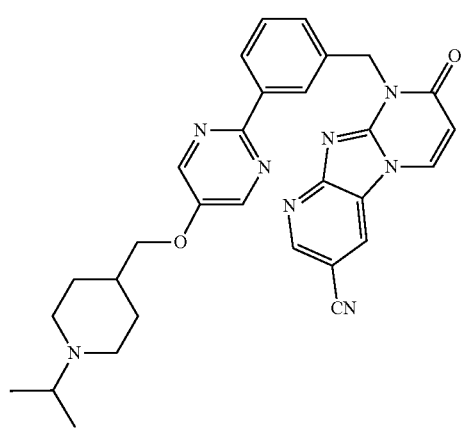
54
-continued
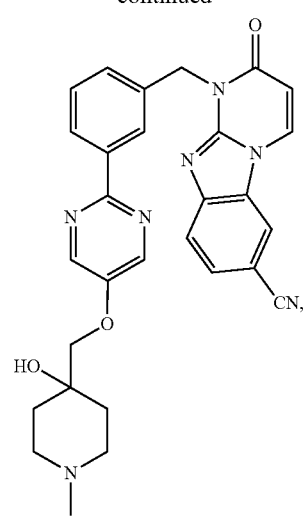
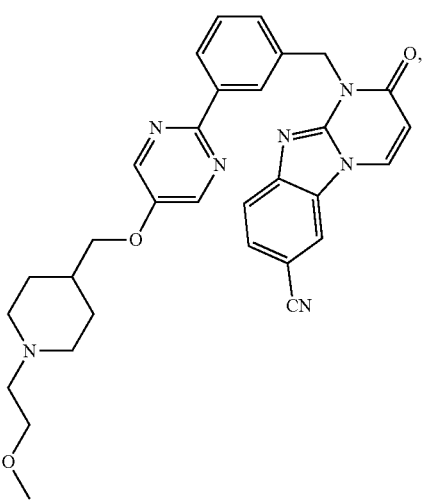
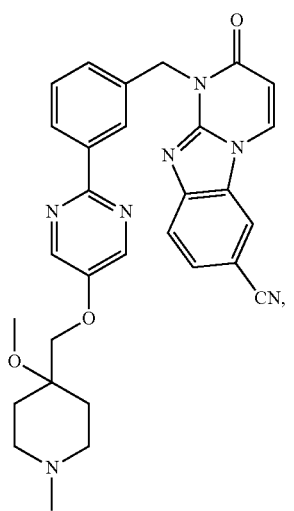

55
-continued
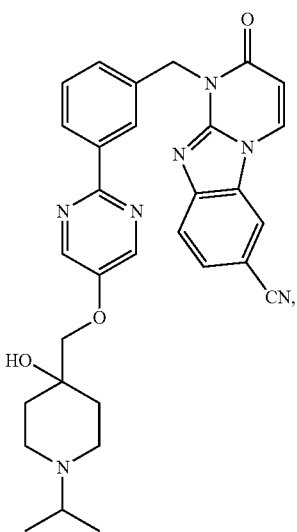
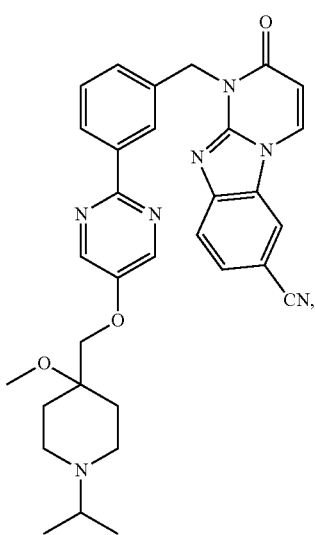
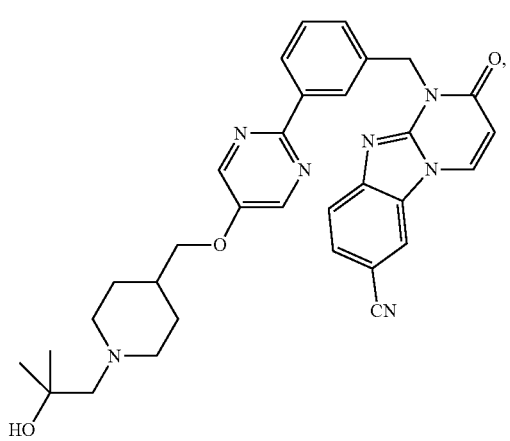
56
-continued
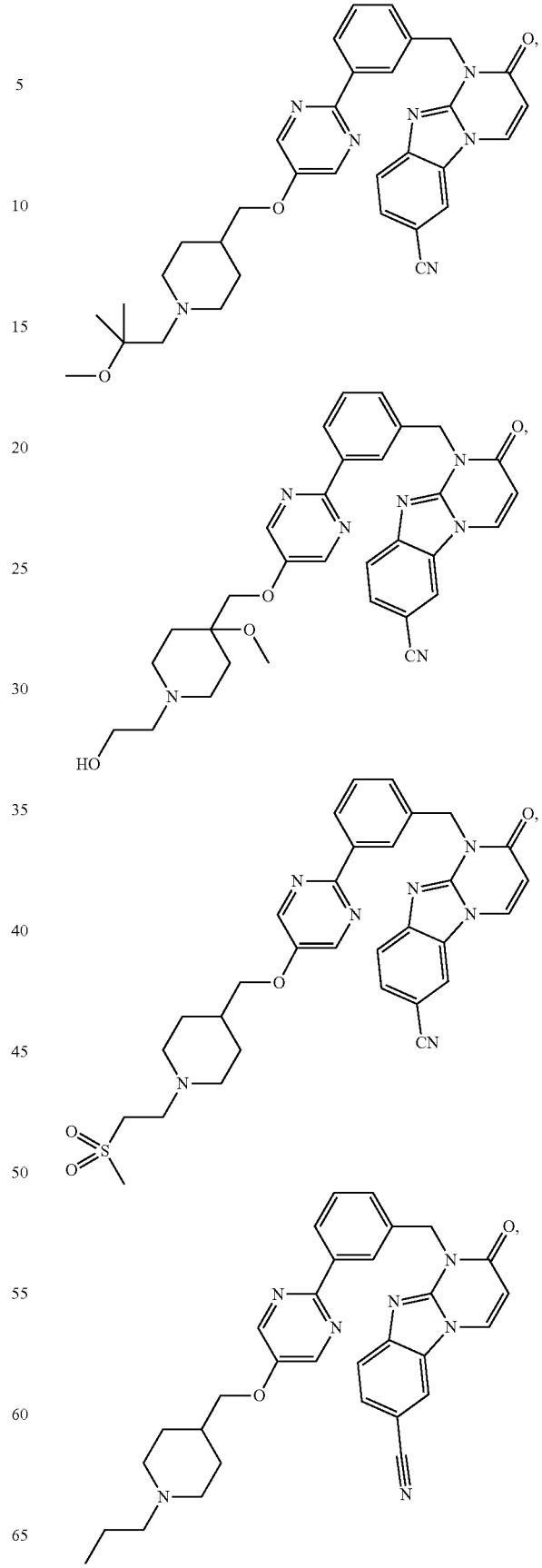

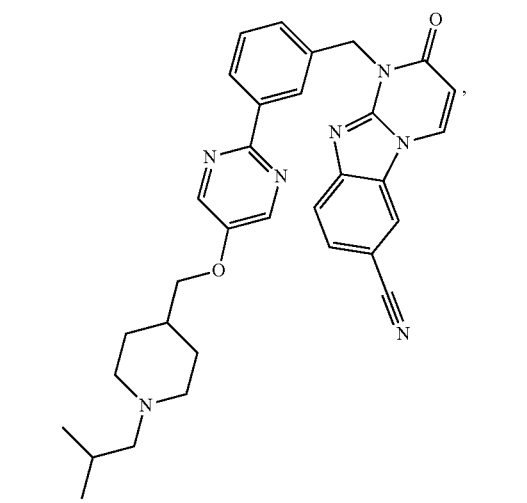
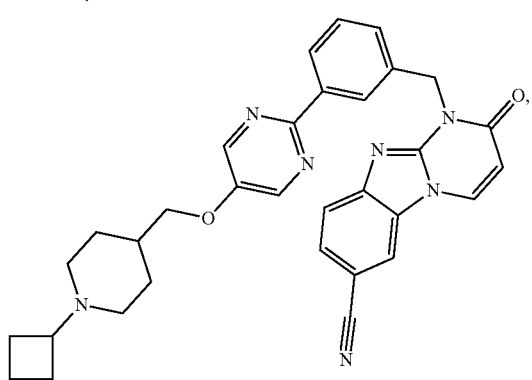
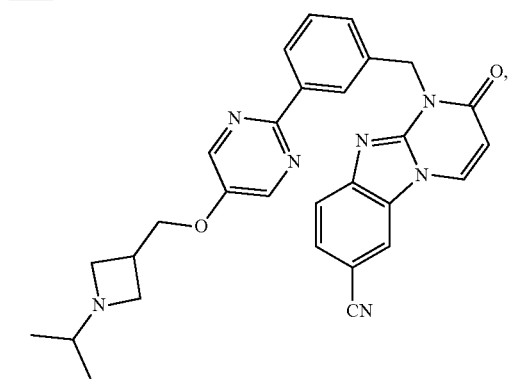
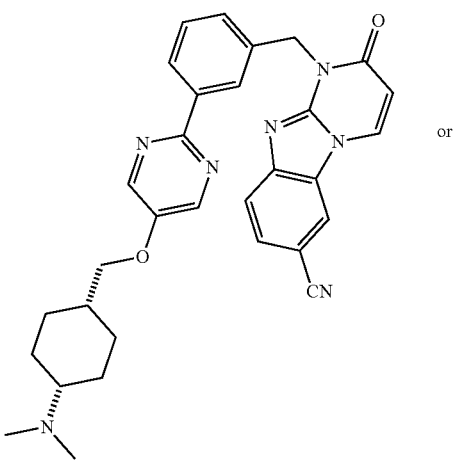
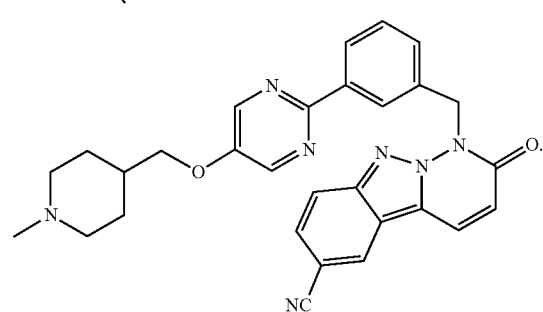
The present disclosure provides a compound represented by the following formula, a pharmaceutically acceptable salt thereof, or an isomer thereof,
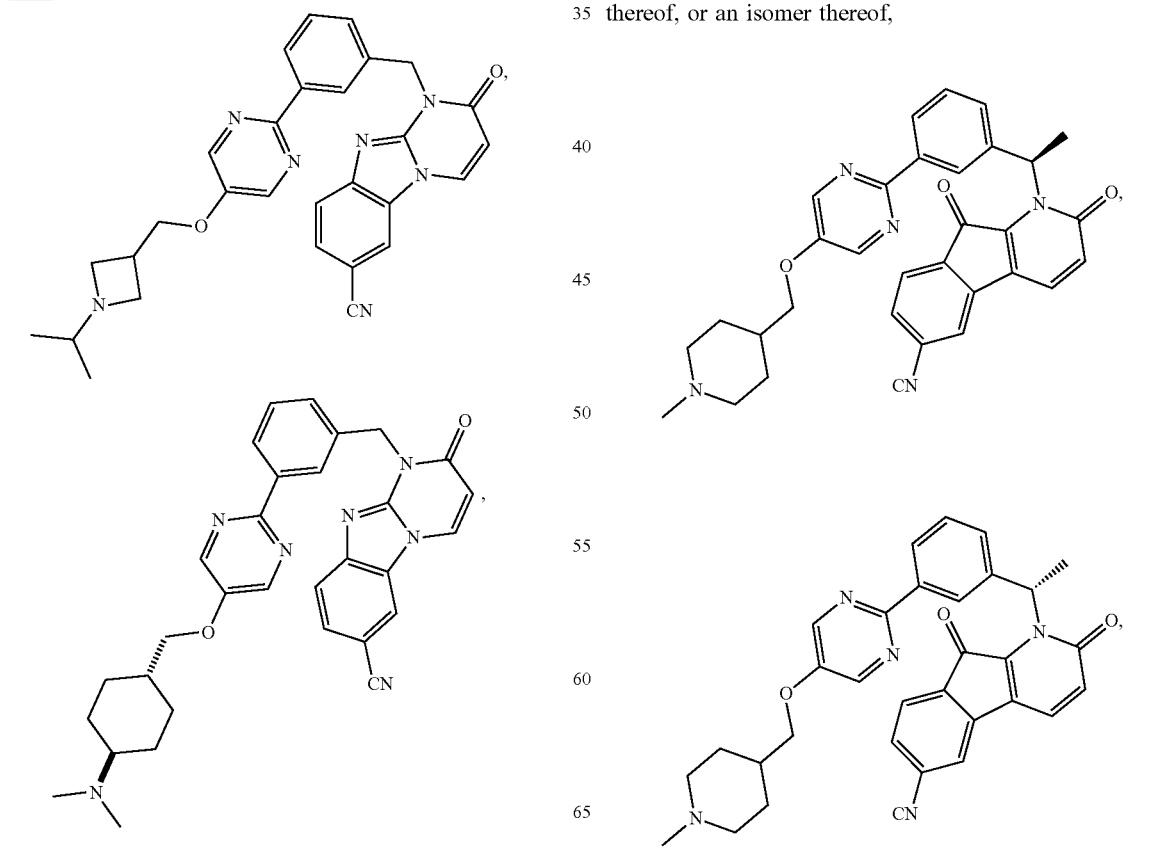

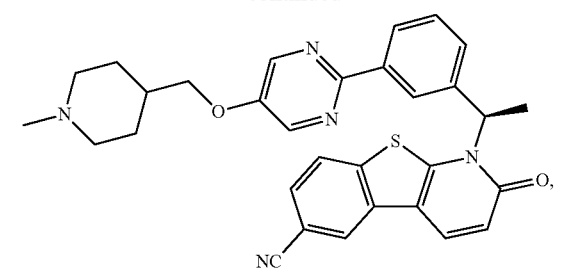
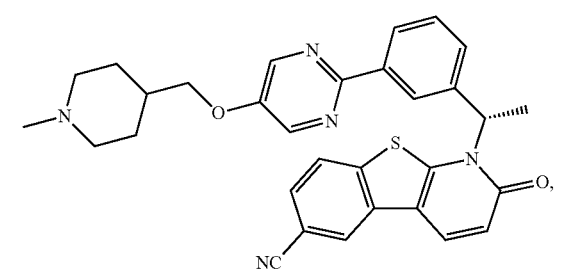
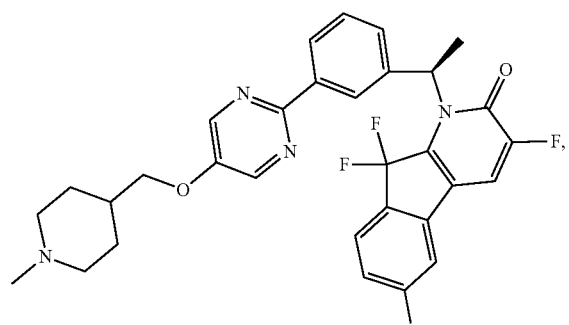
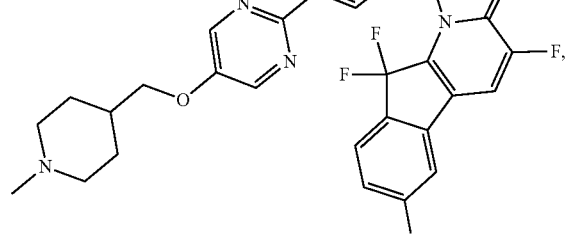
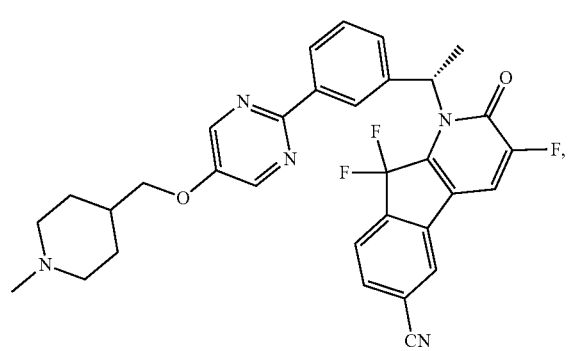
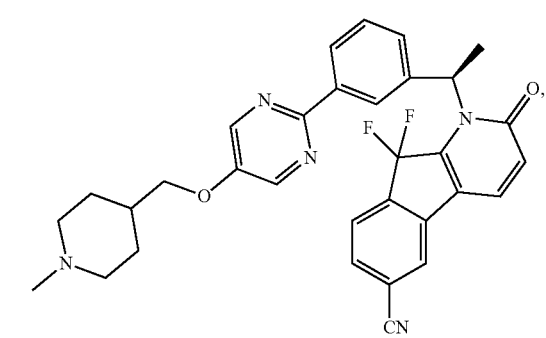
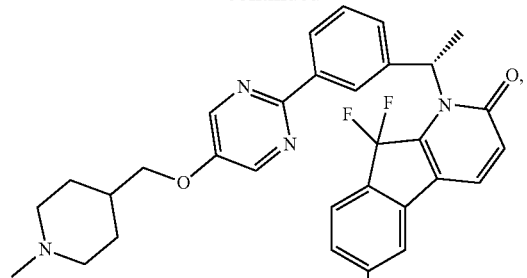
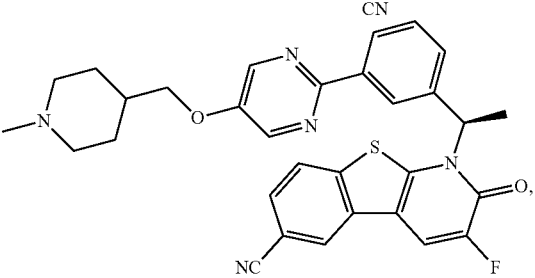
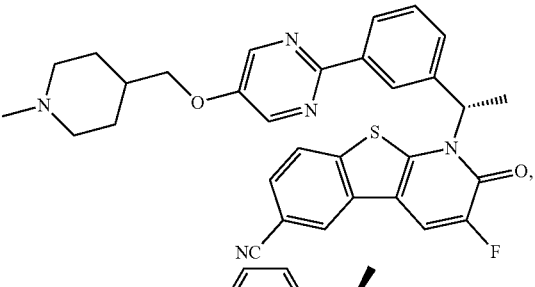
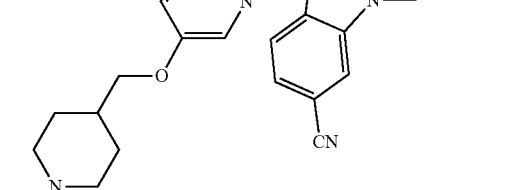
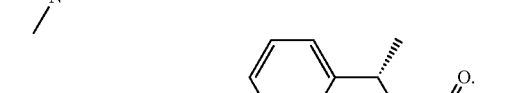
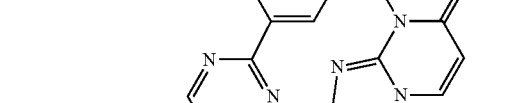
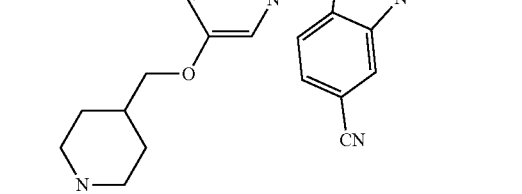
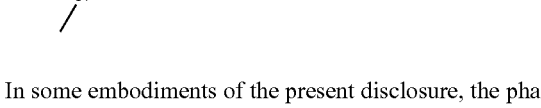
In some embodiments of the present disclosure, the pharmaceutically acceptable salt is formate or hydrochloride.
The present disclosure also provides a pharmaceutical composition containing a therapeutically effective amount of the compound, the pharmaceutically acceptable salt or the isomer thereof, or the formate or hydrochloride, and a pharmaceutically acceptable carrier.

The present disclosure also provides a use of the compound, the pharmaceutically acceptable salt or the isomer thereof, or the formate or hydrochloride, and the pharmaceutical composition in preparing a medicament of c-Met inhibitor.

TECHNICAL EFFECT

The compound of the present disclosure has good selectivity and inhibitory activity on c-Met kinase, and has excellent pharmacokinetic and pharmacodynamic properties. It's expected to be used in the treatment of abnormal c-Met signaling pathways and drug resistance c-Met abnormal expression tumors.

DEFINITION AND DESCRIPTION

Unless otherwise specified, the following terms and phrases used herein are intended to have the following meanings. A specific term or phrase should not be considered indefinite or unclear in the absence of a particular definition, but should be understood in the ordinary sense. When a trading name appears herein, it is intended to refer to its corresponding commodity or active ingredient thereof.

The term "pharmaceutically acceptable" is used herein in terms of those compounds, materials, compositions, and/or dosage forms, which are suitable for use in contact with human and animal tissues within the scope of reliable medical judgment, with no excessive toxicity, irritation, an allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by bringing the compound into contact with a sufficient amount of base in a pure solution or a suitable inert solvent. The pharmaceutically acceptable base addition salt includes a salt of sodium, potassium, calcium, ammonium, organic amine or magnesium, or similar salts. When the compound of the present disclosure contains a relatively basic functional group, an acid addition salt can be obtained by bringing the compound into contact with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid, and the like; and salts of amino acid (such as arginine and the like), and a salt of an organic acid such as glucuronic acid and the like. Certain specific compounds of the present disclosure contain both basic and acidic functional groups, thus can be converted to any base or acid addition salt.

The pharmaceutically acceptable salt of the present disclosure can be prepared from the parent compound that contains an acidic or basic moiety by conventional chemical method. Generally, such salt can be prepared by reacting the free acid or base form of the compound with a stoichiometric amount of an appropriate base or acid in water or an organic solvent or a mixture thereof.

The compounds of the present disclosure may exist in specific geometric or stereoisomeric forms. The present disclosure contemplates all such compounds, including cis and trans isomers, (−)- and (+)-enantiomers, (R)- and (S)-enantiomers, diastereomers isomers, (D)-isomers, (L)-isomers, and racemic and other mixtures thereof, such as enantiomers or diastereomeric enriched mixtures, all of which are within the scope of the present disclosure. Additional asymmetric carbon atoms may be present in substituents such as alkyl. All these isomers and their mixtures are included within the scope of the present disclosure.

Unless otherwise specified, the term "enantiomer" or "optical isomer" refers to stereoisomers that are mirror images of each other.

Unless otherwise specified, the term "cis-trans isomer" or "geometric isomer" is caused by the inability to rotate freely of double bonds or single bonds of ring-forming carbon atoms.

Unless otherwise specified, the term "diastereomer" refers to a stereoisomer in which a molecule has two or more chiral centers and the relationship between the molecules is not mirror images.

Unless otherwise specified, "(+)" refers to dextrorotation, "(−)" refers to levorotation, and "(±)" refers to racemic.

Unless otherwise specified, the absolute configuration of a stereogenic center is represented by a wedged solid bond ( ) and a wedged dashed bond ( ) and the relative configuration of a stereogenic center is represented by a straight solid bond) ( ) and a straight dashed bond ( ), a wave line ( ) is used to represent a wedged dashed bond ( ) or a wedged dashed bond ( ) or the wave line ( ) is used to represent a straight solid bond ( ) and a straight dashed bond ( ).

Unless otherwise specified, the term "tautomer" or "tautomeric form" means that at room temperature, the isomers of different functional groups are in dynamic equilibrium and can be transformed into each other quickly. If tautomers possibly exist (such as in solution), the chemical equilibrium of tautomers can be reached. For example, proton tautomer (also called prototropic tautomer) includes interconversion through proton migration, such as keto-enol isomerization and imine-enamine isomerization. Valence tautomer includes some recombination of bonding electrons for mutual transformation. A specific example of keto-enol tautomerization is the tautomerism between two tautomers of pentane-2,4-dione and 4-hydroxypent-3-en-2-one.

Unless otherwise specified, the terms "enriched in one isomer", "enriched in isomers", "enriched in one enantiomer" or "enriched in enantiomers" refer to the content of one of the isomers or enantiomers is less than 100%, and the content of the isomer or enantiomer is greater than or equal to 60%, or greater than or equal to 70%, or greater than or equal to 80%, or greater than or equal to 90%, or greater than or equal to 95%, or greater than or equal to 96%, or greater than or equal to 97%, or greater than or equal to 98%, or greater than or equal to 99%, or greater than or equal to 99.5%, or greater than or equal to 99.6%, or greater than or equal to 99.7%, or greater than or equal to 99.8%, or greater than or equal to 99.9%.

Unless otherwise specified, the term "isomer excess" or "enantiomeric excess" refers to the difference between the relative percentages of two isomers or two enantiomers. For example, if the content of one isomer or enantiomer is 90%, and the content of the other isomer or enantiomer is 10%, the isomer or enantiomer excess (ee value) is 80%.

Optically active (R)- and (S)-isomer, or D and L isomer can be prepared using chiral synthesis or chiral reagents or other conventional techniques. If one kind of enantiomer of certain compound of the present disclosure is to be obtained, the pure desired enantiomer can be obtained by asymmetric synthesis or derivative action of chiral auxiliary followed by separating the resulting diastereomeric mixture and cleaving the auxiliary group. Alternatively, when the molecule contains a basic functional group (such as amino) or an acidic functional group (such as carboxyl), the compound reacts with an appropriate optically active acid or base to form a salt of the diastereomeric isomer which is then subjected to diastereomeric resolution through the conventional method in the art to give the pure enantiomer. In addition, the enantiomer and the diastereoisomer are generally isolated through chromatography which uses a chiral stationary phase and optionally combines with a chemical derivative method (such as carbamate generated from amine). The compound of the present disclosure may contain an unnatural proportion of atomic isotope at one or more than one atom(s) that constitute the compound. For example, the compound can be radiolabeled with a radioactive isotope, such as tritium ($^3$H), iodine-125 ($^{125}$I) or C-14 ($^{14}$C). For another example, deuterated drugs can be formed by replacing hydrogen with heavy hydrogen, the bond formed by deuterium and carbon is stronger than that of ordinary hydrogen and carbon, compared with non-deuterated drugs, deuterated drugs have the advantages of reduced toxic and side effects, increased drug stability, enhanced efficacy, extended biological half-life of drugs, etc. All isotopic variations of the compound of the present disclosure, whether radioactive or not, are encompassed within the scope of the present disclosure. The term "optional" or "optionally" means that the subsequent event or condition may occur but not requisite, that the term includes the instance in which the event or condition occurs and the instance in which the event or condition does not occur.

The term "substituted" means one or more than one hydrogen atom(s) on a specific atom are substituted with the substituent, including deuterium and hydrogen variables, as long as the valence of the specific atom is normal and the substituted compound is stable. When the substituent is an oxygen (i.e., =O), it means two hydrogen atoms are substituted. Positions on an aromatic ring cannot be substituted with a ketone. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted with 0-2 R, the group can be optionally substituted with up to two R, wherein the definition of R at each occurrence is independent. Moreover, a combination of the substituent and/or the variant thereof is allowed only when the combination results in a stable compound.

When the number of a linking group is 0, such as —(CRR)0-, it means that the linking group is a single bond.

When one of the variables is selected from a single bond, it means that the two groups linked by the single bond are connected directly. For example, when L in A-L-Z represents a single bond, the structure of A-L-Z is actually A-Z.

When a substituent is vacant, it means that the substituent does not exist, for example, when X is vacant in A-X, the structure of A-X is actually A. When the enumerative substituent does not indicate by which atom it is linked to the group to be substituted, such substituent can be bonded by any atom thereof. For example, when pyridyl acts as a substituent, it can be linked to the group to be substituted by any carbon atom on the pyridine ring.

When the enumerative linking group does not indicate the direction for linking, the direction for linking is arbitrary, for example, the linking group L contained in

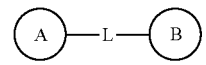

is -M-W-, then -M-W- can link ring A and ring B to form

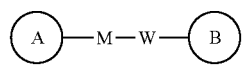

in the direction same as left-to-right reading order, and form

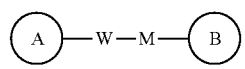

in the direction contrary to left-to-right reading order. A combination of the linking groups, substituents and/or variables thereof is allowed only when such combination can result in a stable compound.

Unless otherwise specified, when a group has one or more linkable sites, any one or more of the sites of that group may be linked to other groups by chemical bonding. The chemical bond between the site and other groups can be represented by a straight solid line bond ( ⟋ ) a straight dashed line bond ( ⟋ ), or a wavy line

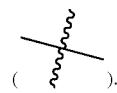

For example, the straight solid line bond in —OCH$_3$ indicates that it is connected to other group through the oxygen atom in the group; the straight dashed line bond in

indicates that it is connected to other group through the end of the nitrogen atom in the group; and the wavy line in

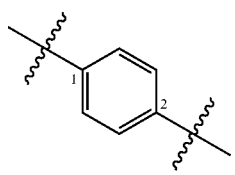 [SMILES: *c1ccc(*)cc1]

indicates that it is connected to other groups through the carbon atoms at positions 1 and 2 in the phenyl group.

Unless otherwise specified, the number of atoms in a ring is generally defined as the number of ring members. For example, "5-7 membered ring" refers to a "ring" in which 5 to 7 atoms are arranged around.

Unless otherwise specified, the term "6-12 membered ring" refers to a cycloalkyl, heterocycloalkyl, cycloalkenyl, or heterocycloalkenyl having 6 to 12 ring atoms. The ring includes single ring, and also includes double ring or multiple ring system such as spiro ring, fused ring, and bridged ring. Unless otherwise specified, the ring optionally contains 1, 2 or 3 heteroatoms independently selected from O, S and N. The 6-12 membered ring includes 6-10 membered, 6-9 membered, 6-8 membered, 6-7 membered rings, etc. The term "6-7 membered heterocycloalkyl" includes piperidyl, but excluding phenyl. The term "ring" also includes a ring system containing at least one ring, wherein each "ring" independently meets the above definition.

Unless otherwise specified, the term "$C_{1-5}$ alkyl" refers to a linear or branched saturated hydrocarbon group containing 1 to 5 carbon atoms. The $C_{1-5}$ alkyl includes $C_{1-4}$, $C_{1-3}$, $C_{1-2}$, $C_{2-6}$, $C_{2-4}$ and $C_5$ alkyl groups and the like. It can be monovalent (such as methyl), divalent (such as methylene) or multivalent (such as methine). Examples of $C_{1-5}$ alkyl include but are not limited to methyl (Me), ethyl (Et), propyl (including n-propyl and isopropyl), butyl (including n-butyl, isobutyl, s-butyl, and t-butyl), pentyl (including n-pentyl, isopentyl and neopentyl), etc.

Unless otherwise specified, the term "$C_{1-4}$ alkyl" refers to a linear or branched saturated hydrocarbon group containing 1 to 4 carbon atoms. The $C_{1-4}$ alkyl includes $C_{1-2}$, $C_{1-3}$ and $C_{2-3}$ alkyl groups and the like; it can be monovalent (such as methyl), divalent (such as methylene) or multivalent (such as methine). Examples of $C_{1-4}$ alkyl include but are not limited to methyl (Me), ethyl (Et), propyl (including n-propyl and isopropyl), butyl (including n-butyl, isobutyl, s-butyl, and t-butyl), etc.

Unless otherwise specified, the term "$C_{1-3}$ alkyl" refers to a linear or branched saturated hydrocarbon group containing 1 to 3 carbon atoms. The $C_{1-3}$ alkyl includes $C_{1-2}$ and $C_{2-3}$ alkyl groups and the like; it can be monovalent (such as methyl), divalent (such as methylene) or multivalent (such as methine). Examples of $C_{1-3}$ alkyl include but are not limited to methyl (Me), ethyl (Et), propyl (including n-propyl and isopropyl), etc.

Unless otherwise specified, the term "$C_{1-3}$ alkoxyl" refers to an alkyl group containing 1 to 3 carbon atoms that are connected to the rest of the molecule through an oxygen atom. The "$C_{1-3}$ alkoxyl" includes $C_{1-2}$, $C_{2-3}$, $C_3$ and $C_2$ alkoxyl groups and the like. Examples of $C_{1-3}$ alkoxyl include but are not limited to methoxyl, ethoxyl, propoxyl (including n-propoxyl and isopropoxyl), etc.

Unless otherwise specified, the term "$C_{3-4}$ cycloalkyl" refers to a saturated cyclic hydrocarbon group having 3 to 4 carbon atoms, which is a monocyclic system, and it may be monovalent, divalent, or multivalent. Examples of $C_{3-4}$ cycloalkyl include, but are not limited to, cyclopropyl, cyclobutyl, etc.

Unless otherwise specified, the term "6-12 membered heterocycloalkyl" by itself or in combination with other terms refers to a saturated cyclic group having 6 to 12 ring atoms, with 1, 2, 3 or 4 ring atoms being heteroatoms independently selected from O, S and N, and the rest are carbon atoms, wherein the N atom is optionally quaternized, and the N and S heteroatoms may optionally be oxidized (i.e. NO and S(O)p, p is 1 or 2). It includes monocyclic, bicyclic and tricyclic systems, wherein the bicyclic and tricyclic systems include spiral rings, fused-rings and bridged rings. In addition, for the "6-12 membered heterocycloalkyl", a heteroatom may occupy the connection position of the heterocycloalkyl with the rest of the molecule. The 6-12 membered heterocycloalkyl includes 6-10 membered, 6-9 membered, 6-8 membered, 6-7 membered, 6-membered, 7-membered and 8-membered heterocycloalkyl, etc. Examples of 6-12 membered heterocycloalkyl include, but are not limited to, tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithiaalkyl, isoxazolidinyl, isothiazolidinyl, 1,2-oxazinyl, 1,2-thiazinyl, hexahydropyridazinyl, homopiperazinyl, homopiperidinyl, dioxepanyl, octahydrocyclopentano[c]pyrrolyl, 8-azabicyclo[3.2.1]octyl, 1-azabicyclo[2.2.1]heptyl, etc.

Unless otherwise specified, the term "6-10 membered heterocycloalkyl" by itself or in combination with other terms refers to a saturated cyclic group having 6 to 10 ring atoms, with 1, 2, 3 or 4 ring atoms being heteroatoms independently selected from O, S and N, and the rest are carbon atoms, wherein the N atom is optionally quaternized, and the N and S heteroatoms may optionally be oxidized (i.e. NO and S(O)p, p is 1 or 2). It includes monocyclic, bicyclic and tricyclic systems, wherein the bicyclic and tricyclic systems include spiral rings, fused-rings and bridged rings. In addition, for the "6-10 membered heterocycloalkyl group", a heteroatom may occupy the connection position of the heterocycloalkyl group with the rest of the molecule. The 6-10 membered heterocycloalkyl includes 6-9 membered, 6-8 membered, 6-membere, 7-membered and 8-membered heterocycloalkyl, etc. Examples of 6-10 membered heterocycloalkyl include, but are not limited to, tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithiaalkyl, isoxazolidinyl, isothiazolidinyl, 1,2-oxazinyl, 1,2-thiazinyl, hexahydropyridazinyl, homopiperazinyl, homopiperidinyl, dioxepanyl, octahydrocyclopentano[c]pyrrolyl, 8-azabicyclo[3.2.1]octyl, 1-azabicyclo[2.2.1]heptyl, etc.

Unless otherwise specified, the term "4-6 membered heterocycloalkyl" by itself or in combination with other terms refers to a saturated cyclic group having 4 to 6 ring atoms, with 1, 2, 3 or 4 ring atoms being heteroatoms independently selected from O, S and N, and the rest are carbon atoms, wherein the N atom is optionally quaternized, and the N and S heteroatoms may optionally be oxidized (i.e. NO and S(O)p, p is 1 or 2). It includes monocyclic and bicyclic systems, wherein the bicyclic system includes spiral rings, fused-rings and bridged rings. In addition, for the "4- to 6-membered heterocycloalkyl group", a heteroatom may occupy the connection position of the heterocycloalkyl group with the rest of the molecule. The 4-6 membered heterocycloalkyl includes 5-6 membered, 4-membered, 5-membered and 6-membered heterocycloalkyl, etc. Examples of 4- to 6-membered heterocycloalkyl include, but are not limited to, azetidinyl, oxetanyl, thietanyl, pyrrolidinyl, pyrazolidinyl, imidazolidinyl, tetrahydrothienyl (including tetrahydrothiophen-2-yl and tetrahydrothiophen-3-yl, etc.), tetrahydrofuranyl (including tetrahydrofuran-2-yl, etc.), tetrahydropyranyl, piperidinyl (including 1-piperidinyl, 2-piperidinyl and 3-piperidinyl, etc.), piperazinyl (including 1-piperazinyl and 2-piperazinyl, etc.), morpholinyl (including 3-morpholinyl and 4-morpholinyl, etc.), dioxanyl, dithiaalkyl, isoxazolidinyl, isothiazolidinyl, 1,2-oxazinyl, 1,2-thiazinyl, hexahydropyridazinyl, homopiperazinyl or homopiperidinyl, etc.

Unless otherwise specified, the term "$C_{1-3}$ alkylamino" refers to an alkyl group containing 1 to 3 carbon atoms that are connected to the rest of the molecule through an amino group. The "$C_{1-3}$ alkylamino" includes $C_{1-2}$, $C_3$ and $C_2$ alkylamino and the like. Examples of $C_{1-3}$ alkylamino groups include, but are not limited to, —NHCH$_3$, —N(CH$_3$)$_2$, —NHCH$_2$CH$_3$, —N(CH$_3$)CH$_2$CH$_3$, —NHCH$_2$CH$_2$CH$_3$, —NHCH$_2$(CH$_3$)$_2$, etc.

Unless otherwise specified, the terms "$C_{6-10}$ aromatic ring" and "$C_{6-10}$ aryl" can be used interchangeably in the present disclosure, and the term "$C_{6-10}$ aromatic ring" or "$C_{6-10}$ aryl" refers a cyclic hydrocarbon group containing 6 to 10 carbon atoms, having a conjugated π-electron system, it can be a single ring, a fused bicyclic ring or a fused tricyclic ring system, wherein each ring is aromatic. It can be monovalent, divalent or multivalent, $C_{6-10}$ aryl groups include $C_{6-9}$, $C_9$, $C_{10}$ and $C_6$ aryl, etc. Examples of $C_{6-10}$ aryl groups include, but are not limited to, phenyl, naphthyl (including 1-naphthyl and 2-naphthyl).

Unless otherwise specified, $C_{n-n+m}$ or $C_{n-Cn+m}$ includes any specific case of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and any range from n to n+m is also included, for example $C_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$, etc.; similarly, n membered to n+m membered means that the number of atoms on the ring is from n to n+m, for example, 3-12 membered ring includes 3 membered ring, 4 membered ring, 5 membered ring, 6 membered ring, 7 membered ring, 8 membered ring, 9 membered ring, 10 membered ring, 11 membered ring, and 12 membered ring, and any range from n to n+m is also included, for example, 3-12 membered ring includes 3-6 membered ring, 3-9 membered ring, 5-6 membered ring, 5-7 membered ring, 6-7 membered ring, 6-8 membered ring, and 6-10 membered ring, etc.

The term "leaving group" refers to a functional group or atom which can be replaced by another functional group or atom through a substitution reaction (such as affinity substitution reaction). For example, representative leaving groups include triflate; chlorine, bromine, and iodine; sulfonate group, such as mesylate, tosylate, p-bromobenzenesulfonate, p-toluenesulfonates and the like; acyloxy, such as acetoxy, trifluoroacetoxy and the like.

The term "protecting group" includes, but is not limited to "amino protecting group", "hydroxy protecting group" or "thio protecting group". The term "amino protecting group" refers to a protecting group suitable for blocking the side reaction on the nitrogen of an amino. Representative amino protecting groups include, but are not limited to: formyl; acyl, such as alkanoyl (e.g., acetyl, trichloroacetyl or trifluoroacetyl); alkoxycarbonyl, such as tert-butoxycarbonyl (Boc); arylmethoxycarbonyl such as benzyloxycarbonyl (Cbz) and 9-fluorenylmethoxycarbonyl (Fmoc); arylmethyl such as benzyl (Bn), trityl (Tr), 1,1-bis-(4'-methoxyphenyl) methyl; silyl such as trimethylsilyl (TMS) and tert-butyldimethylsilyl (TBS) and the like. The term "hydroxy protecting group" refers to a protecting group suitable for blocking the side reaction on hydroxy. Representative hydroxy protecting groups include, but are not limited to: alkyl such as methyl, ethyl, and tert-butyl; acyl such as alkanoyl (e.g., acetyl); arylmethyl such as benzyl (Bn), p-methoxybenzyl (PMB), 9-fluorenylmethyl (Fm), and diphenylmethyl (benzhydryl, DPM); silyl such as trimethylsilyl (TMS) and tert-butyl dimethyl silyl (TBS) and the like.

The compounds of the present disclosure can be prepared by a variety of synthetic methods known to those skilled in the art, including the specific embodiments listed below, the embodiments formed by their combination with other chemical synthesis methods, and equivalent alternatives known to those skilled in the art, preferred implementations include but are not limited to the embodiments of the present disclosure.

The solvents used in the present disclosure are commercially available. It can be used without further purification. The reaction is generally carried out in an anhydrous solvent under inert nitrogen.

The present disclosure uses the following abbreviations: NBS represents for N-bromosuccinimide; Pd(dppf)Cl$_2$ represents for [1,1'-bis(diphenylphosphino)ferrocene]palladium dichloride; BAST represents for bis(2-methoxyethyl) aminosulfur trifluoride; DMF represents for N,N-dimethylformamide; NaBH(OAc)$_3$ represents for sodium triacetoxyborohydride; Pd(PPh$_3$)$_2$Cl$_2$ represents for bis(triphenylphosphine)dichloropalladium; DIPEA represents for N,N-diisopropylethylamine; TBDMSCl represents for tert-butyldimethylchlorosilane; DMSO represents for dimethyl sulfoxide; DME represents for ethylene glycol dimethyl ether; Pd(PPh$_3$)$_4$ represents for tetrakistriphenylphosphine palladium; Boc$_2$O represents for di-tert-butyl dicarbonate; TEA represents for triethylamine; DPPA represents for diphenyl azide phosphate; DMAP represents for 4-dimethylaminopyridine; dppf represents for 1,1'-bis(diphenylphosphino)ferrocene; Pd(dppf)Cl$_2$·CH$_2$Cl$_2$ represents for [1,1'-bis(diphenylphosphino)ferrocene]palladium(II) dichloromethane adduct; Pd$_2$(dba)$_3$ represents for tris(dibenzylideneacetone)dipalladium; NMP represents for N-methylpyrrolidone; TMSCl represents for trimethylchlorosilane; ADDP represents for 1,1'-(azodicarbonyl)-dipiperidine; SFC represents for supercritical fluid chromatography; Xantphos represents for 4,5-bis(diphenylphosphino)-9,9-dimethylxanthene; and LiHMDS represents for lithium hexamethyldisilylamine.

The compounds of the present disclosure are named according to the conventional naming principles in the art or by ChemDraw® software, and the commercially available compounds use the supplier catalog names.

DETAILED DESCRIPTION OF THE EMBODIMENTS

The following embodiments further illustrate the present disclosure, but the present disclosure is not limited thereto. The present disclosure has been described in detail herein, and its specific embodiments have also been disclosed, for one skilled in the art, it is obvious to make various modifications and improvements to the embodiments of the present disclosure without departing from the spirit and scope of the present disclosure. The free base of the compound was obtained by adding saturated sodium bicarbonate solution to the hydrochloride or formate salt of the compound of the present disclosure to adjust the pH to neutral, followed by separation with high-performance liquid chromatography (neutral, ammonium bicarbonate system).

In some embodiments, the compounds represented by formula (I) can be prepared according to the synthetic method described in Scheme A, wherein $R_1$, $R_2$, $R_3$, $R_4$, L, T, ring A and ring B are as defined herein and X is Br or Cl.

Scheme A

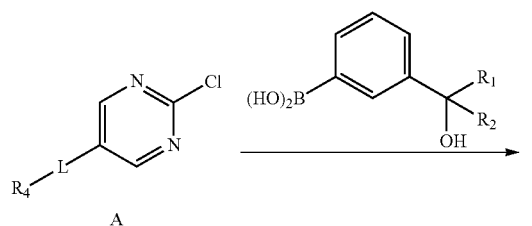

A

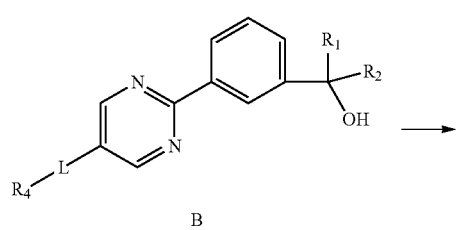

B

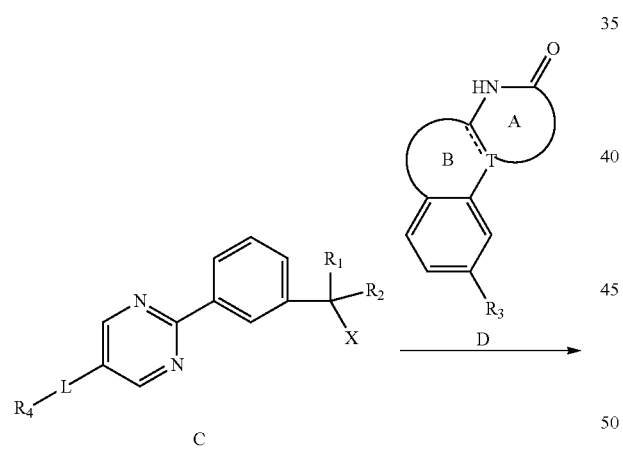

C

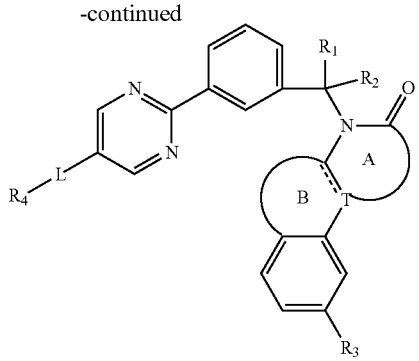

E

The present disclosure is now further described through embodiments. The embodiments given below are for illustrative purposes only and are not limited to the scope of the present disclosure. The compounds of the present disclosure can be prepared by many methods known in the field of organic synthesis. The embodiments of the present disclosure can be synthesized using the methods described below, as well as synthetic methods known in the field of organic synthetic chemistry, or by improved methods based thereon. Preferred methods include, but are not limited to, the methods described below.

DETAILED DESCRIPTION OF THE EMBODIMENTS

In order to illustrate the disclosure in more detail, the following examples are given, but the scope of the disclosure is not limited thereto.

Embodiment 1

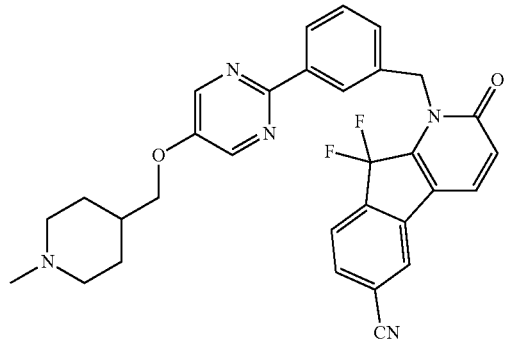

1

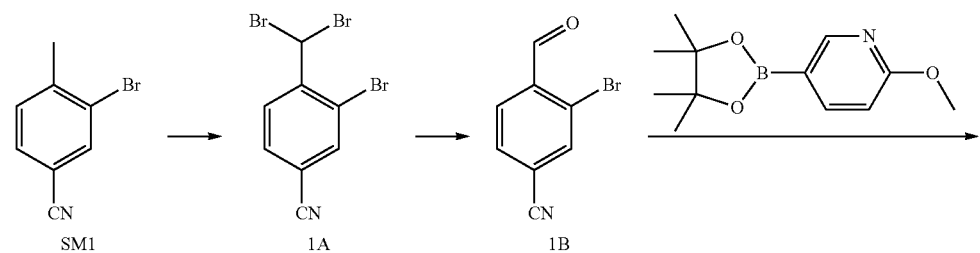

SM1     1A     1B

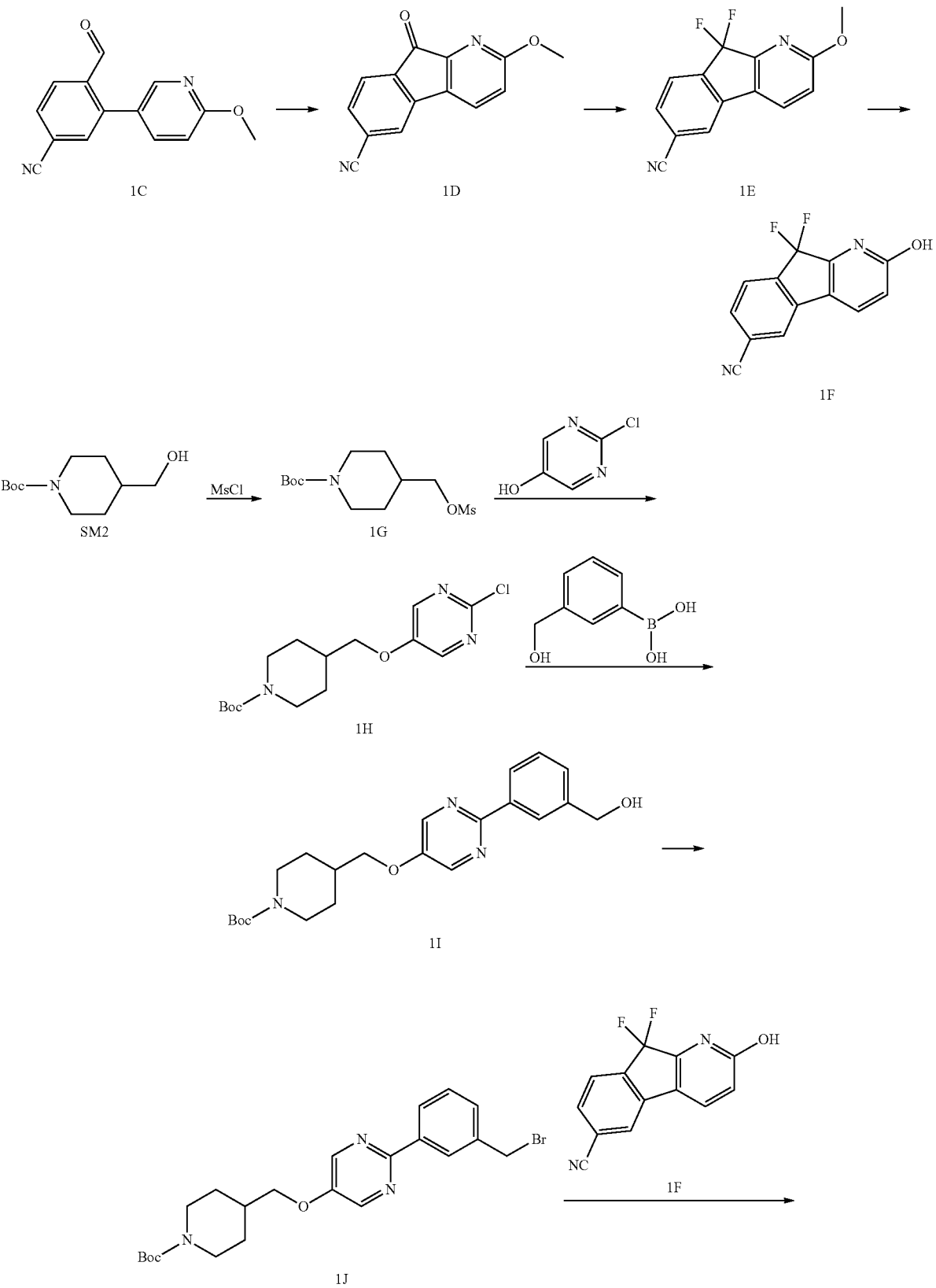

-continued

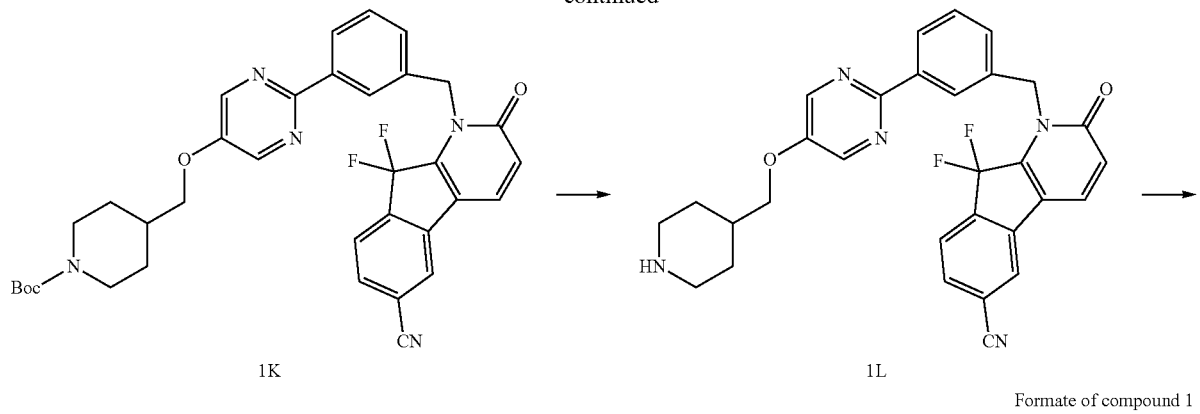

Formate of compound 1

Compound 1A:

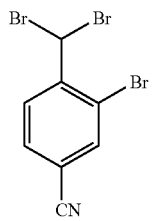

NBS (54.47 g, 306.05 mmol) and peroxybenzoyl (1.85 g, 7.65 mmol) were added to a solution of 3-bromo-4-methylbenzonitrile (15.00 g, 76.51 mmol) in carbon tetrachloride (500 mL). The reaction system was stirred at 80° C. for 16 hours. The reaction mixture was then cooled to 30° C. and filtered. The filtrate was concentrated to obtain a crude product, which was purified by silica gel column chromatography (eluting with petroleum ether:ethyl acetate=40:1-20:1) to obtain the compound 1A. $^1$H NMR (400 MHz, CDCl$_3$) δ=8.14 (d, J=8.2 Hz, 1H), 7.83 (d, J=1.6 Hz, 1H), 7.71 (dd, J=1.6, 8.2 Hz, 1H), 7.02 (s, 1H).

Compound 1B:

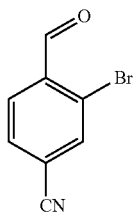 [SMILES: N#Cc1ccc(C=O)c(Br)c1]

A solution of compound 1A (27.78 g, 78.51 mmol) in acetonitrile (300 mL) was added to a solution of silver nitrate (53.35 g, 314.04 mmol) in water (150 mL), the reaction system was stirred at 80° C. for 16 hours, and the reaction mixture was filtered, the filtrate was diluted with ethyl acetate (500 mL), washed with water (300 mL×2 times), the organic phase was dried over anhydrous sodium sulfate, filtered, and the filtrate was concentrated to dryness to obtain the compound 1B. $^1$H NMR (400 MHz, CDCl$_3$) δ=10.32 (s, 1H), 7.96-7.87 (m, 2H), 7.66 (dd, J=1.0, 9.0 Hz, 1H).

Compound 1C:

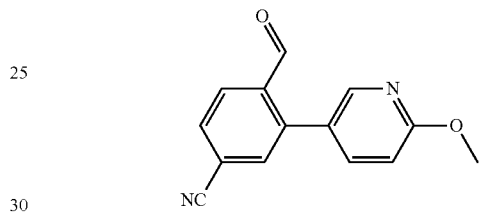

A mixture of compound 1B (16.95 g, 80.70 mmol), 2-methoxy-5-pyridineboronic acid pinacol ester (22.77 g, 96.84 mmol), Pd(dppf)Cl$_2$ (5.91 g, 8.07 mmol), potassium carbonate (22.31 g, 161.41 mmol) in dioxane (180 mL) and water (60 mL) was stirred at 100° C. for 2 hours. The reaction mixture was diluted with ethyl acetate (500 mL) and washed with saturated brine (300 mL×2 times). The organic phase was dried over anhydrous sodium sulfate, filtered, and the filtrate was concentrated. The crude product was purified by silica gel column chromatography (petroleum ether:ethyl acetate=20:1-10:1) to obtain the compound 1C. $^1$H NMR (400 MHz, CDCl$_3$) δ=10.03 (d, J=0.7 Hz, 1H), 8.18 (d, J=2.2 Hz, 1H), 8.13 (d, J=7.8 Hz, 1H), 7.82-7.78 (m, 1H), 7.75 (d, J=1.2 Hz, 1H), 7.62 (dd, J=2.4, 8.6 Hz, 1H), 4.03 (s, 3H).

Compound 1D:

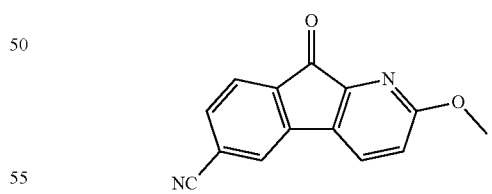

A solution of compound 1C (2.00 g, 8.39 mmol) and peroxy tert-butanol (5.5 mol/L decane solution, 6.11 mL) in 1,2-dichloroethane (8 mL) was stirred at 100° C. for 60 hours, the reaction mixture was diluted with dichloromethane (300 mL), and washed sequentially with saturated sodium thiosulfate aqueous solution (150 mL×3 times), water (100 mL×1 time), saturated brine (150 mL×1 time), and the organic phase was dried over anhydrous sodium sulfate, filtered, and then concentrated to obtain a crude product. The crude product was suspended in petroleum ether (50 mL), stirred at 25° C. for 30 minutes, filtered, and the filter cake was dried to obtain the compound 1D. ¹H NMR (400 MHz, CDCl₃) δ=7.83 (d, J=8.6 Hz, 1H), 7.75 (d, J=7.8 Hz, 1H), 7.65-7.59 (m, 2H), 6.94 (d, J=8.6 Hz, 1H), 4.09 (s, 3H). LCMS (ESI): m/z: 237.1 [M+1].

Compound 1E:

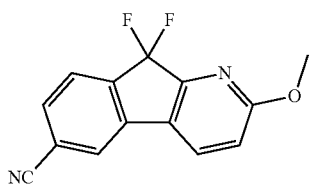 [SMILES: COc1ccc2c(n1)C(F)(F)c1ccc(C#N)cc1-2]

Under the protection of nitrogen, compound 1D (365 mg, 1.55 mmol) and BAST (2.39 g, 10.82 mmol) were stirred at 60° C. for 12 hours, the reaction was quenched with water (100 mL), then the reaction mixture was extracted with ethyl acetate (100 mL×2 times). The combined organic phase was washed with saturated brine (100 mL×1), dried over anhydrous sodium sulfate, filtered and concentrated, the crude product was purified by silica gel column chromatography (petroleum ether:ethyl acetate=20:1-15:1) to obtain the compound 1E. ¹H NMR (400 MHz, CDCl₆) δ=8.35 (d, J=8.6 Hz, 1H), 8.24 (d, J=7.8 Hz, 1H), 7.97-7.86 (m, 2H), 7.13 (d, J=8.3 Hz, 1H), 3.95 (s, 3H). LCMS (ESI): m/z: 259.0 [M+1].

Compound 1F:

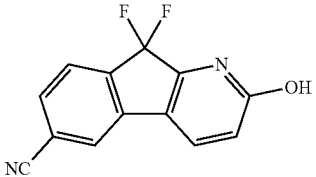 [SMILES: N#Cc1ccc2c(c1)-c1ccc(O)nc1C2(F)F]

Trimethylchlorosilane (416.52 mg, 3.83 mmol) was added to a mixture of compound 1E (165 mg, 0.64 mmol) and sodium iodide (574.68 mg, 3.83 mmol) in acetonitrile (5 mL). The reaction system was stirred at 70° C. for 2 hours, water (150 mL) was added to the reaction mixture, and the mixture was then extracted with ethyl acetate (100 mL×2 times). The combined organic phase was washed sequentially with saturated sodium sulfite aqueous solution (100 mL×2 times) and saturated brine (100 mL×1 time), the organic phase was dried over anhydrous sodium sulfate, filtered, and concentrated to dryness to obtain the compound 1F. ¹H NMR (400 MHz, DMSO-d₆) δ=8.28-8.23 (m, 1H), 8.20-8.15 (m, 1H), 7.92-7.84 (m, 2H), 6.91-6.83 (m, 1H). LCMS (ESI): m/z: 245.0 [M+1].

Compound 1G:

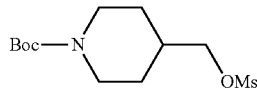

Tert-butyl 4-hydroxymethylpiperidine-1-carboxylate (50 g, 232.25 mmol) was dissolved in 800 mL of anhydrous dichloromethane, then DIEA (60.10 g, 465.04 mmol, 81 mL) was added thereto, and then methanesulfonyl chloride (31.08 g, 271.32 mmol, 21 mL) was added slowly dropwise at 0° C. After the addition, the mixture was stirred and the reaction was carried out for 1 hour under the protection of nitrogen at 27° C. The reaction mixture was washed three times with 200 mL of 0.5 mol/L hydrochloric acid aqueous solution and then washed with 300 mL of saturated sodium bicarbonate aqueous solution. The organic phase was separated and dried over anhydrous sodium sulfate, filtered, and then evaporated to dryness to obtain 1G. ¹H NMR (400 MHz, CDCl₃) δ=4.14 (br s, 2H), 4.07 (d, J=6.4 Hz, 2H), 3.01 (s, 3H), 2.71 (br t, J=12.4 Hz, 2H), 1.97-1.83 (m, 1H), 1.74 (br d, J=12.8 Hz, 2H), 1.46 (s, 9H), 1.32-1.14 (m, 2H). LCMS (ESI): m/z: 238.1 [M-55].

Compound 1H:

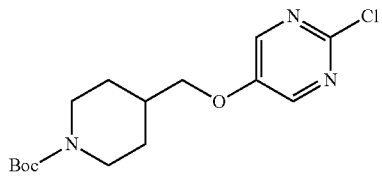 [SMILES: CC(C)(C)OC(=O)N1CCC(COc2cnc(Cl)nc2)CC1]

Compound 1G (109 g, 371.53 mmol), 2-chloro-5-hydroxypyrimidine (40.25 g, 308.37 mmol) and potassium carbonate (85.24 g, 616.75 mmol) were dissolved in 1000 mL of DMF. The mixture was stirred and the reaction was carried out for 16 hours under the protection of nitrogen at 80° C. The reaction mixture was evaporated to dryness to remove the organic solvent. The remaining residue was added with 400 mL of water and then extracted three times with 300 mL of ethyl acetate. The combined organic phase was dried over anhydrous sodium sulfate, filtered, and then evaporated to dryness. The residue was purified by column chromatography (SiO₂, petroleum ether:ethyl acetate=50:1-5:1) to obtain the crude product. The crude product was then slurried with 60 mL of a mixed solvent of petroleum ether:ethyl acetate=5:1 for 15 minutes at 25° C. then filtered, the filter cake was washed three times with 10 mL of a mixed solvent of petroleum ether:ethyl acetate=5:1 and then evaporated to obtain the compound 1H. ¹H NMR (400 MHz, DMSO-d₆) δ=8.53 (s, 2H), 4.02 (d, J=6.5 Hz, 2H), 3.96 (br d, J=12.2 Hz, 2H), 2.87-2.62 (m, 2H), 2.01-1.87 (m, 1H), 1.80-1.66 (m, 2H), 1.39 (s, 9H), 1.10-1.02 (m, 2H). LCMS (ESI): m/z: 272.0 [M-55].

Compound 1I:

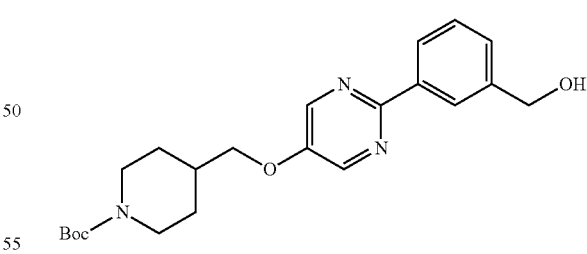

Compound 1H (34 g, 103.72 mmol) and 3-hydroxymethylphenylboronic acid (16 g, 105.29 mmol) were dissolved in 250 mL of dioxane and 50 mL of water, and sodium carbonate (33 g, 311.35 mmol) and Pd(dppf)Cl₂ (3 g, 4.10 mmol) were added thereto. The mixture was stirred and the reaction was carried out for 12 hours under the protection of nitrogen at 90° C., the mixture was evaporated to dryness to remove the organic solvent. The remaining residue was added with 100 mL of water and then extracted three times with 100 mL of ethyl acetate. The combined organic phase was evaporated to dryness, and the residue was slurried with 200 mL of a mixed solvent of petroleum ether:ethyl acetate=1:1 for 30 minutes then filtered, the filter cake was washed three times with 50 mL of a mixed solvent of petroleum ether:ethyl acetate=1:1 to obtain the compound 1I. ¹H NMR (400 MHz, CDCl₃) δ=8.46 (s, 2H), 8.34 (br s, 1H), 8.28 (br s, 1H), 7.47 (br s, 2H), 4.80 (br s, 2H), 4.20 (br s, 2H), 3.95 (br d, J=5.9 Hz, 2H), 2.77 (br s, 2H), 2.02 (br s, 1H), 1.85 (br d, J=13.7 Hz, 2H), 1.48 (s, 9H), 1.32 (1.45-1.12, m, 2H). LCMS (ESI): m/z: 400.1 [M+1].
Compound 1J:

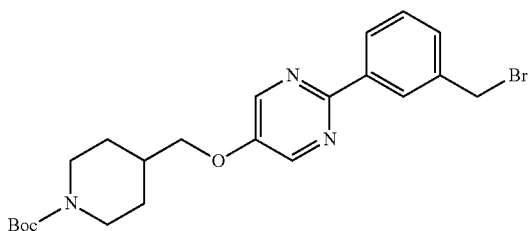 [SMILES: CC(C)(C)OC(=O)N1CCC(COc2cnc(-c3cccc(CBr)c3)nc2)CC1]

Carbon tetrabromide (6.23 g, 18.77 mmol) and triphenylphosphorus (3.94 g, 15.02 mmol) were added to a solution of compound 1I (5 g, 12.52 mmol) in dichloromethane (50 mL) and then the mixture was stirred at 25° C. for 30 minutes. TLC (petroleum ether:ethyl acetate=2:1) showed that there was still raw material left, carbon tetrabromide (2.99 g, 9.01 mmol) and triphenylphosphorus (2.00 g, 7.63 mmol) were added to the reaction mixture and the mixture was stirred at 25° C. for 10 minutes. TLC (petroleum ether:ethyl acetate=2:1) showed that the reaction was complete. The reaction mixture was concentrated, then dichloromethane (10 mL) and ethyl acetate (30 mL) were added to the residue, the mixture was stirred for 10 minutes, then filtered, and the filtrate was concentrated. Methanol (40 mL) was added to the concentrate and stirred for 15 minutes at 25° C. and then the mixture was filtered. The filter cake was washed twice with methanol (5 mL) and dried in air to obtain the compound 1J. ¹H NMR (400 MHz, DMSO-d₆) δ=8.68-8.64 (m, 2H), 8.39 (s, 1H), 8.24 (br d, J=7.7 Hz, 1H), 7.58-7.46 (m, 2H), 4.82 (s, 2H), 4.08 (br d, J=6.4 Hz, 2H), 3.99 (br d, J=10.4 Hz, 2H), 2.76 (br s, 2H), 1.99 (br s, 1H), 1.78 (br d, J=12.0 Hz, 2H), 1.41 (s, 9H), 1.27-1.11 (m, 2H).
Compound 1K:

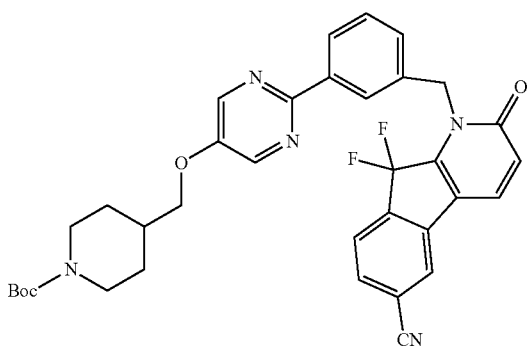 [SMILES: CC(C)(C)OC(=O)N1CCC(COc2cnc(-c3cccc(Cn4c5c(ccc4=O)-c4cc(C#N)ccc4C5(F)F)c3)nc2)CC1]

A suspension of compound 1F (160 mg, 0.66 mmol), compound 1J (393.84 mg, 0.85 mmol) and potassium carbonate (271.66 mg, 1.97 mmol) in DMF (5 mL) were stirred at 65° C. for 1.5 hours, water (50 mL) was added to the reaction mixture and the mixture was extracted with ethyl acetate (100 mL×2 times), the combined organic phases were washed with saturated brine (100 mL×3 times), dried over anhydrous sodium sulfate, filtered, and concentrated. The crude product was purified by silica gel column chromatography (petroleum ether:ethyl acetate=10:1-2:1) to obtain the compound 1K. LCMS (ESI): m/z: 648.2 [M+23].
Compound 1L:

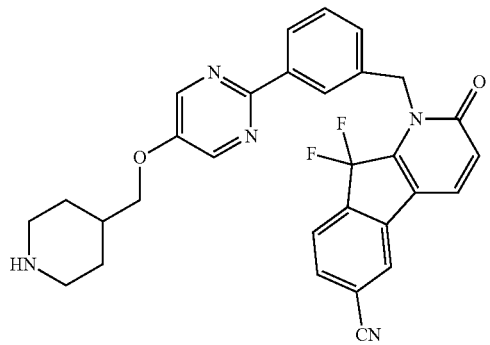 [SMILES: N#Cc1ccc2c(c1)-c1ccc(=O)n(Cc3cccc(-c4ncc(OCC5CCNCC5)cn4)c3)c1C2(F)F]

A solution of hydrochloric acid in ethyl acetate (4 mol/L, 1.5 mL) was added to a solution of compound 1K (55 mg, 0.088 mmol) in dichloromethane (2 mL), and the reaction system was stirred at 25° C. for 2 hours. The pH value was adjusted to 8 with saturated sodium bicarbonate aqueous solution, the mixture was extracted with ethyl acetate (60 mL×2 times), the combined organic phase was washed sequentially with water (100 mL×1 time), saturated brine (100 mL×1 time), the organic phase was dried over anhydrous sodium sulfate, filtered and concentrated to dryness to obtain the compound 1L. LCMS (ESI): m/z: 526.2 [M+1].
Formate of Compound 1:

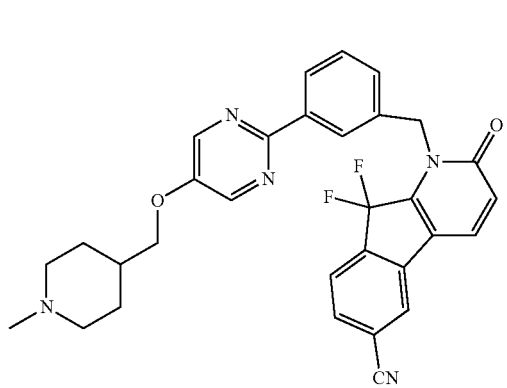

Formaldehyde aqueous solution (80.29 mg, 0.99 mmol) and NaBH(OAc)₃ (41.94 mg, 0.20 mmol) were added to a solution of compound 1L (52 mg, 0.099 mmol) in tetrahydrofuran (3 mL). The reaction system was stirred at 25° C. for 0.5 hours, water (50 mL) was added to the reaction mixture and the mixture was extracted with ethyl acetate (50 mL×2 times), the combined organic phase was washed with saturated brine, dried over anhydrous sodium sulfate, filtered, and concentrated. The crude product was purified by high performance liquid chromatography (formic acid system), and the formate of compound 1 was obtained. ¹H NMR (400 MHz, DMSO-d₆) δ=8.61 (s, 2H), 8.27-8.10 (m, 5H), 7.89-7.79 (m, 2H), 7.45 (t, J=7.8 Hz, 1H), 7.30 (d, J=7.8 Hz, 1H), 6.87 (d, J=9.3 Hz, 1H), 5.38 (s, 2H), 4.10-3.97 (m, 2H), 2.82 (br d, J=11.0 Hz, 2H), 2.19 (s, 3H), 1.95 (br t, J=11.0 Hz, 2H), 1.74 (br d, J=9.5 Hz, 3H), 1.41-1.25 (m, 2H). LCMS (ESI): m/z: 540.2 [M+1].

Embodiment 2

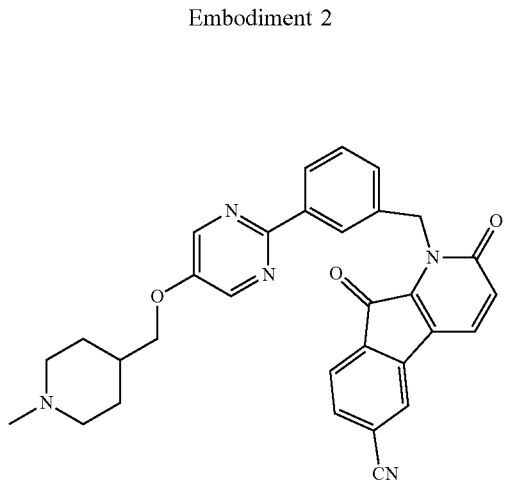

Compound 2A:

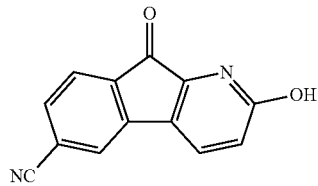 [SMILES: N#Cc1ccc2c(c1)-c1ccc(O)nc1C2=O]

Compound 2A was prepared according to the method of compound 1F by replacing compound 1E with compound 1D. LCMS (ESI): m/z: 223.0 [M+1].

Compound 2B:

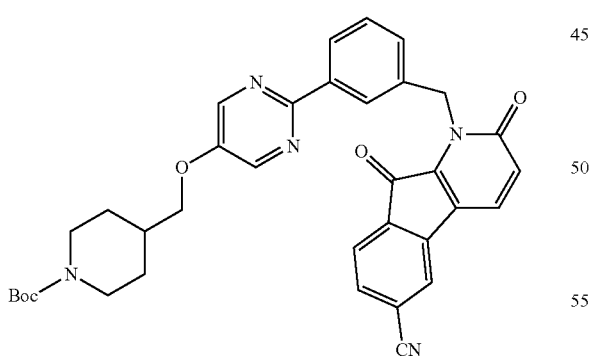

Compound 2B was prepared according to the method of compound 1K by replacing compound 1F with compound 2A. $^1$H NMR (400 MHz, DMSO-$d_6$) δ=8.62 (s, 2H), 8.24-8.15 (m, 2H), 8.09 (d, J=9.3 Hz, 1H), 8.01 (s, 1H), 7.73 (dd, J=1.2, 7.3 Hz, 1H), 7.59 (d, J=7.6 Hz, 1H), 7.46-7.33 (m, 2H), 6.90 (d, J=9.3 Hz, 1H), 5.57 (s, 2H), 4.09-4.02 (m, 2H), 2.83-2.69 (m, 2H), 1.81-1.70 (m, 2H), 1.40 (s, 9H), 1.20 (br s, 3H), 0.89-0.77 (m, 2H). LCMS (ESI): m/z: 604.2 [M+1].

Compound 2C:

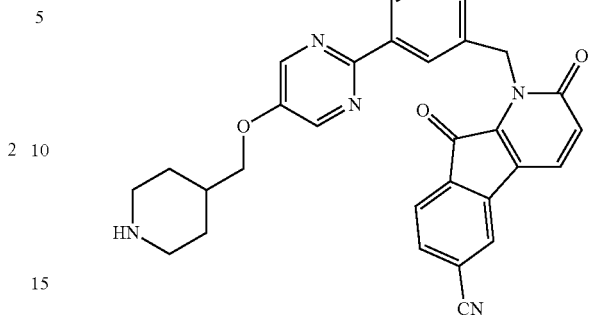

Compound 2C was prepared according to the method of compound 1L by replacing compound 1K with compound 2B. LCMS (ESI): m/z: 504.2 [M+1].

Formate of Compound 2:

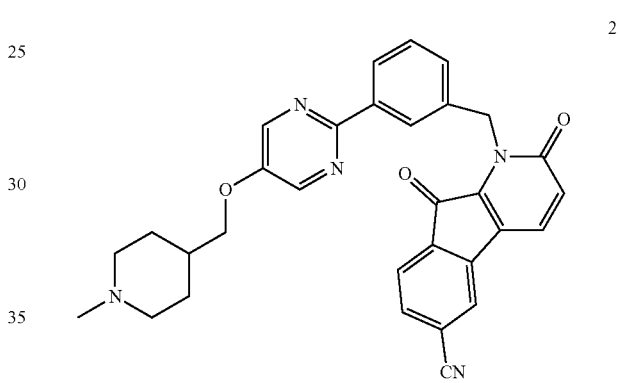

Formate of compound 2 was prepared according to the method of formate of compound 1 by replacing compound 1L with compound 2C. $^1$H NMR (400 MHz, CDCl$_3$) δ=8.50 (s, 1H), 8.43 (s, 3H), 8.23 (td, J=1.5, 7.6 Hz, 1H), 7.61 (d, J=9.3 Hz, 1H), 7.57-7.53 (m, 1H), 7.52-7.48 (m, 1H), 7.46-7.37 (m, 3H), 6.94 (d, J=9.0 Hz, 1H), 5.75 (s, 2H), 3.98 (d, J=5.9 Hz, 2H), 3.33 (br d, J=10.8 Hz, 2H), 2.57 (s, 3H), 2.40 (br s, 2H), 2.08-1.93 (m, 3H), 1.87-1.70 (m, 2H). LCMS (ESI): m/z: 518.2 [M+1].

Embodiment 3

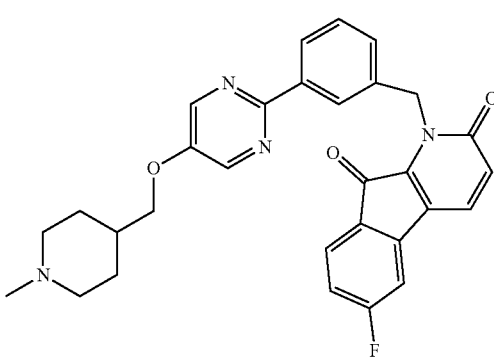

Compound 3A:

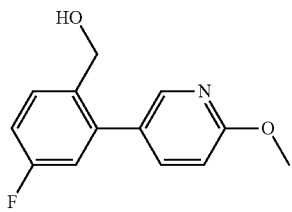 [SMILES: COc1ccc(-c2cc(F)ccc2CO)cn1]

Compound 3A was prepared according to the method of compound 1C by replacing compound 1B with 2-bromo-4-fluorobenzyl alcohol. ¹H NMR (400 MHz, CDCl₃) δ=8.17 (d, J=2.3 Hz, 1H), 7.65 (dd, J=2.4, 8.6 Hz, 1H), 7.53 (dd, J=5.9, 8.4 Hz, 1H), 7.09 (dt, J=2.7, 8.4 Hz, 1H), 6.98 (dd, J=2.6, 9.4 Hz, 1H), 6.82 (d, J=8.4 Hz, 1H), 4.56 (s, 2H), 3.99 (s, 3H), 1.88 (s, 1H). LCMS (ESI): m/z: 234.1 [M+1].

Compound 3B:

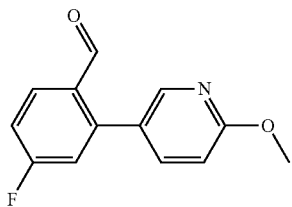 [SMILES: COc1ccc(-c2cc(F)ccc2C=O)cn1]

At 0° C., the Dess-Martin periodinane (24.00 g, 56.59 mmol, 17.52 mL) was added to a solution of compound 3A (12 g, 51.45 mmol) in dichloromethane (200 mL), the mixture was stirred at 0° C. for 0.5 hours, and the reaction mixture was diluted with dichloromethane (1500 mL), washed with saturated sodium sulfite (300 mL×1 time) and saturated sodium bicarbonate (300 mL×1 time), and then dried over anhydrous sodium sulfate, and the filtrate was concentrated. The crude product was purified by column chromatography (petroleum ether:ethyl acetate=20:1, adding 10% dichloromethane) to obtain the compound 3B. ¹H NMR (400 MHz, CDCl₃) δ=10.01-9.86 (m, 1H), 8.18 (d, J=2.3 Hz, 1H), 8.08 (dd, J=6.0, 8.7 Hz, 1H), 7.61 (dd, J=2.5, 8.5 Hz, 1H), 7.21 (dt, J=2.3, 8.2 Hz, 1H), 7.10 (dd, J=2.4, 9.2 Hz, 1H), 6.88 (d, J=8.6 Hz, 1H), 4.02 (s, 3H).

Compound 3C:

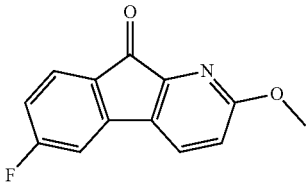 [SMILES: COc1ccc2c(n1)C(=O)c1ccc(F)cc1-2]

Compound 3C was prepared according to the method of compound 1D by replacing compound 1C with compound 3B. ¹H NMR (400 MHz, CDCl₃) δ=7.64 (d, J=8.3 Hz, 1H), 7.58 (dd, J=5.3, 8.1 Hz, 1H), 6.99 (dd, J=2.1, 8.2 Hz, 1H), 6.83 (dt, J=2.1, 8.7 Hz, 1H), 6.77 (d, J=8.4 Hz, 1H), 3.99 (s, 3H).

Compound 3D:

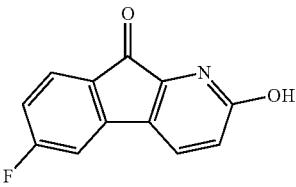 [SMILES: O=C1c2ccc(F)cc2-c2ccc(O)nc21]

Compound 3D was prepared according to the method of compound 1F by replacing compound 1E with compound 3C. ¹H NMR (400 MHz, DMSO-d₆) δ=7.87 (d, J=9.2 Hz, 1H), 7.58-7.51 (m, 1H), 7.12 (d, J=8.8 Hz, 1H), 6.61-6.51 (m, 2H), 6.10 (s, 1H). LCMS (ESI): m/z: 216.0 [M+1].

Compound 3E:

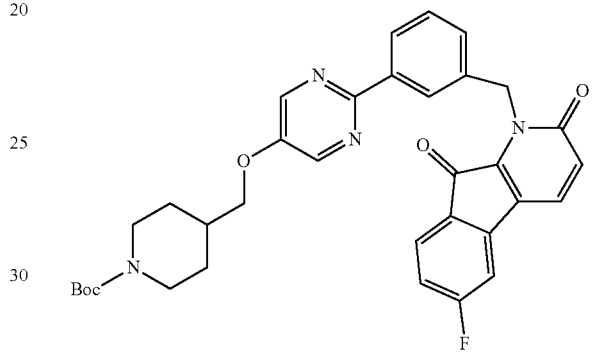

Compound 3E was prepared according to the method of compound 1K by replacing compound 1F with compound 3D. ¹H NMR (400 MHz, DMSO-d₆) δ=8.63 (s, 2H), 8.22 (s, 1H), 8.18 (d, J=7.8 Hz, 1H), 8.04 (d, J=9.2 Hz, 1H), 7.56-7.47 (m, 2H), 7.45-7.39 (m, 1H), 7.38-7.31 (m, 1H), 7.04-6.95 (m, 1H), 6.85 (d, J=9.3 Hz, 1H), 5.59 (s, 2H), 4.15-4.05 (m, 2H), 3.98 (d, J=11.0 Hz, 2H), 2.90-2.64 (m, 2H), 2.07-1.91 (m, 1H), 1.76 (d, J=10.6 Hz, 2H), 1.40 (s, 9H), 1.20-1.11 (m, 2H). LCMS (ESI): m/z: 597.2 [M+1].

Compound 3F:

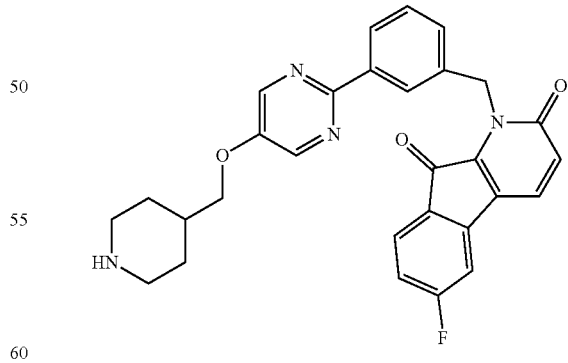

Trifluoroacetic acid (1.54 g, 13.51 mmol, 1 mL) was added to a solution of compound 3E (200 mg, 335.21 μmol) in dichloromethane (2 mL), and the mixture was stirred at 25° C. for 1 hour, the reaction mixture was concentrated and dissolved in ethyl acetate (20 mL), washed once with saturated sodium bicarbonate aqueous solution (10 mL), dried over anhydrous sodium sulfate, and concentrated to obtain the compound 3F, which was used directly in the next step. LCMS (ESI): m/z: 497.2 [M+1].

Formate of Compound 3:

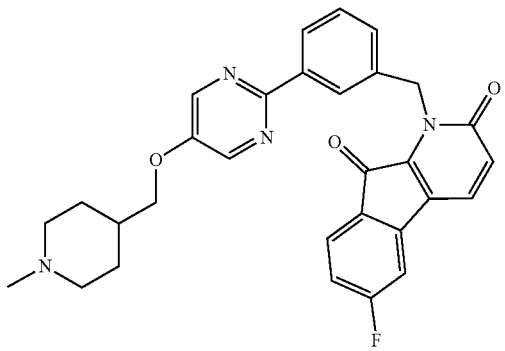

Formate of compound 3 was prepared according to the method of formate of compound 1 by replacing compound 1L with compound 3F. $^1$H NMR (400 MHz, DMSO-d$_6$) δ=8.63 (s, 2H), 8.23-8.16 (m, 3H), 8.05 (d, J=9.3 Hz, 1H), 7.56-7.49 (m, 2H), 7.47-7.41 (m, 1H), 7.38-7.33 (m, 1H), 7.00 (dd, J=2.3, 7.9, 9.7 Hz, 1H), 6.86 (d, J=9.2 Hz, 1H), 5.59 (s, 2H), 4.06 (d, J=5.9 Hz, 2H), 2.96 (s, 2H), 2.34-2.29 (m, 3H), 2.17 (s, 2H), 1.81 (d, J=10.8 Hz, 3H), 1.38 (d, J=12.5 Hz, 2H). LCMS (ESI): m/z: 511.3 [M+1].

Embodiment 4

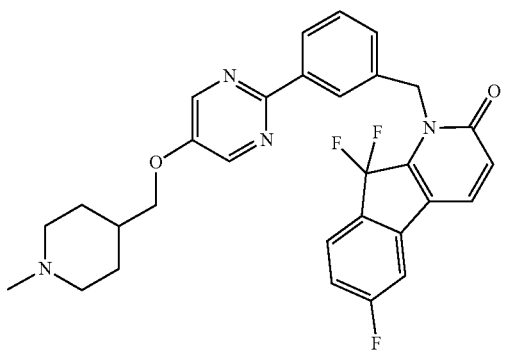

Compound 4A:

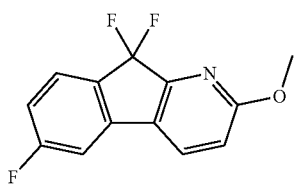 [SMILES: COc1ccc2c(n1)C(F)(F)c1ccc(F)cc1-2]

Compound 4A was prepared according to the method of compound 1E by replacing compound 1D with compound 3C. $^1$H NMR (400 MHz, CDCl$_3$) δ=7.72 (d, J=8.4 Hz, 1H), 7.63-7.57 (m, 1H), 7.14 (dd, J=2.0, 8.3 Hz, 1H), 6.98 (dt, J=2.2, 8.7 Hz, 1H), 6.85 (d, J=8.4 Hz, 1H), 4.06 (s, 3H). LCMS (ESI): m/z: 252.0 [M+1].

Compound 4B:

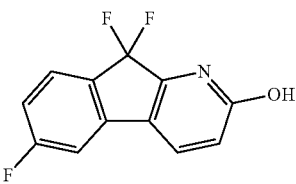

Compound 4B was prepared according to the method of compound 1F by replacing compound 1E with compound 4A. $^1$H NMR (400 MHz, DMSO-d$_6$) δ=12.33-11.06 (m, 1H), 8.13 (d, J=8.6 Hz, 1H), 7.78-7.71 (m, 1H), 7.67 (dd, J=1.8, 9.0 Hz, 1H), 7.23-7.12 (m, 1H), 6.84 (d, J=8.4 Hz, 1H). LCMS (ESI): m/z: 238.0 [M+1].

Compound 4C:

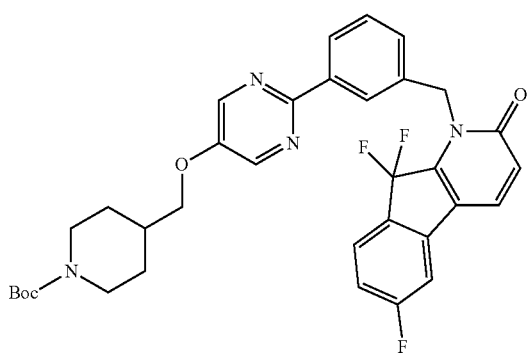 [SMILES: CC(C)(C)OC(=O)N1CCC(COc2cnc(-c3cccc(Cn4c5c(ccc4=O)-c4cc(F)ccc4C5(F)F)c3)nc2)CC1]

Compound 4C was prepared according to the method of compound 1K by replacing compound 1F with compound 4B. $^1$H NMR (400 MHz, DMSO-d$_6$) δ=8.65-8.53 (m, 2H), 8.23-8.15 (m, 2H), 8.07 (d, J=9.5 Hz, 1H), 7.66 (dd, J=4.9, 8.1 Hz, 1H), 7.59 (dd, J=2.3, 8.9 Hz, 1H), 7.44 (t, J=7.8 Hz, 1H), 7.29 (d, J=8.1 Hz, 1H), 7.08 (ddd, J=2.3, 8.3, 9.4 Hz, 1H), 6.81 (d, J=9.3 Hz, 1H), 5.39 (s, 2H), 4.03 (d, J=6.4 Hz, 2H), 4.01-3.94 (m, 2H), 2.81-2.66 (m, 2H), 1.98-1.90 (m, 1H), 1.80-1.71 (m, 2H), 1.39 (s, 9H), 1.15-1.10 (m, 2H). LCMS (ESI): m/z: 641.1 [M+23].

Compound 4D:

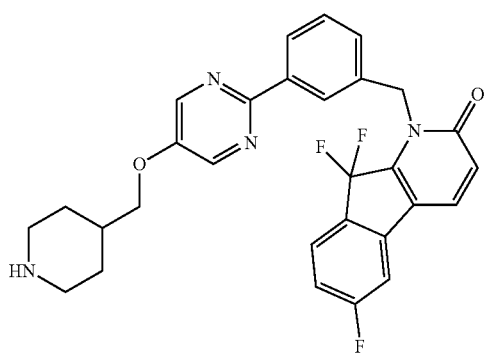 [SMILES: O=c1ccc2c(n1Cc1cccc(-c3ncc(OCC4CCNCC4)cn3)c1)C(F)(F)c1ccc(F)cc1-2]

Compound 4D was prepared according to the method of compound 3F by replacing compound 3E with compound 4C, which was used directly in the next step. LCMS (ESI): m/z: 519.2 [M+1].

Formate of Compound 4:
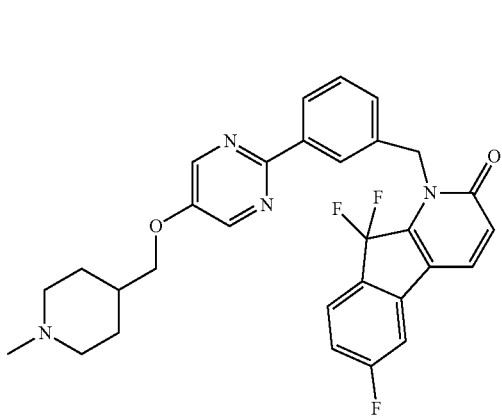
Formate of compound 4 was prepared according to the method of formate of compound 1 by replacing compound 1L with compound 4D. $^1$H NMR (400 MHz, DMSO-$d_6$) δ=8.62 (s, 2H), 8.21-8.19 (m, 1H), 8.19 (s, 1H), 8.15 (s, 1H), 8.12-8.08 (m, 1H), 7.74-7.67 (m, 1H), 7.64 (dd, J=2.3, 9.0 Hz, 1H), 7.46 (t, J=7.8 Hz, 1H), 7.30 (d, J=7.2 Hz, 1H), 7.14-7.07 (m, 1H), 6.84 (d, J=9.4 Hz, 1H), 5.39 (s, 2H), 4.06-4.01 (m, 2H), 2.86-2.80 (m, 2H), 2.20 (s, 3H), 1.95 (t, J=10.8 Hz, 2H), 1.75 (d, J=9.2 Hz, 3H), 1.42-1.25 (m, 2H). LCMS (ESI): m/z: 533.3 [M+1].
Embodiment 5
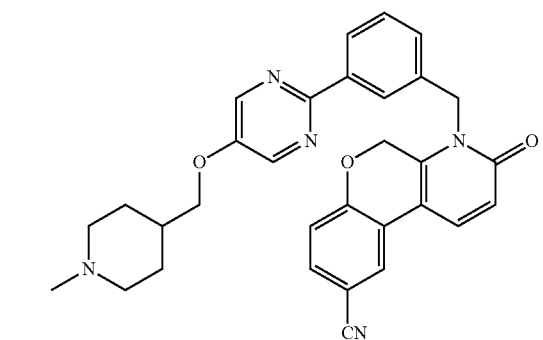
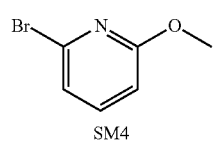
SM4
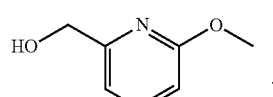
5A
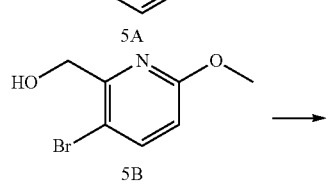
5B
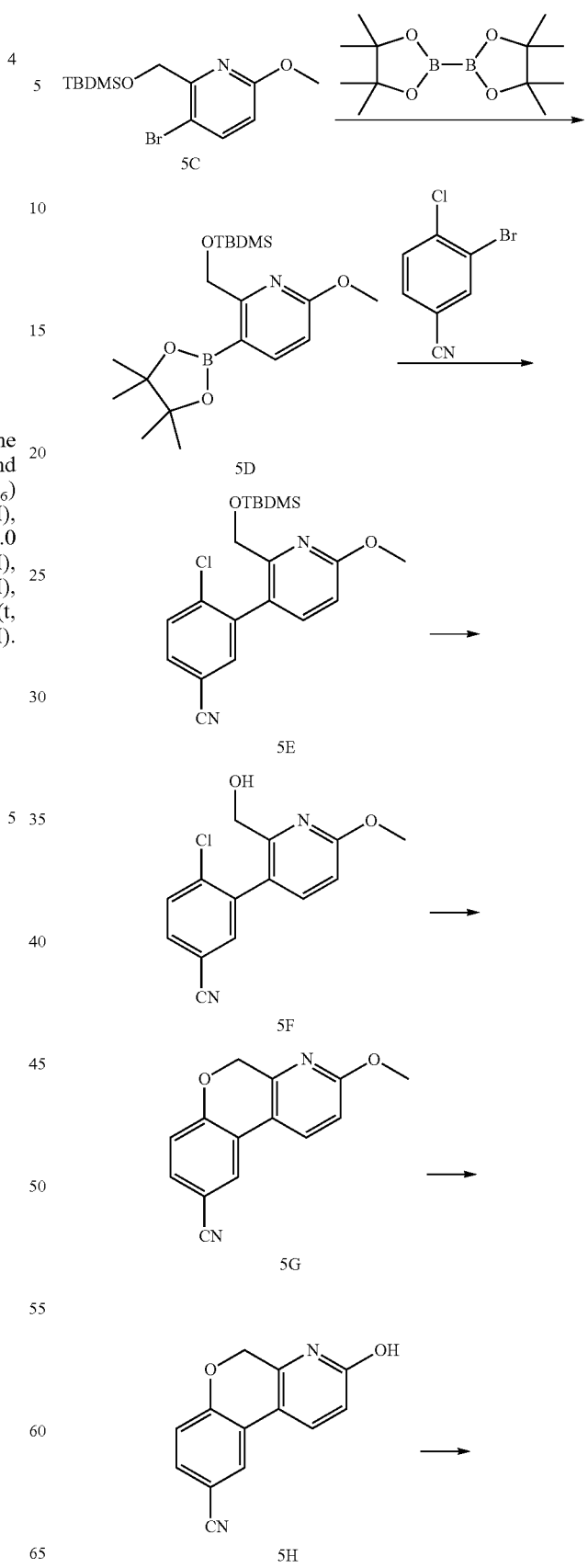

-continued

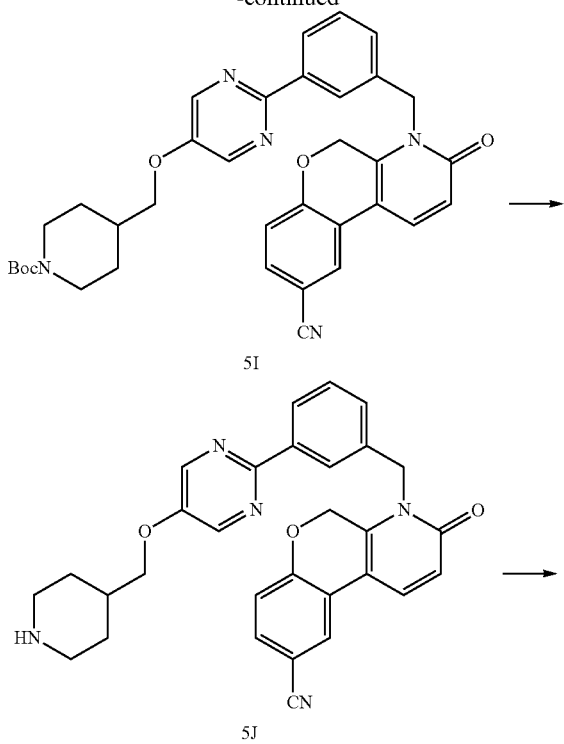

5I

5J

Formate of compound 5

Compound 5A:

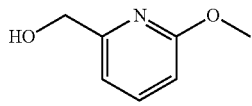

2-bromo-6-methoxypyridine (10 g, 53.19 mmol, 6.54 mL) was dissolved in tetrahydrofuran (100 mL), the mixture was cooled to −60° C., then n-butyllithium solution (2.5 mol/L, 23.40 mL) was slowly added dropwise, and then DMF (4.67 g, 63.83 mmol, 4.9 mL) was continuously added dropwise at this temperature. After the addition, the reaction mixture was heated to −30° C., and methanol (40 mL) was slowly added dropwise, after the addition, the reaction mixture was warmed to 0° C., and sodium borohydride (2.41 g, 63.83 mmol) was added in batches, the reaction mixture was stirred at 0-15° C. for 0.5 hours, concentrated to a volume of about 50 mL, then diluted with ethyl acetate (100 mL), the reaction was quenched with water (50 mL), and then the pH was adjusted to 8-9 with 2 mol/L dilute hydrochloric acid. The organic phase was separated and dried over anhydrous sodium sulfate and concentrated to obtain the compound 5A. $^1$H NMR (400 MHz, CDCl$_3$) δ=7.49 (dd, J=7.2, 8.2 Hz, 1H), 6.73 (dd, J=0.7, 7.3 Hz, 1H), 6.59-6.54 (m, 1H), 4.60 (s, 2H), 3.88 (s, 3H).

Compound 5B:

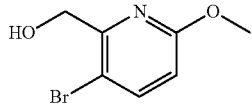

Compound 5A (8.3 g, 53.09 mmol) was dissolved in dichloromethane (100 mL), cooled to −20° C., and liquid bromine (9.33 g, 58.39 mmol, 3.01 mL) was slowly added dropwise, after the addition, the temperature of the reaction mixture was raised to 10° C., and a solution of sodium bicarbonate (8.92 g, 106.17 mmol) in water (100 mL) was slowly added thereto, the mixture was stirred at 10-20° C. for 0.5 hours. The organic phase was separated and dried over anhydrous sodium sulfate, concentrated, then purified by silica gel chromatography (eluting with pure petroleum ether) to obtain the compound 5B. $^1$H NMR (400 MHz, CDCl$_3$) δ=7.70 (d, J=8.8 Hz, 1H), 6.64-6.60 (m, 1H), 4.70 (s, 2H), 3.99 (s, 3H). LCMS (ESI): m/z: 217.9 [M+1].

Compound 5C:

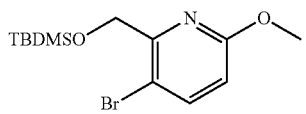 [SMILES: COc1ccc(Br)c(CO[Si](C)(C)C(C)(C)C)n1]

Compound 5B (3 g, 13.76 mmol) and imidazole (1.12 g, 16.51 mmol) were dissolved in dichloromethane, cooled to 10° C., then TBDMSCl (2.49 g, 16.51 mmol, 2.02 mL) was added dropwise thereto, after the addition, the mixture was stirred for 2 hours at 20-30° C., the reaction was quenched with water (20 mL), and the organic phase was separated, the aqueous phase was extracted with dichloromethane (20 mL×1). The organic phase was combined and dried over anhydrous sodium sulfate, concentrated, then purified by silica gel chromatography (eluting with pure petroleum ether) to obtain the compound 5C. $^1$H NMR (400 MHz, CDCl$_3$) δ=7.51 (d, J=8.6 Hz, 1H), 6.42 (d, J=8.6 Hz, 1H), 4.69 (s, 2H), 3.81 (s, 3H), 0.82 (s, 9H), 0.00 (s, 6H). LCMS (ESI): m/z: 332.0 [M+1].

Compound 5D:

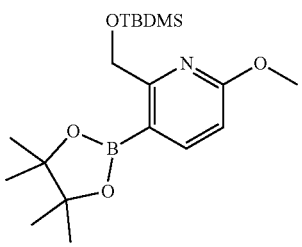

Compound 5C (2.5 g, 7.52 mmol) and bis(pinacolato)diboron (3.82 g, 15.05 mmol) were added to dioxane (40 mL), and then DMSO (7 mL), Pd(dppf)Cl$_2$ (550.48 mg, 752.31 μmol) and potassium acetate (2.21 g, 22.57 mmol) were added thereto, the reaction system was stirred for 3 hours under the protection of nitrogen at 80-90° C., the reaction mixture was diluted with ethyl acetate (20 mL), filtered, the filtrate was dissolved in ethyl acetate (100 mL), and then washed with saturated sodium chloride aqueous solution (20 mL×4), the organic phase was dried over anhydrous sodium sulfate, concentrated, and purified by silica gel chromatography (eluting with pure petroleum ether) to obtain the compound 5D. $^1$H NMR (400 MHz, CDCl$_3$) δ=7.94 (d, J=8.3 Hz, 1H), 6.61 (d, J=8.3 Hz, 1H), 4.99 (s, 2H), 3.99 (s, 3H), 1.35 (s, 12H), 0.94 (s, 9H), 0.10 (s, 6H). LCMS (ESI): m/z: 380.1 [M+1].

Compound 5E:

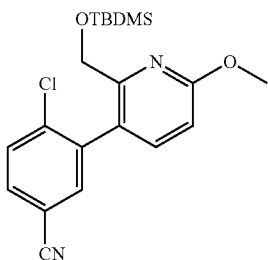 [SMILES: COc1ccc(-c2cc(C#N)ccc2Cl)c(CO[Si](C)(C)C(C)(C)C)n1]

Compound 5D (1.6 g, 4.22 mmol) and 3-bromo-4-chlorobenzonitrile (912.93 mg, 4.22 mmol) were added to DME (30 mL), and then Pd(PPh₃)₄ (487.36 mg, 421.75 μm), sodium carbonate (1.34 g, 12.65 mmol) and water (6 mL) were added thereto, and the reaction system was stirred at 80° C. for 2 hours. The reaction mixture was diluted with ethyl acetate (40 mL), filtered, the filtrate was washed with saturated sodium chloride aqueous solution (10 mL×1), and the aqueous phase was extracted with ethyl acetate (10 mL×2). The organic phase was combined and dried over anhydrous sodium sulfate, concentrated, then purified by silica gel chromatography (eluting with petroleum ether: ethyl acetate=100:1) to obtain the compound 5E. $^1$H NMR (400 MHz, CDCl₃) δ=7.69 (dd, J=0.9, 1.6 Hz, 1H), 7.61-7.58 (m, 2H), 7.40 (d, J=8.3 Hz, 1H), 6.76 (d, J=8.6 Hz, 1H), 4.63-4.46 (m, 2H), 4.02 (s, 3H), 0.84 (s, 9H), 0 (d, J=7.1 Hz, 6H). LCMS (ESI): m/z: 389.0 [M+1].

Compound 5F:

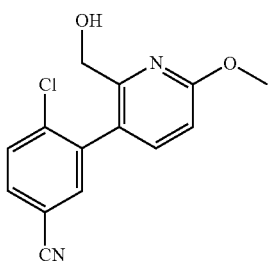 [SMILES: COc1ccc(-c2cc(C#N)ccc2Cl)c(CO)n1]

Compound 5E (1 g, 2.57 mmol) was dissolved in tetrahydrofuran (10 mL), a solution (1 mol/L, 2.6 mL) of tetrabutylammonium fluoride in tetrahydrofuran was added thereto, and the reaction system was stirred at 20-30° C. for 0.5 hours. The reaction mixture was concentrated and diluted with ethyl acetate (30 mL), then washed with saturated sodium chloride aqueous solution (10 mL×1), and the aqueous phase was extracted with ethyl acetate (10 mL×2). The organic phase was combined and dried over anhydrous sodium sulfate, concentrated, then purified by silica gel chromatography (eluting with petroleum ether:ethyl acetate=50:1) to obtain the compound 5F. $^1$H NMR (400 MHz, CDCl₃) δ=7.65 (t, J=1.5 Hz, 2H), 7.56-7.54 (m, 1H), 7.43 (d, J=8.3 Hz, 1H), 6.80 (d, J=8.6 Hz, 1H), 4.41 (d, J=7.3 Hz, 2H), 4.06 (s, 3H), 3.98 (s, 1H).

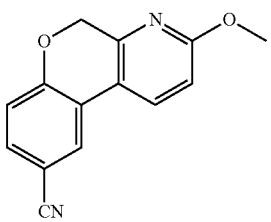 [SMILES: COc1ccc2c(n1)COc1ccc(C#N)cc1-2]

Compound 5G:

Compound 5F (350 mg, 1.27 mmol) was dissolved in tetrahydrofuran (8 mL), a solution of potassium tert-butoxide in tetrahydrofuran (1 mol/L, 1.3 mL) was added thereto, and the reaction system was stirred at 20-30° C. for 0.5 hours. The reaction mixture was diluted with ethyl acetate (30 mL), then washed with saturated ammonium chloride aqueous solution (10 mL×1), and the aqueous phase was extracted with ethyl acetate (10 mL×2). The organic phase was combined, dried over anhydrous sodium sulfate and concentrated to obtain the compound 5G. $^1$H NMR (400 MHz, CDCl₃) δ=7.86 (d, J=8.6 Hz, 1H), 7.84 (d, J=2.0 Hz, 1H), 7.49 (dd, J=2.0, 8.6 Hz, 1H), 7.04 (d, J=8.6 Hz, 1H), 6.81 (d, J=8.8 Hz, 1H), 5.26 (s, 2H), 3.98 (s, 3H). LCMS (ESI): m/z: 239.0 [M+1].

Compound 5H:

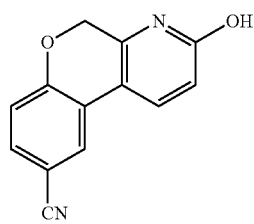 [SMILES: N#Cc1ccc2c(c1)-c1ccc(O)nc1CO2]

Compound 5H was prepared according to the method of compound 1F by replacing compound 1E with compound 5G. $^1$H NMR (400 MHz, DMSO-d₆) δ=8.18 (s, 1H), 8.10 (br d, J=9.5 Hz, 1H), 7.61 (dd, J=2.0, 8.3 Hz, 1H), 7.07 (d, J=8.3 Hz, 1H), 6.47 (br d, J=8.6 Hz, 1H), 5.16 (s, 2H). LCMS (ESI): m/z: 225.1 [M+1].

Compound 5I:

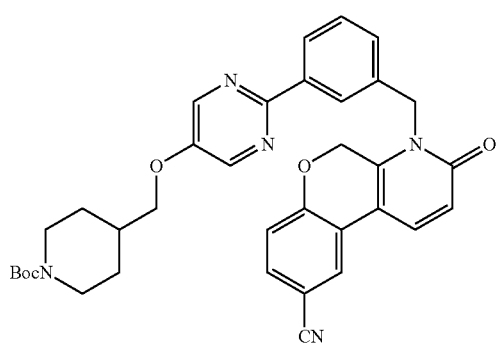

Compound 5I was prepared according to the method of compound 1K by replacing compound 1F with compound 5H and replacing the purification method with preparative high performance liquid chromatography. $^1$H NMR (400 MHz, DMSO-d₆) δ=8.65 (s, 2H), 8.25-8.10 (m, 4H), 7.61 (br d, J=9.5 Hz, 1H), 7.49-7.44 (m, 1H), 7.30 (br d, J=7.1

Hz, 1H), 7.03 (d, J=8.3 Hz, 1H), 6.69 (br d, J=9.5 Hz, 1H), 5.41 (br s, 2H), 5.27 (br s, 2H), 4.06 (br d, J=6.8 Hz, 2H), 2.73 (br s, 4H), 1.98-1.90 (m, 1H), 1.76 (br d, J=9.5 Hz, 4H), 1.40 (s, 9H). LCMS (ESI): m/z: 550.1 [M-55].

Compound 5J:

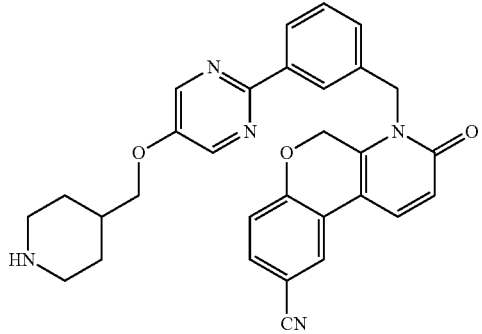 [SMILES: N#Cc1ccc2c(c1)-c1ccc(=O)n(Cc3cccc(-c4ncc(OCC5CCNCC5)cn4)c3)c1CO2]

5

Compound 5I (100 mg, 165.10 mmol) was dissolved in dichloromethane (2 mL), and trifluoroacetic acid (154 mg, 1.35 mmol, 0.1 mL) was added thereto, the reaction system was stirred at 20-30° C. for 2 hours. The reaction system was diluted with dichloromethane (5 mL), washed with saturated sodium bicarbonate aqueous solution (2 mL×1), and the aqueous phase was extracted with dichloromethane (2 mL×2). The organic phase was combined, dried over anhydrous sodium sulfate and concentrated to obtain the compound 5J. $^1$H NMR (400 MHz, CDCl$_3$) δ=8.46 (s, 2H), 8.31 (d, J=7.8 Hz, 1H), 8.27 (s, 1H), 7.75 (d, J=9.8 Hz, 1H), 7.71 (d, J=2.0 Hz, 1H), 7.50-7.48 (m, 1H), 7.46 (d, J=8.1 Hz, 1H), 7.44-7.40 (m, 1H), 7.23 (d, J=8.1 Hz, 1H), 6.93 (d, J=8.3 Hz, 1H), 6.85 (d, J=9.5 Hz, 1H), 5.45 (br s, 2H), 5.13 (s, 2H), 4.00 (br d, J=5.9 Hz, 2H), 3.45 (br d, J=11.7 Hz, 2H), 2.91 (br t, J=12.3 Hz, 4H), 2.17-1.07 (m, 1H), 1.71 (br d, J=12.7 Hz, 2H). LCMS (ESI): m/z: 506.1 [M+1].

Formate of Compound 5:

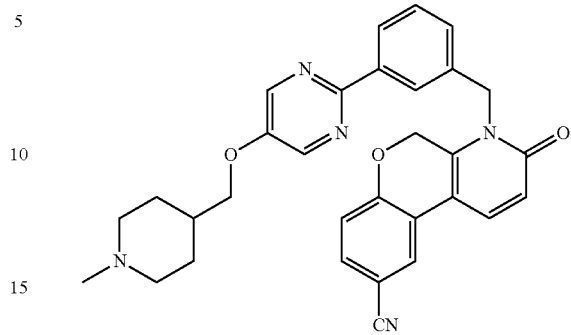

5

Formate of compound 5 was prepared according to the method of formate of compound 1 by replacing compound 1L with compound 5J. $^1$H NMR (400 MHz, DMSO-d$_6$) δ=8.61 (s, 2H), 8.29 (s, 1H), 8.21 (d, J=8.1 Hz, 1H), 8.18 (d, J=2.0 Hz, 1H), 8.16 (d, J=9.8 Hz, 2H), 7.60 (dd, J=1.8, 8.4 Hz, 1H), 7.48 (t, J=7.8 Hz, 1H), 7.30 (d, J=7.8 Hz, 1H), 7.02 (d, J=8.3 Hz, 1H), 6.69 (d, J=9.5 Hz, 1H), 5.41 (br s, 2H), 5.26 (s, 2H), 4.03 (d, J=6.1 Hz, 2H), 2.97 (br d, J=11.7 Hz, 2H), 2.32 (s, 3H), 2.20 (br t, J=10.9 Hz, 2H), 1.87-1.74 (m, 3H), 1.45-1.32 (m, 2H). LCMS (ESI): m/z: 520.1 [M+1].

Embodiment 6

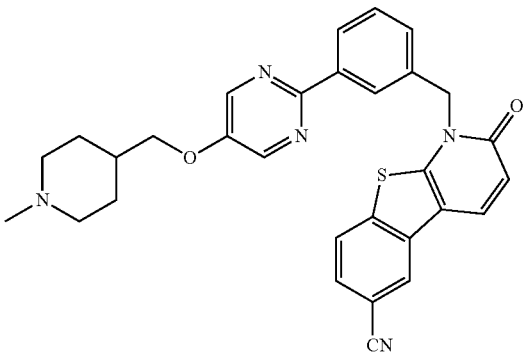

6

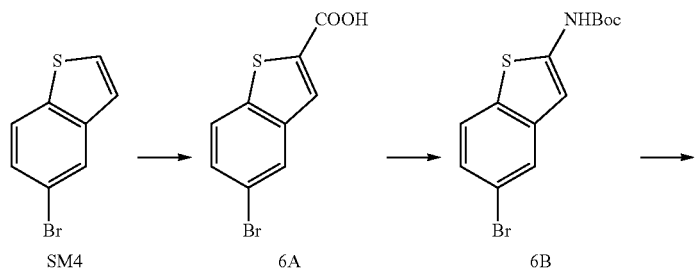

-continued
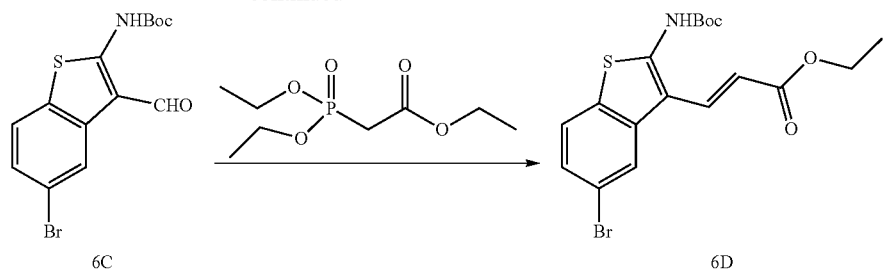
6C → 6D
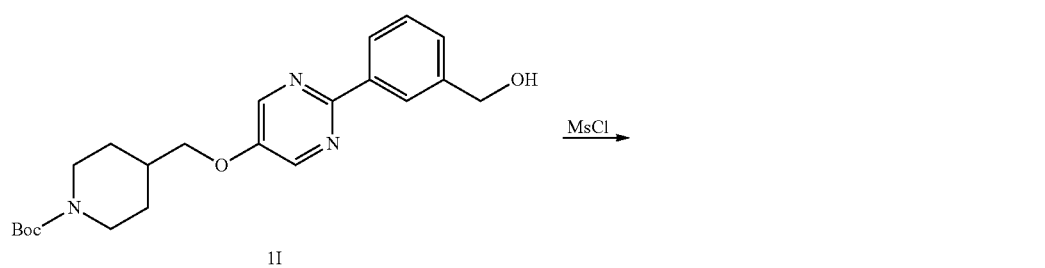
1I
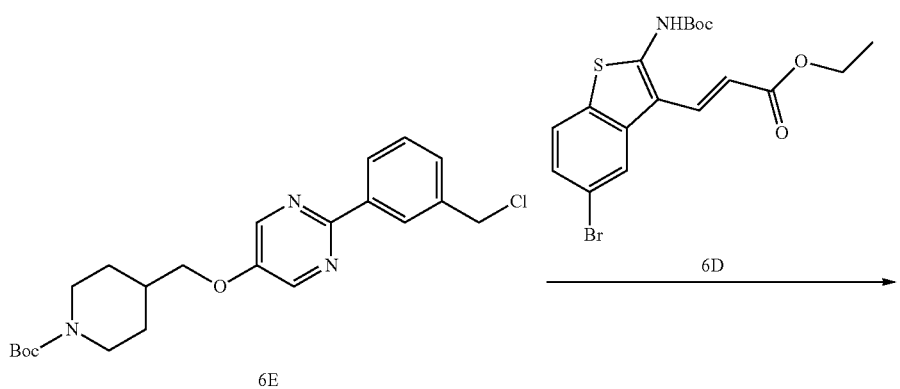
6E + 6D →
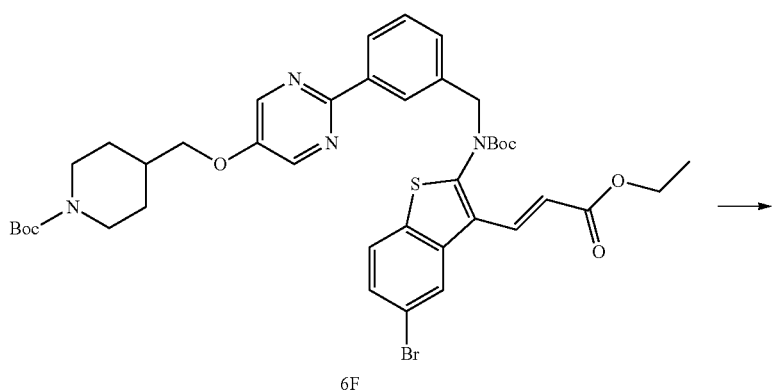
6F →
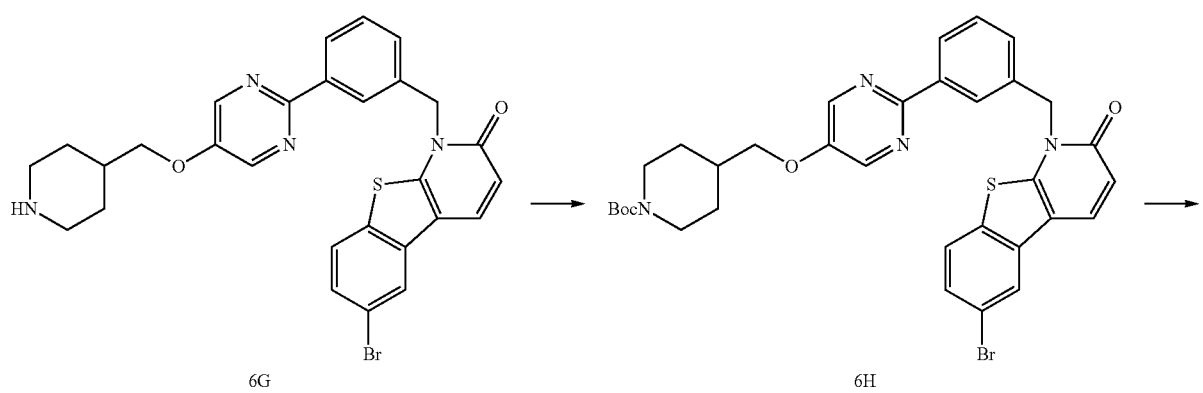
6G → 6H →

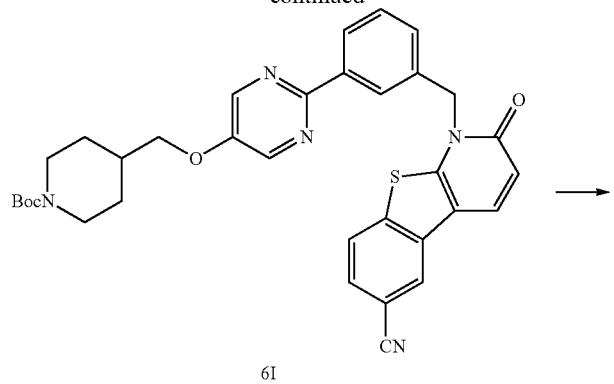

6I

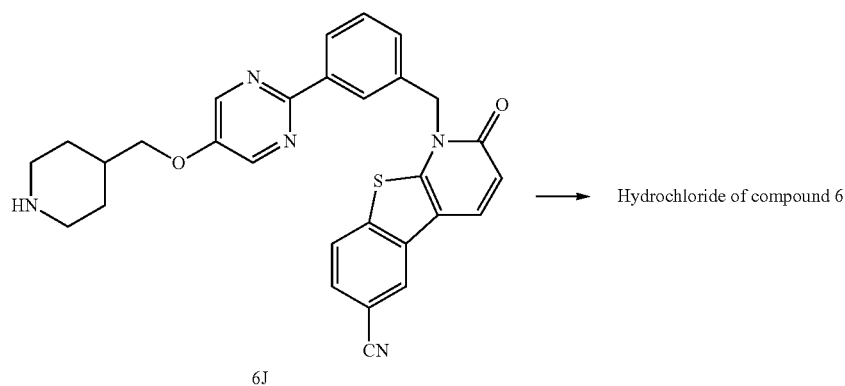

6J

→ Hydrochloride of compound 6

Compound 6A:

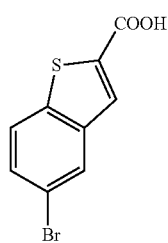 [SMILES: O=C(O)c1cc2cc(Br)ccc2s1]

Compound 6B:

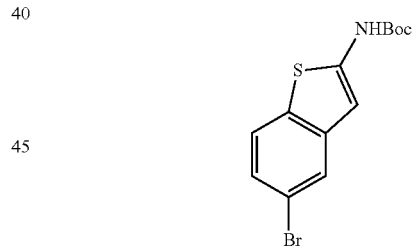

5-bromobenzothiophene (10 g, 46.93 mmol) was dissolved in tetrahydrofuran (100 mL), the mixture was cooled to −60° C., lithium diisopropylamide (2 mol/L, 30.00 mL) was slowly added dropwise under the protection of a nitrogen balloon, after the addition, the mixture was stirred at −60 to −30° C. for 1 hour, then cooled to −60° C., dry ice (20 g, 454.45 mmol) was added thereto in batches. After the addition, the reaction system was stirred at −60 to −30° C. for 0.5 hours under normal pressure, and then stirred at −30 to 0° C. for 0.5 hours, the reaction was quenched with 2 mol/L dilute hydrochloric acid (100 mL), then extracted with ethyl acetate (100 mL×1, 50 mL×2). The organic phase was dried over anhydrous sodium sulfate and concentrated, the crude product was slurried with petroleum ether (30 mL) to obtain the compound 6A. $^1$H NMR (400 MHz, DMSO-$d_6$) δ=8.27 (d, J=2.0 Hz, 1H), 8.09 (s, 1H), 8.04 (d, J=8.6 Hz, 1H), 7.65 (dd, J=2.1, 8.7 Hz, 1H).

Compound 6A (11.8 g, 45.90 mmol), TEA (5.09 g, 50.29 mmol, 7 mL) and DPPA (13.9 g, 50.51 mmol, 10.94 mL) were sequentially added to tert-butanol (150 mL), the reaction system was stirred at 20° C. for 0.5 hours, and then stirred at 80° C. for 8 hours. The reaction mixture was concentrated and diluted with ethyl acetate (200 mL), then washed with saturated sodium bicarbonate aqueous solution (150 mL×1), and the aqueous phase was extracted with ethyl acetate (100 mL×2). The organic phase was combined and dried over anhydrous sodium sulfate, concentrated, then purified by silica gel chromatography (eluting with petroleum ether:ethyl acetate:dichloromethane=50:1:1) to obtain the compound 6B. $^1$H NMR (400 MHz, CDCl$_3$) δ=7.71 (d, J=1.7 Hz, 1H), 7.57 (d, J=8.3 Hz, 1H), 7.32 (dd, J=1.8, 8.4 Hz, 1H), 7.13 (br s, 1H), 6.67 (s, 1H), 1.57 (s, 9H). LCMS (ESI) m/z: 271.9 [M−55].

Compound 6C:

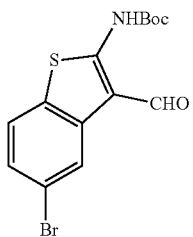 [SMILES: CC(C)(C)OC(=O)Nc1sc2ccc(Br)cc2c1C=O]

DMF (218.50 mg, 2.99 mmol, 0.23 mL) was added to tetrahydrofuran (2 mL), the mixture was cooled to 0° C., and phosphorus oxychloride (693.00 mg, 4.52 mmol, 420.00 μL) was carefully added dropwise, the reaction mixture was stirred at 0° C. for 0.5 hours. Then, compound 6B (0.5 g, 1.52 mmol) was dissolved in tetrahydrofuran (4 mL) and added to the reaction mixture at 0° C. and stirred at 20° C. for 1 hour. The reaction system was diluted with ethyl acetate (20 mL), then quenched with 2 mol/L sodium hydroxide aqueous solution and the pH value was adjusted to 7, the organic phase was separated and the aqueous phase was extracted with ethyl acetate (10 mL×2). The organic phase was combined, dried over anhydrous sodium sulfate and concentrated to obtain the compound 6C. $^1$H NMR (400 MHz, CDCl$_3$) δ=11.17 (br s, 1H), 10.19 (s, 1H), 8.05 (d, J=1.7 Hz, 1H), 7.61 (d, J=8.6 Hz, 1H), 7.43 (dd, J=1.7, 8.3 Hz, 1H), 1.60 (s, 9H). LCMS (ESI) m/z: 299.9 [M-55].

Compound 6D:

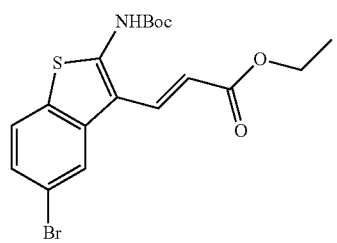 [SMILES: CCOC(=O)/C=C/c1c(NC(=O)OC(C)(C)C)sc2ccc(Br)cc12]

Triethyl phosphonoacetate (2 g, 8.92 mmol, 1.77 mL) was dissolved in tetrahydrofuran (5 mL), cooled to 0° C., sodium hydride (35 mg, 8.88 mmol, 60% purity) was added thereto in batches, and the reaction mixture was stirred at 0° C. for 0.5 hours. Then compound 6C (0.79 g, 2.22 mmol) was dissolved in tetrahydrofuran (10 mL) and added to the reaction mixture at 0° C., after the addition, the mixture was stirred at 0 to 20° C. for 0.5 hours, then heated to 60° C. and stirred at 60° C. for 12 hours. Ethyl acetate (30 mL) was added to the reaction system and then the reaction was quenched with saturated ammonium chloride aqueous solution (10 mL), the organic phase was separated and the aqueous phase was extracted with ethyl acetate (10 mL×2). The organic phase was combined and dried over anhydrous sodium sulfate, concentrated, then purified by silica gel chromatography (eluting with petroleum ether:ethyl acetate=30:1) to obtain the compound 6D. $^1$H NMR (400 MHz, CDCl$_3$) δ=7.86 (d, J=1.7 Hz, 1H), 7.70 (d, J=15.9 Hz, 1H), 7.51 (d, J=8.6 Hz, 1H), 7.40 (br s, 1H), 7.31 (dd, J=1.8, 8.4 Hz, 1H), 6.33 (d, J=16.1 Hz, 1H), 4.26 (q, J=7.1 Hz, 2H), 1.51 (s, 9H), 1.32 (t, J=7.1 Hz, 3H). LCMS (ESI) m/z: 325.8 [M-99].

Compound 6E:

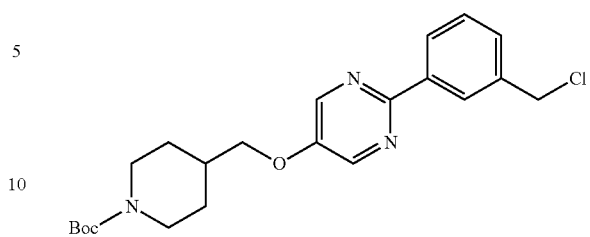

Compound 1I (44 g, 110.14 mmol) was dissolved in 400 mL of dichloromethane, and then DIPEA (57.13 g, 442.08 mmol, 77 mL) was slowly added thereto, and methanesulfonyl chloride (51.80 g, 452.20 mmol, 35 mL) was added thereto at 0° C. After the addition, the reaction mixture was stirred and reacted at 20° C. for 4 hours, 300 mL of dichloromethane was added to the reaction mixture, then the mixture was washed three times with 300 mL of saturated sodium bicarbonate aqueous solution. The organic phase was dried over anhydrous sodium sulfate, filtered, and then evaporated to dryness. The residue was purified by column chromatography (petroleum ether:ethyl acetate=100:1-10:1) to obtain the compound 6E. $^1$H NMR (400 MHz, CDCl$_3$) δ=8.49-8.44 (m, 2H), 8.39 (s, 1H), 8.38-8.29 (m, 1H), 7.50-7.44 (m, 2H), 4.71-4.67 (m, 2H), 4.19 (br s, 2H), 3.96 (d, J=6.4 Hz, 2H), 2.77 (br t, J=12.2 Hz, 2H), 2.08-1.98 (m, 1H), 1.85 (br d, J=12.6 Hz, 2H), 1.48 (s, 9H), 1.39-1.29 (m, 2H). LCMS (ESI): m/z: 418.0 [M+1].

Compound 6F:

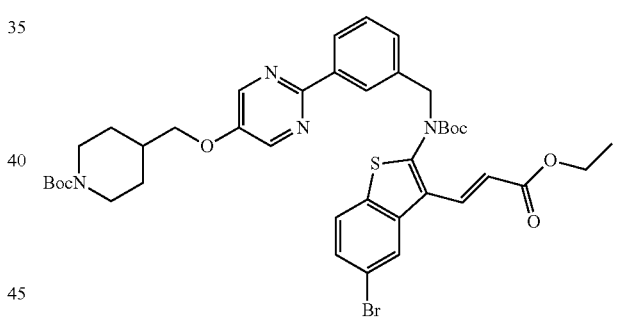

Compound 6D (0.2 g, 469.13 μmol) and compound 6E (235 mg, 562.30 μmol) were added to DMF (4 mL), then cesium carbonate (220 mg, 675.22 μmol) and potassium iodide (80 mg, 481.93 μmol) were added thereto. The reaction system was stirred at 70 to 80° C. for 3 hours. The reaction mixture was diluted with ethyl acetate (8 mL), then washed with saturated sodium chloride aqueous solution (4 mL×1), and the aqueous phase was extracted with ethyl acetate (4 mL×2). The organic phase was combined and dried over anhydrous sodium sulfate, concentrated, then purified by thin layer silica gel chromatography (eluting with petroleum ether:ethyl acetate=2:1) to obtain the compound 6F. $^1$H NMR (400 MHz, CDCl$_3$) δ=8.33 (s, 2H), 8.19 (br d, J=7.3 Hz, 1H), 8.14 (br s, 1H), 7.97 (d, J=2.0 Hz, 1H), 7.49 (d, J=16.4 Hz, 1H), 7.45 (d, J=8.6 Hz, 1H), 7.38-7.35 (m, 1H), 7.32 (d, J=7.6 Hz, 1H), 7.30-7.26 (m, 1H), 6.29 (d, J=16.4 Hz, 1H), 4.84 (s, 2H), 4.16 (m, 4H), 3.86 (d, J=6.4 Hz, 2H), 2.69 (br t, J=12.0 Hz, 2H), 2.00-1.87 (m, 1H), 1.76 (br d, J=13.2 Hz, 2H), 1.45-1.33 (m, 18H), 1.31-1.17 (m, 5H). LCMS (ESI) m/z: 809.0 [M+3].

Hydrochloride of Compound 6G:

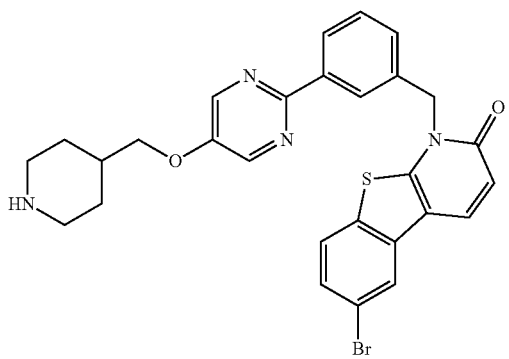

Compound 6F (0.3 g, 371.38 μmol) was dissolved in methanol (5 mL), and a solution of hydrochloric acid in methanol (4 mol/L, 2 mL) was added thereto, then the reaction system was heated to 60° C. and stirred for 1 hour. The reaction system was concentrated to obtain the hydrochloride of compound 6G. LCMS (ESI) m/z: 563.0 [M+3].

Compound 6H:

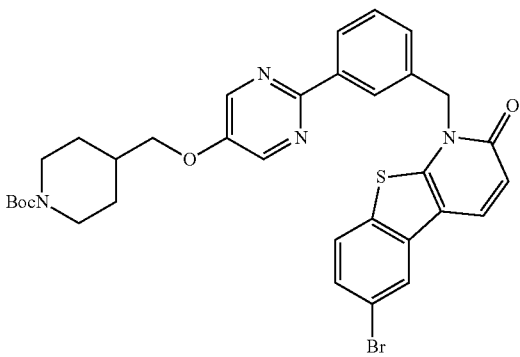 [SMILES: CC(C)(C)OC(=O)N1CCC(COc2cnc(-c3cccc(Cn4c(=O)ccc5c6cc(C#N)ccc6sc54)c3)nc2)CC1]

The hydrochloride of compound 6G (0.22 g, 367.92 μmol) was dissolved in methanol (2 mL) and dichloromethane (2 mL); then triethylamine (181.75 mg, 1.80 mmol, 0.25 mL), DMAP (45 mg, 368.35 mmol) and Boc$_2$O (96 mg, 439.87 mmol, 101.05 μL) were added thereto. The reaction system was stirred at 40 to 50° C. for 1 hour. The reaction mixture was diluted with ethyl acetate (10 mL), then washed with saturated sodium chloride aqueous solution (3 mL×1), and the aqueous phase was extracted with ethyl acetate (2 mL×2). The organic phase was combined and dried over anhydrous sodium sulfate, concentrated, then purified by thin layer silica gel chromatography (dichloromethane:methanol=20:1) to obtain the compound 6H. $^1$H NMR (400 MHz, CDCl$_3$) δ=8.48 (s, 1H), 8.46 (s, 2H), 8.33-8.28 (m, 1H), 7.98-7.94 (m, 2H), 7.57 (d, J=8.5 Hz, 1H), 7.46-7.43 (m, 2H), 7.41 (dd, J=2.0, 8.5 Hz, 1H), 6.77 (d, J=9.3 Hz, 1H), 5.54 (s, 2H), 4.21 (br s, 2H), 3.97 (d, J=6.3 Hz, 2H), 2.79 (br t, J=12.3 Hz, 2H), 2.10-1.97 (m, 1H), 1.86 (br d, J=12.8 Hz, 2H), 1.50 (s, 9H), 1.40-1.28 (m, 2H). LCMS (ESI) m/z: 663.0 [M+3].

Compound 6I:

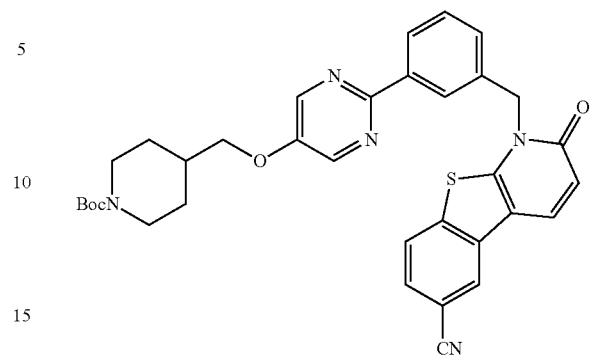

Compound 6H (0.14 g, 211.61 μmol) and zinc cyanide (38 mg, 323.61 μmol) were added to DMF (2 mL), then zinc powder (14 mg, 214.10 μmol), dppf (24 mg, 43.29 μmol) and Pd$_2$(dba)$_3$ (20 mg, 21.84 μmol) were added thereto. The reaction system was stirred at 90 to 100° C. for 12 hours. The reaction mixture was diluted with ethyl acetate (10 mL), filtered, the filtrate was washed with saturated sodium chloride aqueous solution (2 mL×1), and the aqueous phase was extracted with ethyl acetate (2 mL×2). The organic phase was combined and dried over anhydrous sodium sulfate, concentrated, then purified by thin layer silica gel chromatography (dichloromethane:methanol=20:1) to obtain the compound 6I. $^1$H NMR (400 MHz, CDCl$_3$) δ=8.41-8.36 (m, 3H), 8.23 (dt, J=1.7, 4.5 Hz, 1H), 8.03 (d, J=1.2 Hz, 1H), 7.93 (d, J=9.5 Hz, 1H), 7.73 (d, J=8.3 Hz, 1H), 7.46 (dd, J=1.5, 8.3 Hz, 1H), 7.37-7.34 (m, 2H), 6.73 (d, J=9.3 Hz, 1H), 5.47 (s, 2H), 4.13 (m, 2H), 3.88 (d, J=6.4 Hz, 2H), 2.69 (br t, J=12.3 Hz, 2H), 2.01-1.88 (m, 1H), 1.77 (br d, J=12.7 Hz, 2H), 1.40 (s, 9H), 1.25 (dq, 12.4 Hz, 2H). LCMS (ESI) m/z: 552.1 [M-55].

Compound 6J:

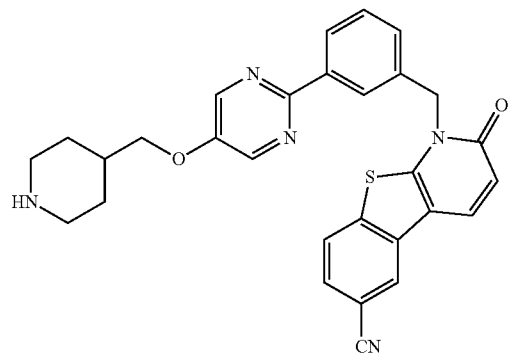 [SMILES: N#Cc1ccc2sc3c(ccc(=O)n3Cc3cccc(-c4ncc(OCC5CCNCC5)cn4)c3)c2c1]

Compound 6J was prepared according to the method of compound 5J by replacing compound 5I with compound 6I, which was used directly in the next step. LCMS (ESI) m/z: 508.1 [M+1].

Hydrochloride of Compound 6:

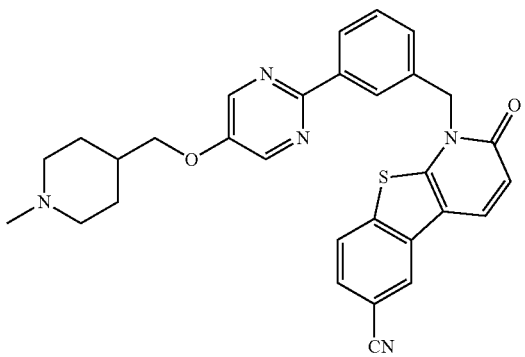

The hydrochloride of compound 6 was prepared according to the method of compound 1 by replacing compound 1L with compound 6J and replacing the high performance liquid chromatography (formic acid system) with high performance liquid chromatography (hydrochloric acid system). $^1$H NMR (400 MHz, DMSO-$d_6$) δ=10.83 (br s, 1H), 8.69-8.60 (m, 3H), 8.47 (d, J=9.3 Hz, 1H), 8.28-8.17 (m, 3H), 7.70 (d, J=8.3 Hz, 1H), 7.51-7.41 (m, 2H), 6.72 (d, J=9.3 Hz, 1H), 5.49 (s, 2H), 4.06 (br d, J=6.4 Hz, 2H), 3.40 (br d, J=11.2 Hz, 2H), 2.95 (q, J=11.1 Hz, 2H), 2.69 (br d, J=4.4 Hz, 3H), 2.05 (m, 1H), 1.94 (br d, J=13.7 Hz, 2H), 1.66 (q, J=11.7 Hz, 2H); LCMS (ESI) m/z: 522.4 [M+1].

Embodiment 7

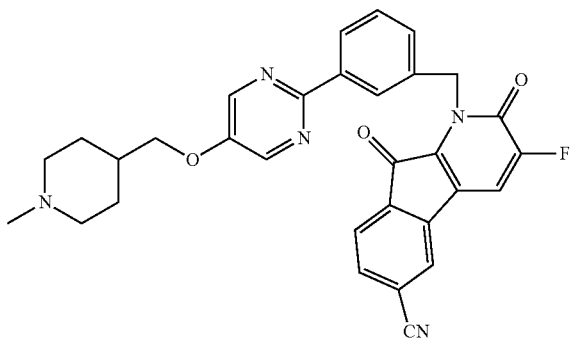

Compound 7A:

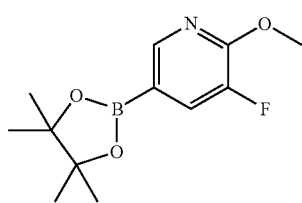

The compound 5-bromo-3-fluoro-2-methoxypyridine (10 g, 48.54 mmol) and bis(pinacolato)diboron (13.56 g, 53.39 mmol) were dissolved in 1,4-dioxane (100 mL), Pd(dppf)Cl$_2$·CH$_2$Cl$_2$ (1.98 g, 2.43 mmol) and potassium acetate (9.53 g, 97.08 mmol) were added thereto, and then the mixture was stirred for 12 hours under the protection of nitrogen at 100° C. After the completion of the reaction, the reaction mixture was filtered, and the filtrate was collected and concentrated to obtain the compound 7A. $^1$HNMR (400 MHz, CDCl$_3$) δ=8.28 (d, J=0.8 Hz, 1H), 7.63 (dd, J=1.4, 10.7 Hz, 1H), 4.04 (s, 3H), 1.33 (s, 12H).

Compound 7B:

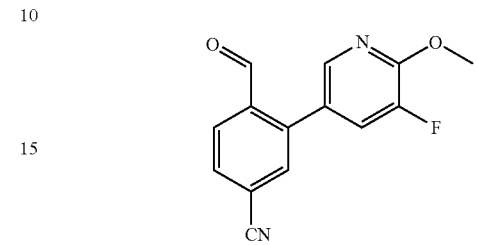

Compound 7B was prepared according to the method of compound 1C by replacing 2-methoxy-5-pyridineboronic acid pinacol ester with compound 7A. $^1$HNMIR (400 MHz, CDCl$_3$) δ=9.97 (s, 1H), 8.05 (d, J=8.1 Hz, 1H), 7.85 (d, J=2.1 Hz, 1H), 7.75 (d, J=8.1 Hz, 1H), 7.66 (d, J=1.3 Hz, 1H), 7.34 (dd, J=2.1, 10.1 Hz, 1H), 4.04 (s, 3H); LCMS (ESI) m/z: 257.1 [M+1].

Compound 7C:

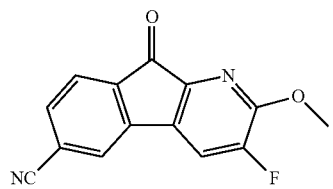 [SMILES: COc1nc2c(cc1F)-c1cc(C#N)ccc1C2=O]

Compound 7B (3.5 g, 13.66 mmol) was dissolved in peroxy tert-butanol (5.5 mol/L decane solution, 19.87 mL), the mixture was heated to 100° C. and stirred for 12 hours. After the reaction was completed, the mixture was cooled to 20° C., and a solid was precipitated. The solid was filtered and dissolved in dichloromethane (50 mL), the mixture was washed three times with saturated sodium carbonate solution (10 mL), the organic phase was dried over anhydrous sodium sulfate and concentrated to obtain the compound 7C. $^1$H NMR (400 MHz, CDCl$_3$) δ=7.66 (br d, J=7.5 Hz, 1H), 7.56 (br d, J=7.3 Hz, 1H), 7.52 (s, 1H), 7.48 (br d, J=8.8 Hz, 1H), 4.09 (s, 3H). LCMS (ESI) m/z: 255.1 [M+1].

Compound 7D:

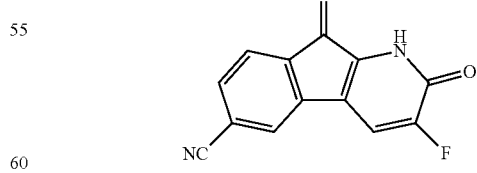

Compound 7C (300 mg, 1.18 mmol) was dissolved in acetonitrile (15 mL) and NMP (1.5 mL), and TMSC1 (384.63 mg, 3.54 mmol, 449.33 μL) and sodium iodide (530.67 mg, 3.54 mmol) were added thereto. The mixture was heated to 70° C. and stirred for another 12 hours, after the reaction was completed, the mixture was cooled to 20°

C. then poured into water, then filtered to obtain a solid, the solid was then collected and dried. The obtained solid was dissolved in acetonitrile (15 mL) and NMP (1.5 mL), peroxy tert-butanol (5.5 mol/L, 227.09 μL) was added thereto, the mixture was heated to 70° C. and stirred for another 12 hours, then cooled to 20° C., the reaction mixture was concentrated to solid, and then slurried with ethyl acetate to obtain the compound 7D. $^1$H NMR (400 MHz, DMSO-$d_6$) δ=8.16-8.02 (m, 1H), 8.02-7.90 (m, 1H), 7.77 (br d, J=7.7 Hz, 1H), 7.61 (br d, J=7.5 Hz, 1H). LCMS (ESI) m/z: 241.0 [M+1].

Compound 7E:

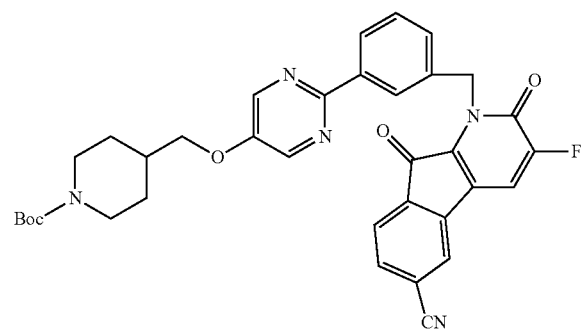 [SMILES: CC(C)(C)OC(=O)N1CCC(COc2cnc(-c3cccc(Cn4c5c(cc(F)c4=O)-c4cc(C#N)ccc4C5=O)c3)nc2)CC1]

Compound 7D (350 mg, 1.46 mmol) was dissolved in DMF (10 mL), cesium carbonate (712.17 mg, 2.19 mmol), potassium iodide (362.84 mg, 2.19 mmol) and compound 6E (913.50 mg, 2.19 mmol) were added thereto, the mixture was heated to 75° C., stirred for 1.5 hours and then cooled to 20° C., the reaction mixture was poured into water and extracted three times with ethyl acetate (150 mL). The organic phase was dried and concentrated to obtain a crude product, the crude product was purified by column chromatography (petroleum ether:ethyl acetate=3:1 to 1:1) to obtain the compound 7E. $^1$H NMR (400 MHz, CDCl$_3$) δ=8.51-8.42 (m, 2H), 8.36 (s, 2H), 8.27 (d, J=7.8 Hz, 1H), 7.58-7.56 (m, 2H), 7.50-7.49 (m, 1H), 7.44-7.42 (m, 1H), 7.39-7.37 (m, 1H), 5.83 (s, 2H), 4.21 (s, 2H), 3.97-3.93 (m, 2H), 2.82-2.75 (m, 2H), 2.12-2.01 (m, 1H), 1.88-1.85 (m, 2H), 1.49 (s, 9H), 1.36-1.28 (m, 2H). LCMS (ESI) m/z: 566.2 [M-55].

Compound 7F:

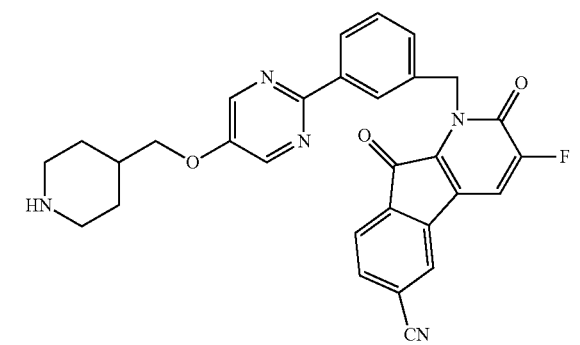 [SMILES: N#Cc1ccc2c(c1)-c1cc(F)c(=O)n(Cc3cccc(-c4ncc(OCC5CCNCC5)cn4)c3)c1C2=O]

Compound 7F was prepared according to the method of compound 5J by replacing compound 5I with compound 7E, which was used directly in the next step. LCMS (ESI) m/z: 522.2 [M+1].

Hydrochloride of Compound 7:

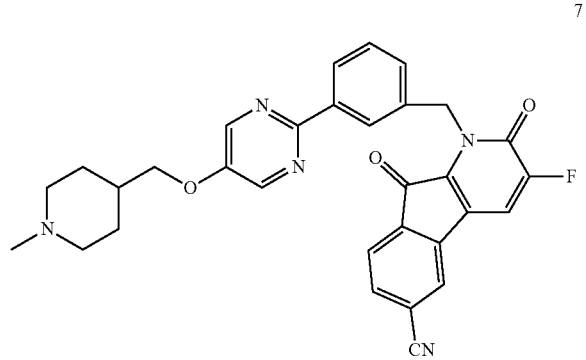 [SMILES: CN1CCC(COc2cnc(-c3cccc(Cn4c5c(cc(F)c4=O)-c4cc(C#N)ccc4C5=O)c3)nc2)CC1]

Hydrochloride of compound 7 was prepared according to the method of compound 1 by replacing compound 1L with compound 7F and replacing the high performance liquid chromatography (formic acid system) with high performance liquid chromatography (hydrochloric acid system). $^1$H NMR (400 MHz, DMSO-$d_6$) δ=10.35-10.24 (m, 1H), 8.68-8.62 (m, 2H), 8.28 (s, 1H), 8.20 (d, J=8.8 Hz, 2H), 8.01 (s, 1H), 7.78 (dd, J=1.3, 7.5 Hz, 1H), 7.62 (d, J=7.4 Hz, 1H), 7.53-7.35 (m, 2H), 5.63 (s, 2H), 4.09 (br d, J=6.3 Hz, 2H), 3.44 (br d, J=11.4 Hz, 2H), 3.02-2.85 (m, 2H), 2.76-2.67 (m, 3H), 2.14-1.90 (m, 2H), 1.69-1.49 (m, 2H); LCMS (ESI) m/z: 536.3 [M+1].

Embodiment 8

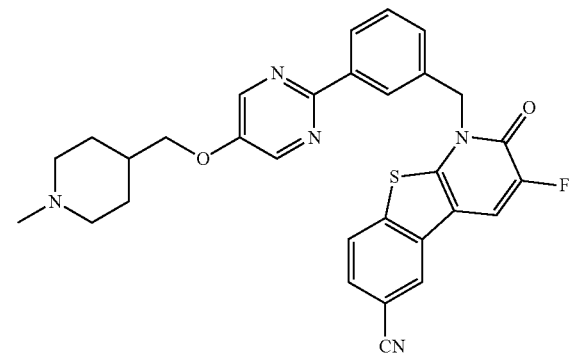

Compound 8A:

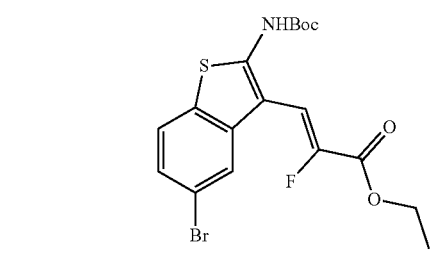 [SMILES: CCOC(=O)/C(F)=C/c1c(NC(=O)OC(C)(C)C)sc2ccc(Br)cc12]

Compound 8A was prepared according to the method of compound 6D by replacing triethyl phosphorylacetate with triethyl 2-fluorophosphorylacetate. $^1$H NMR (400 MHz, CDCl$_3$) δ=7.63 (s, 1H), 7.50 (d, J=8.3 Hz, 1H), 7.30 (dd, J=1.8, 8.4 Hz, 1H), 7.11-6.99 (d, 1H), 4.36 (q, J=7.1 Hz, 2H), 1.49 (s, 9H), 1.37 (t, J=7.2 Hz, 3H); LCMS (ESI) m/z: 345.8 [M-99].

Compound 8B:

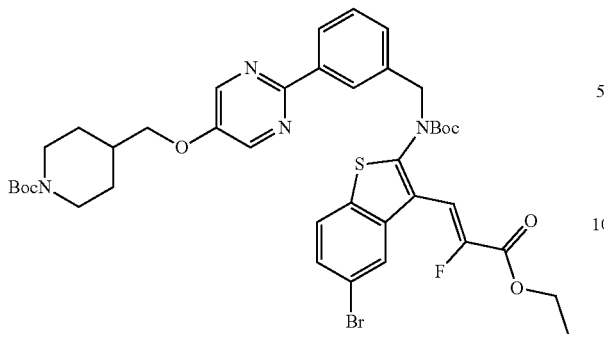

Compound 8B was prepared according to the method of compound 6F by replacing compound 6D with compound 8A. ¹H NMR (400 MHz, CDCl₃) δ=8.36-8.32 (m, 2H), 8.22-8.13 (m, 2H), 7.76-7.72 (m, 1H), 7.45 (d, J=8.6 Hz, 1H), 7.38-7.31 (m, 2H), 7.30-7.25 (m, 1H), 6.80-6.62 (m, 1H), 4.83 (s, 2H), 4.16-4.01 (m, 4H), 3.86 (d, J=6.1 Hz, 2H), 2.75-2.63 (m, 2H), 1.96-1.88 (m, 1H), 1.77 (br d, J=12.7 Hz, 2H), 1.43-1.34 (m, 18H), 1.32-1.24 (m, 5H); LCMS (ESI) m/z: 827.1 [M+3].

Hydrochloride of Compound 8C:

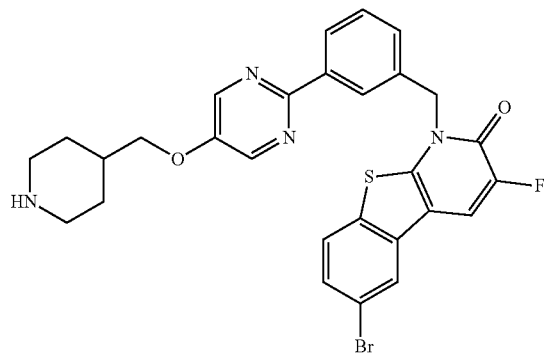 [SMILES: O=c1c(F)cc2c3cc(Br)ccc3sc2n1Cc1cccc(-c2ncc(OCC3CCNCC3)cn2)c1]

The hydrochloride of compound 8C was prepared according to the method of compound 6G by replacing compound 6F with compound 8B. LCMS (ESI) m/z: 580.1 [M+3].

Compound 8D:

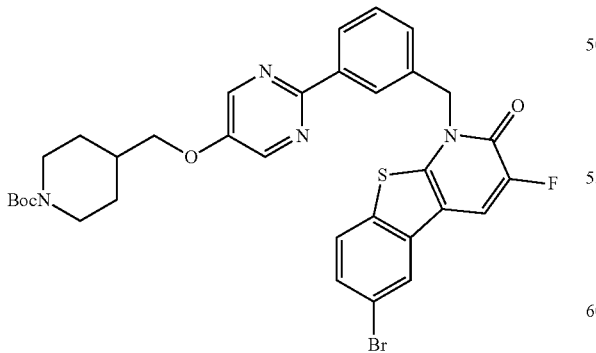

Compound 8D was prepared according to the method of compound 6H by replacing the hydrochloride of compound 6G with the hydrochloride of compound 8C. LCMS (ESI) m/z: 624.9 [M-55].

Compound 8E:

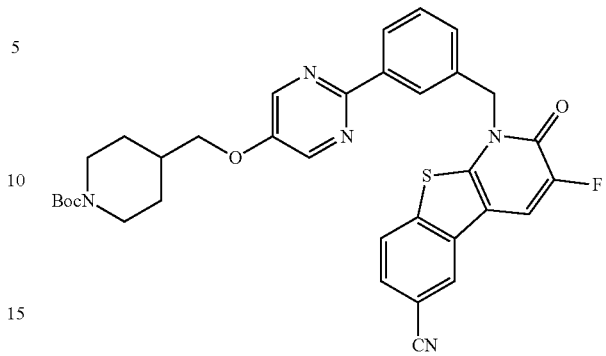

Compound 8E was prepared according to the method of compound 6I by replacing compound 6H with compound 8D. LCMS (ESI) m/z: 570.1 [M-55].

Compound 8F:

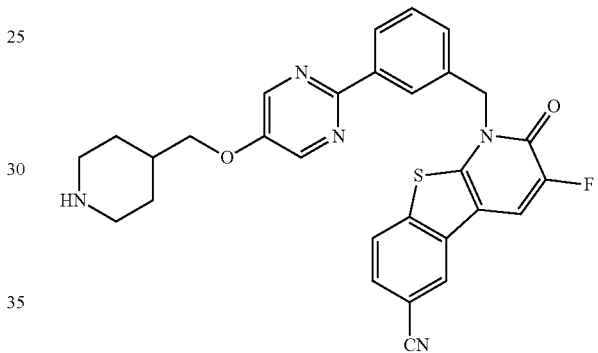

Compound 8F was prepared according to the method of compound 5J by replacing compound 5I with compound 8E. LCMS (ESI) m/z: 526.1 [M+1].

Hydrochloride of Compound 8:

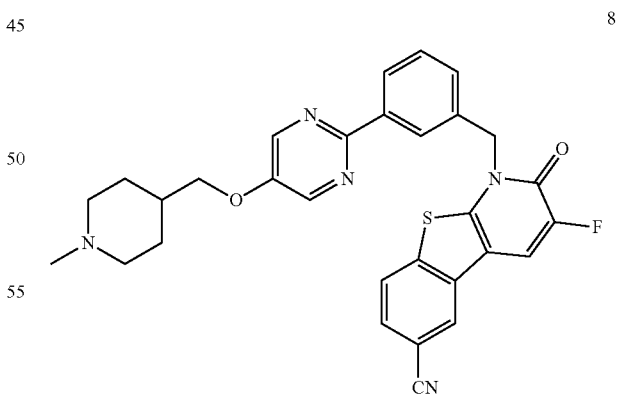

8

Hydrochloride of compound 8 was prepared according to the method of compound 1 by replacing compound 1L with compound 8F and replacing the high performance liquid chromatography (formic acid system) with high performance liquid chromatography (hydrochloric acid system). ¹H NMR (400 MHz, DMSO-d₆) δ=10.54 (br s, 1H), 8.70 (d, J=1.0 Hz, 1H), 8.67-8.63 (m, 2H), 8.62 (d, J=10.0 Hz, 1H), 8.28 (s, 1H), 8.27-8.22 (m, 2H), 7.76 (dd, J=1.6, 8.4 Hz, 1H), 7.53-7.44 (m, 2H), 5.57 (s, 2H), 4.07 (d, J=6.4 Hz, 2H), 3.42 (br d, J=11.2 Hz, 2H), 3.02-2.89 (m, 2H), 2.71 (d, J=4.6 Hz, 3H), 2.08-2.00 (m, 1H), 1.96 (br d, J=13.9 Hz, 2H), 1.70-1.57 (m, 2H); LCMS (ESI) m/z: 540.1 [M+1].
Embodiment 9
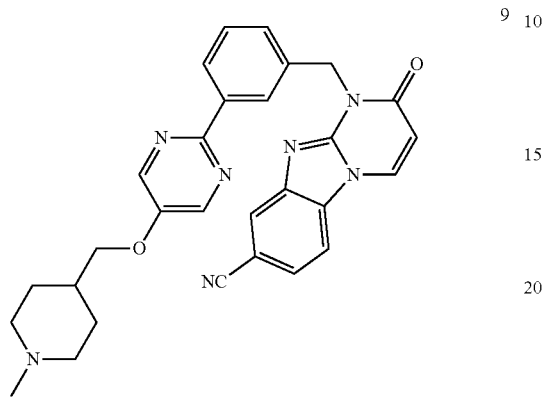
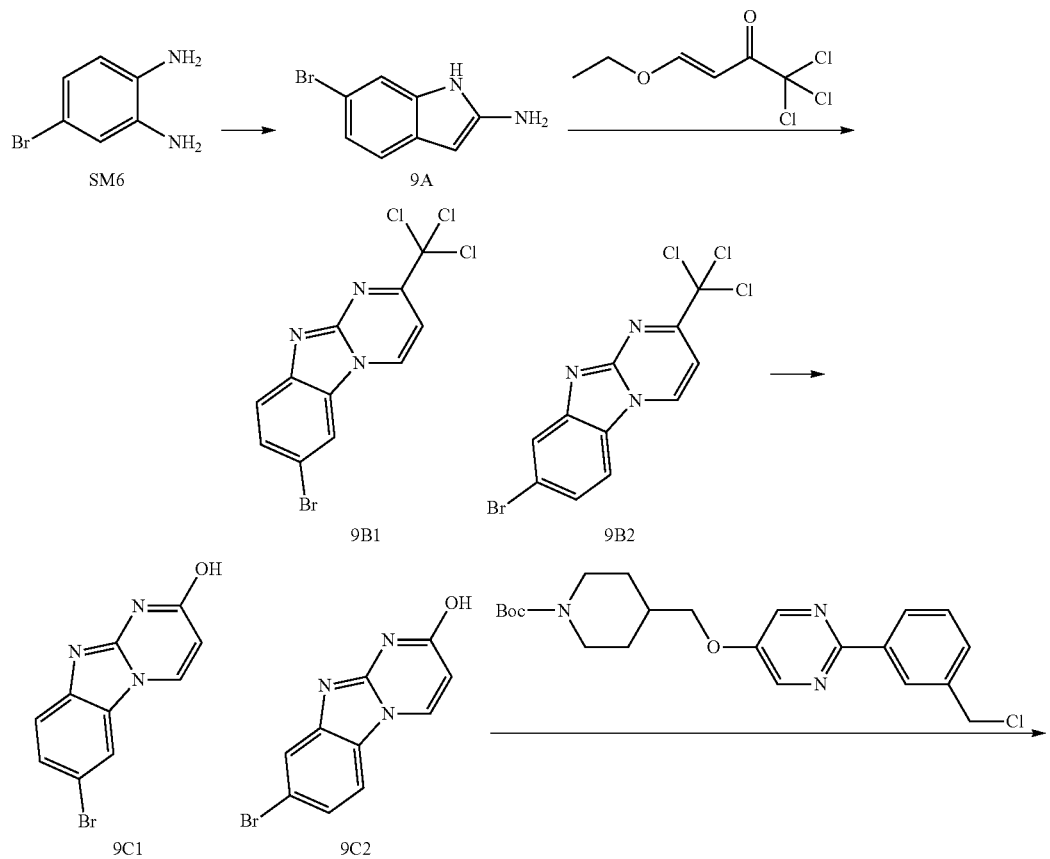

109 110
-continued
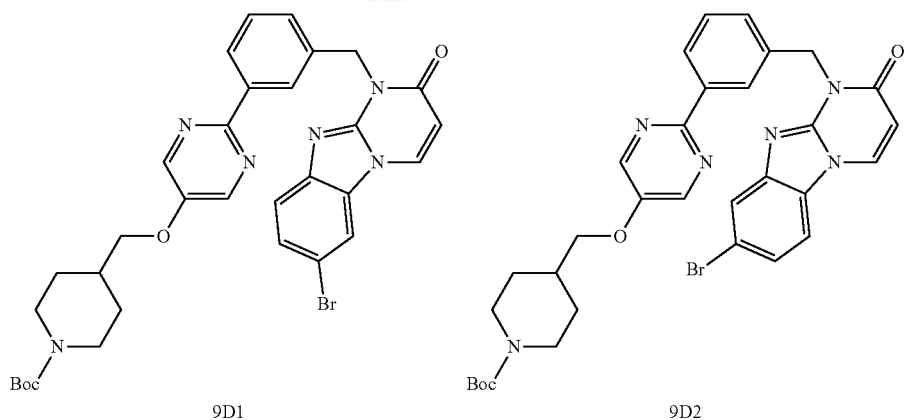
9D1　　9D2
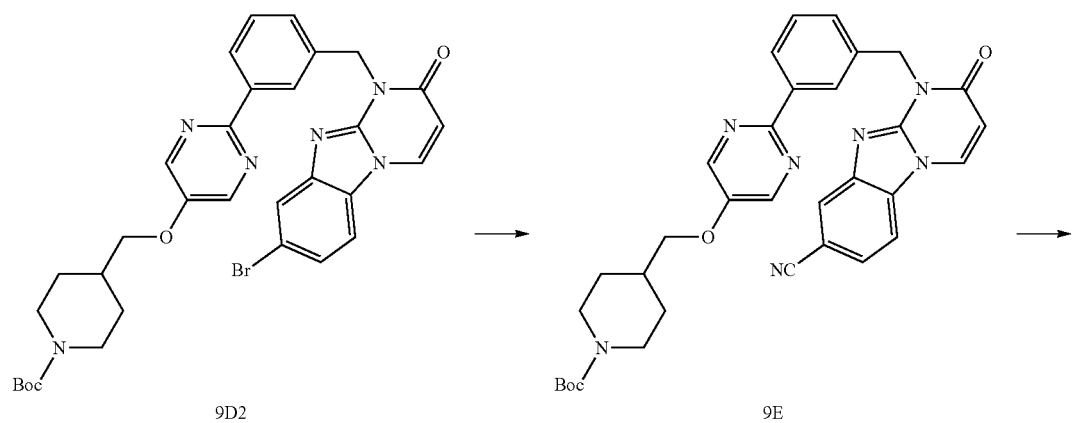
9D2 → 9E →
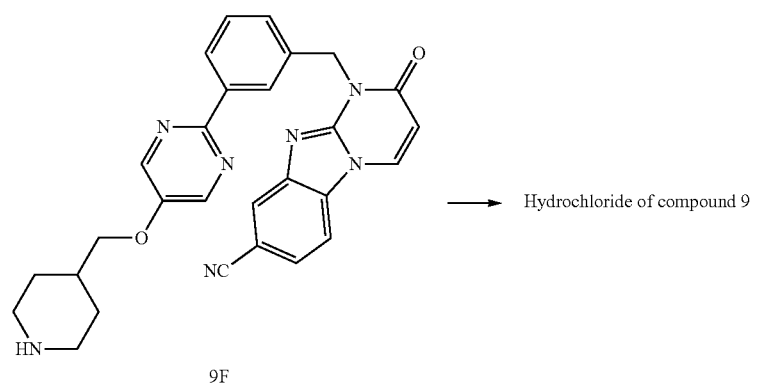 [SMILES: N#Cc1ccc2c(c1)nc1n(Cc3cccc(-c4ncc(OCC5CCNCC5)cn4)c3)c(=O)ccn21]
9F → Hydrochloride of compound 9

Compound 9A:

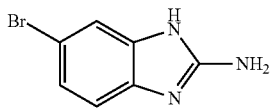

4-Bromophenyl-1,2-diamine (10 g, 53.47 mmol) and bromine cyanide (5.66 g, 53.47 mmol, 3.93 mL) were dissolved in ethanol (50 mL) and water (50 mL), and then the mixture was stirred at 70° C. for 12 hours under the protection of nitrogen. After the completion of the reaction, the reaction mixture was concentrated, and sodium hydroxide aqueous solution (2 mol/L) was added to adjust the pH value to about 9. Then the solid was filtered, and the filter cake was collected and dried to obtain the compound 9A. $^1$HNMR (400 MHz, CD$_3$OD) δ=7.39 (d, J=1.6 Hz, 1H), 7.24-7.19 (m, 1H), 7.18-7.12 (m, 1H); LCMS (ESI) m/z: 212.0 [M+1].

Compound 9B1, 9B2:

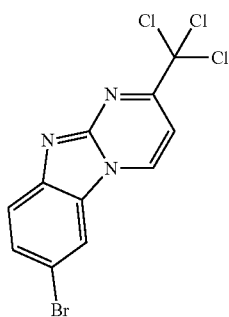

9B1

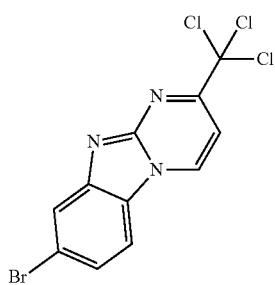

9B2

Compound 9A (7 g, 33.01 mmol) and 1,1,1-trichloro-4-ethoxy-3-butene-2-one (7.18 g, 33.01 mmol) were dissolved in toluene (70 mL), triethylamine (3.34 g, 33.01 mmol, 4.59 mL) was added thereto, and then the mixture was stirred at 100° C. for 2 hours under the protection of nitrogen. After the completion of the reaction, the reaction mixture was filtered, and the filtrate was collected and concentrated to obtain the crude product. The crude product was slurried with methanol (150 mL), then filtered and dried to obtain a mixture of compounds 9B1 and 9B2. $^1$H NMR (400 MHz, CDCl$_3$) δ=8.79 (d, J=7.3 Hz, 1H), 8.06 (d, J=1.7 Hz, 1H), 7.88 (d, J=8.8 Hz, 1H), 7.66 (dd, J=1.8, 8.8 Hz, 1H), 7.50 (d, J=7.2 Hz, 1H); LCMS (ESI) m/z: 365.9 [M+3].

Compound 9C1, 9C2:

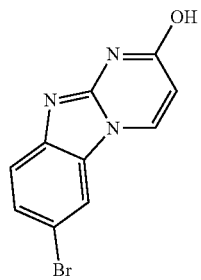

9C1

9C2

The mixture of compounds 9B1 and 9B2 (0.6 g, 1.64 mmol) was dissolved in acetonitrile (2 mL), and sodium hydroxide (85.37 mg, 2.13 mmol) was added thereto. The mixture was heated to 70° C. and stirred for another 0.5 hours. After the completion of the reaction, the mixture was concentrated to solid, then dilute hydrochloric acid (2 mol/L) was added to adjust the pH value to about 3, and a solid was precipitated. The solid was filtered and dried to obtain a mixture of compounds 9C1 and 9C2. $^1$H NMR (400 MHz, DMSO-d$_6$) δ=8.85-8.70 (m, 1H), 8.24 (d, J=1.5 Hz, 0.4H), 7.89 (d, J=8.5 Hz, 0.6H), 7.72 (d, J=1.8 Hz, 0.5H), 7.48-7.38 (m, 1.5H), 6.15 (dd, J=2.3, 7.8 Hz, 1H); LCMS (ESI) m/z: 264.0 [M+1].

Compound 9D1, 9D2:

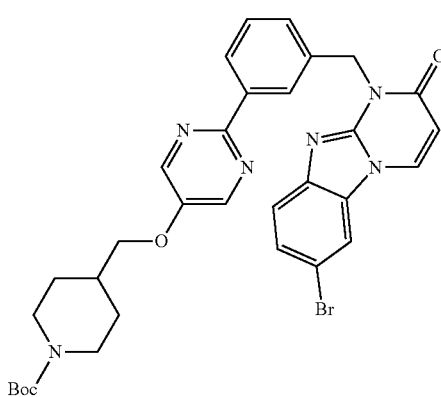

9D1

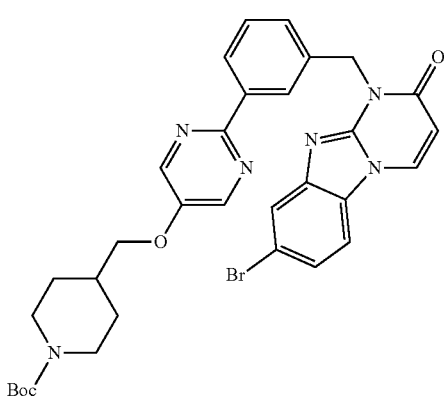 [SMILES: CC(C)(C)OC(=O)N1CCC(COc2cnc(-c3cccc(Cn4c(=O)ccn5c6ccc(C#N)cc6nc45)c3)nc2)CC1]

9D2

The mixture of compounds 9C1 and 9C2 (100 mg, 378.68 mmol) and compound 6E (158.26 mg, 378.68 mmol) were dissolved in DMF (3 mL), and cesium carbonate (61.63 mg, 189.15 mmol) and potassium iodide (31.40 mg, 189.15 µmol) were added thereto. The mixture was heated to 70° C. and stirred for another 1 hour. The reaction mixture was concentrated to obtain a crude product, the crude product was purified by thin layer silica gel chromatography (petroleum ether:ethyl acetate=1:2) to obtain the compound 9D1 and 9D2, respectively. The compound 9D1 is characterized as: $^1$H NMR (400 MHz, CDCl$_3$) δ=8.51 (s, 1H), 8.36 (s, 2H), 8.17 (d, J=7.9 Hz, 1H), 7.90 (d, J=7.8 Hz, 1H), 7.60-7.55 (m, 2H), 7.52 (d, J=8.6 Hz, 1H), 7.40 (dd, J=1.8, 8.6 Hz, 1H), 7.33 (t, J=7.8 Hz, 1H), 6.17 (d, J=7.8 Hz, 1H), 5.64-5.43 (m, 2H), 4.12 (br s, 2H), 3.86 (d, J=6.4 Hz, 2H), 2.69 (br t, J=12.3 Hz, 2H), 2.02-1.89 (m, 1H), 1.77 (br d, J=12.5 Hz, 2H), 1.40 (s, 9H), 1.31-1.20 (m, 2H). LCMS (ESI) m/z: 647.3 [M+3]. Compound 9D2 is characterized as: $^1$H NMR (400 MHz, CDCl$_3$) δ=8.52 (s, 1H), 8.40-8.32 (m, 2H), 8.22-8.12 (m, 1H), 7.93 (d, J=7.8 Hz, 1H), 7.81 (d, J=1.6 Hz, 1H), 7.59 (d, J=7.8 Hz, 1H), 7.40-7.27 (m, 3H), 6.17 (d, J=7.8 Hz, 1H), 5.50 (s, 2H), 4.28-4.00 (m, 2H), 3.87 (d, J=6.3 Hz, 2H), 2.69 (br t, J=11.1 Hz, 2H), 2.02-1.88 (m, 1H), 1.77 (br d, J=12.6 Hz, 2H), 1.40 (s, 9H), 1.29-1.16 (m, 2H). LCMS (ESI) m/z: 647.3 [M+3].

Compound 9E:

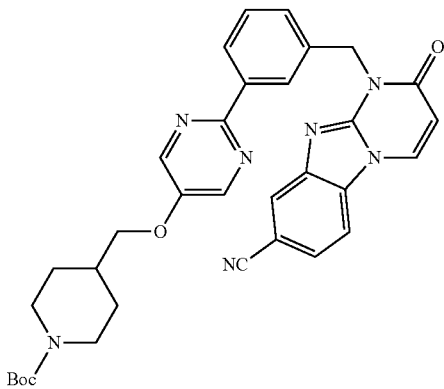

Compound 9E was prepared according to the method of compound 6I by replacing compound 6H with compound 9D2. $^1$H NMR (400 MHz, CDCl$_3$) δ=8.55 (s, 1H), 8.18 (d, J=7.9 Hz, 1H), 8.01-7.91 (m, 3H), 7.60 (d, J=7.6 Hz, 1H), 7.55-7.47 (m, 2H), 7.38-7.30 (m, 2H), 6.25 (d, J=7.8 Hz, 1H), 5.51 (s, 2H), 4.22-4.03 (m, 2H), 3.87 (d, J=6.3 Hz, 2H), 2.78-2.62 (m, 2H), 2.11-1.90 (m, 1H), 1.77 (br d, J=13.1 Hz, 2H), 1.40 (s, 9H), 1.31-1.21 (m, 2H). LCMS (ESI) m/z: 536.2 [M-55].

Compound 9F:

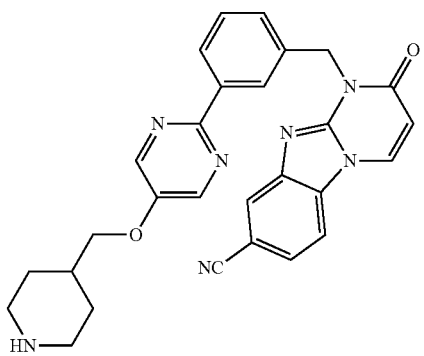 [SMILES: N#Cc1ccc2c(c1)nc1n(Cc3cccc(-c4ncc(OCC5CCNCC5)cn4)c3)c(=O)ccn21]

Compound 9F was prepared according to the method of compound 5J by replacing compound 5I with compound 9E, which was used directly in the next step. LCMS (ESI) m/z: 492.2 [M+1].

Hydrochloride of Compound 9:

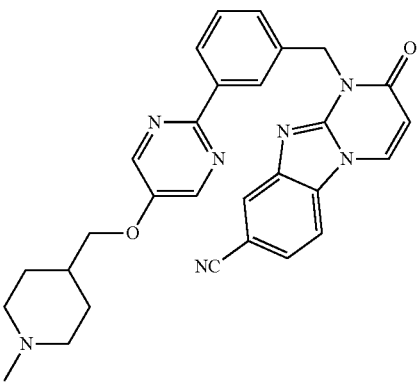

9

The hydrochloride of compound 9 was prepared according to the method of compound 1 by replacing compound 1L with compound 9F and replacing the high performance liquid chromatography (formic acid system) with high performance liquid chromatography (hydrochloric acid system). $^1$H NMR (400 MHz, DMSO-d$_6$) δ=9.70-9.57 (m, 1H), 8.99 (d, J=7.8 Hz, 1H), 8.67-8.62 (m, 2H), 8.35 (s, 1H), 8.22-8.12 (m, 3H), 7.74 (dd, J=1.1, 8.4 Hz, 1H), 7.54-7.49 (m, 1H), 7.47-7.41 (m, 1H), 6.44 (d, J=7.8 Hz, 1H), 5.45 (s, 2H), 4.09 (d, J=6.1 Hz, 2H), 3.48-3.43 (m, 2H), 3.04-2.85 (m, 2H), 2.74 (d, J=4.4 Hz, 3H), 2.13-1.94 (m, 3H), 1.63-1.44 (m, 2H). LCMS (ESI) m/z: 506.2 [M+1].

Embodiment 10

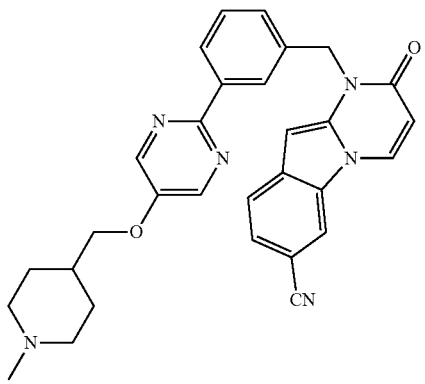

Compound 10A:

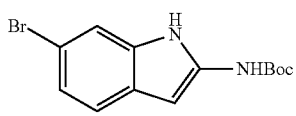 [SMILES: CC(C)(C)OC(=O)Nc1cc2ccc(Br)cc2[nH]1]

Compound 10A was prepared according to the method of compound 6B by replacing compound 6A with 6-bromo-1H-indole-2-carboxylic acid. ¹H NMR (400 MHz, CDCl₃) δ=9.91 (s, 1H), 7.38 (s, 1H), 7.25 (d, J=2.9 Hz, 1H), 7.14 (dd, J=1.7, 8.4 Hz, 1H), 6.90 (br s, 1H), 5.71 (d, J=1.3 Hz, 1H), 1.53 (s, 9H). LCMS (ESI): m/z: 254.9 [M-55].

Trifluoroacetate of Compound 10B:

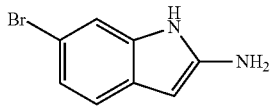

Compound 10A (2 g, 6.43 mmol) was dissolved in dichloromethane (20 mL), trifluoroacetic acid (3.85 g, 33.77 mmol, 2.5 mL) was added thereto, the mixture was stirred at 15° C. for 64 hours, the reaction solvent was evaporated to dryness to obtain the trifluoroacetate salt of compound 10B. ¹H NMR (400 MHz, CDCl₃) δ=12.71-12.12 (m, 1H), 11.54-10.93 (m, 1H), 9.95 (br s, 1H), 8.40 (br s, 1H), 7.31 (d, J=1.2 Hz, 1H), 7.29-7.24 (m, 1H), 7.20-7.13 (m, 1H). LCMS (ESI) m/z: 213.5 [M+3].

Compound 10C:

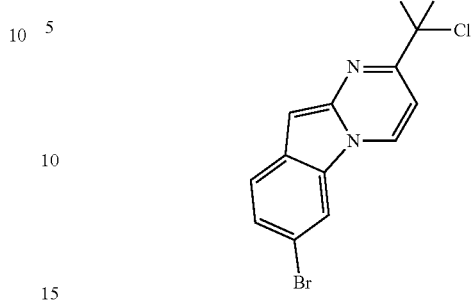

Compound 10C was prepared according to the method of compound 9B1, 9B2 by replacing compound 9A with compound 10B. LCMS (ESI) m/z: 364.9 [M+3].

Compound 10D:

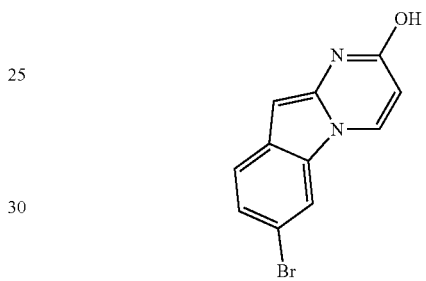

Compound 10D was prepared according to the method of compounds 9C1, 9C2 by replacing the mixture of compounds 9B1 and 9B2 with compound 10C. LCMS (ESI) m/z: 264.6 [M+3].

Compound 10E:

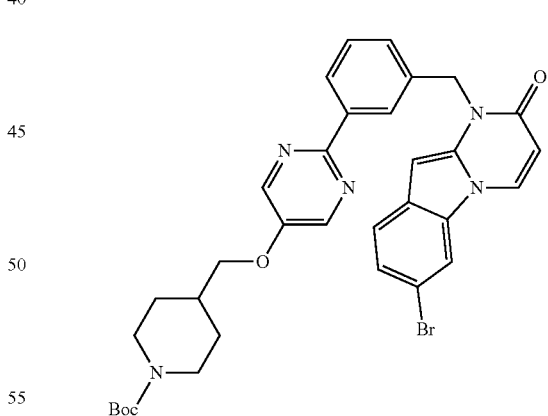

Compound 10E was prepared according to the method of compound 9D1, 9D2 by replacing the mixture of compounds 9C1 and 9C2 with compound 10D. ¹H NMR (400 MHz, CDCl₃) δ=8.49-8.44 (m, 2H), 8.41 (s, 1H), 8.28 (br d, J=7.1 Hz, 1H), 8.04 (d, J=7.7 Hz, 1H), 7.64 (s, 1H), 7.47-7.37 (m, 2H), 7.37-7.30 (m, 2H), 7.28 (s, 1H), 6.09 (d, J=7.8 Hz, 1H), 5.33 (d, J=8.2 Hz, 2H), 4.35-4.16 (m, 2H), 3.96 (d, J=6.4 Hz, 2H), 2.90-2.67 (m, 2H), 2.06-1.97 (m, 1H), 1.86 (br d, J=11.9 Hz, 2H), 1.50 (s, 9H), 1.41-1.30 (m, 2H). LCMS (ESI) m/z: 646.3 [M+3].

Compound 10F:

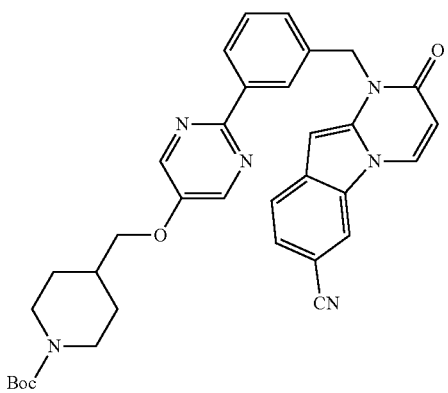 [SMILES: CC(C)(C)OC(=O)N1CCC(COc2cnc(-c3cccc(Cn4c(=O)ccn5c6cc(C#N)ccc6cc45)c3)nc2)CC1]

Compound 10F was prepared according to the method of compound 61 by replacing compound 6H with compound 10E. LCMS (ESI) m/z: 535.1 [M-55].

Compound 10G:

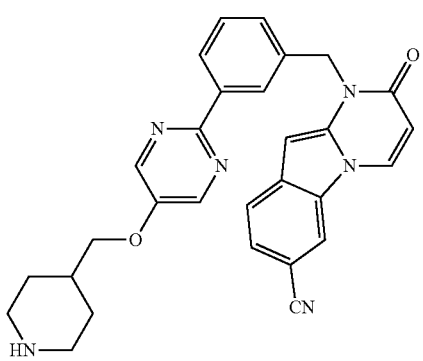

Compound 10G was prepared according to the method of compound 5J by replacing compound 5I with compound 10F, which was used directly in the next step. LCMS (ESI) m/z: 491.1 [M+1].

Hydrochloride of Compound 10:

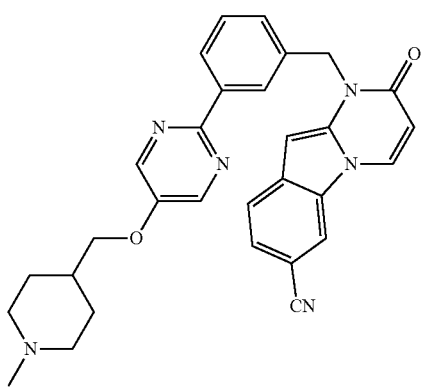

The hydrochloride of compound 10 was prepared according to the method of compound 1 by replacing compound 1L with compound 10G and replacing the high performance liquid chromatography (formic acid system) with high performance liquid chromatography (hydrochloric acid system). $^1$H NMR (400 MHz, CD$_3$OD) δ=8.59 (d, J=7.8 Hz, 1H), 8.42 (s, 2H), 8.20 (s, 1H), 8.16-8.04 (m, 2H), 7.49 (d, J=8.3 Hz, 1H), 7.42-7.33 (m, 3H), 6.09-6.00 (m, 1H), 5.26 (s, 2H), 4.00 (d, J=5.5 Hz, 2H), 3.48 (br d, J=12.5 Hz, 2H), 2.97 (br t, J=12.5 Hz, 2H), 2.84-2.74 (m, 3H), 2.05 (br d, J=13.5 Hz, 3H), 1.60 (q, J=12.6 Hz, 2H). LCMS (ESI) m/z: 505.5 [M+1].

Embodiment 11

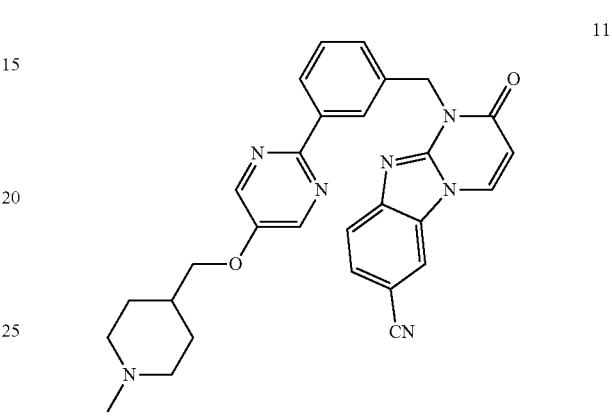

Compound 11A:

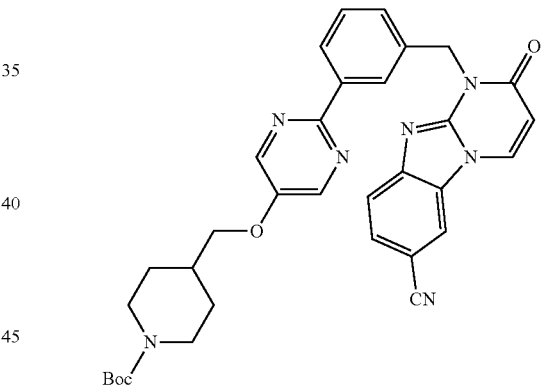

Pd (PPh$_3$)$_4$ (1.00 g, 865.38 μmol) was added to and a solution of compound 9D1 (1.00 g, 1.55 mmol) and zinc cyanide (1.00 g, 8.52 mmol) in DMF (20 mL), and the mixture was stirred at 120° C. for 1.5 hours. The reaction mixture was diluted with water (120 mL) and extracted with ethyl acetate (80 mL×3 times), and the combined organic phase was washed with water (100 mL×3 times). The organic phase was dried over anhydrous sodium sulfate, filtered, and the filtrate was concentrated. Ethyl acetate (30 mL) was added to the residue, the mixture was stirred at 20° C. for 15 minutes, and filtered, the filter cake was washed with ethyl acetate (5 mL×2 times) and dried in air to obtain the compound 11A. $^1$H NMR (400 MHz, DMSO-d$_6$) δ=8.92 (d, J=7.8 Hz, 1H), 8.63 (s, 2H), 8.57 (s, 1H), 8.36 (s, 1H), 8.20 (d, J=7.8 Hz, 1H), 7.81-7.73 (m, 2H), 7.53-7.50 (m, 1H), 7.46-7.42 (m, 1H), 6.47 (d, J=7.8 Hz, 1H), 5.47 (s, 2H), 4.09-4.03 (m, 2H), 4.02-3.93 (m, 2H), 2.81-2.68 (m, 2H), 2.00-1.90 (m, 1H), 1.76 (br d, J=11.6 Hz, 2H), 1.40 (s, 9H), 1.24-1.11 (m, 2H); LCMS (ESI) m/z: 592.2 [M+1].

119

Hydrochloride of Compound 11:

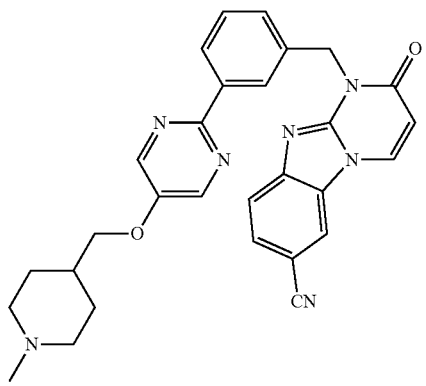

11

37% Formaldehyde aqueous solution (7.5 mL) was added to a solution of compound 11A (720 mg, 1.55 mmol) in formic acid (7.5 mL)], the mixture was stirred at 120° C. for 1 hour, the reaction mixture was concentrated, and methanol (30 mL) was added to the residue, the pH value of the residue was adjusted to 9-10 with 28% ammonia water, then the mixture was stirred at 20° C. for 15 hours and then filtered, the filter cake was added to a mixed solution of dichloromethane (60 mL) and methanol (20 mL) and the stirred at 20° C. for 1 hour, the filtrate was combined with the previous filtrate and purified by column chromatography (eluting with dichloromethane:methanol=25:1 to dichloromethane:methanol=10:1 with 0.1% ammonia). The obtained compound was purified by silica gel preparation plate (dichloromethane:methanol=10:1 with 0.1% ammonia water), the obtained product was concentrated, and acetonitrile (10 mL), water (30 mL) and 2 mol/L of hydrochloric acid aqueous solution (0.5 mL) were added to the residue, then concentrated, and the residue was freeze-dried to obtain the hydrochloride of compound 11. $^1$H NMR (400 MHz, CD$_3$OD) δ=8.75 (d, J=7.8 Hz, 1H), 8.54 (s, 2H), 8.41 (s, 1H), 8.31 (d, J=0.9 Hz, 1H), 8.24 (d, J=7.8 Hz, 1H), 7.81-7.75 (m, 1H), 7.74-7.69 (m, 1H), 7.62 (d, J=7.3 Hz, 1H), 7.50-7.41 (m, 1H), 6.38 (d, J=7.8 Hz, 1H), 5.59 (s, 2H), 4.13 (d, J=5.6 Hz, 2H), 3.67-3.58 (m, 2H), 3.14-3.03 (m, 2H), 2.91 (s, 3H), 2.27-2.12 (m, 3H), 1.78-1.61 (m, 2H); LCMS (ESI) m/z: 506.2 [M+1].

Embodiment 12

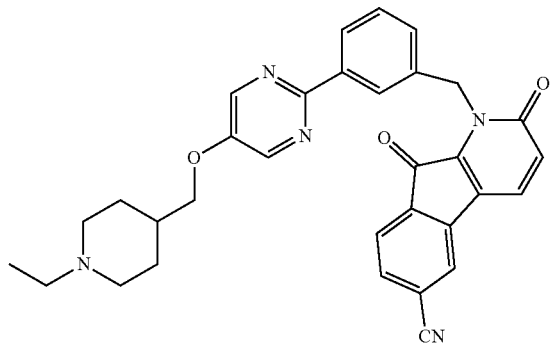

12

120

The hydrochloride of compound 12 was prepared according to the method of the formate of compound 1, by replacing the compound 1L with compound 2C, and replacing the formaldehyde aqueous solution with acetaldehyde, and replacing the purification method with thin-layer silica gel chromatography (dichloromethane:methanol=5:1), and compound 12 was obtained, then water (10 mL) and hydrochloric acid (2 mol/L, 0.2 mL) was added thereto, and the mixture was concentrated to dryness to obtain the hydrochloride of compound 12. $^1$H NMR (400 MHz, DMSO-d$_6$) δ=10.37-10.02 (m, 1H), 8.67-8.63 (m, 2H), 8.23 (s, 1H), 8.17 (d, J=7.8 Hz, 1H), 8.09 (d, J=9.3 Hz, 1H), 8.02 (d, J=0.8 Hz, 1H), 7.73 (dd, J=1.3, 7.5 Hz, 1H), 7.59 (d, J=7.5 Hz, 1H), 7.45-7.40 (m, 1H), 7.38-7.34 (m, 1H), 6.91 (d, J=9.3 Hz, 1H), 5.57 (s, 2H), 4.09 (d, J=6.5 Hz, 2H), 3.49-3.46 (m, 2H), 3.05 (br dd, J=5.3, 7.3 Hz, 2H), 2.95-2.84 (m, 2H), 2.14-1.91 (m, 3H), 1.72-1.56 (m, 2H), 1.28-1.22 (m, 3H); LCMS (ESI): m/z: 532.2 [M+1].

Embodiment 13

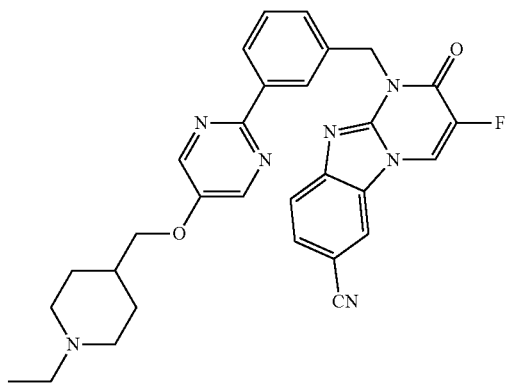

13

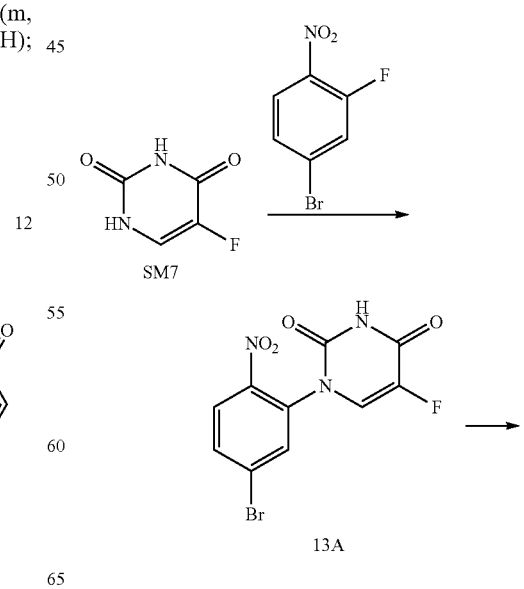

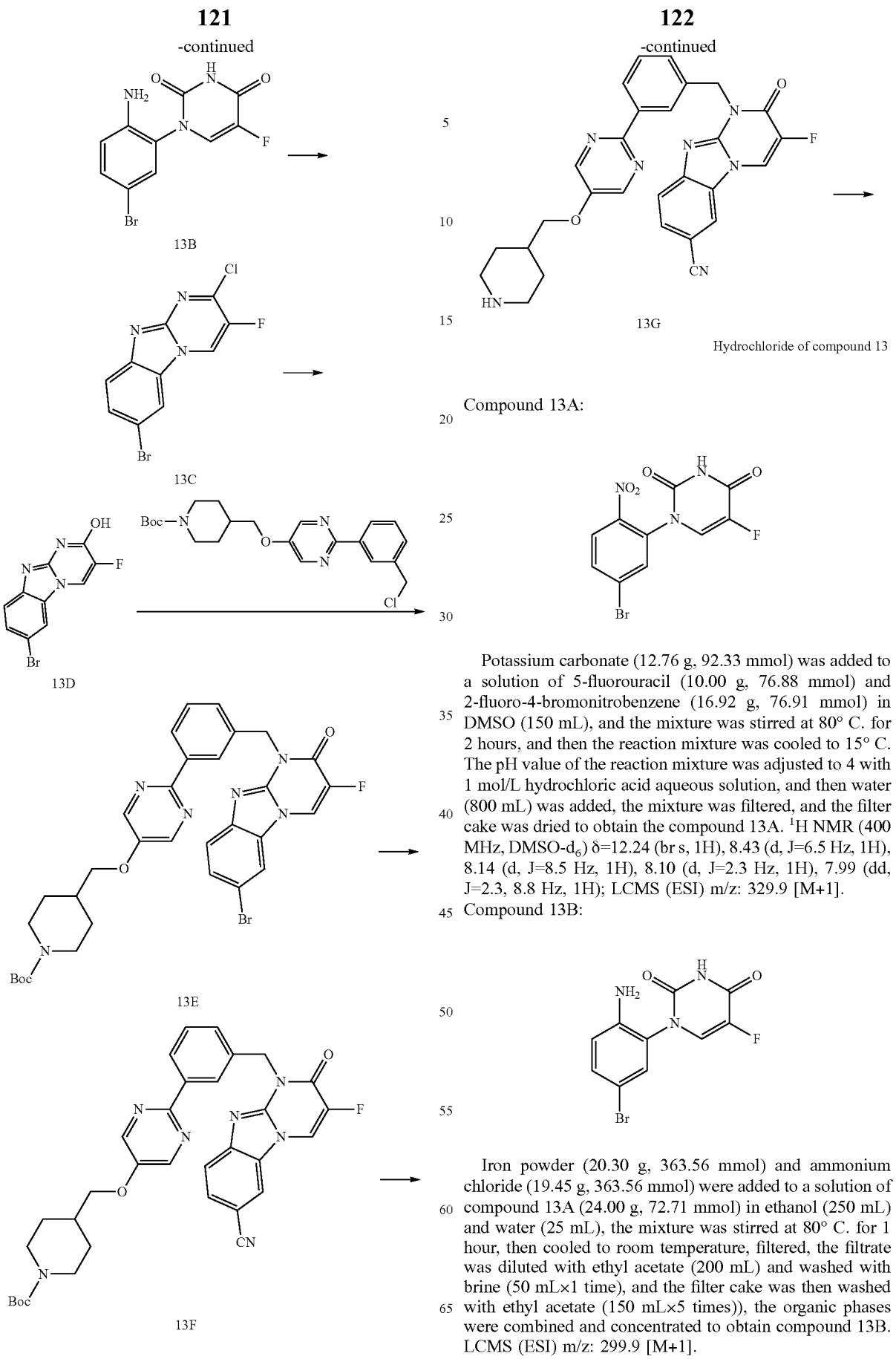

Hydrochloride of compound 13

Compound 13A:

Potassium carbonate (12.76 g, 92.33 mmol) was added to a solution of 5-fluorouracil (10.00 g, 76.88 mmol) and 2-fluoro-4-bromonitrobenzene (16.92 g, 76.91 mmol) in DMSO (150 mL), and the mixture was stirred at 80° C. for 2 hours, and then the reaction mixture was cooled to 15° C. The pH value of the reaction mixture was adjusted to 4 with 1 mol/L hydrochloric acid aqueous solution, and then water (800 mL) was added, the mixture was filtered, and the filter cake was dried to obtain the compound 13A. $^1$H NMR (400 MHz, DMSO-$d_6$) δ=12.24 (br s, 1H), 8.43 (d, J=6.5 Hz, 1H), 8.14 (d, J=8.5 Hz, 1H), 8.10 (d, J=2.3 Hz, 1H), 7.99 (dd, J=2.3, 8.8 Hz, 1H); LCMS (ESI) m/z: 329.9 [M+1].

Compound 13B:

Iron powder (20.30 g, 363.56 mmol) and ammonium chloride (19.45 g, 363.56 mmol) were added to a solution of compound 13A (24.00 g, 72.71 mmol) in ethanol (250 mL) and water (25 mL), the mixture was stirred at 80° C. for 1 hour, then cooled to room temperature, filtered, the filtrate was diluted with ethyl acetate (200 mL) and washed with brine (50 mL×1 time), and the filter cake was then washed with ethyl acetate (150 mL×5 times)), the organic phases were combined and concentrated to obtain compound 13B. LCMS (ESI) m/z: 299.9 [M+1].

Compound 13C:

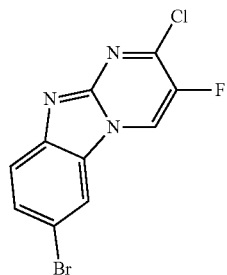

A solution of compound 13B (10.00 g, 33.32 mmol) and phosphorus oxychloride (165 g, 1.08 mol, 100 mL) was stirred at 100° C. for 12 hours, and the reaction mixture was cooled and added to water (1 L), the mixture was then filtered, and the filter cake was dried in vacuum to obtain compound 13C. $^1$H NMR (400 MHz, DMSO-d$_6$) δ=9.98 (d, J=4.4 Hz, 1H), 8.61 (d, J=2.0 Hz, 1H), 7.85 (d, J=8.8 Hz, 1H), 7.71 (dd, J=2.0, 8.6 Hz, 1H); LCMS (ESI) m/z: 301.8 [M+3].

Compound 13D:

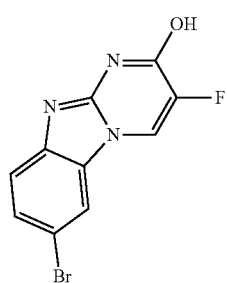 [SMILES: Fc1cn2c(nc1Cl)nc1ccc(Br)cc12]

Sodium hydroxide aqueous solution (2 mol/L, 88 mL) was added to a solution of compound 13C (3.52 g, 11.71 mmol) in THF (30 mL). The mixture was stirred at 80° C. for 1 hour, then cooled and the pH value of the reaction mixture was adjusted to 5 with 1 mol/L hydrochloric acid aqueous solution and then concentrated. Acetonitrile (50 mL) was added to the residue and stirred for 30 minutes at 20° C. The mixture was then filtered, and the filter cake was dried in vacuum to obtain the compound 13D. LCMS (ESI) m/z: 283.9 [M+3].

Compound 13E:

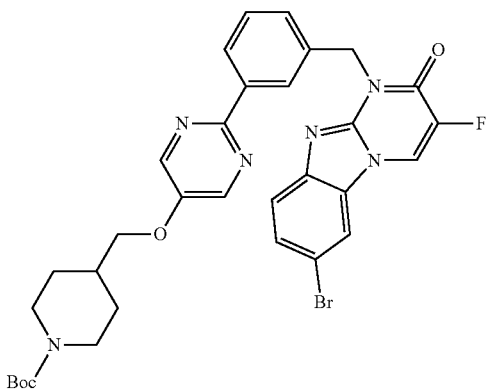

Compound 13E was prepared according to the method of compounds 9D1, 9D2 by replacing the mixture of compounds 9C1 and 9C2 with compound 13D. $^1$H NMR (400 MHz, CDCl$_3$) δ=8.44 (s, 2H), 8.38 (s, 1H), 8.30 (td, J=2.1, 6.3 Hz, 1H), 8.01 (d, J=3.5 Hz, 1H), 7.64 (d, J=1.5 Hz, 1H), 7.47-7.38 (m, 3H), 7.18 (d, J=8.8 Hz, 1H), 5.49 (s, 2H), 4.28-4.10 (m, 2H), 3.95 (d, J=6.5 Hz, 2H), 2.77 (br t, J=12.1 Hz, 2H), 2.07-1.95 (m, 1H), 1.85 (br d, J=12.5 Hz, 2H), 1.48 (s, 9H), 1.40-1.26 (m, 2H); LCMS (ESI) m/z: 663.1 [M+1].

Compound 13F:

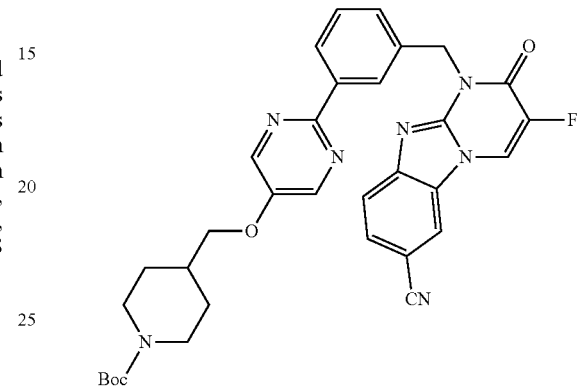

Pd(PPh$_3$)$_4$ (105 mg, 90.87 μmol) was added to a solution of compound 13E (200 mg, 301.42 μmol) and zinc cyanide (200 mg, 1.70 mmol) in DMF (10 mL). The mixture was stirred at 100° C. for 2 hours. The reaction mixture was cooled, then water (50 mL) was added thereto, the mixture was extracted with ethyl acetate (30 mL×3 times). The combined organic phase was concentrated, ethyl acetate (20 mL) was added to the residue, and the mixture was stirred at 20° C. for 0.5 hours. The mixture was then filtered, and the filter cake was dried in vacuum to obtain the compound 13F. LCMS (ESI) m/z: 610.2 [M+1].

Compound 13G:

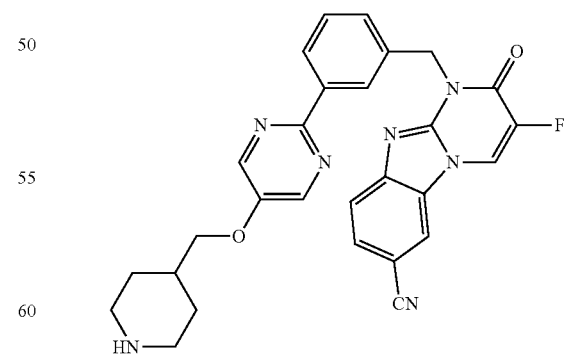

Compound 13G was prepared according to the method of compound 5J by replacing compound 5I with compound 13F, which was used directly in the next step. LCMS (ESI) m/z: 510.2 [M+1].

125

Hydrochloride of Compound 13:

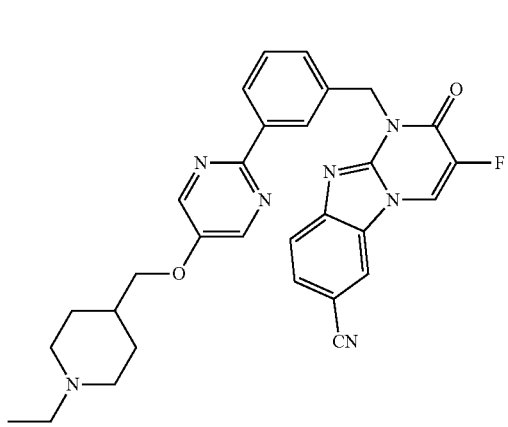

The hydrochloride of compound 13 was prepared according to the method of the formate of compound 1, by replacing the compound 1L with compound 2C, and replacing the formaldehyde aqueous solution with acetaldehyde, and replacing the purification method with thin-layer silica gel chromatography (dichloromethane:methanol=10:1), and the compound 13 was obtained, then water (10 mL) and hydrochloric acid (2 mol/1, 0.2 mL) was added thereto, and the mixture was concentrated to obtain the hydrochloride of compound 13. $^1$H NMR (400 MHz, DMSO-$d_6$) δ=10.51 (br s, 1H), 9.21 (br s, 1H), 8.74-8.46 (m, 3H), 8.40-8.13 (m, 2H), 7.93-7.72 (m, 2H), 7.45 (br s, 2H), 5.54 (br s, 2H), 4.08 (br s, 2H), 3.54-3.47 (m, 2H), 3.14-2.81 (m, 4H), 2.16-1.88 (m, 3H), 1.82-1.59 (m, 2H), 1.26 (br s, 3H); LCMS (ESI) m/z: 538.2 [M+1].

126

Embodiment 14

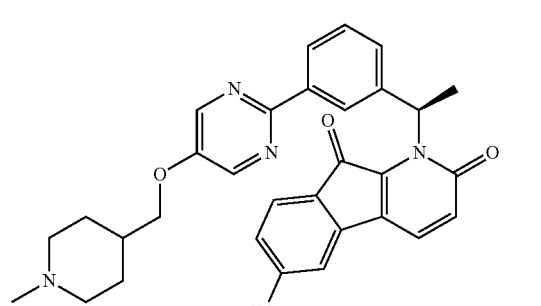

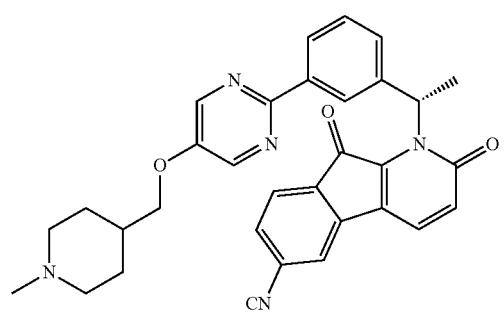

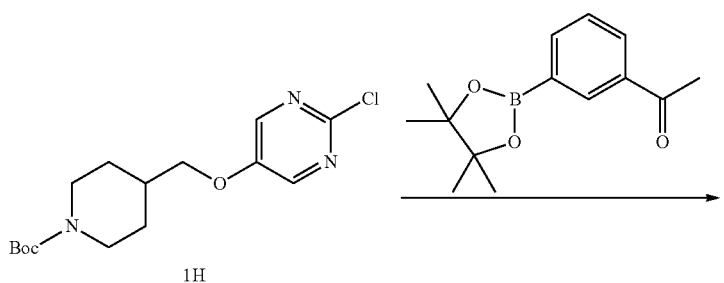

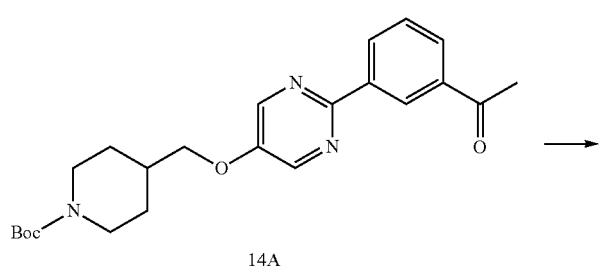

-continued

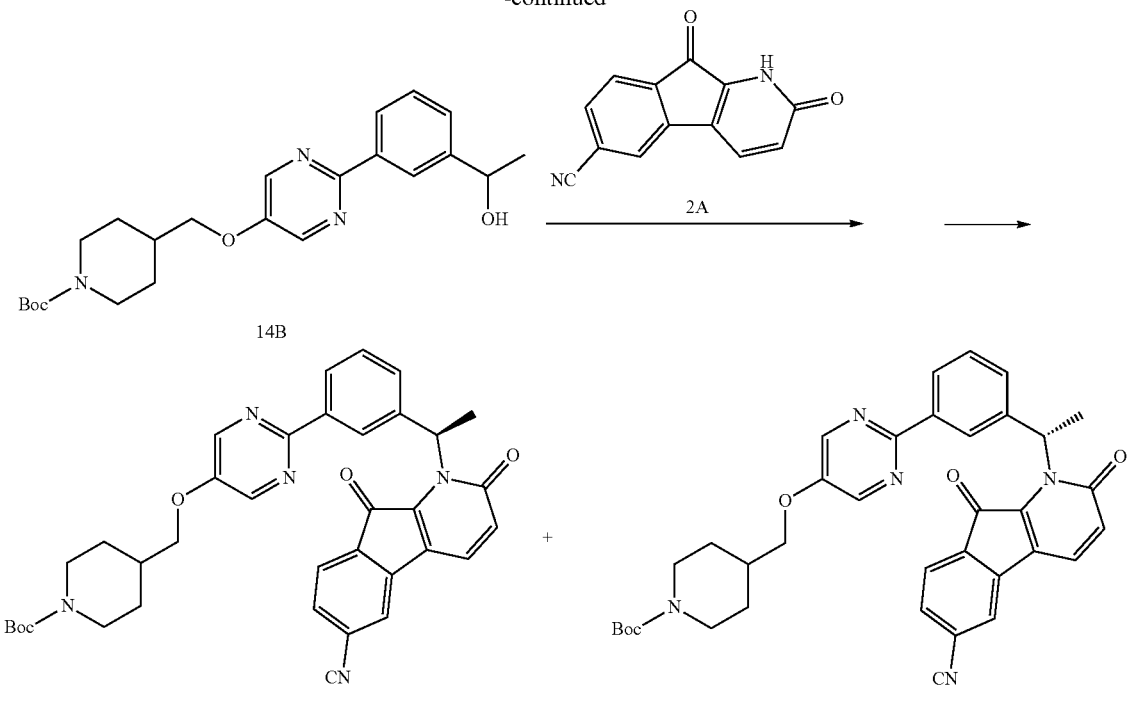

14C-1 ──→ 14D-1 ──→ Hydrochloride of 14-1
14C-2 ──→ 14D-2 ──→ Hydrochloride of 14-2

Compound 14A:

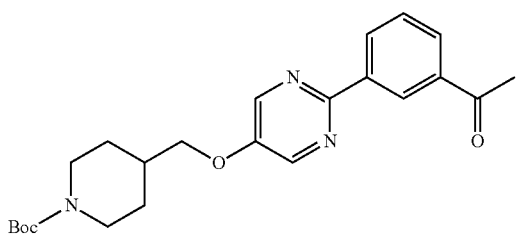 [SMILES: CC(=O)c1cccc(-c2ncc(OCC3CCN(C(=O)OC(C)(C)C)CC3)cn2)c1]

Pd(dppf)Cl$_2$·CH$_2$Cl$_2$ (2.24 g, 2.75 mmol) and potassium carbonate (25.30 g, 183.04 mmol) were added to a mixed solution of compound 1H (30.00 g, 91.52 mmol) and 1-[3-(4,4,5,5-tetramethyl-1,3,2-dioxoborapentan-2-yl)phenyl]ethanone (18.02 g, 73.21 mmol) in dioxane (300 mL) and water (50 mL), the reaction mixture was stirred at 100° C. for 12 hours, then cooled to 15° C. and filtered, the filter cake was discarded, and ethyl acetate (400 mL) was added to the filtrate and washed with brine (300 mL×2 times), the organic phase was concentrated, ethyl acetate (500 mL) was added to the residue, the mixture was stirred at 80° C. for 1 hour and then cooled to 15° C. and stirred for 1 hour. The mixture was then filtered, and the filter cake was dried to obtain the compound 14A. $^1$H NMR (400 MHz, CDCl$_3$) δ=8.95 (t, J=1.6 Hz, 1H), 8.57 (td, J=1.4, 7.8 Hz, 1H), 8.49 (s, 2H), 8.05 (td, J=1.5, 7.8 Hz, 1H), 7.58 (t, J=7.8 Hz, 1H), 4.31-4.13 (m, 2H), 3.98 (d, J=6.3 Hz, 2H), 2.84-2.73 (m, 2H), 2.71 (s, 3H), 2.09-2.00 (m, 1H), 1.86 (br d, J=13.0 Hz, 2H), 1.48 (s, 9H), 1.41-1.30 (m, 2H); LCMS (ESI) m/z: 434.1 [M+23].

Compound 14B:

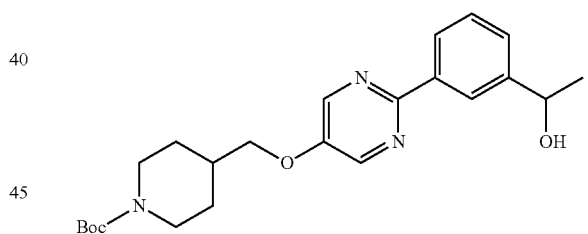

Sodium borohydride (3.31 g, 87.49 mmol) was added to a mixed solution of compound 14A (24.00 g, 58.32 mmol) in methanol (100 mL) and tetrahydrofuran (200 mL) under the protection of nitrogen at 0° C. The reaction mixture was stirred at 15° C. for 2.5 hours, water (300 mL) was slowly added to the reaction mixture and then extracted with ethyl acetate (250 mL×2 times). The combined organic phase was washed with brine (300 mL×2 times), dried over anhydrous sodium sulfate, filtered, and concentrated to obtain the compound 14B. $^1$H NMR (400 MHz, CDCl$_3$) δ=8.44 (s, 2H), 8.34 (s, 1H), 8.25 (td, J=1.7, 7.1 Hz, 1H), 7.50-7.41 (m, 2H), 5.00 (q, J=6.4 Hz, 1H), 4.28-4.14 (m, 2H), 3.93 (d, J=6.3 Hz, 2H), 2.76 (br t, J=12.0 Hz, 2H), 2.16 (br s, 1H), 2.03-1.95 (m, 1H), 1.83 (br d, J=11.3 Hz, 2H), 1.56 (d, J=6.5 Hz, 3H), 1.47 (s, 9H), 1.37-1.29 (m, 2H); LCMS (ESI) m/z: 414.1 [M+1].

Compound 14C-1 and 14C-2:

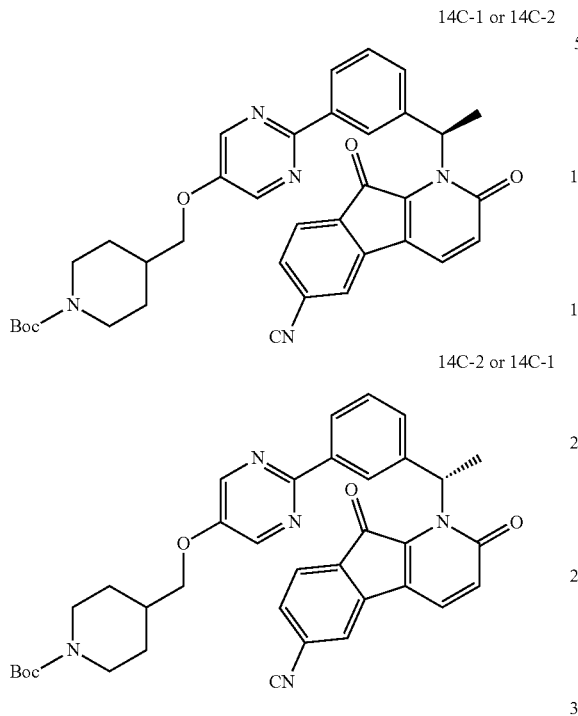

Compound 14D-1 and 14D-2:

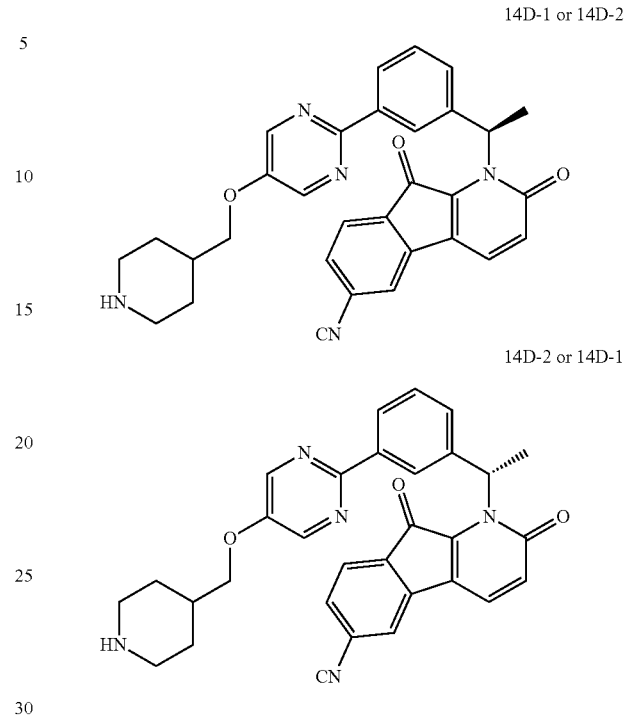

ADDP (680 mg, 2.70 mmol) was added to a mixed solution of compound 2A (400 mg, 1.80 mmol), compound 14B (1.12 g, 2.70 mmol) and tributylphosphine (548 mg, 2.71 mmol) in toluene (15 mL). The reaction mixture was stirred at 15° C. for 0.5 hours under the protection of nitrogen and then stirred at 100° C. for 12 hours. Ethyl acetate (100 mL) was added to the reaction mixture, washed with brine (30 mL×2 times), concentrated, and the crude product was purified by high performance liquid chromatography (formic acid system) to obtain a mixture of compounds 14C-1 and 14C-2, characterized as: $^1$H NMR (400 MHz, CDCl$_3$) δ=8.43 (s, 2H), 8.38 (s, 1H), 8.28-8.21 (m, 1H), 7.60-7.47 (m, 3H), 7.44-7.37 (m, 3H), 6.91 (q, J=7.2 Hz, 1H), 6.79 (dt, J=2.2, 3.4 Hz, 1H), 4.28-4.11 (m, 2H), 3.94 (d, J=6.4 Hz, 2H), 2.84-2.71 (m, 2H), 2.06 (d, J=6.8 Hz, 3H), 2.01-1.97 (m, 1H), 1.84 (br d, J=13.7 Hz, 2H), 1.48 (s, 9H), 1.37-1.26 (m, 2H); LCMS (ESI) m/z: 618.3 [M+1].

The mixture of 14C-1 and 14C-2 was purified by chiral SFC (separation column: Chiralpak IC-3 50×4.6 mm ID, 3 μm; mobile phase: phase A was carbon dioxide, phase B was isopropanol+acetonitrile (containing 0.05% of diethylamine); gradient elution: 60% isopropanol+acetonitrile (containing 0.05% diethylamine) in carbon dioxide; flow rate: 3 mL/min; detection wavelength: 220 nm; column temperature: 35° C.; pressure: 100 bar), the compound with a retention time of 2.091 minutes was obtained as compound 14C-1. LCMS (ESI) m/z: 618.3 [M+1].

The compound with a retention time of 3.435 minutes was compound 14C-2. $^1$H NMR (400 MHz, CDCl$_3$) δ=8.43 (s, 2H), 8.38 (s, 1H), 8.24 (dd, J=2.0, 6.3 Hz, 1H), 7.61-7.47 (m, 3H), 7.45-7.39 (m, 3H), 6.91 (q, J=7.0 Hz, 1H), 6.84-6.74 (m, 1H), 4.29-4.11 (m, 2H), 3.94 (d, J=6.3 Hz, 2H), 2.77 (br t, J=12.5 Hz, 2H), 2.14-1.95 (m, 4H), 1.84 (br d, J=13.3 Hz, 2H), 1.48 (s, 9H), 1.39-1.27 (m, 2H).

Compound 14D-1 was prepared according to the method of compound 5J by replacing compound 5I with compound 14C-1. LCMS (ESI) m/z: 518.2 [M+1]. Compound 14D-2 was prepared according to the method of compound 5J by replacing compound 5I with compound 14C-2. LCMS (ESI) m/z: 518.2 [M+1].

Hydrochloride of Compounds 14-1 and 14-2:

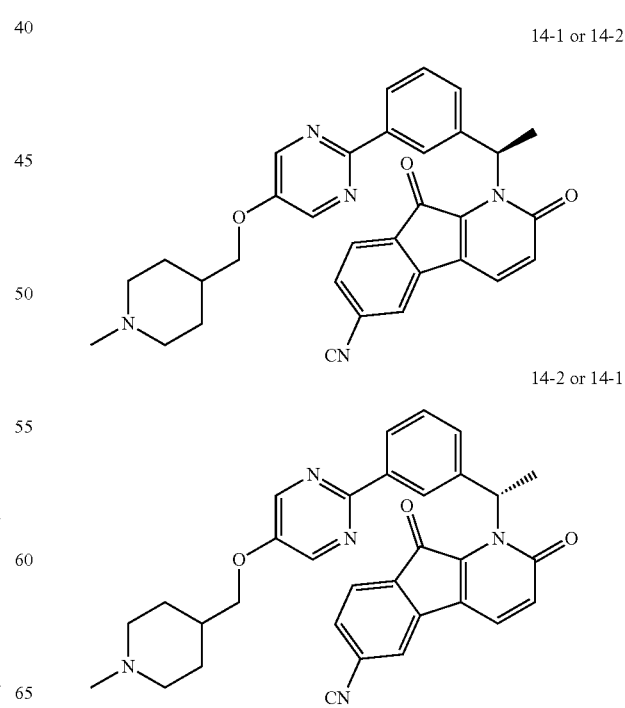

The hydrochloride of compound 14-1 was prepared according to the method of compound 1 by replacing compound 1L with compound 14D-1 and replacing the high performance liquid chromatography (formic acid system) with high performance liquid chromatography (hydrochloric acid system). $^1$H NMR (400 MHz, DMSO-$d_6$) δ=8.73-8.58 (m, 2H), 8.28 (br d, J=1.5 Hz, 1H), 8.20-8.10 (m, 1H), 8.08-7.97 (m, 2H), 7.74 (br d, J=7.3 Hz, 1H), 7.68-7.57 (m, 1H), 7.48-7.33 (m, 2H), 6.83-6.51 (m, 2H), 4.08 (d, J=6.3 Hz, 2H), 3.43 (br d, J=11.3 Hz, 2H), 3.01-2.87 (m, 2H), 2.71 (d, J=4.8 Hz, 3H), 2.05-1.88 (m, 6H), 1.68-1.53 (m, 2H); LCMS (ESI) m/z: 532.3 [M+1].

The hydrochloride of compound 14-2 was prepared according to the method of compound 1 by replacing compound 1L with compound 14D-2 and replacing the high performance liquid chromatography (formic acid system) with high performance liquid chromatography (hydrochloric acid system). $^1$H NMR (400 MHz, DMSO-$d_6$) δ=8.68-8.64 (m, 2H), 8.28 (br s, 1H), 8.20-8.15 (m, 1H), 8.08-8.01 (m, 2H), 7.75 (br d, J=7.3 Hz, 1H), 7.69-7.59 (m, 1H), 7.49-7.34 (m, 2H), 6.83-6.58 (m, 2H), 4.08 (d, J=6.1 Hz, 2H), 3.43 (br d, J=11.0 Hz, 2H), 3.02-2.89 (m, 2H), 2.72 (d, J=4.6 Hz, 3H), 2.05-1.91 (m, 6H), 1.65-1.51 (m, 2H); LCMS (ESI) m/z: 532.3 [M+1].

Embodiment 15

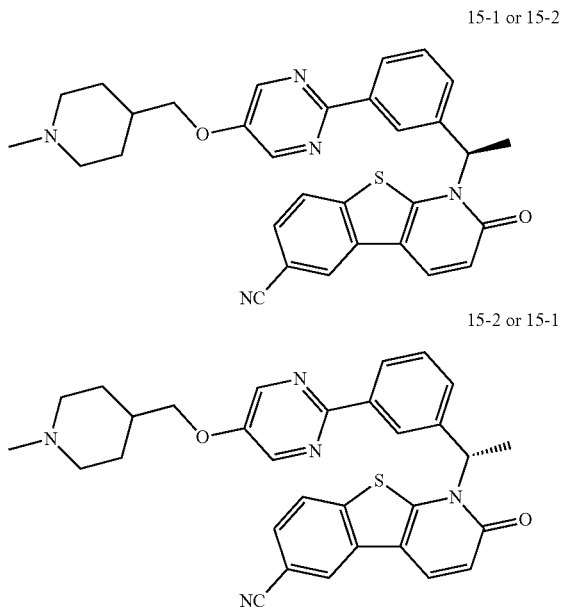

15-1 or 15-2

15-2 or 15-1

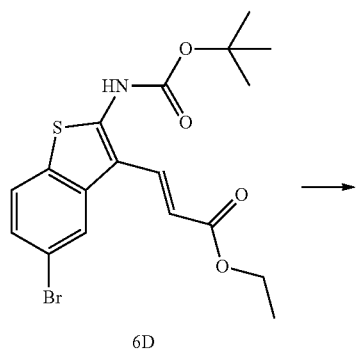

6D

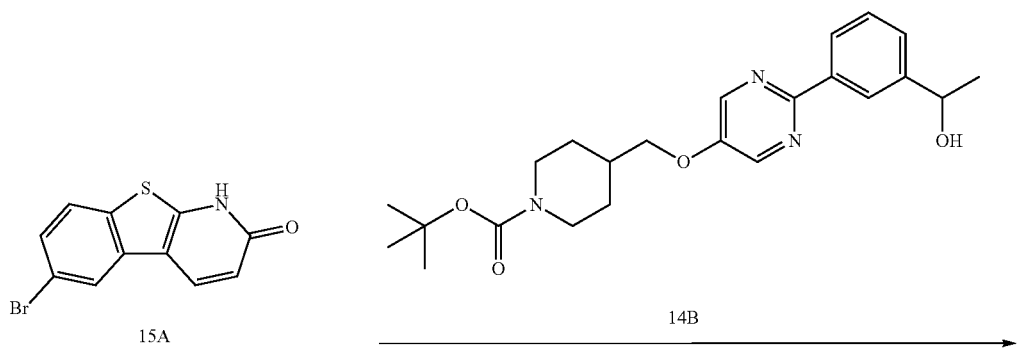

15A    14B

-continued

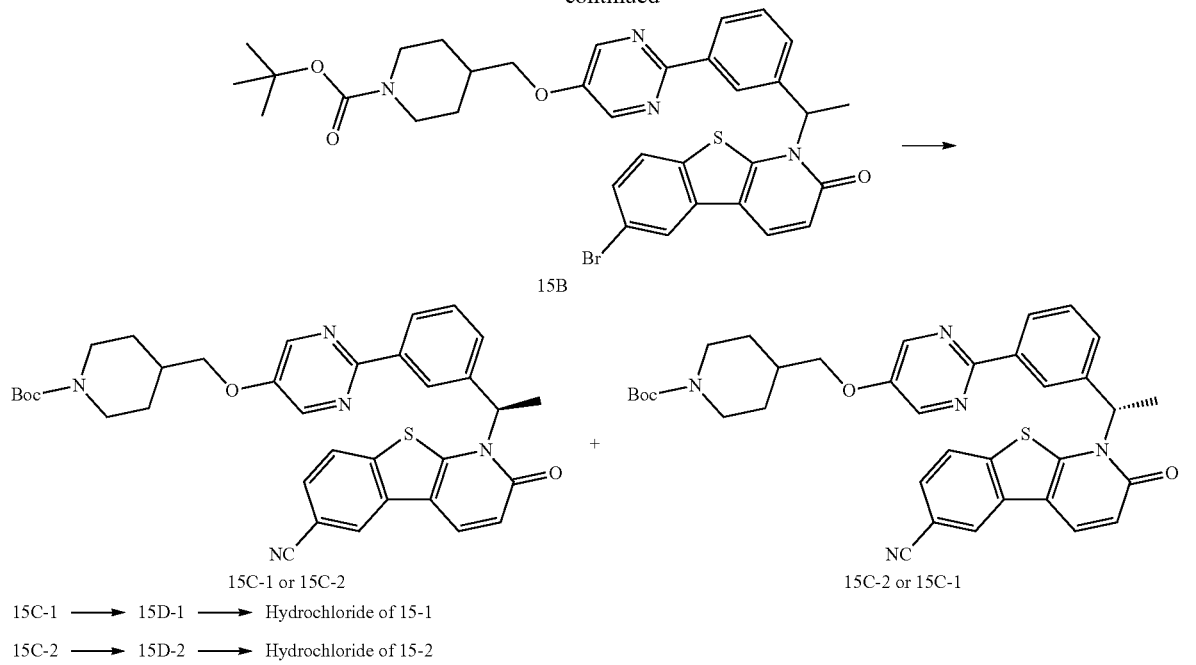

15C-1 ⟶ 15D-1 ⟶ Hydrochloride of 15-1
15C-2 ⟶ 15D-2 ⟶ Hydrochloride of 15-2

Compound 15A:

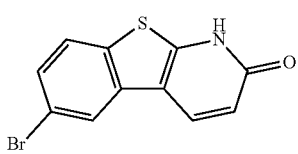 [SMILES: O=c1ccc2c([nH]1)sc1ccc(Br)cc12]

The compound 6D (2.68 g, 6.29 mmol) and hydrochloric acid gas in methanol (4 mol/L, 53.60 mL) were stirred at 15° C. for 14 hours, saturated sodium bicarbonate aqueous solution was added to the reaction mixture until the pH value of the mixture reached 9, a solid was precipitated out. The mixture was then filtered, and the filter cake was dried to obtain the compound 15A. $^1$H NMR (400 MHz, DMSO-$d_6$) δ=8.51 (br d, J=9.3 Hz, 1H), 8.43 (d, J=1.5 Hz, 1H), 7.94 (d, J=8.5 Hz, 1H), 7.55 (dd, J=2.0, 8.5 Hz, 1H), 6.67 (td, J=2.2, 4.8 Hz, 1H); LCMS (ESI) m/z: 279.9 [M+1].

Compound 15B:

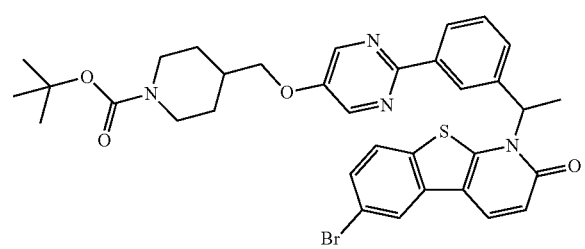 [SMILES: CC(c1cccc(-c2ncc(OCC3CCN(C(=O)OC(C)(C)C)CC3)cn2)c1)n1c(=O)ccc2c3cc(Br)ccc3sc21]

Compound 15B was prepared according to the method of compound 14C by replacing compound 2A with compound 15A. $^1$H MNR (400 MHz, CDCl$_3$) δ=8.49-8.43 (m, 3H), 8.33 (d, J=7.6 Hz, 1H), 7.96-7.87 (m, 2H), 7.48-7.38 (m, 3H), 7.35-7.30 (m, 1H), 6.97 (br d, J=5.6 Hz, 1H), 6.75 (d, J=9.5 Hz, 1H), 4.29-4.11 (m, 2H), 3.95 (d, J=6.4 Hz, 2H), 2.84-2.67 (m, 2H), 2.07-2.01 (m, 4H), 1.84 (br d, J=12.5 Hz, 2H), 1.48 (s, 9H), 1.38-1.28 (m, 2H).

Compound 15C-1, 15C-2:

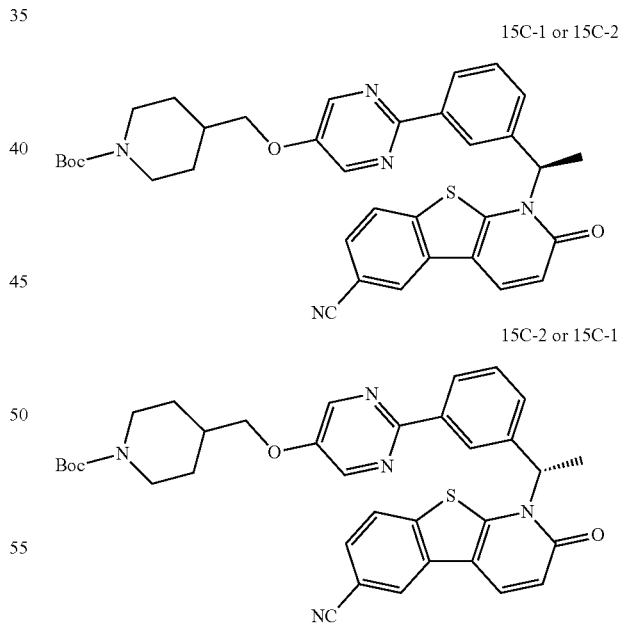

The mixture of compounds 15C-1 and 15C-2 was prepared according to the method of compound 61 by replacing compound 6H with compound 15B, characterized as: $^1$H NMR (400 MHz, CDCl$_3$) δ=8.51-8.44 (m, 3H), 8.36 (d, J=7.3 Hz, 1H), 8.07 (s, 1H), 7.98 (d, J=9.3 Hz, 1H), 7.65 (d, J=8.3 Hz, 1H), 7.51-7.41 (m, 3H), 7.06-6.95 (m, 1H), 6.82 (d, J=9.5 Hz, 1H), 4.21 (ddd, J=3.9, 5.2, 8.5 Hz, 2H), 3.96 (d, J=6.4 Hz, 2H), 2.83-2.69 (m, 2H), 2.05-1.97 (m, 4H), 1.84 (br d, J=11.5 Hz, 2H), 1.48 (s, 9H), 1.38-1.29 (m, 2H); LCMS (ESI) m/z: 622.2 [M+1].

The mixture of 15C-1 and 15C-2 was purified by chiral SFC (separation column: Chiralpak AD-3 50×4.6 mm ID, 3 μm; mobile phase: phase A was carbon dioxide, phase B was isopropanol+acetonitrile (containing 0.05% of diethylamine); gradient elution: 40% isopropanol+acetonitrile (containing 0.05% diethylamine) in carbon dioxide; flow rate: 3 mL/min; detection wavelength: 220 nm; column temperature: 35° C.; pressure: 100 bar), the compound with a retention time of 1.557 minutes was compound 15C-1, LCMS (ESI) m/z: 622.3 [M+1];

The compound with a retention time of 1.889 minutes was compound 15C-2. LCMS (ESI) m/z: 622.3 [M+1].

Compound 15D-1 and 15D-2:

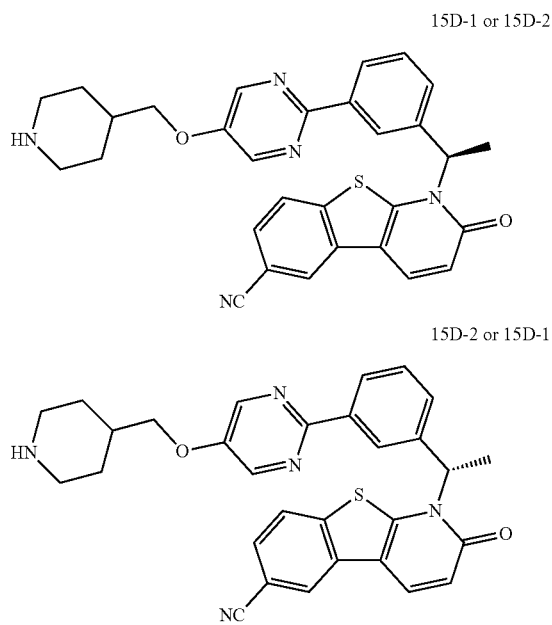

15D-1 or 15D-2

15D-2 or 15D-1

Compound 15D-1 was prepared according to the method of compound 5J by replacing compound 5I with compound 15C-1. LCMS (ESI) m/z: 522.3 [M+1]. Compound 15D-2 was prepared according to the method of compound 5J by replacing compound 5I with compound 15C-2. LCMS (ESI) m/z: 522.3 [M+1].

Hydrochloride of Compounds 15-1 and 15-2:

15-1 or 15-2

15-2 or 15-1

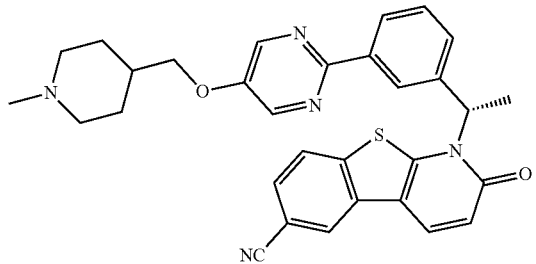

The hydrochloride of compound 15-1 was prepared according to the method of compound 1 by replacing compound 1L with compound 15D-1 and replacing the high performance liquid chromatography (formic acid system) with high performance liquid chromatography (hydrochloric acid system). $^1$H NMR (400 MHz, DMSO-$d_6$) δ=10.33-10.20 (m, 1H), 8.68 (d, J=1.0 Hz, 1H), 8.66-8.62 (m, 2H), 8.47 (d, J=9.5 Hz, 1H), 8.29-8.25 (m, 2H), 8.12 (d, J=8.3 Hz, 1H), 7.68 (dd, J=1.4, 8.4 Hz, 1H), 7.58-7.46 (m, 2H), 6.74 (d, J=9.3 Hz, 2H), 4.07 (d, J=6.3 Hz, 2H), 3.42 (br d, J=12.3 Hz, 2H), 3.03-2.87 (m, 2H), 2.71 (d, J=4.8 Hz, 3H), 2.05-1.90 (m, 6H), 1.67-1.51 (m, 2H); LCMS (ESI) m/z: 536.2 [M+1].

The hydrochloride of compound 15-2 was prepared according to the method of compound 1 by replacing compound 1L with compound 15D-2 and replacing the high performance liquid chromatography (formic acid system) with high performance liquid chromatography (hydrochloric acid system). $^1$H NMR (400 MHz, DMSO-$d_6$) δ=10.41-10.27 (m, 1H), 8.70-8.60 (m, 3H), 8.46 (d, J=9.5 Hz, 1H), 8.30-8.23 (m, 2H), 8.11 (d, J=8.3 Hz, 1H), 7.67 (dd, J=1.1, 8.4 Hz, 1H), 7.58-7.45 (m, 2H), 6.74 (d, J=9.3 Hz, 2H), 4.06 (d, J=6.3 Hz, 2H), 3.41 (br d, J=12.3 Hz, 2H), 3.01-2.86 (m, 2H), 2.75-2.67 (m, 3H), 2.05-1.91 (m, 6H), 1.70-1.52 (m, 2H); LCMS (ESI) m/z: 536.2 [M+1].

Embodiment 16

16

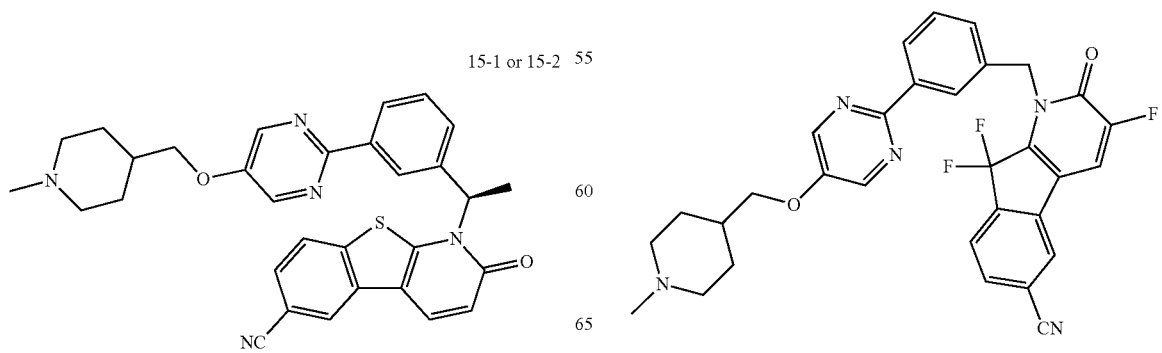

Compound 16A:

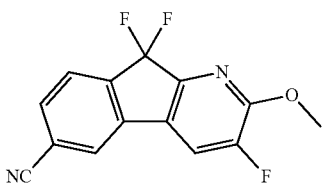 [SMILES: COc1nc2c(cc1F)-c1cc(C#N)ccc1C2(F)F]

Compound 16A was prepared according to the method of compound 1E by replacing compound 1D with compound 7C. $^1$H NMR (400 MHz, CDCl$_3$) δ=7.80-7.72 (m, 1H), 7.71-7.65 (m, 2H), 7.57 (d, J=9.2 Hz, 1H); LCMS (ESI): m/z: 277.1 [M+1].

Compound 16B:

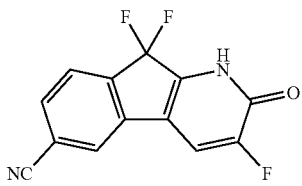 [SMILES: N#Cc1ccc2c(c1)-c1cc(F)c(=O)[nH]c1C2(F)F]

Compound 16A (260 mg, 941.30 µmol) was dissolved in acetonitrile (6 mL), and TMSCl (513.60 mg, 4.73 mmol, 0.60 mL) and sodium iodide (710 mg, 4.74 mmol) were added thereto. The mixture was heated to 80° C. and stirred for 18 hours, after the completion of the reaction, the mixture was cooled to 20° C., the reaction mixture was poured into water (18 mL) and filtered to obtain solid, the filter cake was washed twice with water (5 mL/time) and dried to obtain the compound 16B. $^1$H NMR (400 MHz, DMSO-d$_6$) δ=8.38-8.18 (m, 2H), 8.01-7.91 (m, 2H). LCMS (ESI) m/z: 263.6 [M+1].

Compound 16C:

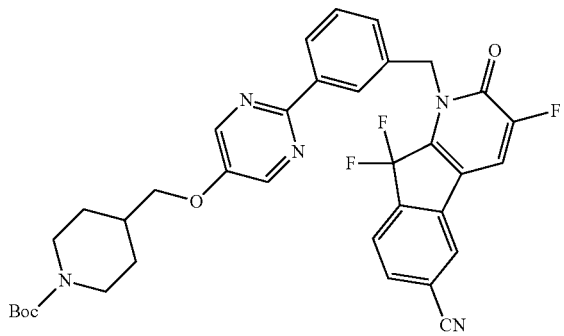 [SMILES: CC(C)(C)OC(=O)N1CCC(COc2cnc(-c3cccc(Cn4c5c(cc(F)c4=O)-c4cc(C#N)ccc4C5(F)F)c3)nc2)CC1]

Compound 16C was prepared according to the method of compound 1K by replacing compound 1F with compound 16B. $^1$H NMR (400 MHz, DMSO-d$_6$) δ=8.52-8.48 (m, 2H), 8.41 (s, 1H), 8.30 (d, J=7.6 Hz, 1H), 7.65-7.58 (m, 2H), 7.52 (s, 1H), 7.47-7.35 (m, 3H), 5.55 (s, 2H), 4.28-4.12 (m, 2H), 4.02-3.92 (m, 2H), 2.90-2.69 (m, 2H), 2.06-1.97 (m, 1H), 1.90-1.78 (m, 2H), 1.50 (s, 9H), 1.38-1.27 (m, 2H); LCMS (ESI): m/z: 644.3 [M+1].

Compound 16D:

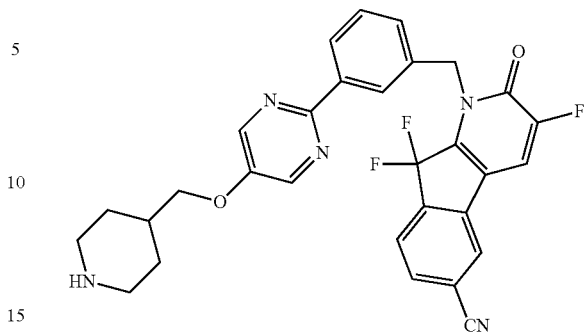

A hydrochloric acid gas in methanol solution (4 mol/L, 1 mL) was added to a solution of compound 16C (60 mg, 93.22 µmol) in methanol (2 mL), and the reaction system was stirred at 15° C. for 30 minutes. Water (30 mL) was added to the reaction mixture, and the pH value of the mixture was adjusted to 10 with 1 mol/L of sodium hydroxide aqueous solution, the mixture was extracted with dichloromethane (15 mL×3 times), and the combined organic phase was dried over anhydrous sodium sulfate, filtered and concentrated to dryness to obtain compound 16D. LCMS (ESI): m/z: 544.3 [M+1].

Hydrochloride of Compound 16:

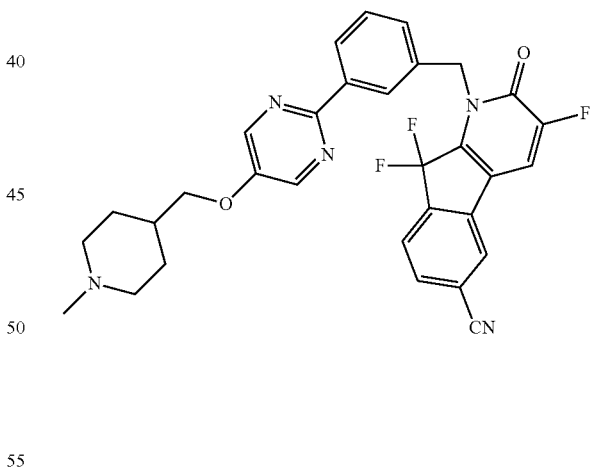

The hydrochloride of compound 16 was prepared according to the method of compound 1 by replacing compound 1L with compound 16D and replacing the high performance liquid chromatography (formic acid system) with high performance liquid chromatography (hydrochloric acid system). $^1$H NMR (400 MHz, CD$_3$OD) δ=8.55 (s, 2H), 8.32-8.20 (m, 2H), 8.03-7.91 (m, 2H), 7.76 (s, 2H), 7.53-7.39 (m, 2H), 5.56 (s, 2H), 4.13 (d, J=5.6 Hz, 2H), 3.69-3.52 (m, 2H), 3.09 (br t, J=11.9 Hz, 2H), 2.96-2.89 (m, 3H), 2.28-2.11 (m, 3H), 1.81-1.62 (m, 2H); LCMS (ESI) m/z: 558.3 [M+1].

Embodiment 17
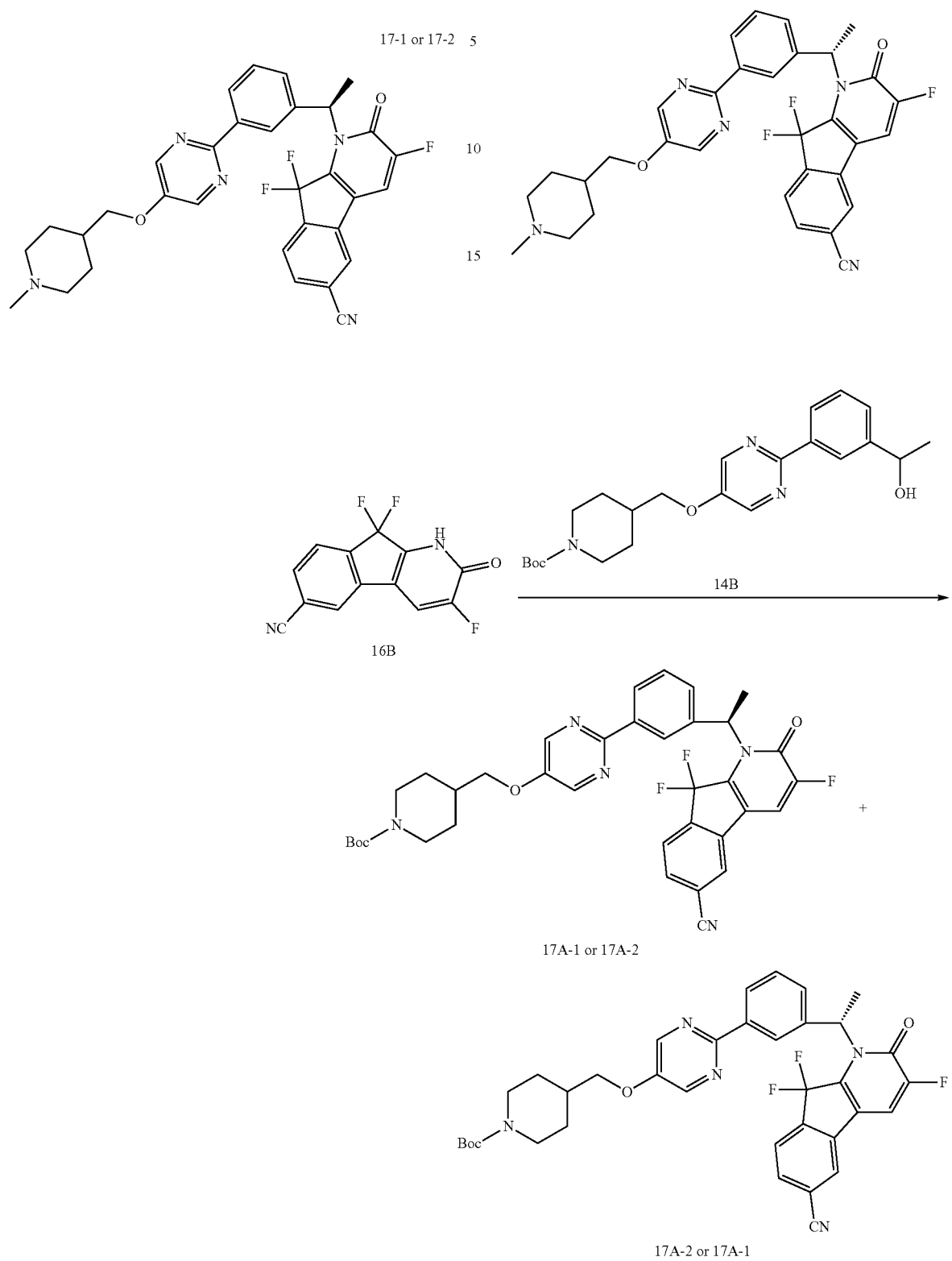
17A-1 → 17B-1 → Hydrochloride of 17-1
17A-2 → 17B-2 → Hydrochloride of 17-2

Compounds 17A-1 and 17A-2:

Compounds 17B-1 and 17B-2:

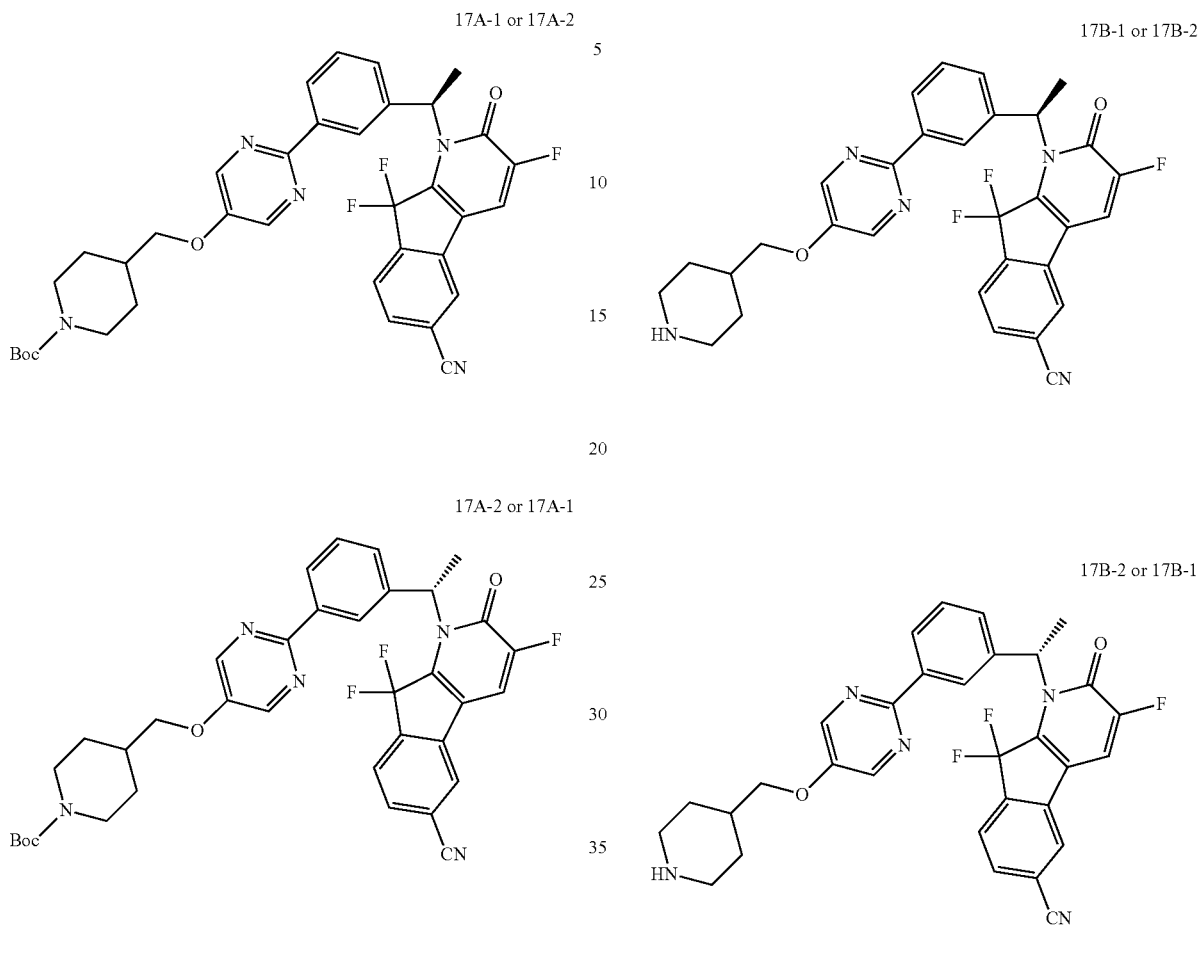

The mixture of compounds 17A-1 and 17A-2 was prepared according to the method of compound 14C by replacing compound 2A with compound 16B, characterized as: $^1$H NMR (400 MHz, CDCl$_3$) δ=8.51 (s, 1H), 8.44 (s, 2H), 8.30 (d, J=7.8 Hz, 1H), 7.72-7.66 (m, 1H), 7.66-7.61 (m, 1H), 7.56 (br d, J=7.7 Hz, 1H), 7.51 (s, 1H), 7.49-7.44 (m, 1H), 7.31 (d, J=7.3 Hz, 1H), 5.79 (br d, J=4.6 Hz, 1H), 4.29-4.15 (m, 2H), 3.94 (d, J=6.2 Hz, 2H), 2.78 (br t, J=11.4 Hz, 2H), 2.20 (d, J=6.8 Hz, 3H), 2.03 (br dd, J=3.4, 6.8 Hz, 1H), 1.85 (br d, J=12.2 Hz, 2H), 1.49 (s, 9H), 1.39-1.31 (m, 2H); LCMS (ESI): m/z: 658.3 [M+1]. The mixture of 17A-1 and 17A-2 was purified by chiral SFC (separation method: separation column: Chiralpak AS-3 50×4.6 mm ID, 3 μm; mobile phase: phase A was carbon dioxide, phase B was ethanol (containing 0.05% of diethylamine); gradient elution: ethanol (containing 0.05% diethylamine) in carbon dioxide from 5% to 40%; flow rate: 3 mL/min; detection wavelength: 220 nm; column temperature: 35° C.; pressure: 100 bar.), the compound with a retention time of 1.542 minutes was obtained as compound 17A-1, and the compound with a retention time of 1.644 minutes was obtained as compound 17A-2.

Compound 17B-1 was prepared according to the method of compound 5J by replacing compound 5I with compound 17A-1. LCMS (ESI) m/z: 558.1 [M+1]. Compound 17B-2 was prepared according to the method of compound 5J by replacing compound 5I with compound 17A-2. LCMS (ESI) m/z: 558.1 [M+1].

Hydrochloride of Compounds 17-1 and 17-2:

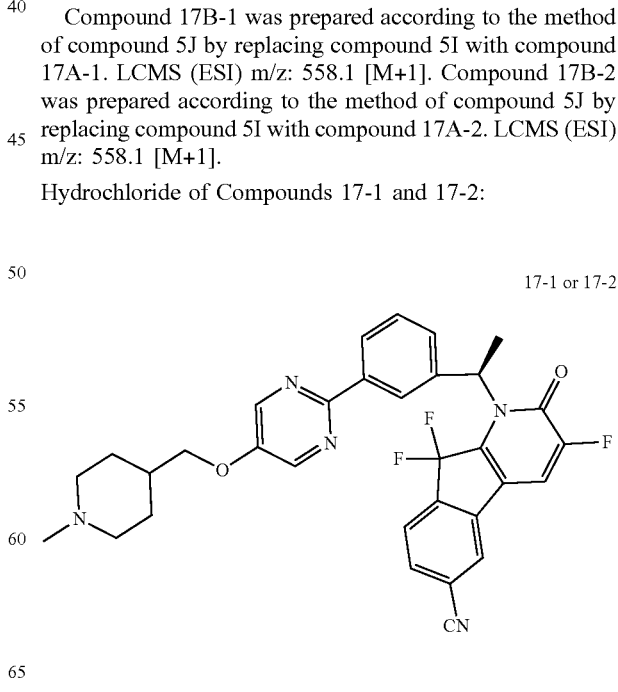

-continued 17-2 or 17-1

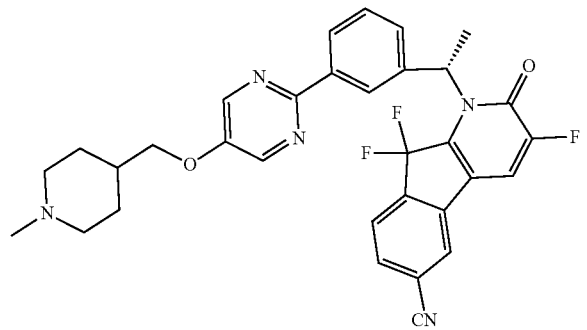

The hydrochloride of compound 17-1 was prepared according to the method of compound 1 by replacing compound 1L with compound 17B-1 and replacing the high performance liquid chromatography (formic acid system) with high performance liquid chromatography (hydrochloric acid system). $^1$H NMR (400 MHz, DMSO-$d_6$) δ=10.62-10.01 (m, 1H), 8.72-8.61 (m, 2H), 8.33 (s, 1H), 8.27-8.20 (m, 1H), 8.20-8.12 (m, 2H), 8.03-7.85 (m, 2H), 7.54-7.41 (m, 2H), 5.67 (br d, J=6.0 Hz, 1H), 4.08 (br d, J=6.1 Hz, 2H), 3.31-3.07 (m, 1H), 3.03-2.88 (m, 2H), 2.83-2.64 (m, 4H), 2.15-1.90 (m, 6H), 1.70-1.50 (m, 2H); LCMS (ESI) m/z: 572.4 [M+1].

The hydrochloride of compound 17-2 was prepared according to the method of compound 1 by replacing compound 1L with compound 17B-2 and replacing the high performance liquid chromatography (formic acid system) with high performance liquid chromatography (hydrochloric acid system). $^1$H NMR (400 MHz, DMSO-$d_6$) δ=10.67-10.14 (m, 1H), 8.66 (s, 2H), 8.33 (s, 1H), 8.29-8.10 (m, 3H), 8.02-7.82 (m, 2H), 7.48 (br d, J=7.7 Hz, 2H), 5.68 (br d, J=5.7 Hz, 1H), 4.08 (br d, J=6.1 Hz, 2H), 3.29-3.11 (m, 1H), 3.04-2.88 (m, 2H), 2.82-2.60 (m, 4H), 2.14-1.89 (m, 6H), 1.71-1.53 (m, 2H); LCMS (ESI) m/z: 572.4 [M+1].

Embodiment 18

18-1 or 18-2

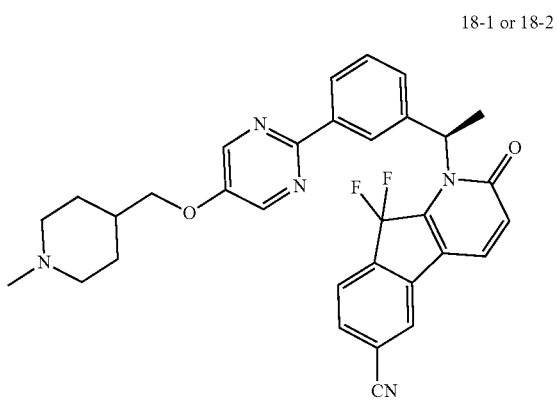

18-2 or 18-1

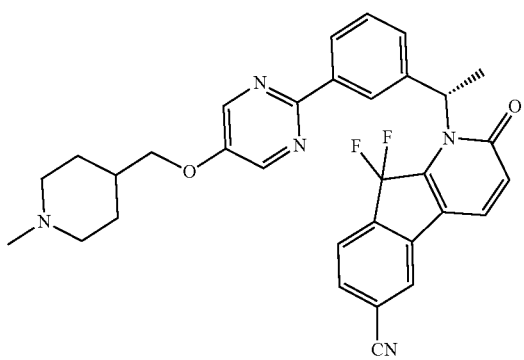

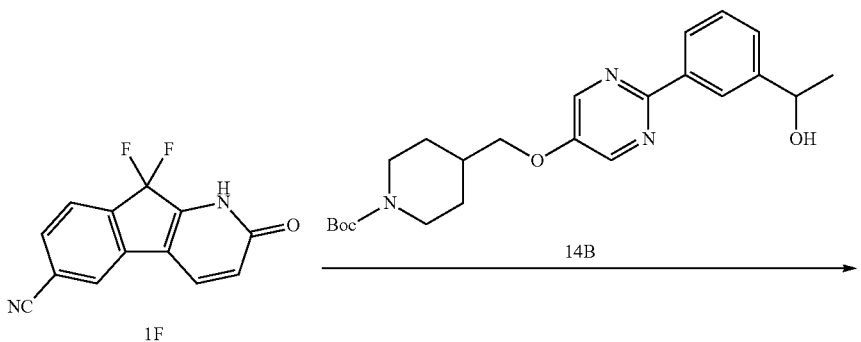

-continued

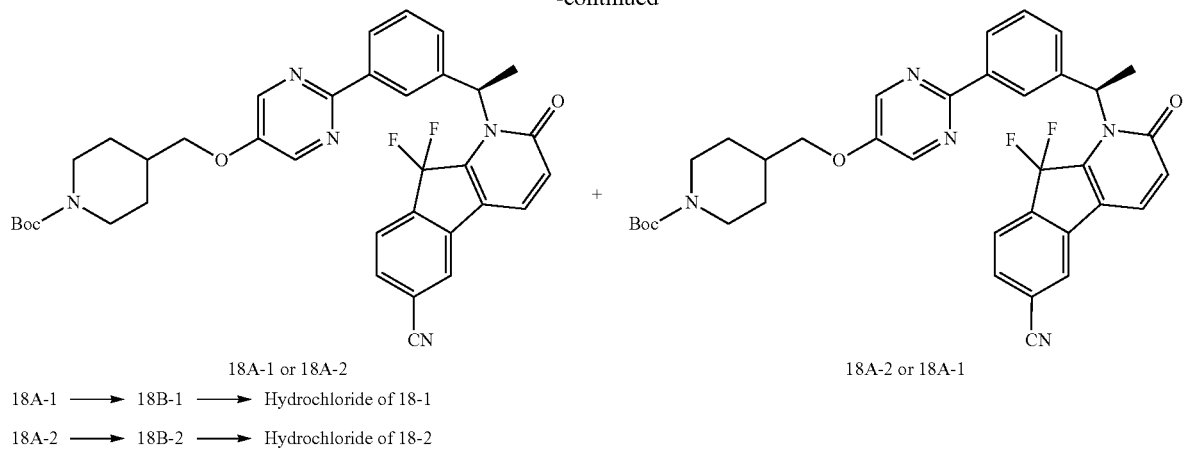

18A-1 or 18A-2              18A-2 or 18A-1

18A-1 ⟶ 18B-1 ⟶ Hydrochloride of 18-1
18A-2 ⟶ 18B-2 ⟶ Hydrochloride of 18-2

Compounds 18A-1 and 18A-2:

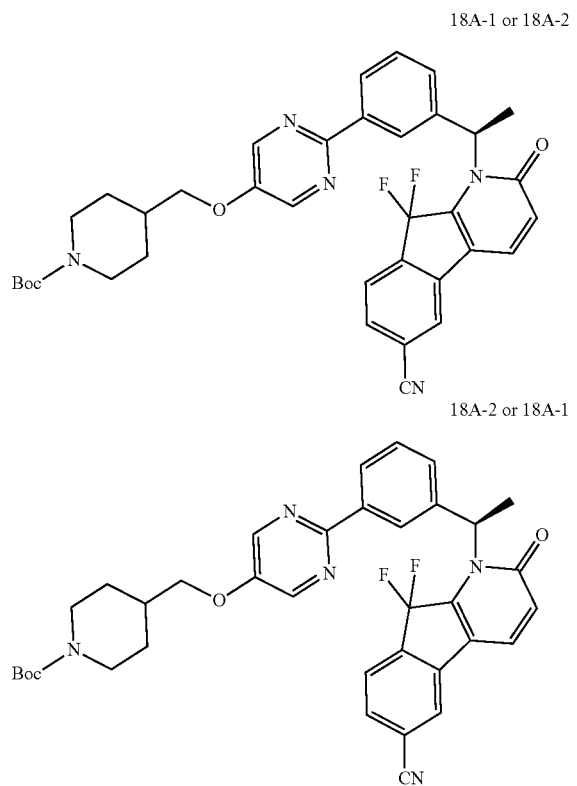

18A-1 or 18A-2

18A-2 or 18A-1

The mixture of compounds 18A-1 and 18A-2 was prepared according to the method of compound 14C by replacing compound 2A with compound 1F. Characterized as: ¹H NMR (400 MHz, CDCl$_3$) δ=8.49 (s, 1H), 8.43 (s, 2H), 8.28 (d, J=7.6 Hz, 1H), 7.69-7.65 (m, 1H), 7.62-7.57 (m, 1H), 7.55-7.48 (m, 3H), 7.47-7.41 (m, 1H), 6.63 (d, J=9.3 Hz, 1H), 5.81-5.68 (m, 1H), 4.26-4.14 (m, 2H), 3.94 (d, J=6.4 Hz, 2H), 2.87-2.67 (m, 2H), 2.17 (d, J=6.8 Hz, 3H), 2.04-1.96 (m, 1H), 1.84 (br d, J=13.0 Hz, 2H), 1.48 (s, 9H), 1.38-1.28 (m, 2H); LCMS (ESI): m/z: 640.3 [M+1]. The mixture of compounds 18A-1 and 18A-2 was purified by chiral SFC (separation column: Chiralcel OD-3 50×4.6 mm ID, 3 μm; mobile phase: phase A was carbon dioxide, phase B was methanol+acetonitrile (containing 0.05% of diethylamine); gradient elution: 40% methanol+acetonitrile (containing 0.05% diethylamine) in carbon dioxide; flow rate: 3 mL/min; detection wavelength: 220 nm; column temperature: 35° C.; pressure: 100 bar), the compound with a retention time of 1.716 minutes was obtained as compound 18A-1, and the compound with a retention time of 2.381 minutes was obtained as compound 18A-2.

Compound 18B-1 and 18B-2:

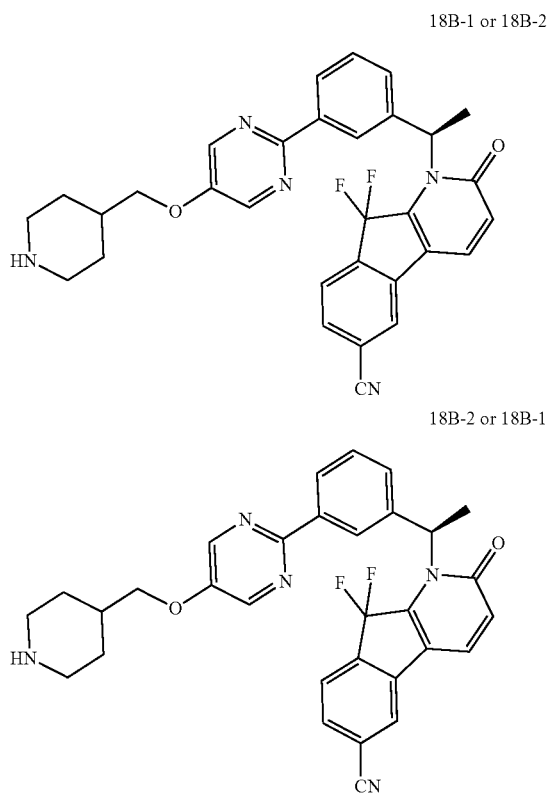

18B-1 or 18B-2

18B-2 or 18B-1

Compound 18B-1 was prepared according to the method of compound 5J by replacing compound 5I with compound 18A-1. LCMS (ESI) m/z: 540.3 [M+1]. Compound 18B-2 was prepared according to the method of compound 5J by replacing compound 5I with compound 18A-2. LCMS (ESI) m/z: 540.3 [M+1].

Hydrochloride of Compounds 18-1 and 18-2:

18-1 or 18-2

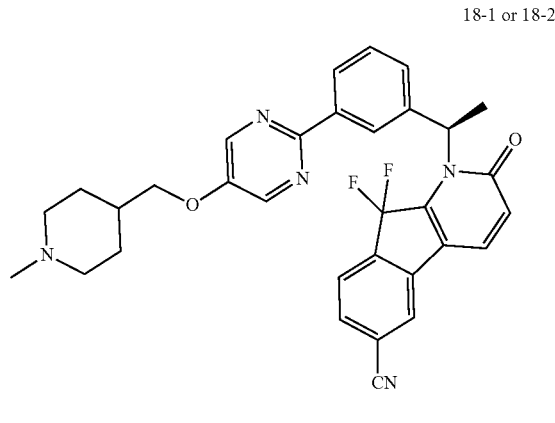

18-2 or 18-1

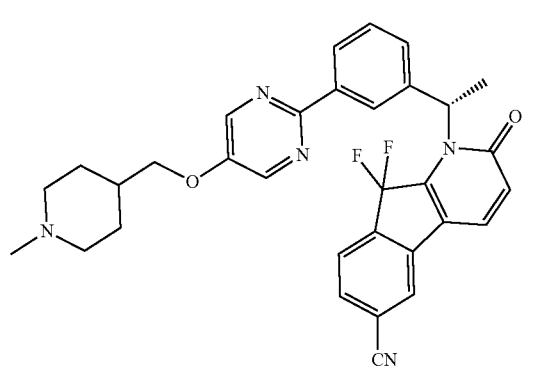

The hydrochloride of compound 18-1 was prepared according to the method of compound 1 by replacing compound 1L with compound 18B-1 and replacing the high performance liquid chromatography (formic acid system) with high performance liquid chromatography (hydrochloric acid system). $^1$H NMR (400 MHz, DMSO-$d_6$) δ=10.97-10.65 (m, 1H), 8.67-8.61 (m, 2H), 8.27 (s, 1H), 8.22-8.16 (m, 2H), 8.05 (d, J=9.3 Hz, 1H), 7.93 (br d, J=7.8 Hz, 1H), 7.88-7.80 (m, 1H), 7.51-7.42 (m, 2H), 6.62 (br d, J=9.3 Hz, 1H), 5.59 (br d, J=6.3 Hz, 1H), 4.06 (br d, J=6.3 Hz, 2H), 3.43-3.37 (m, 2H), 3.02-2.88 (m, 2H), 2.74-2.65 (m, 3H), 2.03 (br d, J=6.8 Hz, 4H), 1.94 (br d, J=12.3 Hz, 2H), 1.72-1.57 (m, 2H); LCMS (ESI) m/z: 554.3 [M+1].

The hydrochloride of compound 18-2 was prepared according to the method of compound 1 by replacing compound 1L with compound 18B-2 and replacing the high performance liquid chromatography (formic acid system) with high performance liquid chromatography (hydrochloric acid system). $^1$H NMR (400 MHz, DMSO-$d_6$) δ=10.77-10.02 (m, 1H), 8.67-8.62 (m, 2H), 8.28 (s, 1H), 8.22-8.16 (m, 2H), 8.05 (d, J=9.3 Hz, 1H), 7.94 (br d, J=7.5 Hz, 1H), 7.86 (d, J=7.8 Hz, 1H), 7.53-7.34 (m, 2H), 6.63 (br d, J=9.3 Hz, 1H), 5.69-5.53 (m, 1H), 4.07 (br d, J=6.3 Hz, 2H), 3.46-3.38 (m, 2H), 3.01-2.88 (m, 2H), 2.70 (br d, J=4.5 Hz, 3H), 2.03 (br d, J=6.8 Hz, 4H), 1.96 (br d, J=14.5 Hz, 2H), 1.60 (br d, J=12.8 Hz, 2H); LCMS (ESI) m/z: 554.3 [M+1].

Embodiment 19

19

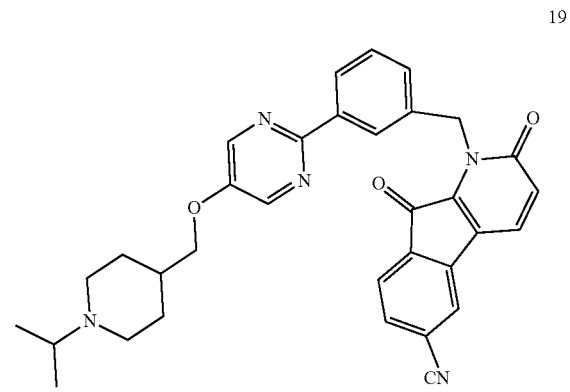

According to the method of the formate of compound 1, by replacing the cmpound 1L with compound 2C, and replacing the formaldehyde aqueous solution with acetone, and the obtained product was purified by high performance liquid chromatography (formic acid system), then purified by thin-layer silica gel chromatography (dichloromethane: methanol=5:1) to obtain compound 19 (30 mg), then water (10 mL) and hydrochloric acid aqueous solution (0.5 mol/L, 0.44 mL) were added, the mixture was stirred at 15° C. for 30 minutes, then subjected to freeze-dring to obtain the hydrochloride of compound 19. $^1$H NMR (400 MHz, DMSO-$d_6$) δ=8.64 (s, 2H), 8.23 (s, 1H), 8.18 (d, J=7.5 Hz, 1H), 8.10 (d, J=9.3 Hz, 1H), 8.03 (s, 1H), 7.77-7.73 (m, 1H), 7.60 (d, J=7.5 Hz, 1H), 7.46-7.41 (m, 1H), 7.39-7.34 (m, 1H), 6.91 (d, J=9.3 Hz, 1H), 5.58 (s, 2H), 4.11-3.99 (m, 3H), 3.47-3.39 (m, 2H), 3.12-2.80 (m, 2H), 2.19-2.06 (m, 1H), 2.04-1.89 (m, 2H), 1.75-1.55 (m, 2H), 1.33-1.16 (m, 6H); LCMS (ESI): m/z: 546.3 [M+1].

Embodiment 20

20

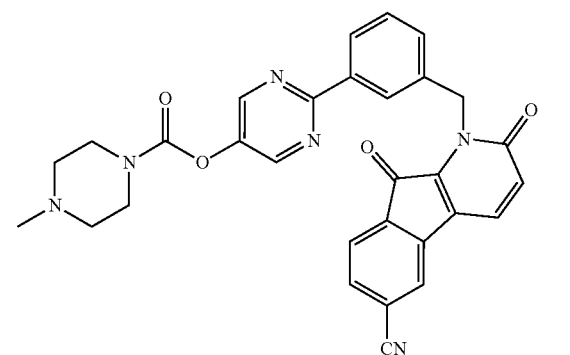

Compound 20A:

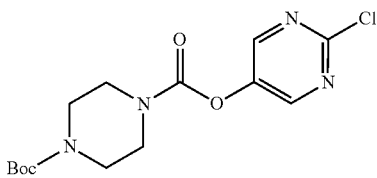 [SMILES: CC(C)(C)OC(=O)N1CCN(C(=O)Oc2cnc(Cl)nc2)CC1]

Triphosgene (5.46 g, 18.39 mmol) was added to a solution of 2-chloro-5-hydroxypyrimidine (2 g, 15.32 mmol), N-Boc piperazine (3.14 g, 16.85 mmol) and triethylamine (3.10 g, 30.64 mmol, 4.27 mL) in dichloromethane (20 mL) at 0° C. The reaction mixture was stirred at 15° C. for 1 hour. Saturated sodium bicarbonate aqueous solution (30 mL) was added to the reaction mixture, and the mixture was extracted, the aqueous phase was separated and extracted with dichloromethane (20 mL×1 time). The organic phases were combined and dried over sodium sulfate, then concentrated, the residue was purified by column chromatography (petroleum ether:ethyl acetate=10:1-4:1) to obtain the compound 20A. LCMS (ESI): m/z: 287.1 [M-55].

Compound 20B:

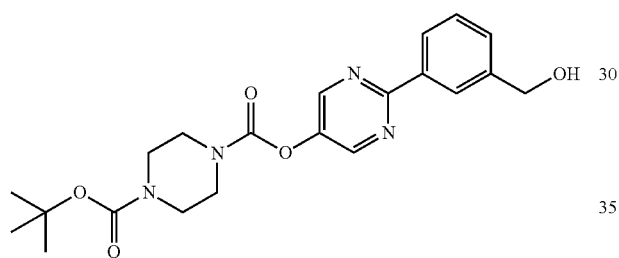

Compound 20A (1 g, 2.40 mmol) and 3-hydroxymethylphenylboronic acid (400 mg, 2.63 mmol) were dissolved in 10 mL of dioxane and 2 mL of water, and potassium carbonate (660 mg, 4.78 mmol) and Pd(dppf)Cl$_2$ (90 mg, 123.00 μmol) were added thereto. The mixture was stirred and the reaction was carried out for 2 hours under the protection of nitrogen at 110° C., the mixture was concentrated to remove the organic solvent. Ethyl acetate (30 mL) was added to the residue, and then washed with water (20 mL×1 time) and brine (20 mL×1 time), and the organic phase was concentrated to dryness to obtain the compound 20B, which was used directly in the next step.

Compound 20C:

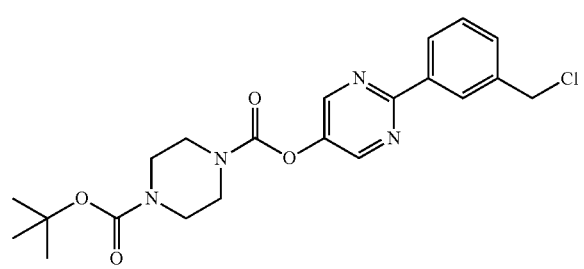 [SMILES: CC(C)(C)OC(=O)N1CCN(C(=O)Oc2cnc(-c3cccc(CCl)c3)nc2)CC1]

Compound 20C was prepared according to the method of compound 6E by replacing compound 1I with compound 20B. LCMS (ESI): m/z: 433.0 [M+1].

Compound 20D:

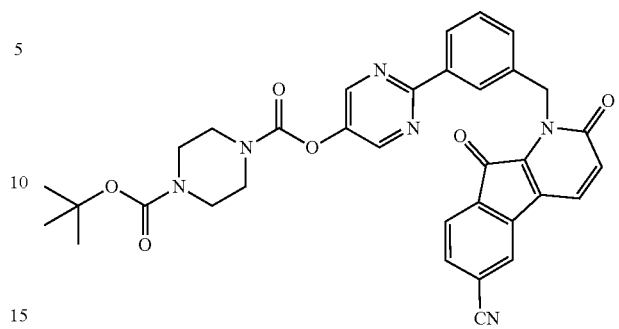

Compound 20D was prepared according to the method of compound 1K by replacing compound 1F with compound 2A and replacing the compound 1J with compound 20C. $^1$H NMR (400 MHz, CDCl$_3$) δ=8.64 (s, 2H), 8.48 (s, 1H), 8.29 (d, J=7.8 Hz, 1H), 7.61 (d, J=9.3 Hz, 1H), 7.57-7.53 (m, 1H), 7.49 (dd, J=1.2, 7.4 Hz, 2H), 7.43 (d, J=7.8 Hz, 1H), 7.39 (s, 1H), 6.94 (d, J=9.3 Hz, 1H), 5.76 (s, 2H), 3.70 (br s, 2H), 3.55 (br s, 6H), 1.50 (s, 9H). LCMS (ESI): m/z: 619.2 [M+1].

Compound 20E:

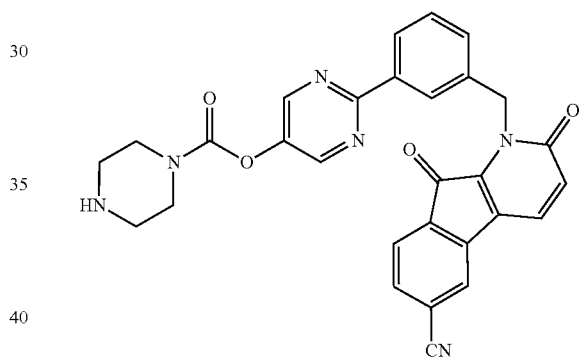

Compound 20E was prepared according to the method of compound 5J by replacing compound 5I with compound 20D. LCMS (ESI) m/z: 519.3 [M+1].

Hydrochloride of Compound 20:

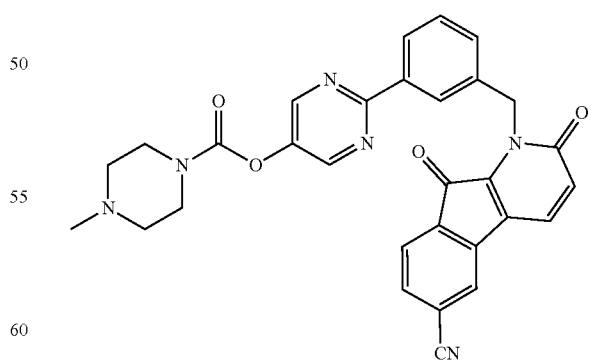

The hydrochloride of compound 20 was prepared according to the method of compound 1 by replacing compound 1L with compound 20E and replacing the high performance liquid chromatography (formic acid system) with high performance liquid chromatography (hydrochloric acid system). ¹H NMR (400 MHz, CD₃OD) δ=8.72 (s, 2H), 8.35 (s, 1H), 8.29 (br d, J=7.6 Hz, 1H), 8.01 (d, J=9.3 Hz, 1H), 7.76 (s, 1H), 7.67-7.57 (m, 2H), 7.54-7.48 (m, 1H), 7.48-7.41 (m, 1H), 6.91 (d, J=9.3 Hz, 1H), 5.74 (s, 2H), 4.60-4.31 (m, 2H), 3.68-3.52 (m, 3H), 3.47-3.37 (m, 1H), 3.31-3.19 (m, 2H), 3.00 (s, 3H); LCMS (ESI) m/z: 533.3 [M+1].
Embodiment 21
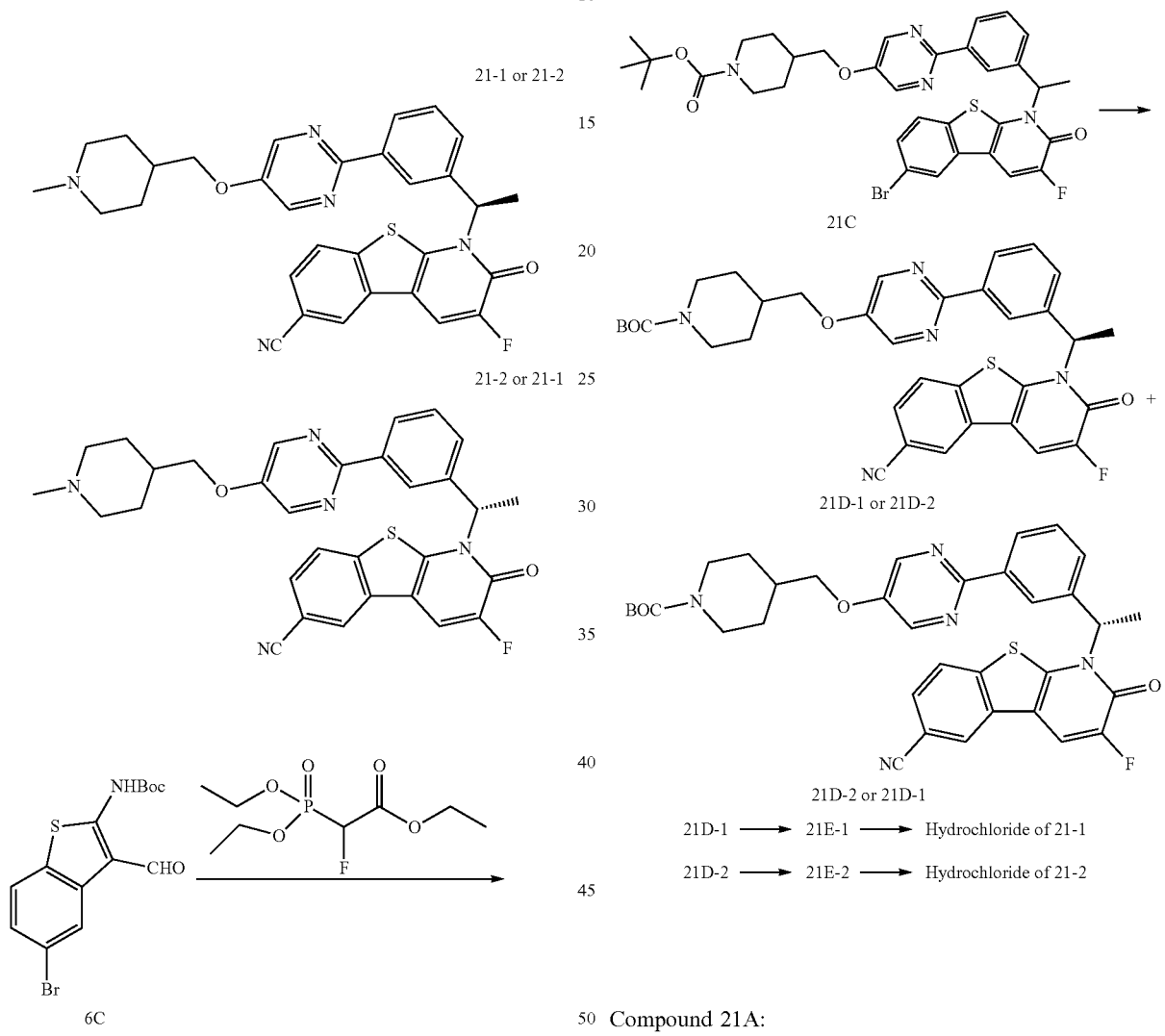
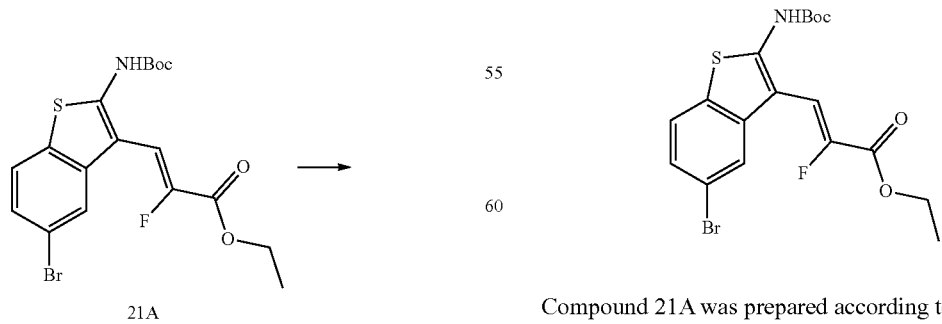
Compound 21A was prepared according to the method of compound 6D by replacing triethyl phosphonoacetate with ethyl 2-diethoxyphosphoryl-2-fluoroacetate. LCMS (ESI) m/z: 343.7 [M-100].

Compound 21B:

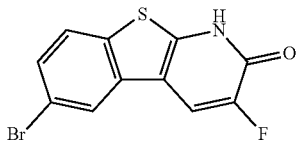 [SMILES: O=c1[nH]c2sc3ccc(Br)cc3c2cc1F]

Hydrochloric acid gas in methanol (4 mol/L, 10 mL) was added to a mixed solution of compound 21A (0.93 g, 2.09 mmol) in methanol (10 mL) and dichloromethane (10 mL). The reaction mixture was stirred at 20° C. for 16 hours, then concentrated to dryness. The residue was diluted with ethyl acetate (3 mL) and filtered, and the filter cake was dried to obtain the compound 21B. $^1$H NMR (400 MHz, DMSO-$d_6$) δ=8.52 (br d, J=9.8 Hz, 1H), 8.41 (br s, 1H), 7.96 (d, J=8.6 Hz, 1H), 7.55 (dd, J=1.6, 8.4 Hz, 1H); LCMS (ESI) m/z: 297.7 [M+1].

Compound 21C:

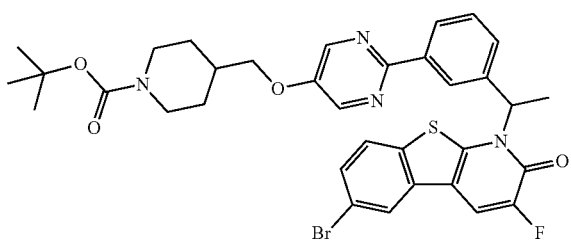 [SMILES: CC(c1cccc(-c2ncc(OCC3CCN(C(=O)OC(C)(C)C)CC3)cn2)c1)n1c(=O)c(F)cc2c3cc(Br)ccc3sc21]

Compound 21C was prepared according to the method of compound 14C by replacing compound 2A with compound 21B, replacing the high performance liquid chromatography (formic acid system) with thin layer silica gel chromatography (dichloromethane:methanol=20:1). $^1$H NMR (400 MHz, CDCl$_3$) δ=8.39 (s, 1H), 8.37 (s, 2H), 8.27 (d, J=7.3 Hz, 1H), 7.80 (d, J=1.7 Hz, 1H), 7.66 (d, J=8.6 Hz, 1H), 7.42-7.32 (m, 3H), 7.31-7.27 (m, 1H), 6.89 (q, J=6.8 Hz, 1H), 4.12 (m, 2H), 3.87 (d, J=6.1 Hz, 2H), 2.69 (br t, J=12.3 Hz, 2H), 1.98 (d, J=7.1 Hz, 3H), 1.96-1.88 (m, 1H), 1.76 (br d, J=12.0 Hz, 2H), 1.40 (s, 9H), 1.30-1.18 (m, 2H); LCMS (ESI) m/z: 639.3 [M-55].

Compound 21D-1 and 21D-2:

21D-1 or 21D-2

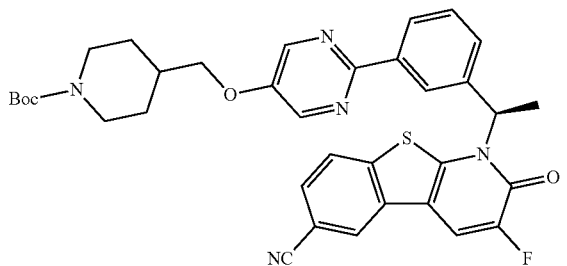

21D-2 or 21D-1

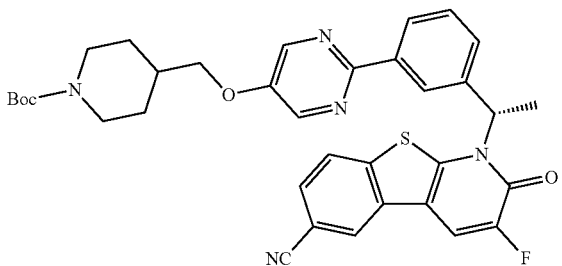

The mixture of compounds 21D-1 and 21D-2 was prepared according to the method of compound 61 by replacing compound 6H with compound 21C, characterized as: LCMS (ESI) m/z: 584.1 [M-55]. The mixture of 21D-1 and 21D-2 was purified by chiral SFC (separation method: separation column: Chiralpak AD-3 50×4.6 mm ID, 3 μm; mobile phase: phase A was carbon dioxide, phase B was isopropanol+acetonitrile (containing 0.05% of diethylamine); gradient elution: 40% isopropanol+acetonitrile (containing 0.05% diethylamine) in carbon dioxide; flow rate: 3 mL/min; detection wavelength: 220 nm; column temperature: 35° C.; pressure: 100 bar), the compound with a retention time of 0.845 minutes was compound 21D-1. $^1$H NMR (400 MHz, CDCl$_3$) δ=8.47 (s, 1H), 8.45 (s, 2H), 8.36 (d, J=7.6 Hz, 1H), 8.03 (s, 1H), 7.79 (d, J=8.3 Hz, 1H), 7.67 (d, J=8.3 Hz, 1H), 7.51-7.45 (m, 2H), 7.44-7.39 (m, 1H), 7.01 (q, J=7.1 Hz, 1H), 4.19 (m, 2H), 3.95 (d, J=6.4 Hz, 2H), 2.77 (br t, J=12.0 Hz, 2H), 2.06 (d, J=7.1 Hz, 3H), 2.02 (m, 1H), 1.84 (br d, J=12.5 Hz, 2H), 1.48 (s, 9H), 1.37-1.26 (m, 2H). The compound with a retention time of 1.077 minutes was compound 21D-2. $^1$H NMR (400 MHz, CDCl$_3$) δ=8.47 (s, 1H), 8.45 (s, 2H), 8.37 (d, J=7.8 Hz, 1H), 8.03 (s, 1H), 7.79 (d, J=8.6 Hz, 1H), 7.67 (d, J=8.3 Hz, 1H), 7.51-7.45 (m, 2H), 7.45-7.40 (m, 1H), 7.01 (q, J=7.1 Hz, 1H), 4.19 (br s, 2H), 3.95 (d, J=6.4 Hz, 2H), 2.77 (br t, J=12.0 Hz, 2H), 2.06 (d, J=7.3 Hz, 3H), 2.02-1.95 (m, 1H), 1.84 (br d, J=13.0 Hz, 2H), 1.48 (s, 9H), 1.38-1.26 (m, 2H).

Compound 21E-1 and 21E-2:

21E-1 or 21E-2

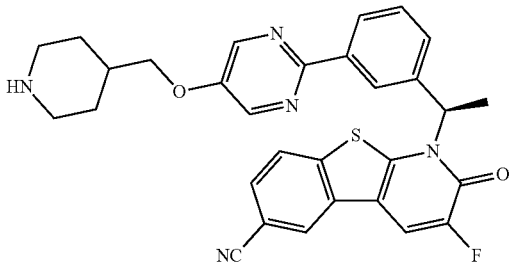

-continued 21E-2 or 21E-1

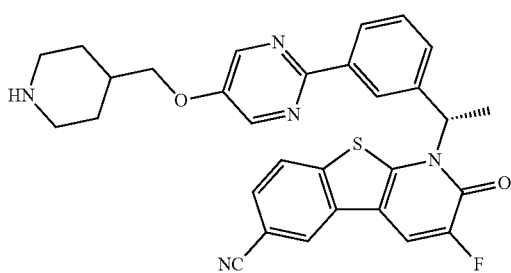

Compound 21E-1 or 21E-2 was prepared according to the method of compound 5J by replacing compound 5I with compound 21D-1 or 21D-2. LCMS (ESI) m/z: 540.1 [M+1]. Compound 21E-2 or 21E-1 was prepared according to the method of compound 5J by replacing compound 5I with compound 21E-2 or 21E-1. LCMS (ESI) m/z: 522.3 [M+1]. Hydrochloride of Compounds 21-1 and 21-2:

21-1 or 21-2

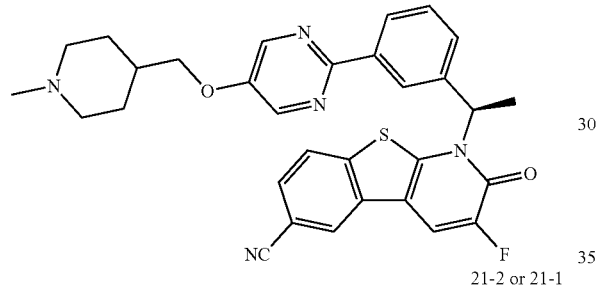

21-2 or 21-1

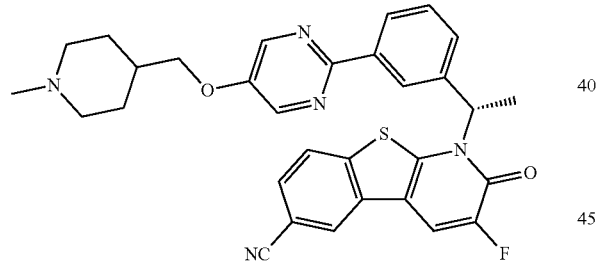

The hydrochloride of compound 21-1 was prepared according to the method of compound 1 by replacing compound 1L with compound 21E-1 and replacing the high performance liquid chromatography (formic acid system) with high performance liquid chromatography (hydrochloric acid system). $^1$H NMR (400 MHz, DMSO-d$_6$) δ=10.50-9.97 (m, 1H), 8.73-8.64 (m, 3H), 8.60 (d, J=9.8 Hz, 1H), 8.34-8.25 (m, 2H), 8.15 (d, J=8.3 Hz, 1H), 7.72 (dd, J=1.5, 8.4 Hz, 1H), 7.61-7.44 (m, 2H), 6.88-6.61 (m, 1H), 4.08 (d, J=6.2 Hz, 2H), 3.44 (br d, J=12.0 Hz, 2H), 3.03-2.86 (m, 2H), 2.72 (d, J=4.8 Hz, 3H), 2.13-1.88 (m, 6H), 1.69-1.50 (m, 2H); LCMS (ESI) m/z: 554.3 [M+1].

The hydrochloride of compound 21-2 was prepared according to the method of compound 1 by replacing compound 1L with compound 21E-2 and replacing the high performance liquid chromatography (formic acid system) with high performance liquid chromatography (hydrochloric acid system). $^1$H NMR (400 MHz, DMSO-d$_6$) δ=10.86-10.40 (m, 1H), 8.72-8.62 (m, 3H), 8.60 (d, J=9.8 Hz, 1H), 8.36-8.22 (m, 2H), 8.14 (d, J=8.3 Hz, 1H), 7.71 (dd, J=1.3, 8.4 Hz, 1H), 7.60-7.45 (m, 2H), 6.74 (br s, 1H), 4.07 (d, J=6.2 Hz, 2H), 3.44-3.38 (m, 2H), 3.03-2.86 (m, 2H), 2.80-2.64 (m, 3H), 2.14-1.87 (m, 6H), 1.71-1.54 (m, 2H); LCMS (ESI) m/z: 554.3 [M+1].

Embodiment 22

22-1 or 22-2

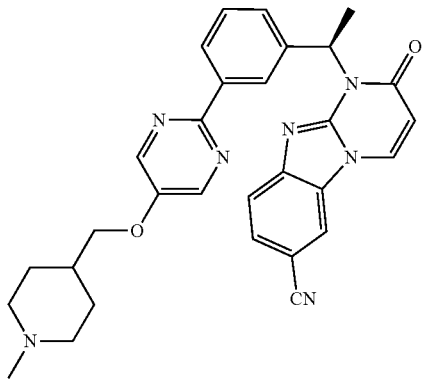

22-2 or 22-1

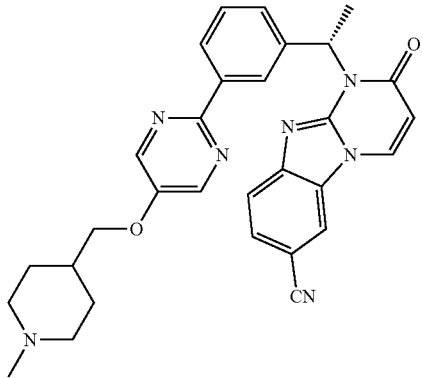

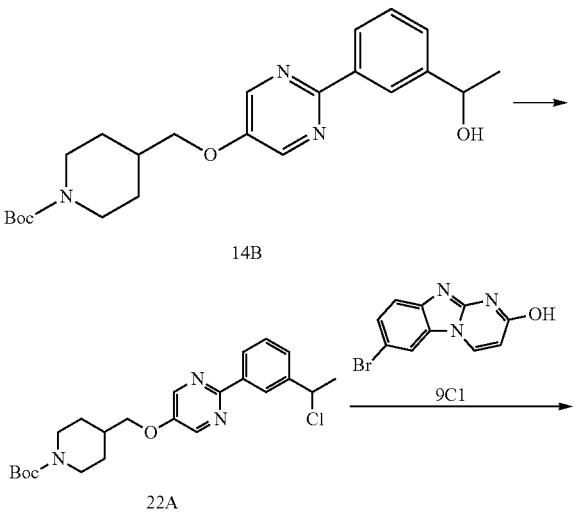

-continued

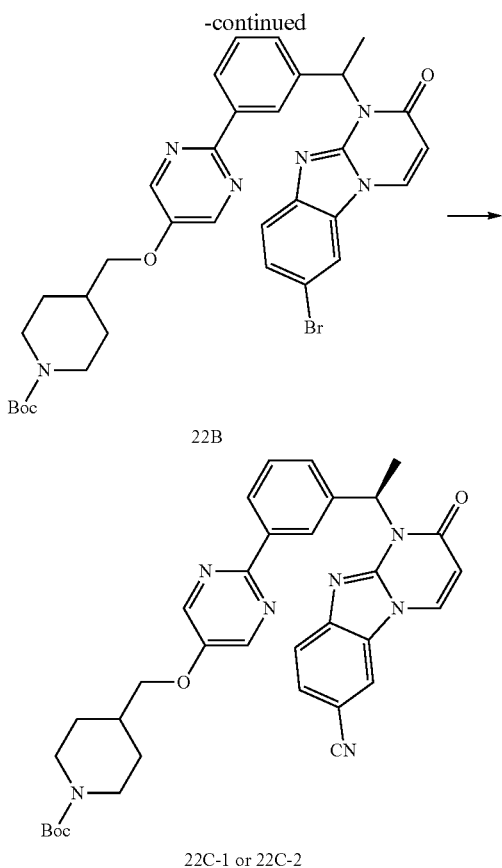

22B

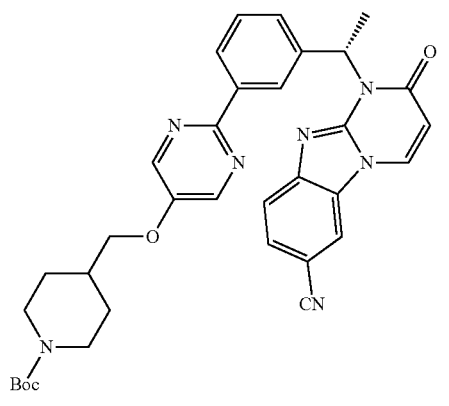

22C-1 or 22C-2

22C-2 or 22C-1

22C-1 ⟶ 22D-1 ⟶ Hydrochloride of 22-1

22C-2 ⟶ 22D-2 ⟶ Hydrochloride of 22-2

Compound 22A:

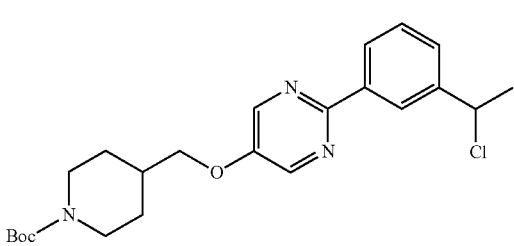 [SMILES: CC(Cl)c1cccc(-c2ncc(OCC3CCN(C(=O)OC(C)(C)C)CC3)cn2)c1]

Compound 22A was prepared according to the method of compound 6E by replacing compound 6D with compound 14B. ¹H NMR (400 MHz, CDCl₃) δ=8.46 (s, 2H), 8.41 (t, J=1.8 Hz, 1H), 8.30 (td, J=1.5, 7.5 Hz, 1H), 7.58-7.40 (m, 2H), 5.20 (q, J=6.9 Hz, 1H), 4.31-4.08 (m, 2H), 3.96 (d, J=6.5 Hz, 2H), 2.77 (br t, J=12.6 Hz, 2H), 2.10-1.97 (m, 1H), 1.92 (d, J=6.8 Hz, 3H), 1.85 (br d, J=12.5 Hz, 2H), 1.48 (s, 9H), 1.41-1.27 (m, 2H); LCMS (ESI) m/z: 432.1 [M+1].

Compound 22B:

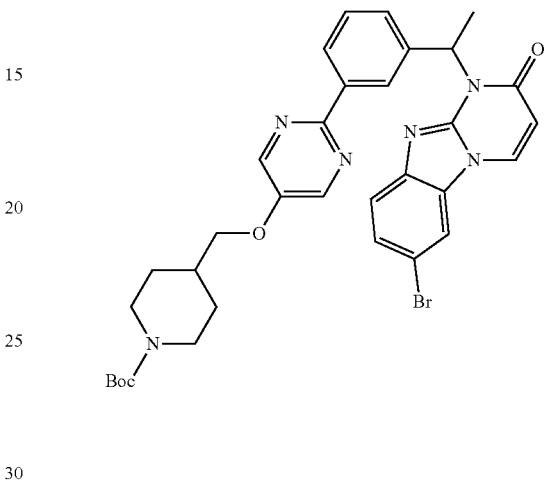

Compound 22B was prepared according to the method of compound 6F by replacing compound 6D with compound 9C1 and replacing the compound 6E with compound 22A. ¹H NMR (400 MHz, CDCl₃) δ=8.55 (s, 1H), 8.43 (s, 2H), 8.24 (d, J=8.0 Hz, 1H), 7.95 (d, J=7.8 Hz, 1H), 7.66-7.61 (m, 2H), 7.58-7.53 (m, 1H), 7.49-7.38 (m, 2H), 6.65 (q, J=6.9 Hz, 1H), 6.16 (d, J=7.5 Hz, 1H), 4.26-4.13 (m, 2H), 3.94 (d, J=6.5 Hz, 2H), 2.85-2.68 (m, 2H), 2.16 (d, J=7.3 Hz, 3H), 2.00 (br dd, J=3.4, 7.9 Hz, 1H), 1.88-1.79 (m, 2H), 1.48 (s, 9H), 1.35-1.29 (m, 2H); LCMS (ESI) m/z: 661.1 [M+3].

Compounds 22C-1 and 22C-2:

22C-1 or 22C-2

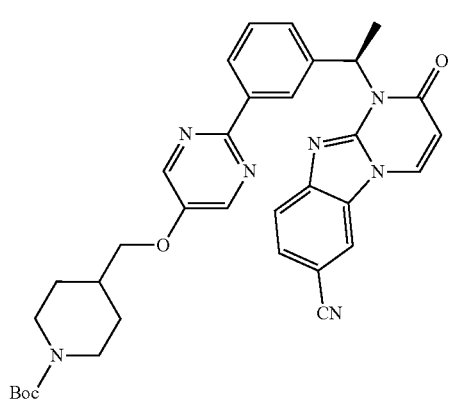 [SMILES: CC(c1cccc(-c2ncc(OCC3CCN(C(=O)OC(C)(C)C)CC3)cn2)c1)n1c(=O)ccn2c3cc(Br)ccc3nc12]

-continued 22C-2 or 22C-1

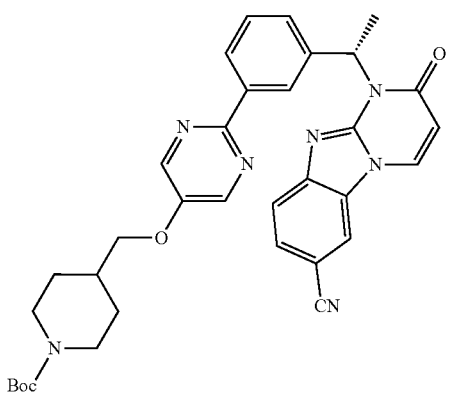

A mixture of compounds 22C-1 and 22C-2 was prepared according to the method of compound 6I by replacing compound 6H with compound 22B. The mixture of 22C-1 and 22C-2 was purified by chiral SFC (separation method: separation column: Chiralcel OJ-3 50×4.6 mm ID, 3 μm; mobile phase: phase A was carbon dioxide, phase B was ethanol (containing 0.05% of diethylamine); gradient elution: 40% ethanol (containing 0.05% diethylamine) in carbon dioxide; flow rate: 3 mL/min; detector: PDA; column temperature: 35° C.; pressure: 100 bar), the compound with a retention time of 1.591 minutes was obtained as compound 22C-1, and the compound with a retention time of 2.636 minutes was obtained as compound 22C-2.

Compounds 22D-1 and 22D-2:

22D-1 or 22D-2

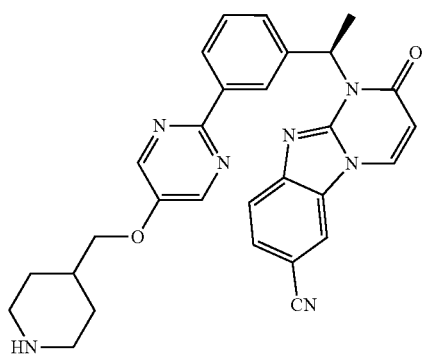

22D-2 or 22D-1

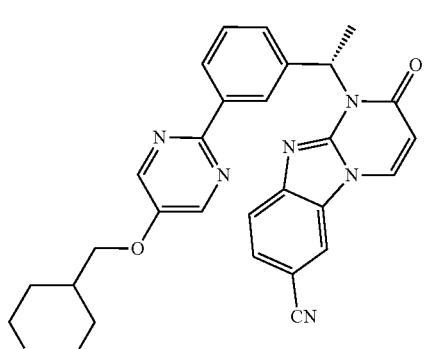

Compound 22D-1 was prepared according to the method of compound 5J by replacing compound 5I with compound 22C-1. LCMS (ESI) m/z: 506.2 [M+1]. Compound 22D-2 was prepared according to the method of compound 5J by replacing compound 5I with compound 22C-2. LCMS (ESI) m/z: 506.2 [M+1].

Hydrochloride of Compounds 22-1 and 22-2:

22-1 or 22-2

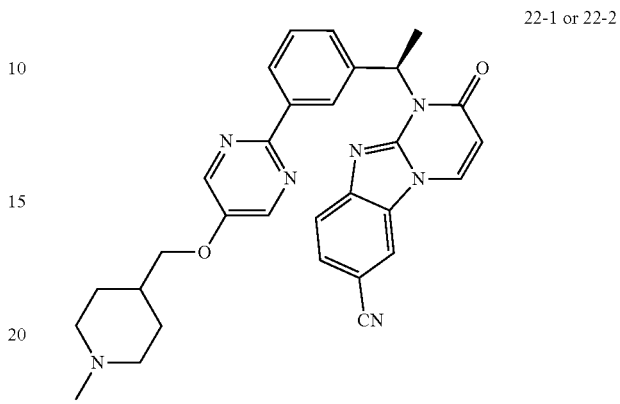

22-2 or 22-1

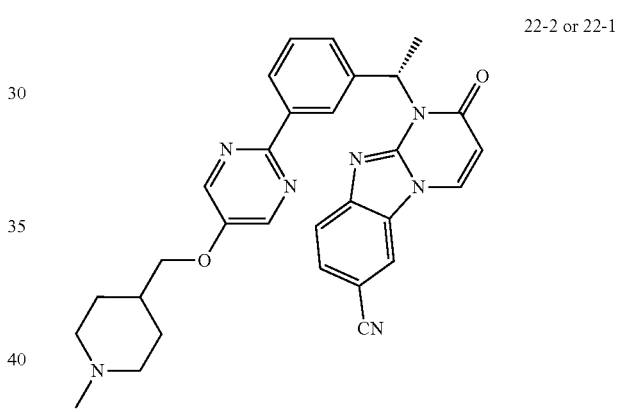

The hydrochloride of compound 22-1 was prepared according to the method of compound 1 by replacing compound 1L with compound 22D-1 and replacing the high performance liquid chromatography (formic acid system) with high performance liquid chromatography (hydrochloric acid system). $^1$H NMR (400 MHz, CDCl$_3$) δ=8.55 (s, 1H), 8.42 (s, 2H), 8.24 (d, J=7.8 Hz, 1H), 8.05 (d, J=7.8 Hz, 1H), 7.82 (s, 1H), 7.73 (d, J=8.3 Hz, 1H), 7.67-7.58 (m, 2H), 7.42 (t, J=7.8 Hz, 1H), 6.67 (q, J=7.1 Hz, 1H), 6.24 (d, J=7.8 Hz, 1H), 4.01 (br d, J=3.8 Hz, 2H), 3.60-3.46 (m, 2H), 2.77 (s, 5H), 2.16 (d, J=7.3 Hz, 3H), 2.09 (br s, 5H); LCMS (ESI) m/z: 520.2 [M+1].

The hydrochloride of compound 22-2 was prepared according to the method of compound 1 by replacing compound 1L with compound 22D-2 and replacing the high performance liquid chromatography (formic acid system) with high performance liquid chromatography (hydrochloric acid system). $^1$H NMR (400 MHz, CDCl$_3$) δ=8.56 (s, 1H), 8.44 (s, 2H), 8.25 (d, J=7.8 Hz, 1H), 8.05 (d, J=7.5 Hz, 1H), 7.82 (s, 1H), 7.74 (d, J=8.5 Hz, 1H), 7.68-7.62 (m, 2H), 7.43 (t, J=7.8 Hz, 1H), 6.68 (q, J=7.2 Hz, 1H), 6.25 (d, J=7.5 Hz, 1H), 4.03 (br d, J=3.3 Hz, 2H), 3.68-3.59 (m, 2H), 2.91-2.66 (m, 5H), 2.16 (d, J=7.3 Hz, 3H), 2.14-2.06 (m, 3H), 1.88-1.86 (m, 2H); LCMS (ESI) m/z: 520.2 [M+1].

Embodiment 23

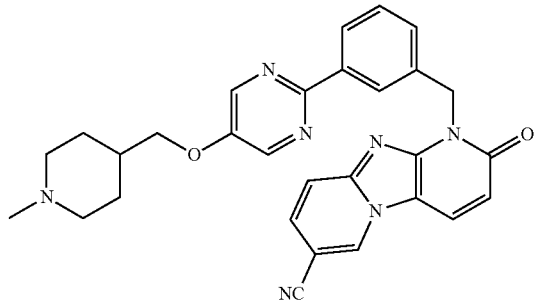

23

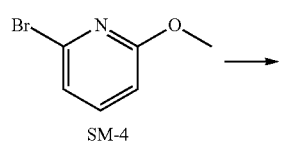

SM-4

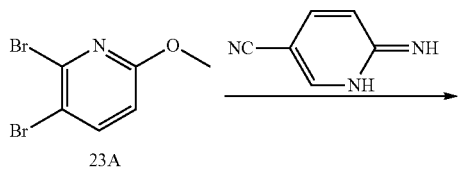

23A

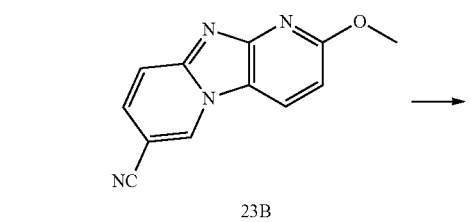

23B

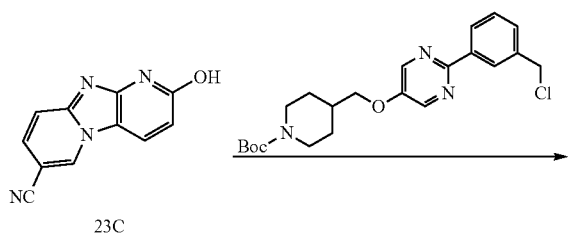

23C

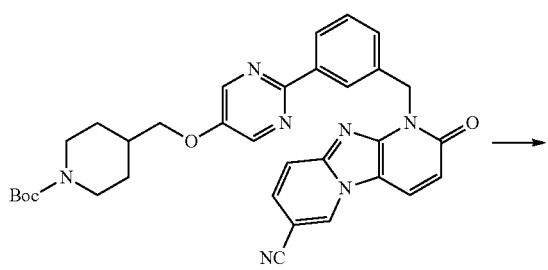

23D

Hydrochloride of compound 23

Compound 23A:

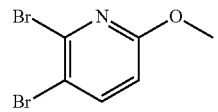

NBS (9.47 g, 53.19 mmol) was added to a solution of 2-bromo-6-methoxypyridine (5 g, 26.59 mmol) in DMF (50 mL) at 15° C., and the mixture was stirred at 90° C. for 0.5 hours, water (50 mL) was added to the reaction mixture, then extracted with ethyl acetate (50 mL×1 time), the organic phase was washed with brine (50 mL×5 times), dried over sodium sulfate, filtered and concentrated, and the crude product was purified by silica gel column chromatography (eluting with pure petroleum ether) to obtain the compound 23A. $^1$H NMR (400 MHz, CDCl$_3$) δ=7.62 (d, J=8.5 Hz, 1H), 6.54 (d, J=8.5 Hz, 1H), 3.85 (s, 3H); LCMS (ESI) m/z: 267.9 [M+3].

Compound 23B:

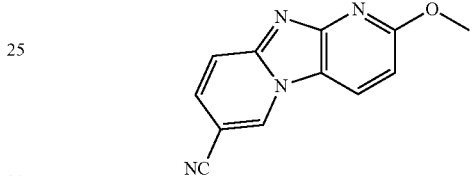

Pd$_2$(dba)$_3$ (138 mg, 150.70 mmol) and Xantphos (174 mg, 300.72 μmol) were added to a 50 mL round bottom flask containing NMP (5 mL) at 25° C., and the mixture was purged with nitrogen while stirring for 10 minutes. Cuprous iodide (45 mg, 236.28 μmol), compound 23A (1 g, 3.75 mmol), 6-imino-1H-pyridine-3-carbonitrile (540 mg, 4.53 mmol) and cesium carbonate (4.88 g, 14.98 mmol) were added in another 10 mL round-bottomed flask, the previously prepared catalyst was added into the reaction flask under the protection of nitrogen, the mixture was purged with nitrogen for 5 minutes, and the mixture was stirred at 90° C. for 45 minutes. The reaction mixture was cooled to room temperature and filtered, and the filter cake was washed with dichloromethane:methanol=10:1 (15 mL×3 times). The pH value of the obtained filtrate was adjusted to 1 with hydrochloric acid aqueous solution (2 mol/L), and the aqueous phase was washed with dichloromethane (15 mL×3 times), the organic phase was discarded, and pH value of the aqueous phase was adjusted to 8 with saturated sodium bicarbonate aqueous solution, the precipitated solid was filtered and dried under reduced pressure to obtain the compound 23B. $^1$H NMR (400 MHz, DMSO-d$_6$) δ=9.92 (s, 1H), 8.65 (d, J=8.9 Hz, 1H), 7.88-7.75 (m, 2H), 6.95 (d, J=8.9 Hz, 1H), 3.99 (s, 3H); LCMS (ESI) m/z: 225.6 [M+1].

Compound 23C:

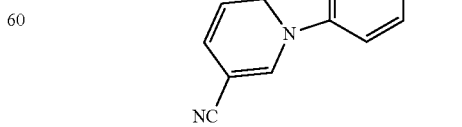

Compound 23C was prepared according to the method of compound 1F by replacing compound 1E with compound 23B, the obtained crude product was purified by high-performance liquid chromatography (formic acid system). ¹H NMR (400 MHz, DMSO-d₆) δ=9.54 (s, 1H), 8.09 (br d, J=9.3 Hz, 1H), 7.60-7.47 (m, 2H), 6.16 (d, J=9.3 Hz, 1H).
Compound 23D:

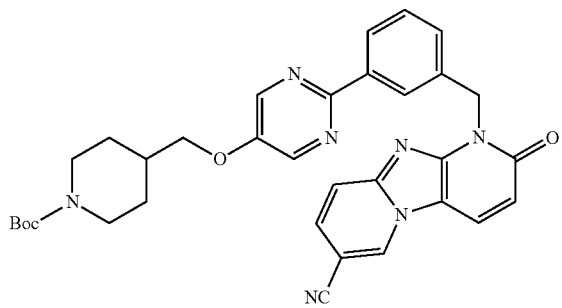 [SMILES: CC(C)(C)OC(=O)N1CCC(COc2cnc(-c3cccc(Cn4c(=O)ccc5c4nc4ccc(C#N)cn45)c3)nc2)CC1]

Compound 23D was prepared according to the method of compound 6F by replacing compound 6D with compound 23C. ¹H NMR (400 MHz, DMSO-d₆) δ=9.78 (s, 1H), 8.63-8.57 (m, 2H), 8.43 (d, J=9.5 Hz, 1H), 8.28 (s, 1H), 8.15 (br d, J=7.2 Hz, 1H), 7.92-7.72 (m, 2H), 7.50-7.35 (m, 2H), 6.50 (d, J=9.5 Hz, 1H), 5.52 (s, 2H), 4.04 (d, J=6.5 Hz, 2H), 3.96 (br d, J=11.4 Hz, 2H), 2.80-2.65 (m, 2H), 1.96 (br s, 1H), 1.77-1.72 (m, 2H), 1.38 (s, 9H), 1.18-1.10 (m, 2H); LCMS (ESI) m/z: 592.4 [M+1].
Hydrochloride of Compound 23:

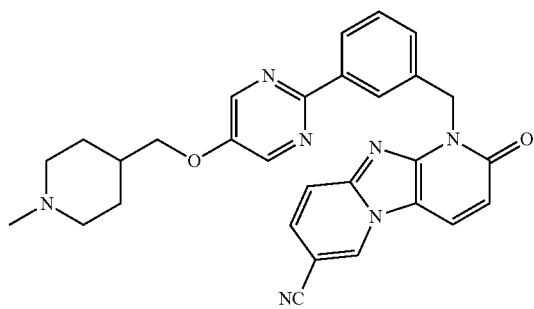 [SMILES: CN1CCC(COc2cnc(-c3cccc(Cn4c(=O)ccc5c4nc4ccc(C#N)cn45)c3)nc2)CC1]

37% Formaldehyde aqueous solution (0.5 mL) was added to a solution of compound 23D (50 mg, 84.51 μmol) in formic acid (0.5 mL) at 25° C., and the mixture was stirred at 100° C. for 0.5 hours and concentrated to dryness under reduced pressure. The residue was dissolved in methanol (4 mL), 37% formaldehyde aqueous solution (0.1 mL) and NaBH(OAc)₃ (36 mg, 169.86 μmol) were added to the reaction mixture, the mixture was stirred at 25° C. for 0.5 hours and then concentrated to dryness, the residue was purified by high performance liquid chromatography (hydrochloric acid system), the pH value of the obtained mixture was adjusted to 8 with saturated sodium bicarbonate aqueous solution, and then the mixture was extracted with dichloromethane:methanol=10:1 (20 mL×3 times), the organic phase was combined and concentrated under reduced pressure. Water (10 mL) and acetonitrile (0.5 mL) were added to the residue, then hydrochloric acid aqueous solution (0.5 mol/L, 0.1 mL) was added thereto and stirred at 25° C. for 0.5 hours, the mixture was concentrated under reduced pressure to obtain hydrochloride of compound 23. ¹H NMR (400 MHz, DMSO-d₆) δ=10.14-9.70 (m, 2H), 8.68-8.55 (m, 2H), 8.44 (d, J=9.5 Hz, 1H), 8.29 (s, 1H), 8.16 (br d, J=7.1 Hz, 1H), 7.88-7.76 (m, 2H), 7.48-7.38 (m, 2H), 6.50 (d, J=9.5 Hz, 1H), 5.53 (s, 2H), 4.08 (br d, J=6.0 Hz, 2H), 3.28-3.08 (m, 2H), 3.07-2.86 (m, 2H), 2.80-2.70 (m, 3H), 2.09-1.88 (m, 3H), 1.65-1.47 (m, 2H); LCMS (ESI) m/z: 506.2 [M+1].

Embodiment 24

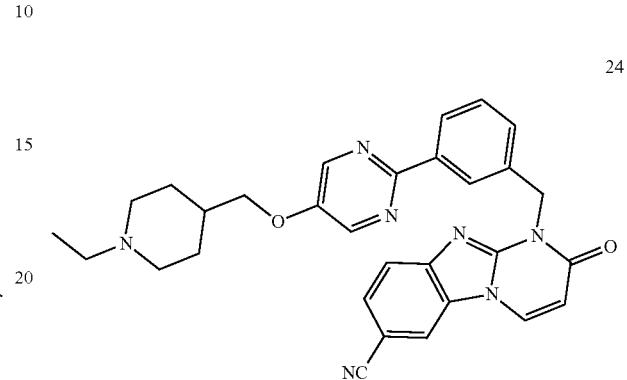

24

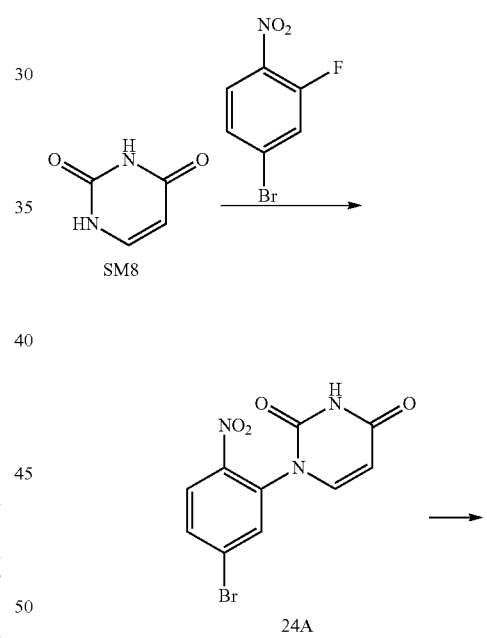

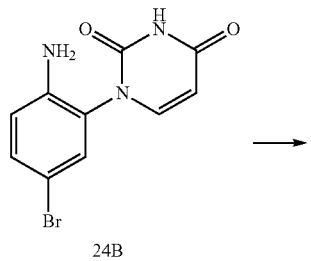

-continued

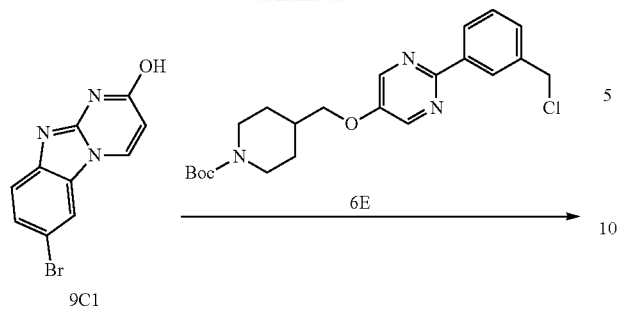

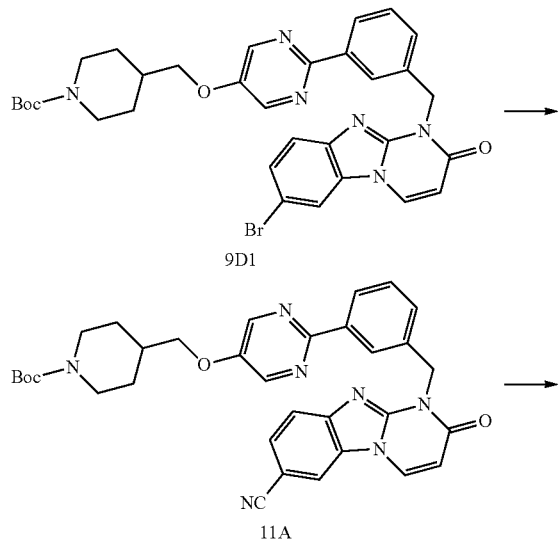

Hydrochloride of compound 24

Compound 24A:

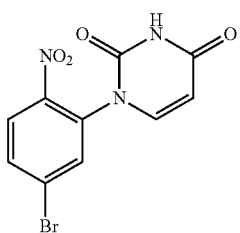 [SMILES: O=c1ccn(-c2cc(Br)ccc2[N+](=O)[O-])c(=O)[nH]1]

Compound 24A was prepared according to the method of compound 13A by replacing 5-fluorouracil with uracil. ¹H NMR (400 MHz, DMSO-d$_6$) δ=11.69 (s, 1H), 8.16-8.10 (m, 2H), 8.02-7.95 (m, 1H), 7.89 (d, J=7.9 Hz, 1H), 5.82 (dd, J=2.1, 8.0 Hz, 1H).

Compound 24B:

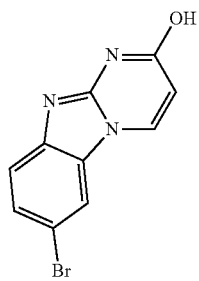 [SMILES: Oc1ccn2c(n1)nc1ccc(Br)cc12]

Reduced iron powder (4.47 g, 80.11 mmol) was added to a solution of compound 24A (5 g, 16.02 mmol) in acetic acid (100 mL) at 25° C. The mixture was stirred at 90° C. for 1 hour, cooled to room temperature and filtered, the filtrate was concentrated under reduced pressure to dryness, water (50 mL) was added, and the pH value of the mixture was adjusted to 8 with sodium hydroxide aqueous solution (1 mol/L), and then the mixture was extracted with dichloromethane:methanol=10:1 (100 mL×3 times). The organic phase was combined, dried and concentrated, then purified by silica gel column chromatography (dichloromethane:methanol=1:0 to 20:1) to obtain the compound 24B. ¹H NMR (400 MHz, DMSO-d$_6$) δ=11.29 (d, J=1.6 Hz, 1H), 7.38 (d, J=7.9 Hz, 1H), 7.31-7.21 (m, 2H), 6.72 (d, J=8.6 Hz, 1H), 5.61 (dd, J=2.3, 7.8 Hz, 1H), 5.54 (s, 2H); LCMS (ESI) m/z: 284.1 [M+3].

Compound 9C1:

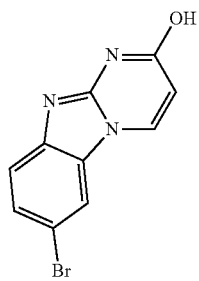 [SMILES: Oc1ccn2c(n1)nc1ccc(Br)cc12]

A mixture of compound 24B (2.9 g, 10.28 mmol) and polyphosphoric acid (15 g) was stirred at 170° C. for 2 hours, then cooled to room temperature, water (40 mL) was added thereto, and then the pH value of the mixture was adjusted to 5-6 with saturated sodium carbonate aqueous solution, the precipitated solid was filtered and evaporated to dryness, ethyl acetate (20 mL) was added to the obtained solid and filtered, the filter cake was dried to obtain the compound 9C1. ¹H NMR (400 MHz, DMSO-d$_6$) δ=8.77 (d, J=7.7 Hz, 1H), 8.24 (d, J=1.6 Hz, 1H), 7.51-7.40 (m, 2H), 6.14 (d, J=7.8 Hz, 1H); LCMS (ESI) m/z: 264.2 [M+1].

Compound 9D1:

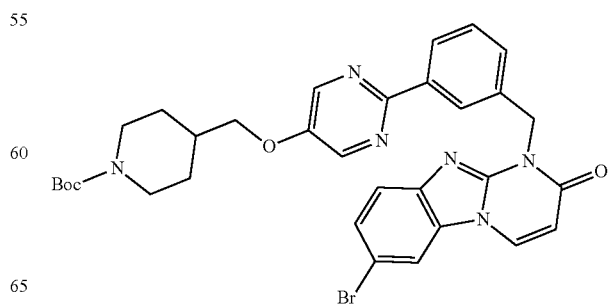

Compound 9D1 was prepared according to the method of compound 6F by replacing compound 6D with compound 9C1. $^1$H NMR (400 MHz, DMSO-$d_6$) δ=8.90 (d, J=7.8 Hz, 1H), 8.63 (s, 2H), 8.41-8.30 (m, 2H), 8.26-8.10 (m, 1H), 7.62-7.55 (m, 1H), 7.53-7.41 (m, 3H), 6.37 (d, J=7.8 Hz, 1H), 5.44 (s, 2H), 4.06 (d, J=6.4 Hz, 2H), 3.98 (br d, J=11.9 Hz, 2H), 2.75 (br s, 2H), 1.97 (br dd, J=6.8, 12.6 Hz, 1H), 1.76 (br d, J=11.0 Hz, 2H), 1.41 (s, 9H), 1.17 (dq, J=4.3, 12.3 Hz, 2H); LCMS (ESI) m/z: 645.4 [M+1].

Trifluoroacetate of Compound 24C:

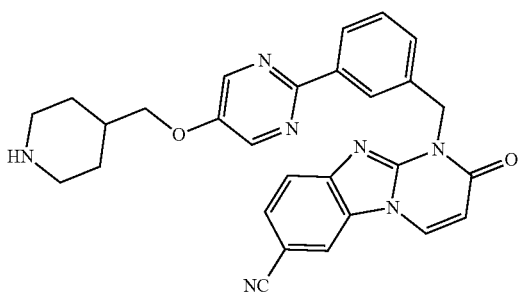 [SMILES: N#Cc1ccc2nc3n(Cc4cccc(-c5ncc(OCC6CCNCC6)cn5)c4)c(=O)ccn3c2c1]

Trifluoroacetic acid (0.9 mL) was added to the solution of compound 11A (0.9 g, 1.52 mmol) in dichloromethane (3 mL), the mixture was stirred at 25° C. for 15 minutes, and then concentrated under reduced pressure to dryness to obtain the trifluoroacetate of compound 24C. $^1$H NMR (400 MHz, CD$_3$OD) δ=8.74 (d, J=7.7 Hz, 1H), 8.53 (s, 2H), 8.41 (s, 1H), 8.30 (d, J=0.9 Hz, 1H), 8.24 (d, J=7.9 Hz, 1H), 7.79-7.75 (m, 1H), 7.74-7.69 (m, 1H), 7.61 (d, J=7.6 Hz, 1H), 7.45 (t, J=7.7 Hz, 1H), 6.38 (d, J=7.8 Hz, 1H), 5.59 (s, 2H), 4.12 (d, J=6.0 Hz, 2H), 3.48 (br d, J=12.7 Hz, 2H), 3.13-3.04 (m, 2H), 2.31-2.18 (m, 1H), 2.13 (br d, J=13.2 Hz, 2H), 1.73-1.58 (m, 2H); LCMS (ESI) m/z: 492.4 [M+1].

Hydrochloride of Compound 24:

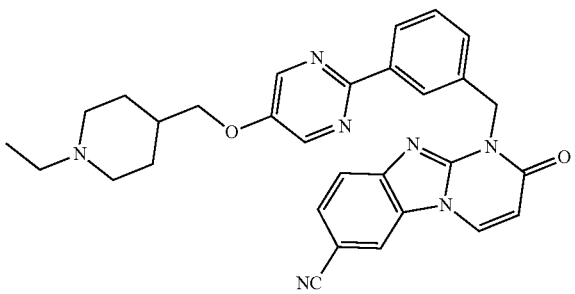 [SMILES: CCN1CCC(COc2cnc(-c3cccc(Cn4c(=O)ccn5c6cc(C#N)ccc6nc45)c3)nc2)CC1]

Acetaldehyde aqueous solution (2.55 g, 23.14 mmol, 40% purity), sodium bicarbonate (832 mg, 9.91 mmol) and NaBH(OAc)$_3$ (558 mg, 2.63 mmol) were sequentially added to a mixture of trifluoroacetate of compound 24C (0.4 g, 660.54 μmol, trifluoroacetate) in ethanol (10 mL) and dichloromethane (10 mL). The reaction mixture was stirred at 25° C. for 0.5 hours and then concentrated to dryness, saturated sodium bicarbonate aqueous solution (20 mL) was added to the residue, the mixture was extracted with dichloromethane:methanol=10:1 (50 mL×3 times), and the organic phase was combined and washed with brine (20 mL×1 time), dried over sodium sulfate, filtered and concentrated to dryness. The residue was purified by high performance liquid chromatography (formic acid system), the pH value of the obtained mixture was adjusted to 8 with saturated sodium bicarbonate aqueous solution and extracted with dichloromethane:methanol=10:1 (20 mL×3 times), and the organic phase was washed with brine (20 mL×1 time), dried over sodium sulfate, filtered and concentrated to dryness to obtain the compound 24. Water (5 mL) and acetonitrile (10 mL) and hydrochloric acid aqueous solution (0.5 mol/1, 1 mL) were sequentially added to compound 24 and stirred at 25° C. for 15 minutes, the mixture was concentrated under reduced pressure to obtain the hydrochloride of compound 24. $^1$H NMR (400 MHz, DMSO-$d_6$) δ=9.65 (br s, 1H), 8.94 (d, J=7.8 Hz, 1H), 8.65 (s, 2H), 8.59 (s, 1H), 8.36 (s, 1H), 8.20 (d, J=7.8 Hz, 1H), 7.82-7.72 (m, 2H), 7.55-7.50 (m, 1H), 7.48-7.40 (m, 1H), 6.47 (d, J=7.7 Hz, 1H), 5.47 (s, 2H), 4.10 (br d, J=5.7 Hz, 2H), 3.49 (br s, 2H), 3.17-2.80 (m, 4H), 2.14-1.89 (m, 3H), 1.60 (br d, J=12.8 Hz, 2H), 1.24 (br t, J=7.0 Hz, 3H); LCMS (ESI) m/z: 520.2 [M+1].

Embodiment 25

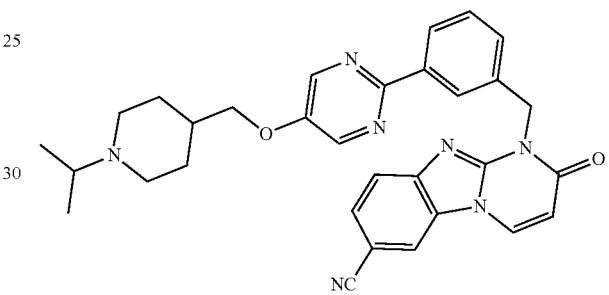

Potassium carbonate (912 mg, 6.60 mmol) and 2-iodopropane (896 mg, 5.27 mmol) were sequentially added to the mixture of trifluoroacetate of compound 24C (0.4 g, 660.54 mmol, trifluoroacetate) in ethanol (10 mL) and DMF (7 mL). The reaction mixture was stirred at 70° C. for 1 hour and then cooled to room temperature, water (20 mL) was added thereto, the precipitated solid was filtered, the filter cake was slurried with ethanol (20 mL) and filtered, then the filter cake was dried and purified by high performance liquid chromatography (formic acid system), the pH value of the obtained mixture was adjusted to 8 with saturated sodium bicarbonate aqueous solution and extracted with dichloromethane:methanol=10:1 (40 mL×3 times), the combined organic phase was dried over anhydrous sodium sulfate, filtered and concentrated to dryness to obtain the compound 25. Water (5 mL) and acetonitrile (10 mL) and hydrochloric acid aqueous solution (1 mol/1, 0.6 mL) were sequentially added to compound 25 and the mixture was stirred at 25° C. for 15 minutes, the mixture was concentrated under reduced pressure to obtain the hydrochloride of compound 25. $^1$H NMR (400 MHz, DMSO-$d_6$) δ=9.44 (br s, 1H), 8.94 (d, J=7.8 Hz, 1H), 8.65 (s, 2H), 8.59 (s, 1H), 8.36 (s, 1H), 8.20 (d, J=7.8 Hz, 1H), 7.84-7.71 (m, 2H), 7.55-7.49 (m, 1H), 7.48-7.41 (m, 1H), 6.47 (d, J=7.8 Hz, 1H), 5.47 (s, 2H), 4.10 (br d, J=6.1 Hz, 2H), 3.40 (br d, J=10.8 Hz, 3H), 2.99 (br d, J=10.9 Hz, 2H), 2.10 (br d, J=15.2 Hz, 1H), 2.00 (br d, J=13.8 Hz, 2H), 1.73-1.57 (m, 2H), 1.26 (br d, J=6.6 Hz, 6H); LCMS (ESI) m/z: 534.2 [M+1].

Embodiment 26

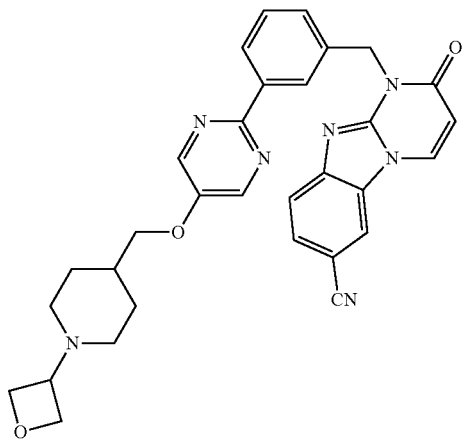

Compound 24C:

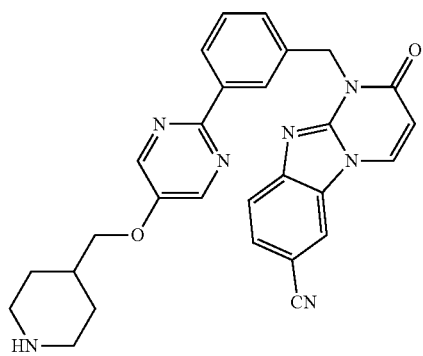 [SMILES: N#Cc1ccc2nc3n(Cc4cccc(-c5ncc(OCC6CCNCC6)cn5)c4)c(=O)ccn3c2c1]

Saturated sodium bicarbonate aqueous solution (20 mL) was added to the trifluoroacetate of compound 24C (335 mg, 569.64 mmol), the mixture was extracted with dichloromethane:methanol=10:1 (20 mL×3 times), and the organic phase was combined and dried over sodium sulfate, filtered and concentrated to dryness to obtain the compound 24C, which was used directly in the next step.

Hydrochloride of Compound 26:

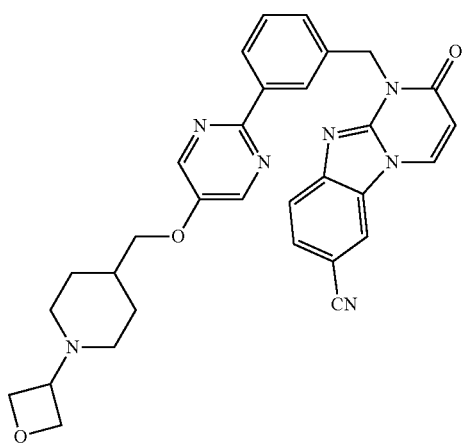 [SMILES: N#Cc1ccc2nc3n(Cc4cccc(-c5ncc(OCC6CCN(C7COC7)CC6)cn5)c4)c(=O)ccn3c2c1]

3-Iodooxetane (838 mg, 4.56 mmol) and potassium carbonate (787 mg, 5.70 mmol) were added sequentially to a solution of compound 24C (280 mg, 569.64 μmol) in DMF (10 mL). The reaction mixture was stirred at 90° C. for 16 hours and then cooled to room temperature, the reaction mixture was added to water (80 mL), the precipitated solid was filtered, and the filter cake was dissolved in dichloromethane (250 mL) and washed with brine (150 mL×2), the organic phase was dried over sodium sulfate, filtered and concentrated, and the residue was purified by column chromatography (eluting with dichloromethane:methanol=40:1). The obtained crude product was purified by high performance liquid chromatography (hydrochloric acid system), the pH value of the obtained mixture was adjusted to 8 with saturated sodium bicarbonate aqueous solution and extracted with dichloromethane:methanol=10:1 (40 mL×3 times), and the organic phase was dried over sodium sulfate, filtered and concentrated to dryness to obtain the compound 26. Water (10 mL), acetonitrile (3 mL) and hydrochloric acid aqueous solution (0.5 mol/L, 0.2 mL) were sequentially added to compound 26, and the mixture was stirred at 25° C. for 15 minutes, and then freeze-dried to obtain the hydrochloride of compound 26. $^1$H NMR (400 MHz, DMSO-$d_6$) δ=10.83-10.45 (m, 1H), 8.93 (d, J=7.8 Hz, 1H), 8.65 (s, 2H), 8.58 (s, 1H), 8.36 (s, 1H), 8.20 (d, J=7.8 Hz, 1H), 7.79-7.75 (m, 2H), 7.55-7.50 (m, 1H), 7.48-7.43 (m, 1H), 6.46 (d, J=7.8 Hz, 1H), 5.47 (s, 2H), 4.86-4.76 (m, 2H), 4.74-4.66 (m, 2H), 4.40-4.28 (m, 1H), 4.11 (d, J=6.1 Hz, 2H), 2.95-2.75 (m, 2H), 2.07-1.92 (m, 2H), 1.74-1.55 (m, 5H); LCMS (ESI) m/z: 548.2 [M+1].

Embodiment 27

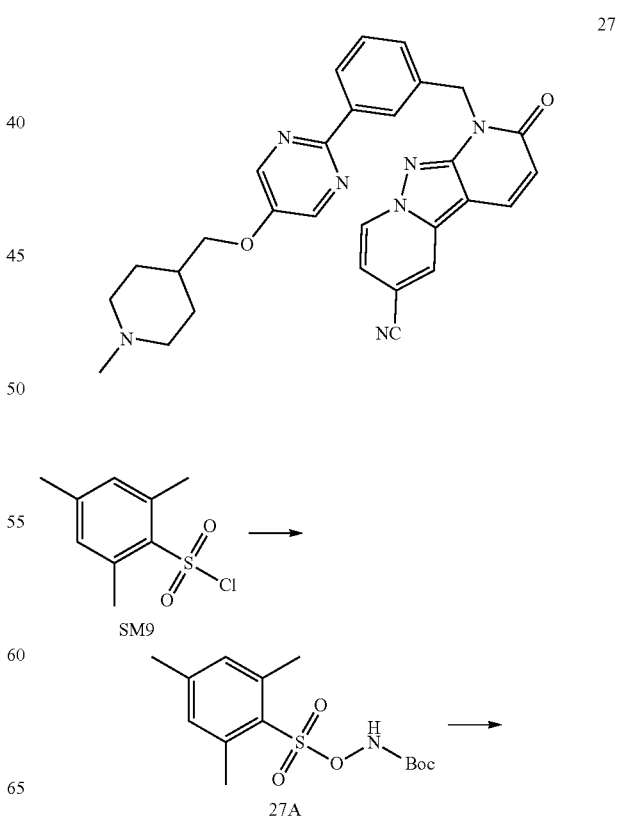

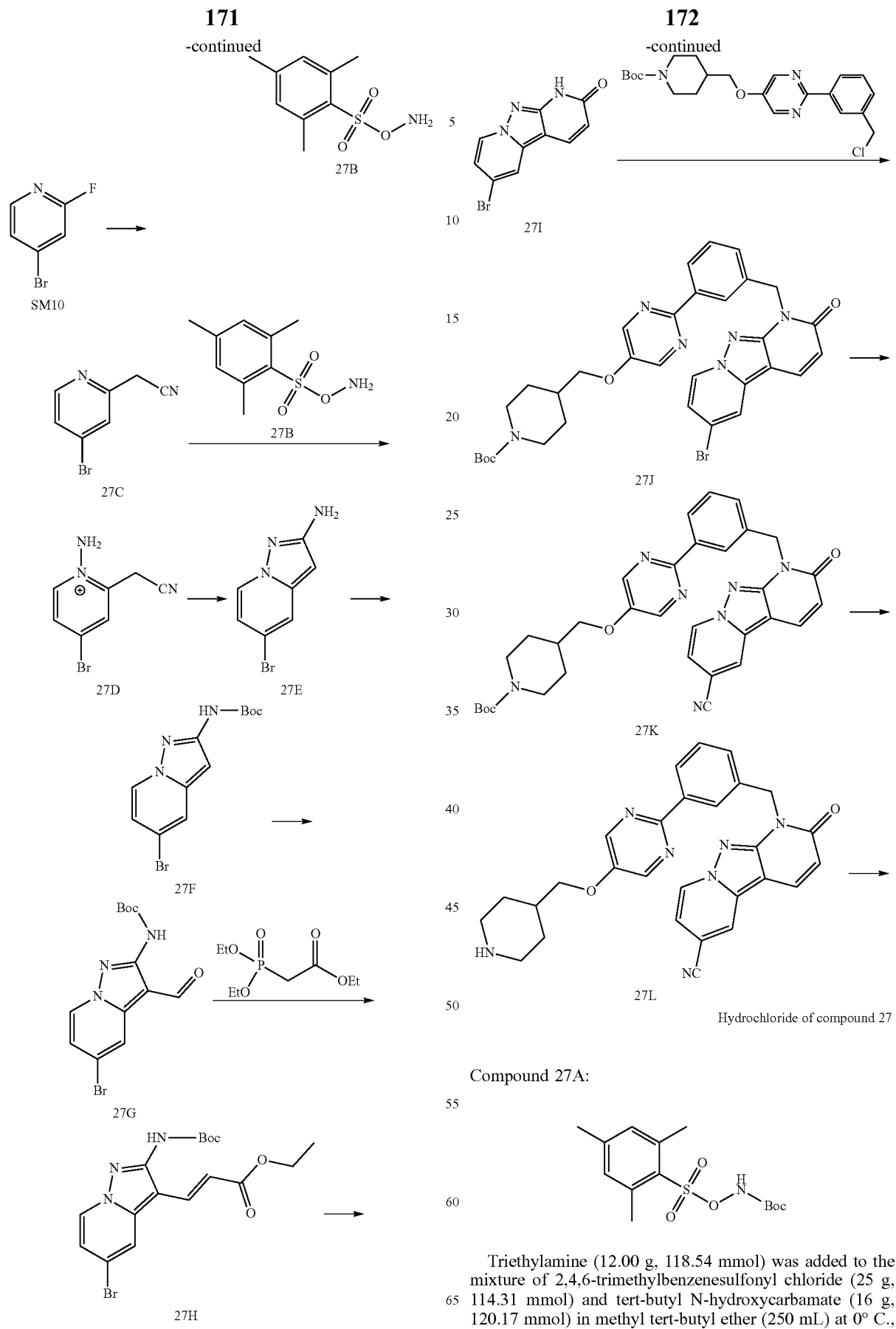
Compound 27A:
Triethylamine (12.00 g, 118.54 mmol) was added to the mixture of 2,4,6-trimethylbenzenesulfonyl chloride (25 g, 114.31 mmol) and tert-butyl N-hydroxycarbamate (16 g, 120.17 mmol) in methyl tert-butyl ether (250 mL) at 0° C., the mixture was stirred at 0-10° C. for 2 hours, then filtered, the filtrate was concentrated to dryness under reduced pressure, and the residue was slurried with n-hexane (50 mL×2 times), filtered and the filter cake was dried to obtain the compound 27A. $^1$H NMR (400 MHz, CDCl$_3$) δ=7.99-7.46 (m, 1H), 6.99 (s, 2H), 2.68 (s, 6H), 2.32 (s, 3H), 1.32 (s, 9H).
Compound 27B:

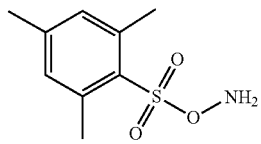

At 0° C., compound 33A (19 g, 60.24 mmol) was added to trifluoroacetic acid (57 mL), the mixture was stirred at 0° C. for 0.5 hours, water (20 mL) was added to the reaction mixture, the precipitated solid was filtered and dissolved in dichloromethane (100 mL), the organic phase was washed with saturated sodium bicarbonate aqueous solution (50 mL×1 time) and dried over sodium sulfate, filtered and concentrated, and the residue was dissolved in dichloromethane (50 mL), which was used directly used in the next step.
Compound 27C:

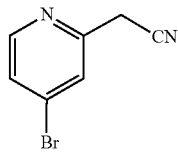

Under the protection of nitrogen at −78° C., LiHMDS (1 mol/L, tetrahydrofuran solution, 89.78 mL, 89.78 mmol) was added to a solution of 4-bromo-2-fluoropyridine (7.9 g, 44.89 mmol) and acetonitrile (3.69 g, 89.87 mmol) in tetrahydrofuran (90 mL). The mixture was stirred at −78° C. for 2 hours, the temperature was raised to 25° C., and the mixture was stirred at 25° C. for 2 hours, then saturated ammonium chloride aqueous solution (25 mL) was added thereto, then the mixture was extracted with (20 mL×3 times), the combined organic phase was washed with brine (20 mL×2 times), dried over sodium sulfate, filtered and concentrated, and the residue was purified by column chromatography (eluting with petroleum ether:ethyl acetate=50:1-20:1) to obtain the compound 27C. $^1$H NMR (400 MHz, CDCl$_3$) δ=8.34 (d, J=5.3 Hz, 1H), 7.57 (d, J=1.3 Hz, 1H), 7.39 (dd, J=1.8, 5.4 Hz, 1H), 3.86 (s, 2H); LCMS (ESI) m/z: 197.1 [M+1].
Compound 27D:

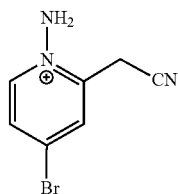 [SMILES: N#CCc1cc(Br)cc[n+]1N]

A solution of compound 27B (13 g, 60.39 mmol) in dichloromethane (50 mL) was added to a solution of compound 27C (6.3 g, 31.97 mmol) in dichloromethane (50 mL) at 25° C., and the mixture was heated to 25° C. and stirred for 2 hours, then filtered, the filter cake was washed with dichloromethane (40 mL×3 times) and dried to obtain the compound 27D. $^1$H NMR (400 MHz, DMSO-d$_6$) δ=8.44 (d, J=7.3 Hz, 1H), 7.78 (d, J=1.6 Hz, 1H), 6.87 (dd, J=2.3, 7.3 Hz, 1H), 6.76 (s, 2H), 6.48-6.28 (m, 2H).
Compound 27E:

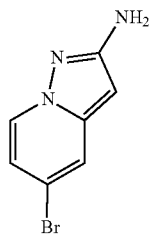

Potassium carbonate (5.38 g, 38.90 mmol) was added to a solution of compound 27D (8 g, 19.40 mmol) in methanol (70 mL) at 0° C., the mixture was stirred at 25° C. for 2 hours and concentrated to dryness under reduced pressure, water (40 mL) was added to the residue and extracted with dichloromethane:methanol=10:1 (50 mL×4 times), the organic phases were combined and dried over sodium sulfate, filtered, and concentrated to dryness under reduced pressure to obtain the compound 27E. $^1$H NMR (400 MHz, DMSO-d$_6$) δ=8.21 (d, J=7.3 Hz, 1H), 7.53 (d, J=1.8 Hz, 1H), 6.60 (dd, J=2.3, 7.2 Hz, 1H), 5.63 (s, 1H), 5.44 (s, 2H); LCMS (ESI) m/z: 212.0 [M+1].
Compound 27F:

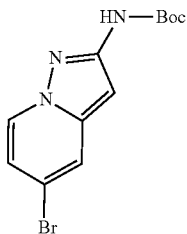 [SMILES: CC(C)(C)OC(=O)Nc1cc2cc(Br)ccn2n1]

DMAP (260 mg, 2.13 mmol) and Boc$_2$O (5.42 g, 24.83 mmol) were added to a solution of compound 27E (8 g, 19.40 mmol) in dioxane (45 mL) at 25° C., and the mixture was stirred at 25° C. for 0.5 hours, the reaction mixture was diluted with water (40 mL) and extracted with dichloromethane (70 mL×2 times), the organic phase was combined and concentrated to dryness under reduced pressure, and the residue was purified by column chromatography (eluting with petroleum ether:ethyl acetate=50:1-10:1) to obtain the compound 27F. $^1$H NMR (400 MHz, DMSO-d$_6$) δ=10.13 (br s, 1H), 8.44 (d, J=7.3 Hz, 1H), 7.85 (d, J=1.8 Hz, 1H), 6.87 (dd, J=2.1, 7.3 Hz, 1H), 6.62 (s, 1H), 1.48 (s, 9H); LCMS (ESI) m/z: 314.2 [M+3].

Compound 27G:

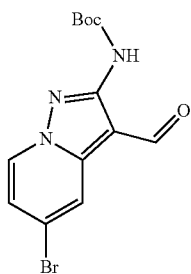 [SMILES: CC(C)(C)OC(=O)Nc1nn2ccc(Br)cc2c1C=O]

DMF (329 mg, 4.50 mmol, 0.35 mL) was added to tetrahydrofuran (10 mL), cooled to 0° C., and phosphorus oxychloride (1.03 g, 6.71 mmol, 0.62 mL) was slowly added dropwise under the protection of nitrogen, the mixture was stirred at 0° C. for 0.5 hours. Then compound 27F (0.7 g, 2.24 mmol) was dissolved in tetrahydrofuran (2 mL) and added dropwise to the reaction mixture at 0° C., after the addition, the mixture was stirred at 40° C. for 0.5 hours. Saturated sodium bicarbonate aqueous solution (15 mL) was added to the reaction mixture, and the mixture was extracted with dichloromethane (20 mL×2). The organic phases were combined, dried over anhydrous sodium sulfate, filtered and concentrated to dryness, and the residue was purified by column chromatography (eluting with petroleum ether:dichloromethane=10:1 to 1:1) to obtain the compound 27G. $^1$H NMR (400 MHz, DMSO-$d_6$) δ=9.95 (s, 1H), 9.91 (s, 1H), 8.68 (d, J=7.2 Hz, 1H), 8.30-8.21 (m, 1H), 7.30 (dd, J=2.3, 7.2 Hz, 1H), 1.43 (s, 9H).

Compound 27H:

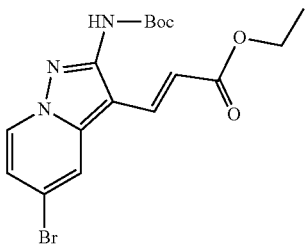 [SMILES: CCOC(=O)/C=C/c1c(NC(=O)OC(C)(C)C)nn2ccc(Br)cc12]

Compound 27H was prepared according to the method of compound 6D by replacing compound 6C with compound 27G. $^1$H NMR (400 MHz, DMSO-$d_6$) δ=9.67 (s, 1H), 8.65 (d, J=7.2 Hz, 1H), 8.38-8.28 (m, 1H), 7.70 (d, J=16.3 Hz, 1H), 7.22-7.16 (m, 1H), 6.34 (d, J=16.3 Hz, 1H), 4.17 (q, J=7.1 Hz, 2H), 1.45 (s, 9H), 1.20 (t, J=7.1 Hz, 3H).

Compound 27I:

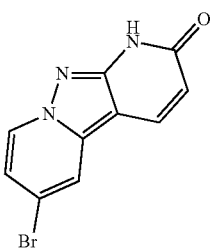 [SMILES: O=c1ccc2c(nn3ccc(Br)cc23)[nH]1]

Compound 27I was prepared according to the method of hydrochloride of compound 6G by replacing compound 6F with compound 27H. $^1$H NMR (400 MHz, DMSO-$d_6$) δ=12.11 (br s, 1H), 8.73 (d, J=7.3 Hz, 1H), 8.44 (d, J=1.5 Hz, 1H), 8.13 (d, J=9.4 Hz, 1H), 7.23 (dd, J=1.9, 7.2 Hz, 1H), 6.16 (d, J=9.4 Hz, 1H); LCMS (ESI) m/z: 266.1 [M+3].

Compound 27J:

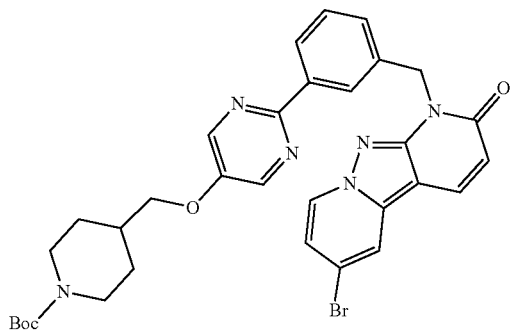 [SMILES: CC(C)(C)OC(=O)N1CCC(COc2cnc(-c3cccc(Cn4c(=O)ccc5c4nn4ccc(Br)cc54)c3)nc2)CC1]

Compound 27J was prepared according to the method of compound 6F by replacing compound 6D with compound 27I. $^1$H NMR (400 MHz, DMSO-$d_6$) δ=8.81 (d, J=7.4 Hz, 1H), 8.61 (s, 2H), 8.52 (d, J=1.6 Hz, 1H), 8.28-8.22 (m, 2H), 8.20-8.14 (m, 1H), 7.49-7.40 (m, 2H), 7.32-7.23 (m, 1H), 6.37 (d, J=9.4 Hz, 1H), 5.43 (s, 2H), 4.05 (d, J=6.4 Hz, 2H), 4.02-3.92 (m, 2H), 2.74 (br s, 2H), 1.97 (br d, J=3.8 Hz, 1H), 1.76 (br d, J=10.8 Hz, 2H), 1.20-1.12 (m, 2H); LCMS (ESI) m/z: 647.4 [M+3].

Compound 27K:

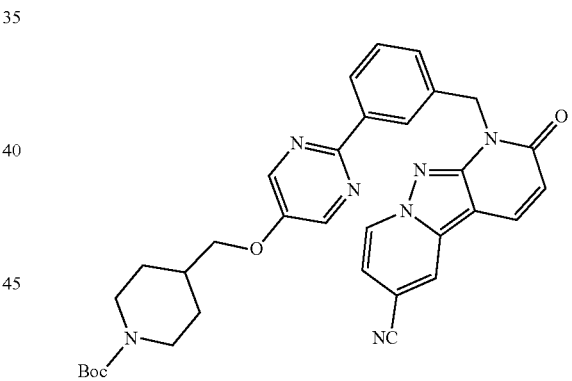

Compound 27K was prepared according to the method of compound 6I by replacing compound 6H with compound 27J, and replacing the thin-layer silica gel chromatography with silica gel column chromatography (eluting with dichloromethane:methanol=1:0-50:1). $^1$H NMR (400 MHz, DMSO-$d_6$) δ=9.48 (dd, J=0.8, 7.2 Hz, 1H), 9.40 (s, 1H), 9.30 (s, 2H), 9.09 (d, J=7.7 Hz, 1H), 8.97-8.92 (m, 1H), 8.72 (d, J=9.4 Hz, 1H), 8.47 (br s, 1H), 8.04-8.00 (m, 1H), 7.92 (dd, J=1.9, 7.2 Hz, 1H), 7.47 (d, J=9.4 Hz, 1H), 6.45 (s, 2H), 4.80 (d, J=6.3 Hz, 2H), 3.63 (br s, 2H), 2.88 (br s, 1H), 2.71 (br d, J=12.8 Hz, 2H), 2.34-2.33 (m, 9H), 2.24-2.13 (m, 4H); LCMS (ESI) m/z: 592.3 [M+1].

Trifluoroacetate of Compound 27L:

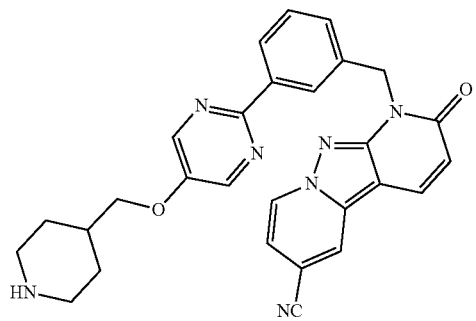 [SMILES: N#Cc1ccn2nc3c(ccc(=O)n3Cc3cccc(-c4ncc(OCC5CCNCC5)cn4)c3)c2c1]

Embodiment 28

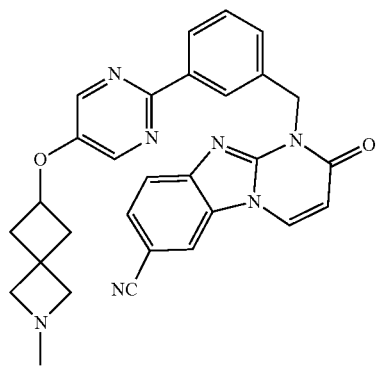

The trifluoroacetate of compound 27L was prepared according to the method of trifluoroacetate of compound 24C by replacing compound 11A with compound 27K. $^1$H NMR (400 MHz, CD$_3$OD) δ=8.88 (dd, J=0.8, 7.2 Hz, 1H), 8.60-8.57 (m, 1H), 8.53 (s, 2H), 8.39 (s, 1H), 8.26 (d, J=9.3 Hz, 1H), 8.21 (d, J=8.0 Hz, 1H), 7.56 (s, 1H), 7.45-7.39 (m, 1H), 7.31 (dd, J=1.8, 7.2 Hz, 1H), 6.55 (d, J=9.4 Hz, 1H), 5.61 (s, 2H), 4.11 (d, J=5.9 Hz, 2H), 3.48 (br d, J=12.4 Hz, 2H), 3.13-3.02 (m, 2H), 2.32-2.19 (m, 1H), 2.13 (br d, J=13.9 Hz, 2H), 1.70-1.58 (m, 2H); LCMS (ESI) m/z: 492.4 [M+1].

Hydrochloride of Compound 27:

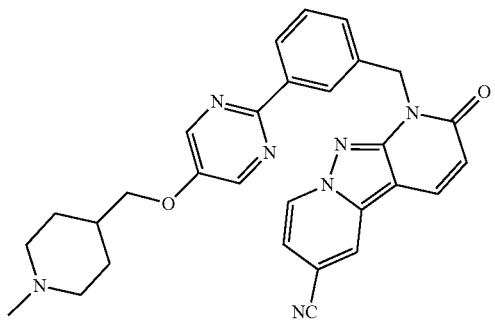 [SMILES: CN1CCC(COc2cnc(-c3cccc(Cn4c(=O)ccc5c4nn4ccc(C#N)cc54)c3)nc2)CC1]

Hydrochloride of compound 27 was prepared according to the method of hydrochloride of compound 24 by replacing trifluoroacetate of compound 24C with trifluoroacetate of compound 27L. $^1$H NMR (400 MHz, DMSO-d$_6$) δ=10.02 (br s, 1H), 9.04 (d, J=7.0 Hz, 1H), 8.87 (s, 1H), 8.69-8.58 (m, 2H), 8.36-8.23 (m, 2H), 8.17 (br s, 1H), 7.46-7.33 (m, 3H), 6.50 (d, J=9.4 Hz, 1H), 5.47 (s, 2H), 4.08 (br d, J=6.0 Hz, 2H), 3.47-3.45 (m, 2H), 3.03-2.89 (m, 2H), 2.78-2.60 (m, 3H), 2.12-1.93 (m, 3H), 1.69-1.50 (m, 2H); LCMS (ESI) m/z: 506.4 [M+1].

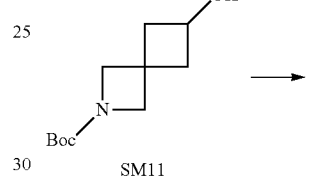

SM11

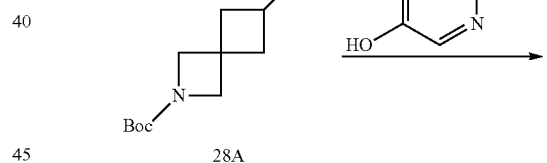

28A

28B

-continued

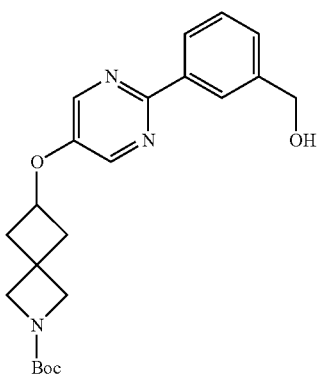
28C

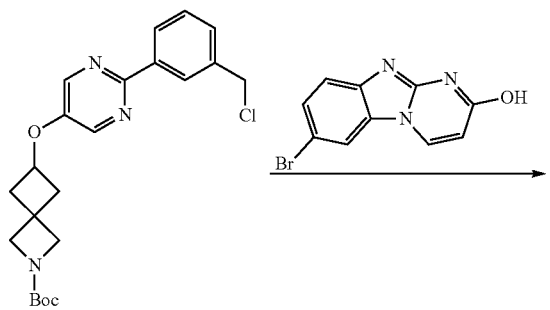
28D

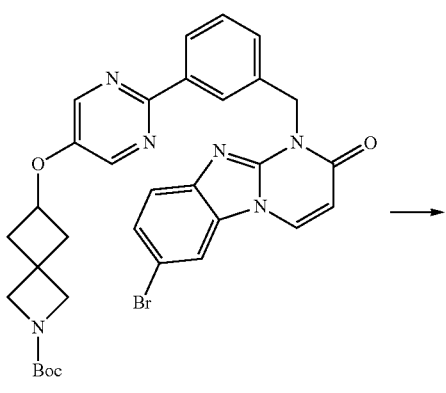
28E

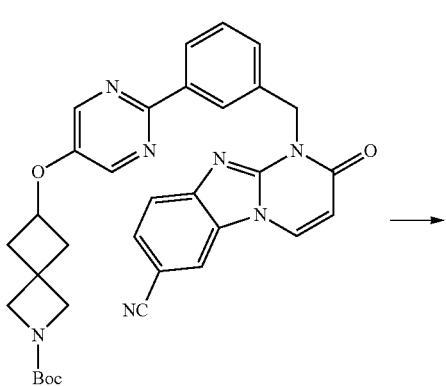
28F

-continued

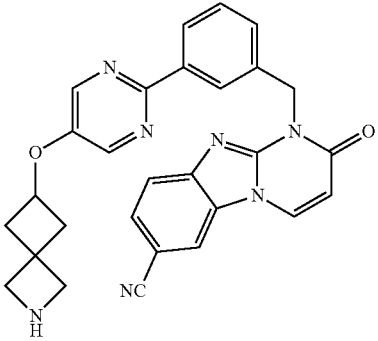
28G

Hydrochloride of compound 28

Compound 28A:

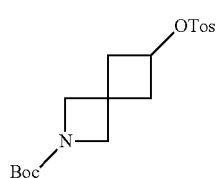

Triethylamine (1.2 mL, 8.62 mmol) was added to a mixture of 6-hydroxy-2-azaspiro[3.3]heptane-2-carboxylic acid tert-butyl ester (1.18 g, 5.53 mmol) and DMAP (180 mg, 1.47 mmol) in dichloromethane (20 mL), the mixture was cooled to 0° C., then p-toluenesulfonyl chloride (1.27 g, 6.64 mmol) was added to the reaction mixture at 0° C., after the addition, the temperature was raised to 25° C. and the mixture was stirred at 25° C. for 1 hour, ethyl acetate (80 mL) was added thereto, and the mixture was successively washed with hydrochloric acid aqueous solution (0.5 mol/L, 60 mL×2 times) and saturated sodium bicarbonate aqueous solution (50 mL×2 times) and brine (50 mL×2 times), dried over sodium sulfate, filtered, and the filtrate was concentrated to obtain the compound 28A. $^1$H NMR (400 MHz, CDCl$_3$) δ=7.76 (d, J=8.3 Hz, 2H), 7.34 (d, J=8.1 Hz, 2H), 4.77-4.58 (m, 1H), 3.84 (d, J=1.2 Hz, 4H), 2.51-2.43 (m, 5H), 2.35-2.24 (m, 2H), 1.40 (s, 9H). LCMS (ESI) m/z: 312.1 [M-55].

Compound 28B:

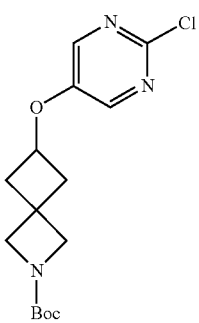 [SMILES: CC(C)(C)OC(=O)N1CC2(CC(Oc3cnc(Cl)nc3)C2)C1]

Compound 28B was prepared according to the method of compound 1H by replacing compound 1G with compound 28A. LCMS (ESI) m/z: 270.3 [M-55].

Compound 28C:

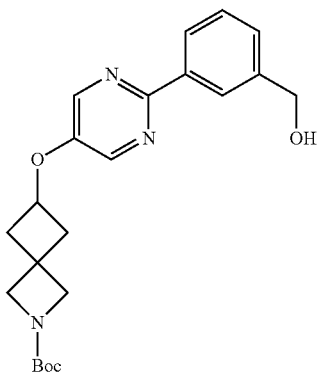 [SMILES: CC(C)(C)OC(=O)N1CC2(CC(Oc3cnc(-c4cccc(CO)c4)nc3)C2)C1]

Compound 28C was prepared according to the method of compound 11 by replacing compound 1H with compound 28B, and replacing the purification method with silica gel column chromatography (eluting with petroleum ether:ethyl acetate=5:1-2:1). $^1$H NMR (400 MHz, CDCl$_3$) δ=8.35 (s, 2H), 8.33 (s, 1H), 8.29-8.22 (m, 1H), 7.49-7.44 (m, 2H), 4.78 (br s, 2H), 4.72-4.61 (m, 1H), 3.99 (s, 2H), 3.96 (s, 2H), 2.84-2.71 (m, 2H), 2.46-2.34 (m, 2H), 1.44 (s, 9H); LCMS (ESI) m/z: 398.2 [M+1].

Compound 28D:

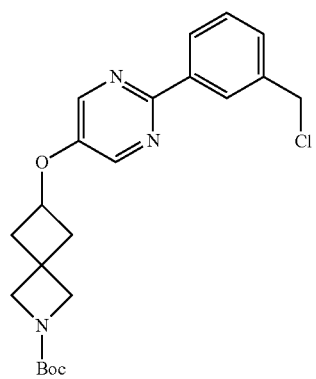 [SMILES: CC(C)(C)OC(=O)N1CC2(CC(Oc3cnc(-c4cccc(CCl)c4)nc3)C2)C1]

Compound 28D was prepared according to the method of compound 6E by replacing compound 11 with compound 28C. $^1$H NMR (400 MHz, CDCl$_3$) δ=8.38 (s, 1H), 8.37 (s, 2H), 8.34-8.27 (m, 1H), 7.53-7.43 (m, 2H), 4.76-4.63 (m, 3H), 4.01 (s, 2H), 3.97 (s, 2H), 2.86-2.72 (m, 2H), 2.50-2.36 (m, 2H), 1.45 (s, 9H); LCMS (ESI) m/z: 416.2 [M+1].

Compound 28E:

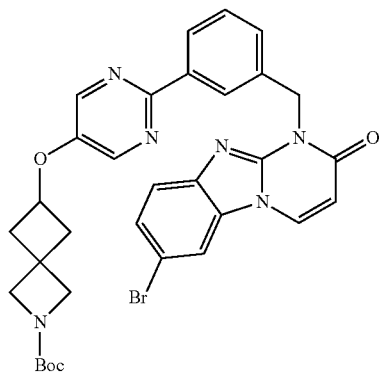 [SMILES: CC(C)(C)OC(=O)N1CC2(CC(Oc3cnc(-c4cccc(Cn5c(=O)ccn6c7cc(Br)ccc7nc56)c4)nc3)C2)C1]

Compound 28E was prepared according to the method of compound 6F by replacing compound 6D with compound 9C1 and replacing the compound 6E with compound 28D. $^1$H NMR (400 MHz, CDCl$_3$) δ=8.56 (s, 1H), 8.33 (s, 2H), 8.23 (d, J=7.6 Hz, 1H), 7.97 (d, J=7.6 Hz, 1H), 7.68-7.62 (m, 2H), 7.58 (d, J=8.6 Hz, 1H), 7.50-7.44 (m, 1H), 7.41 (t, J=7.8 Hz, 1H), 6.23 (d, J=7.8 Hz, 1H), 5.57 (s, 2H), 4.68 (quin, J=6.7 Hz, 1H), 4.00 (s, 2H), 3.96 (s, 2H), 2.77 (ddd, J=3.1, 7.0, 10.5 Hz, 2H), 2.44-2.35 (m, 2H), 1.45 (s, 9H); LCMS (ESI) m/z: 645.3 [M+3].

Compound 28F

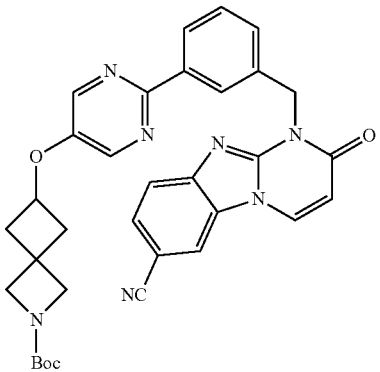 [SMILES: CC(C)(C)OC(=O)N1CC2(CC(Oc3cnc(-c4cccc(Cn5c(=O)ccn6c7cc(C#N)ccc7nc56)c4)nc3)C2)C1]

Compound 28F was prepared according to the method of compound 6I by replacing compound 6H with compound 28E, replacing thin-layer silica gel chromatography with silica gel column chromatography (eluting with petroleum ether:ethyl acetate=3:1 to 1:1). LCMS (ESI) m/z: 590.2 [M+1].

Compound 28G:

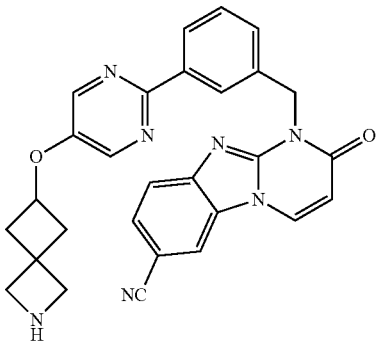 [SMILES: N#Cc1ccc2nc3n(Cc4cccc(-c5ncc(OC6CC7(CNC7)C6)cn5)c4)c(=O)ccn3c2c1]

Compound 28G was prepared according to the method of compound 5J by replacing compound 5I with compound 28F. LCMS (ESI) m/z: 490.1 [M+1].

183

Hydrochloride of Compound 28:

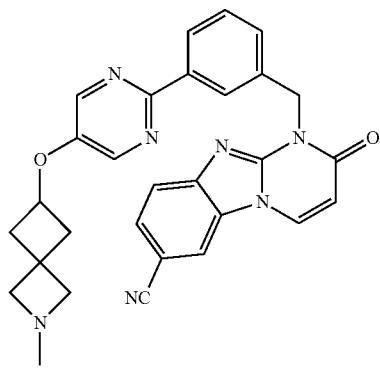 [SMILES: CN1CC2(CC(Oc3cnc(-c4cccc(Cn5c(=O)ccn6c7cc(C#N)ccc7nc56)c4)nc3)C2)C1]

The hydrochloride of compound 28 was prepared according to the method of compound 1 by replacing compound 1L with compound 28G and replacing the high performance liquid chromatography (formic acid system) with high performance liquid chromatography (hydrochloric acid system). $^1$H NMR (400 MHz, CD$_3$OD) δ=8.76 (d, J=7.9 Hz, 1H), 8.42 (s, 2H), 8.40 (s, 1H), 8.32 (s, 1H), 8.27-8.21 (m, 1H), 7.80-7.76 (m, 1H), 7.75-7.71 (m, 1H), 7.64-7.59 (m, 1H), 7.49-7.42 (m, 1H), 6.38 (d, J=7.9 Hz, 1H), 5.59 (s, 2H), 4.13 (s, 1H), 3.37 (s, 4H), 2.93 (s, 3H), 2.92-2.87 (m, 2H), 2.58-2.45 (m, 2H); LCMS (ESI) m/z: 504.0 [M+1].

Embodiment 29

29

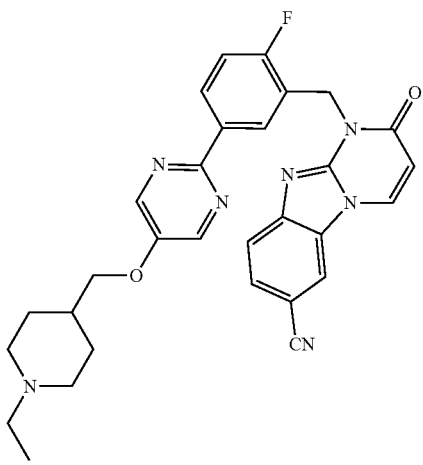

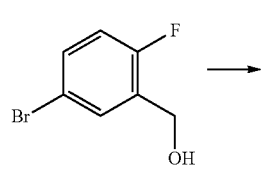

SM12

184

-continued

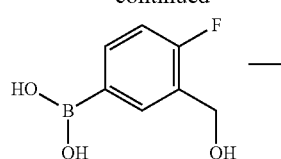

29A

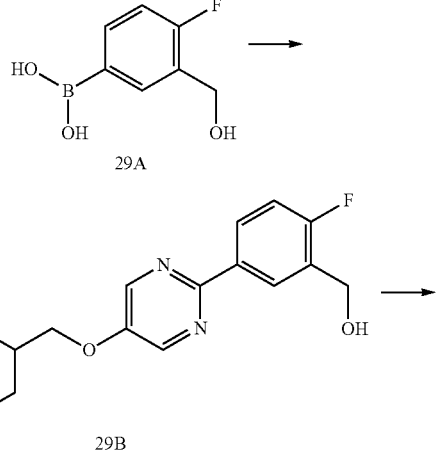

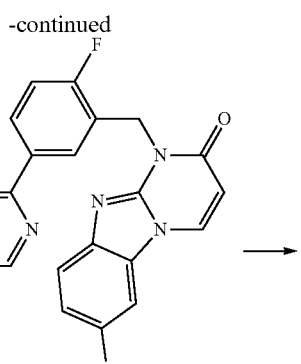

29F

Hydrochloride of compound 29

Compound 29A:

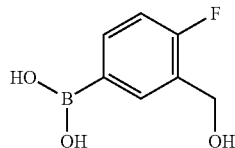 [SMILES: OCc1cc(B(O)O)ccc1F]

Under the protection of nitrogen at −78° C., n-butyl lithium (2.5 mol/L hexane solution, 21.46 mL, 53.65 mmol) was added to a solution of (5-bromo-2-fluoro-phenyl)methanol (5 g, 24.39 mmol) in tetrahydrofuran (50 mL), 21.46 mL, 53.65 mmol). The mixture was stirred at −78° C. for 15 minutes, triisopropyl borate (10.09 g, 53.65 mmol) was added thereto at −78° C., after the addition, the reaction mixture was heated to 25° C. and stirred at 25° C. for 1 hour, water (30 mL) was added to the reaction mixture at 25° C., the mixture was extracted with ethyl acetate (20 mL×2 times), the pH value of the aqueous phase was adjusted to 3 with hydrochloric acid aqueous solution (2 mol/L), then extracted with ethyl acetate (250 mL×2 times), the organic phase was dried over sodium sulfate, filtered and concentrated to obtain the compound 29A. $^1$H NMR (400 MHz, DMSO-$d_6$) δ=7.97-7.90 (m, 1H), 7.75-7.70 (m, 1H), 7.13-7.05 (m, 1H), 4.54 (s, 2H).

Compound 29B:

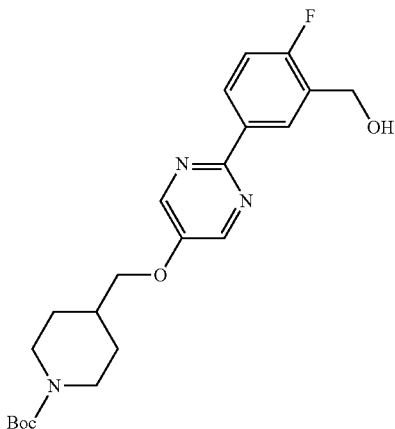 [SMILES: CC(C)(C)OC(=O)N1CCC(COc2cnc(-c3ccc(F)c(CO)c3)nc2)CC1]

According to the method of compound 1I by replacing the compound 3-hydroxymethyl phenylboronic acid with compound 29A, and replacing the purification method with silica gel column chromatography purification (eluting with petroleum ether:ethyl acetate=4:1 to dichloromethane:methanol=30:1), and then slurried with a mixed solvent of petroleum ether:ethyl acetate=10:1 to obtain the compound 29B. $^1$H NMR (400 MHz, CDCl$_3$) δ=8.50-8.40 (m, 3H), 8.35-8.23 (m, 1H), 7.20-7.07 (m, 1H), 4.90-4.80 (m, 2H), 4.18 (br s, 2H), 3.98-3.90 (m, 2H), 2.85-2.65 (m, 2H), 1.97-2.02 (m, 1H), 1.88-1.77 (m, 2H), 1.44 (s, 9H), 1.40-1.23 (m, 2H); LCMS (ESI) m/z: 418.1 [M+1].

Compound 29C:

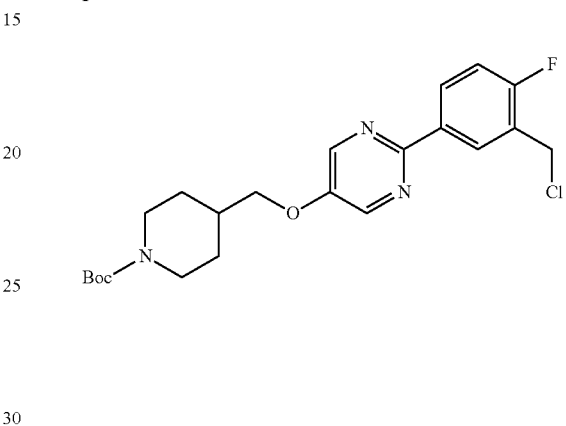

Compound 29C was prepared according to the method of compound 6E by replacing compound 1I with compound 29B. $^1$H NMR (400 MHz, CDCl$_3$) δ=8.49-8.42 (m, 3H), 8.39-8.27 (m, 1H), 7.20-7.14 (m, 1H), 4.70 (s, 2H), 4.19 (br s, 2H), 3.96 (d, J=6.4 Hz, 2H), 2.73 (br t, J=12.2 Hz, 2H), 2.10-1.98 (m, 1H), 1.80 (br d, J=12.6 Hz, 2H), 1.48 (s, 9H), 1.38-1.20 (m, 2H); LCMS (ESI) m/z: 380.2 [M-55].

Compound 29D:

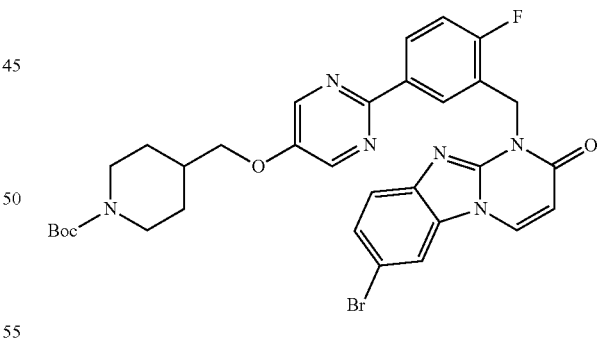

Compound 29D was prepared according to the method of compound 6F by replacing compound 6D with compound 9C1 and replacing the compound 6E with compound 29C. $^1$H NMR (400 MHz, DMSO-$d_6$) δ ppm 8.92 (d, J=7.82 Hz, 1H) 8.54 (s, 2H) 8.31 (d, J=1.71 Hz, 1H) 8.26-8.17 (m, 1H) 8.08 (dd, J=7.46, 2.08 Hz, 1H) 7.56-7.53 (m, 1H) 7.46 (dd, J=8.56, 1.96 Hz, 1H) 7.35 (dd, J=9.78, 8.80 Hz, 1H) 6.40 (d, J=7.83 Hz, 1H) 5.46 (s, 2H) 4.02-3.98 (m, 2H) 3.94 (d, J=10.88 Hz, 2H) 2.75-2.66 (m, 2H) 1.96-1.85 (m, 1H) 1.76-1.67 (m, 2H) 1.38 (s, 9H) 1.18-1.09 (m, 2H); LCMS (ESI) m/z: 664.9 [M+3].

Compound 29E:

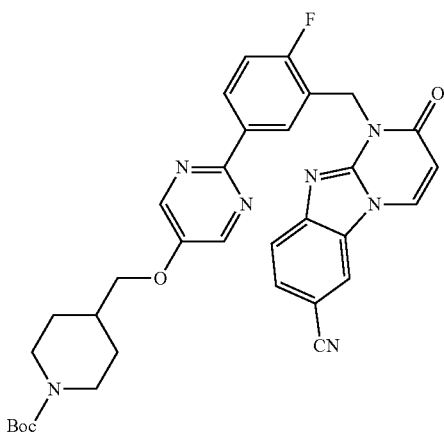 [SMILES: CC(C)(C)OC(=O)N1CCC(COc2cnc(-c3ccc(F)c(Cn4c(=O)ccn5c6cc(C#N)ccc6nc45)c3)nc2)CC1]

Compound 29E was prepared according to the method of compound 61 by replacing the compound 6H with compound 29D, and replacing thin-layer silica gel chromatography with silica gel column chromatography purification (eluting with petroleum ether:ethyl acetate=10:1 to 2:1 to dichloromethane:methanol=80:1). $^1$H NMR (400 MHz, DMSO-$d_6$) δ ppm 8.96 (d, J=7.83 Hz, 1H) 8.59-8.53 (m, 3H) 8.33-8.20 (m, 1H) 8.13 (dd, J=7.46, 2.08 Hz, 1H) 7.78-7.70 (m, 2H) 7.44-7.33 (m, 1H) 6.51 (d, J=7.70 Hz, 1H) 5.49 (s, 2H) 4.01 (d, J=6.48 Hz, 2H) 3.96 (d, J=11.25 Hz, 2H) 2.82-2.65 (m, 2H) 1.99-1.87 (m, 1H) 1.78-1.68 (m, 2H) 1.39 (s, 9H) 1.20-1.07 (m, 2H); LCMS (ESI) m/z: 554.9 [M-55].

Compound 29F:

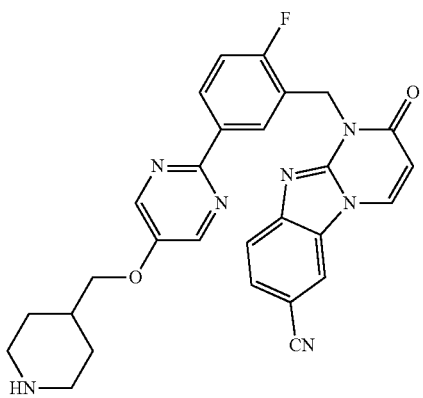 [SMILES: N#Cc1ccc2nc3n(Cc4cc(-c5ncc(OCC6CCNCC6)cn5)ccc4F)c(=O)ccn3c2c1]

Compound 29F was prepared according to the method of compound 5J by replacing compound 5I with compound 29E. $^1$H NMR (400 MHz, DMSO-$d_6$) δ ppm 8.96 (d, J=7.88 Hz, 1H) 8.61-8.54 (m, 3H) 8.27-8.20 (m, 1H) 8.13 (dd, J=7.38, 2.13 Hz, 1H) 7.80-7.74 (m, 2H) 7.39-7.31 (m, 1H) 6.50 (d, J=7.75 Hz, 1H) 5.49 (s, 2H) 3.97 (d, J=6.50 Hz, 2H) 2.98 (d, J=11.88 Hz, 2H) 1.95-1.78 (m, 1H) 1.69 (d, J=10.88 Hz, 2H) 1.22-1.10 (m, 4H); LCMS (ESI) m/z: 510.4 [M+1].

Hydrochloride of Compound 29:

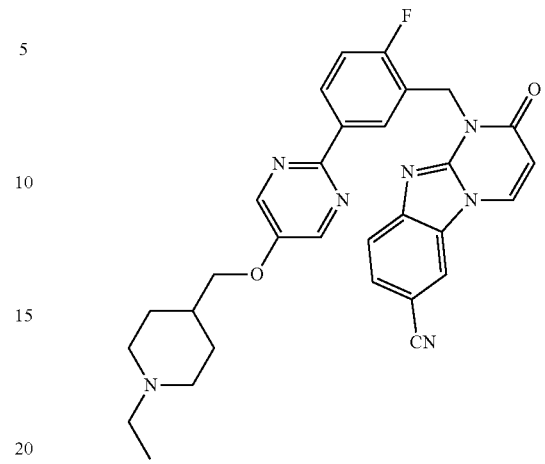

According to the method of compound 1 by replacing compound 1L with compound 29F and replacing the formaldehyde aqueous solution with acetaldehyde aqueous solution, the pH value of the mixture purified by high performance liquid preparative chromatography (formic acid system) was adjusted to 8 with saturated sodium bicarbonate aqueous solution, then extracted with dichloromethane:methanol=10:1 (20 mL×3 times), and the organic phases were combined and concentrated under reduced pressure to obtain compound 29. Water (30 mL) and acetonitrile (6 mL) were added to compound 29 (360 mg), then hydrochloric acid aqueous solution (1 mol/1, 0.8 mL) was added thereto and stirred at 25° C. for 0.5 hours, the mixture was freeze-dried to obtain the hydrochloride of compound 29. $^1$H NMR (400 MHz, CD$_3$OD) δ ppm 8.78 (d, J=7.83 Hz, 1H) 8.44 (s, 2H) 8.31 (s, 1H) 8.30-8.25 (m, 1H) 8.12 (dd, J=7.40, 2.02 Hz, 1H) 7.75-7.67 (m, 2H) 7.25 (dd, J=9.72, 8.86 Hz, 1H) 6.39 (d, J=7.82 Hz, 1H) 5.62 (s, 2H) 4.06 (d, J=5.62 Hz, 2H) 3.63 (d, J=12.59 Hz, 2H) 3.19 (q, J=7.42 Hz, 2H) 3.08-2.92 (m, 2H) 2.24-2.08 (m, 3H) 1.75-1.61 (m, 2H) 1.36 (t, J=7.34 Hz, 3H); LCMS (ESI) m/z: 538.5 [M+1].

Embodiment 30

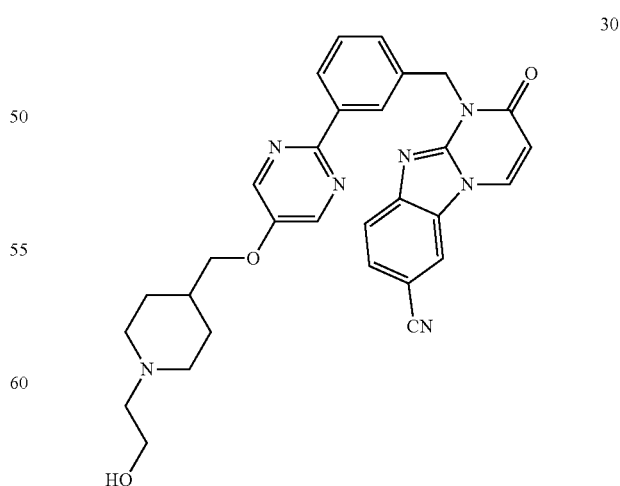

Potassium carbonate (70 mg, 506.49 μmol) was added to a mixture of trifluoroacetate of compound 24C (100 mg, 165.13 μmol, trifluoroacetate) and 2-bromoethanol (32 mg, 256.07 μmol) in DMF (3 mL). The reaction mixture was stirred at 80° C. for 0.5 hours and then cooled to room temperature, then filtered, the filtrate was concentrated to dryness, the residue was purified by high performance liquid chromatography (trifluoroacetic acid system), the pH value of the obtained mixture was adjusted to 8 by adding saturated sodium bicarbonate aqueous solution, then extracted with dichloromethane:methanol=10:1 (20 mL×3 times), the organic phases were combined and dried over anhydrous sodium sulfate, then concentrated under reduced pressure to obtain compound 30, then water (5 mL), acetonitrile (10 mL) and hydrochloric acid aqueous solution (1 mol/L, 0.13 mL) were sequentially added to compound 30, and stirred at 25° C. for 15 minutes, the mixture was concentrated under reduced pressure to obtain the hydrochloride of compound 30. $^1$H NMR (400 MHz, DMSO-$d_6$) δ=9.60 (br s, 1H), 8.94 (d, J=7.7 Hz, 1H), 8.71-8.62 (m, 2H), 8.60-8.55 (m, 1H), 8.58 (s, 1H), 8.36 (s, 1H), 8.20 (d, J=7.7 Hz, 1H), 7.84-7.71 (m, 2H), 7.55-7.49 (m, 1H), 7.48-7.41 (m, 1H), 6.47 (d, J=7.8 Hz, 1H), 5.47 (s, 2H), 4.09 (d, J=6.1 Hz, 2H), 3.85-3.72 (m, 2H), 3.57 (br d, J=11.5 Hz, 2H), 3.14 (br d, J=4.8 Hz, 2H), 3.07-2.93 (m, 2H), 2.08 (br s, 1H), 1.98 (br d, J=13.4 Hz, 2H), 1.77-1.58 (m, 2H); LCMS (ESI) m/z: 536.3 [M+1].

Embodiment 31

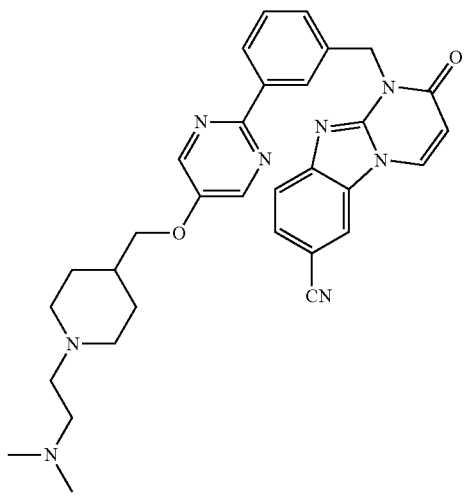

31

Compound 31A:

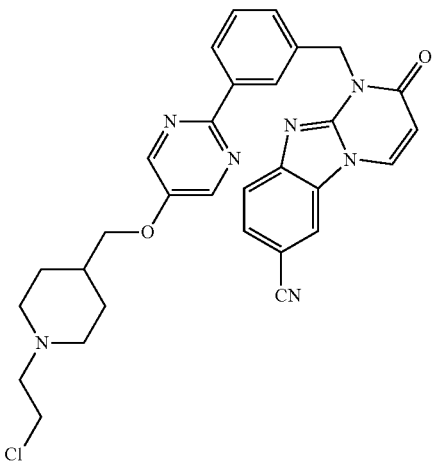 [SMILES: N#Cc1ccc2nc3n(Cc4cccc(-c5ncc(OCC6CCN(CCCl)CC6)cn5)c4)c(=O)ccn3c2c1]

NaBH(OAc)$_3$ (26 mg, 122.06 μmol) and acetic acid (5 mg, 81.38 μmol) were added to a mixture of compound 24C (40 mg, 81.38 μmol) and 2-chloroacetaldehyde (16 mg, 81.38 μmol) in dichloromethane (5 mL) and methanol (0.5 mL). The reaction mixture was stirred at 25° C. for 2 hours, then the pH value was adjusted to 9 with sodium bicarbonate aqueous solution, extracted with dichloromethane:methanol=10:1 (20 mL×3 times), and the combined organic phase was dried over sodium sulfate, filtered and concentrated to dryness. The residue was purified by thin-layer silica gel chromatography (dichloromethane:methanol=10:1) to obtain the compound 31A. LCMS (ESI) m/z: 554.3 [M+1].

Compound 31:

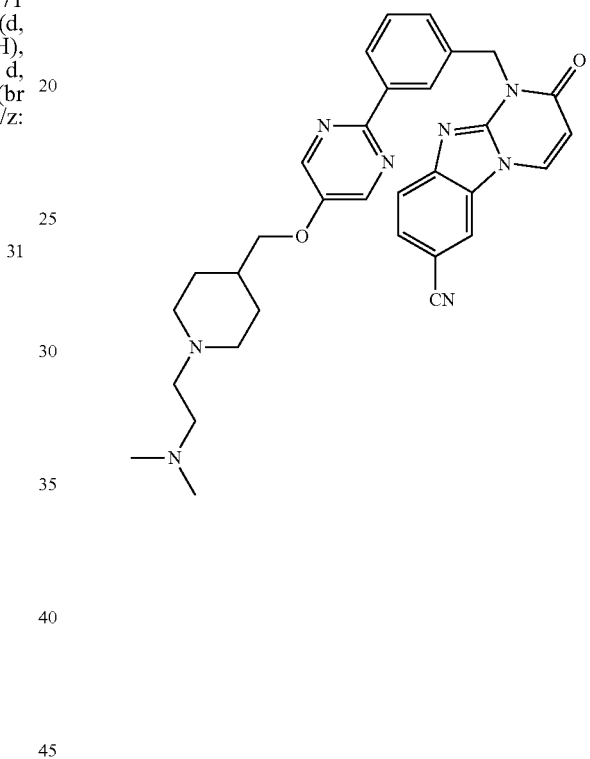

A solution of dimethylamine in tetrahydrofuran (2 mol/L, 0.1 mL, 0.2 mmol) was added to a mixture of compound 31A (10 mg, 18.05 μmol) in ethanol (2 mL). The reaction solution was stirred at 90° C. for 1 hour in a muffled tank and then cooled to room temperature and concentrated to dryness, the obtained crude product was purified by high performance liquid chromatography preparative chromatography (formic acid system), and the pH value of the obtained mixture was adjusted to 8 with saturated sodium bicarbonate aqueous solution then extracted with dichloromethane:methanol=10:1 (20 mL×3 times), the organic phase was combined and dried over anhydrous sodium sulfate, then concentrated to obtain the compound 31. LCMS (ESI) m/z: 563.4 [M+1].

Embodiment 32

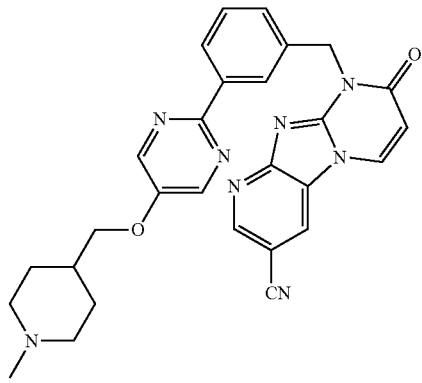

32

According to the method of compound 1 by replacing compound 1L with 8-oxo-9-(3-(5-(piperidin-4-ylmethoxy)pyrimidin-2-yl)benzyl)-8,9-dihydropyridine[2',3':4,5]imidazole[1,2-a]pyrimidine-3-carbonitrile, and replacing high performance liquid preparative chromatography (formic acid system) with high performance liquid preparative chromatography separation (trifluoroacetic acid system), saturated sodium bicarbonate aqueous solution (30 mL) was added to the obtained mixture, the pH value of the mixture was adjusted to 10 with 2 mol/L sodium hydroxide aqueous solution, and the mixture was extracted with dichloromethane (30 mL×3 times), the organic phase was combined and concentrated under reduced pressure to obtain the compound 32. Water (10 mL) was added to the obtained compound 32, the pH value of the mixture was adjusted to 2 with hydrochloric acid aqueous solution (3 mol/L), then freeze-dried to obtain the hydrochloride of compound 32. $^1$H NMR (400 MHz, CD$_3$OD) δ=8.69 (d, J=7.9 Hz, 1H), 8.66 (d, J=1.8 Hz, 1H), 8.54 (s, 2H), 8.41 (s, 1H), 8.35 (d, J=1.8 Hz, 1H), 8.23 (d, J=7.9 Hz, 1H), 7.63 (d, J=7.5 Hz, 1H), 7.44 (t, J=7.8 Hz, 1H), 6.44 (d, J=7.8 Hz, 1H), 5.56 (s, 2H), 4.32-4.06 (m, 2H), 3.65-3.55 (m, 2H), 3.17-3.03 (m, 2H), 2.91 (s, 3H), 2.28-2.12 (m, 3H), 1.79-1.65 (m, 2H); LCMS (ESI) m/z: 507.1 [M+1].

Embodiment 33

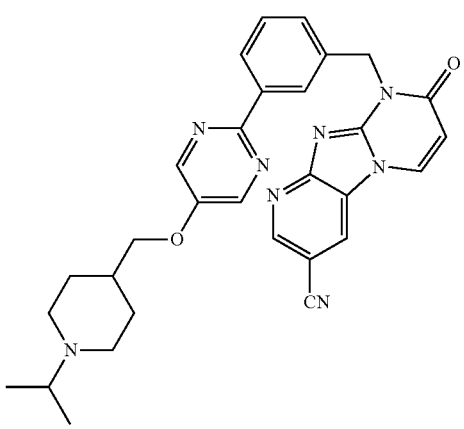 [SMILES: CC(C)N1CCC(COc2cnc(-c3cccc(Cn4c(=O)ccn5c6cc(Br)cnc6nc45)c3)nc2)CC1]

33

Compound 33A:

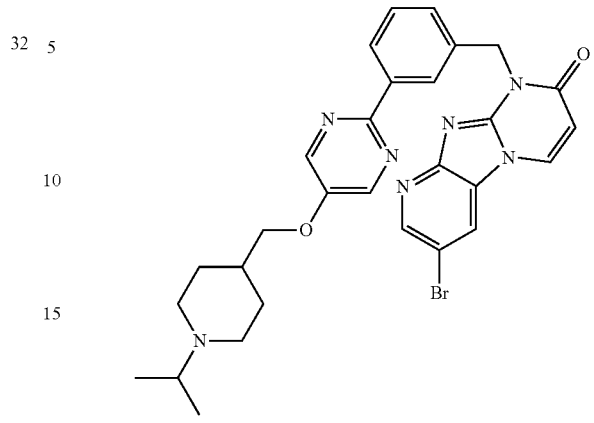

Potassium carbonate (50 mg, 361.77 μmol) and 2-iodopropane (80 mg, 470.61 μmol) were sequentially added to a mixture of trifluoroacetate of the compound 3-bromo-9-(3-(5-(piperidin-4-ylmethoxy)pyrimidin-2-yl)benzyl)pyridine[2',3':4,5]imidazole[1,2-a]pyrimidine-8(9H)-one (70 mg, 128.11 μmol, trifluoroacetate) in DMF (2 mL), the reaction mixture was stirred at 100° C. for 1 hour, then cooled to room temperature, and concentrated to dryness to obtain a crude product of the compound 33A. LCMS (ESI) m/z: 590.2 [M+3].

Hydrochloride of Compound 33:

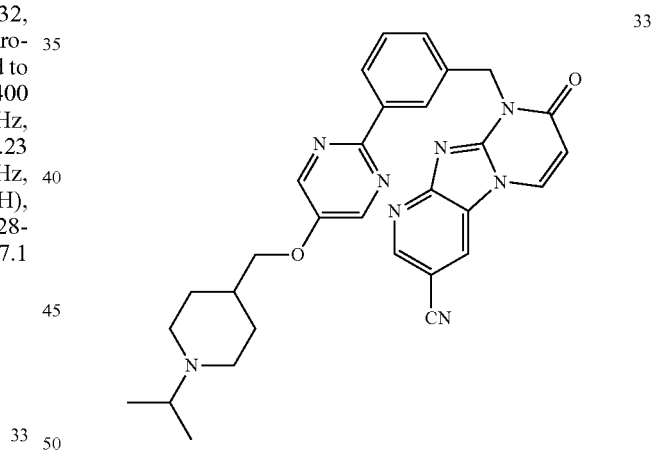

33

Compound 33A (75 mg, 127.44 μmol) and zinc cyanide (75 mg, 638.71 μmol) were added to DMF (2 mL), then zinc powder (30 mg, 458.79 μmol), dppf (35 mg, 63.13 μmol) and Pd$_2$(dba)$_3$ (30 mg, 32.76 μmol) were added thereto. The reaction system was stirred at 110° C. for 2 hours. The reaction system was diluted with saturated sodium bicarbonate aqueous solution (30 mL), and then extracted with dichloromethane (20 mL×3). The organic phases were combined, dried over anhydrous sodium sulfate, concentrated, purified by thin-layer silica gel chromatography (dichloromethane:methanol=7:1), and then purified by high performance liquid chromatography (trifluoroacetic acid system), then saturated sodium bicarbonate aqueous solution (30 mL) was added to the obtained mixture, and the pH value of the mixture was adjusted to 10 with 2 mol/L sodium hydroxide aqueous solution, then the mixture was extracted with dichloromethane (30 mL×3 times), the organic phases were combined and concentrated under reduced pressure to obtain compound 33. Water (10 mL) was added to compound 33, the pH value of the mixture was adjusted to 2 with hydrochloric acid aqueous solution (3 mol/L), the mixture was freeze-dried to obtain the hydrochloride of compound 33. $^1$H NMR (400 MHz, CD$_3$OD) δ=8.70 (d, J=7.8 Hz, 1H), 8.67 (d, J=1.8 Hz, 1H), 8.54 (s, 2H), 8.43 (s, 1H), 8.37 (d, J=1.8 Hz, 1H), 8.25 (d, J=7.9 Hz, 1H), 7.64 (d, J=7.5 Hz, 1H), 7.49-7.42 (m, 1H), 6.45 (d, J=7.8 Hz, 1H), 5.58 (s, 2H), 4.13 (d, J=5.6 Hz, 2H), 3.57-3.53 (m, 2H), 3.18-3.09 (m, 2H), 2.21 (br d, J=13.1 Hz, 3H), 1.73 (br dd, J=1.9, 13.9 Hz, 3H), 1.40 (d, J=6.8 Hz, 6H); LCMS (ESI) m/z: 535.2 [M+1].

Embodiment 34

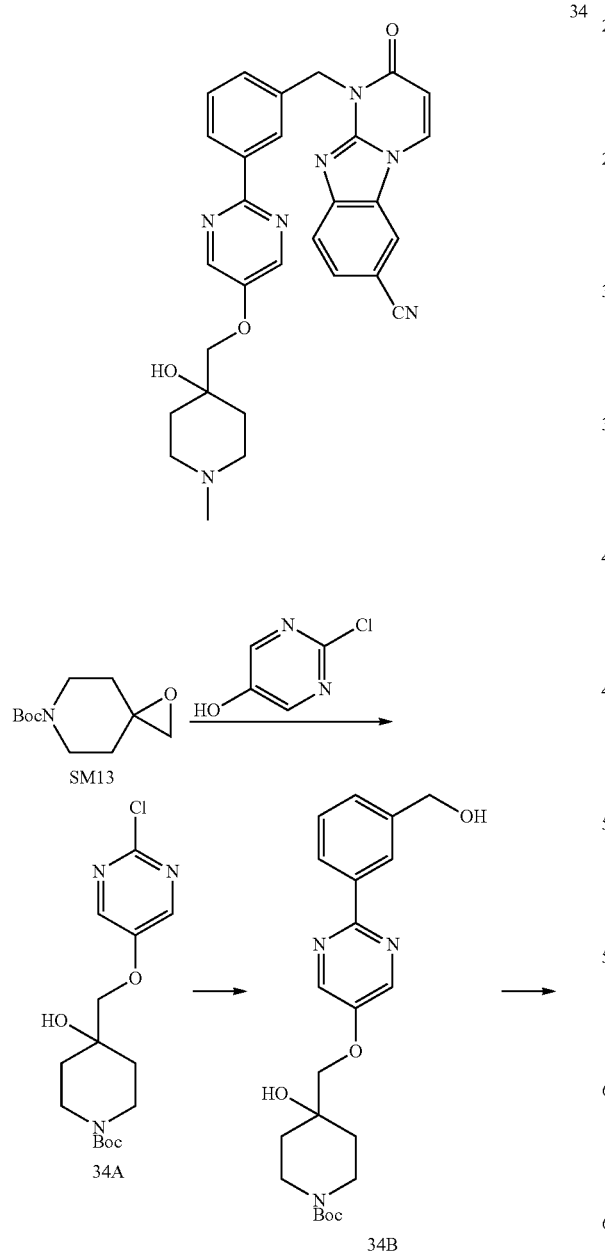

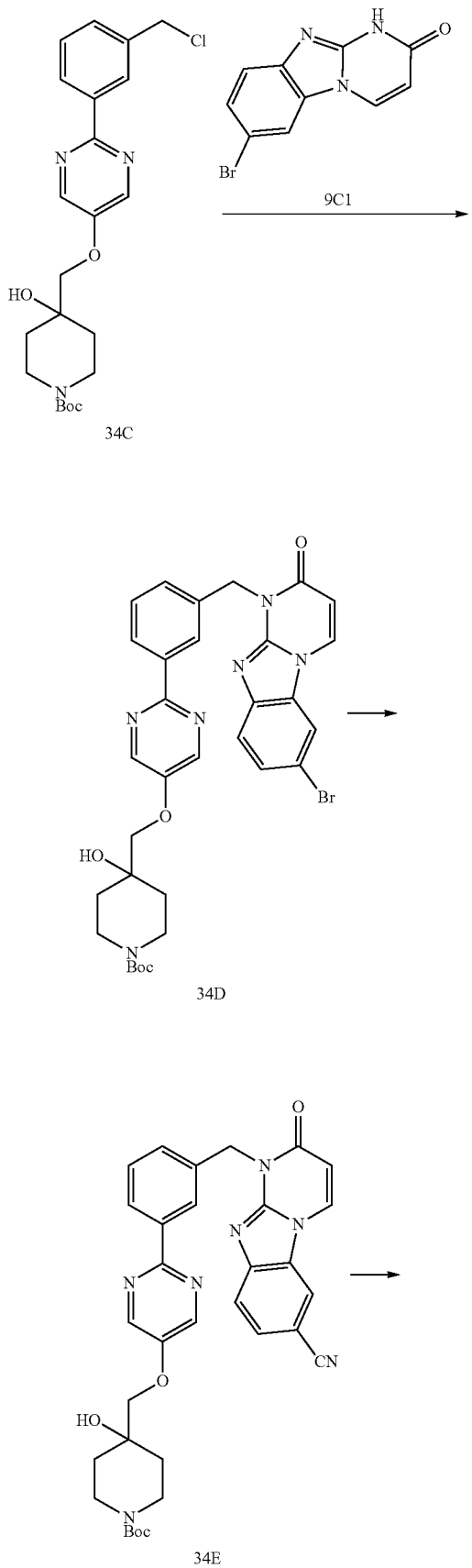

-continued

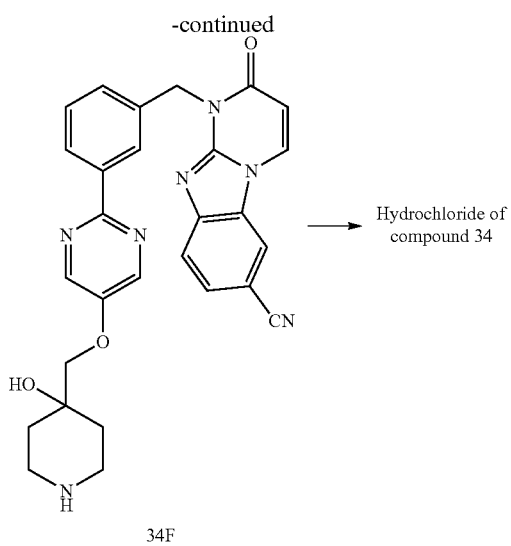

34F

Hydrochloride of compound 34

Compound 34A:

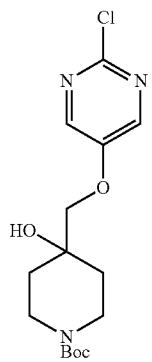

Under the protection of nitrogen, potassium carbonate (6.36 g, 46.01 mmol) was added to a solution of 2-chloro-5-hydroxypyrimidine (3 g, 22.98 mmol) and 1-oxa-6-azaspiro[2.5]octane-6-carboxylic acid tert-butyl ester (8.82 g, 41.37 mmol) in DMF (50 mL). The mixture was stirred at 70-80° C. for 12 hours, the reaction mixture was cooled to 25° C., ethyl acetate (80 mL) was added thereto at 25° C., and then the mixture was filtered, the filtrate was washed with saturated ammonium chloride aqueous solution (50 mL×1 time), the aqueous phase was extracted with ethyl acetate (50 mL×2 times). The combined organic phase was dried over sodium sulfate, filtered and concentrated, and the residue was purified by silica gel column (petroleum ether:ethyl acetate=5:1) to obtain the compound 34A. $^1$H NMR (400 MHz, DMSO-$d_6$) δ=8.56 (s, 2H), 3.99 (s, 2H), 3.78-3.66 (m, 2H), 3.18-3.00 (m, 2H), 1.59-1.50 (m, 4H), 1.41 (s, 9H). LCMS (ESI) m/z: 344.2 [M+1].

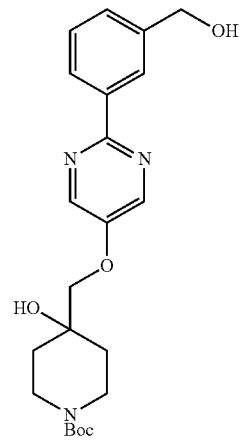 [SMILES: CC(C)(C)OC(=O)N1CCC(O)(COc2cnc(-c3cccc(CO)c3)nc2)CC1]

Compound 34B:

Compound 34A (1 g, 2.91 mmol) and 3-hydroxymethyl phenylboronic acid pinacol ester (820 mg, 3.50 mmol) were dissolved in 20 mL of ethylene glycol dimethyl ether, and Pd(PPh$_3$)$_4$ (170 mg, 147.11 μmol), sodium carbonate (33 g, 311.35 mmol) and water (5 mL) were added thereto. The mixture was stirred and the reaction was carried out at 70-80° C. for 2 hours under a nitrogen atmosphere, the reaction mixture was diluted with ethyl acetate (40 mL) and washed with saturated brine (10 mL×1 time). The organic phases were combined and dried over anhydrous sodium sulfate, concentrated, then the residue was purified by silica gel chromatography (petroleum ether:ethyl acetate:dichloromethane=10:1:1) to obtain the compound 34B. $^1$H NMR (400 MHz, CDCl$_3$) δ=8.50 (s, 2H), 8.37 (s, 1H), 8.32-8.28 (m, 1H), 7.52-7.48 (m, 2H), 4.82 (s, 2H), 3.97 (m, 4H), 3.31-3.18 (m, 2H), 1.82-1.75 (m, 2H), 1.70 (m, 2H), 1.50 (s, 9H). LCMS (ESI) m/z: 416.2 [M+1].

Compound 34C:

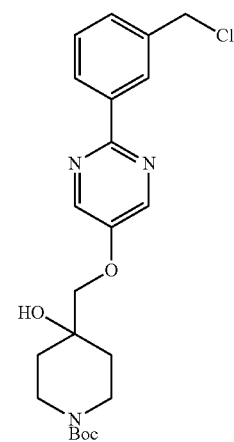 [SMILES: CC(C)(C)OC(=O)N1CCC(O)(COc2cnc(-c3cccc(CCl)c3)nc2)CC1]

Compound 34C was prepared according to the method of compound 6E by replacing compound 11 with compound 34B. $^1$H NMR (400 MHz, CDCl$_3$) δ=8.43 (s, 2H), 8.32 (s, 1H), 8.27-8.22 (m, 1H), 7.44-7.39 (m, 2H), 4.61 (s, 2H), 3.89 (m, 4H), 3.22-3.10 (m, 2H), 1.74-1.67 (m, 2H), 1.62 (m, 2H), 1.41 (s, 9H). LCMS (ESI) m/z: 434.2 [M+1].

Compound 34D:

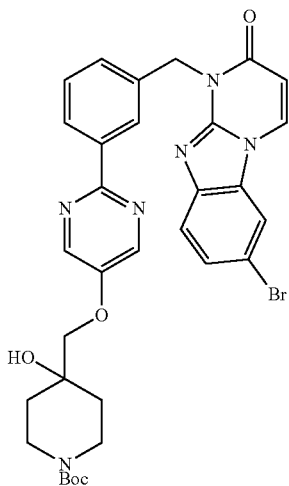 [SMILES: CC(C)(C)OC(=O)N1CCC(O)(COc2cnc(-c3cccc(Cn4c(=O)ccn5c6cc(Br)ccc6nc45)c3)nc2)CC1]

Compound 34D was prepared according to the method of compound 6F by replacing compound 6D with compound 9C1 and replacing the compound 6E with compound 34C. $^1$H NMR (400 MHz, DMSO-$d_6$) δ=8.90 (d, J=7.8 Hz, 1H), 8.64 (s, 2H), 8.37-8.30 (m, 2H), 8.20 (d, J=7.8 Hz, 1H), 7.58 (d, J=8.6 Hz, 1H), 7.56-7.48 (m, 2H), 7.47-7.42 (m, 1H), 6.37 (d, J=7.8 Hz, 1H), 5.44 (s, 2H), 4.01 (s, 2H), 3.79-3.69 (m, 2H), 3.18-3.01 (m, 2H), 1.57 (br dd, J=3.9, 6.8 Hz, 4H), 1.41 (s, 9H); LCMS (ESI) m/z: 663.0 [M+3].

Compound 34E:

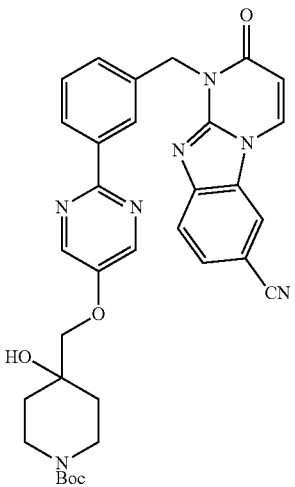 [SMILES: N#Cc1ccc2nc3n(Cc4cccc(-c5ncc(OCC6(O)CCNCC6)cn5)c4)c(=O)ccn3c2c1]

Compound 34D (0.2 g, 302.32 μmol) and zinc cyanide (178 mg, 1.52 mmol) were added to DMF (5 mL), then zinc powder (40 mg, 611.71 μmol), dppf (67 mg, 120.86 μmol) and Pd$_2$(dba)$_3$ (56 mg, 61.15 μmol) were added thereto. The reaction system was stirred at 90 to 100° C. for 12 hours. The reaction system was diluted with dichloromethane (10 mL) and then filtered, the filtrate was washed with saturated sodium chloride aqueous solution (5 mL×1), and the aqueous phase was extracted with dichloromethane (5 mL×2). The organic phase was combined, dried over anhydrous sodium sulfate and concentrated. Dichloromethane (2 mL) was added to the residue and filtered, the filter cake was washed with ethyl acetate (1 mL×2) and dried to obtain the compound 34E. $^1$H NMR (400 MHz, DMSO-$d_6$) δ=8.93 (d, J=7.8 Hz, 1H), 8.64 (s, 2H), 8.58 (s, 1H), 8.37 (s, 1H), 8.20 (d, J=7.6 Hz, 1H), 7.80-7.74 (m, 2H), 7.54-7.49 (m, 1H), 7.47-7.41 (m, 1H), 6.47 (d, J=7.6 Hz, 1H), 5.47 (s, 2H), 4.88 (s, 1H), 4.01 (s, 2H), 3.79-3.67 (m, 2H), 3.18-3.04 (m, 2H), 1.57 (m, 4H), 1.41 (s, 9H); LCMS (ESI) m/z: 608.2 [M+1].

Compound 34F:

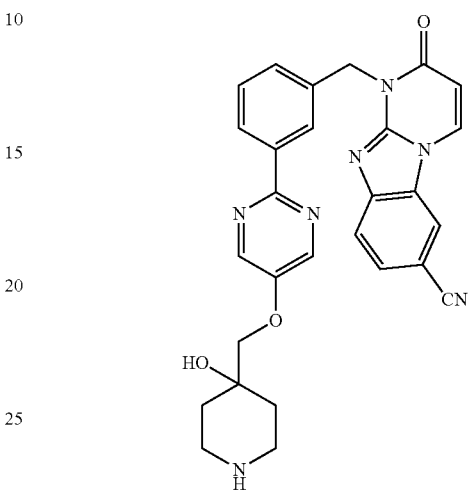

Compound 34F was prepared according to the method of compound 5J by replacing compound 5I with compound 34E. LCMS (ESI) m/z: 508.2 [M+1].

Hydrochloride of Compound 34:

34

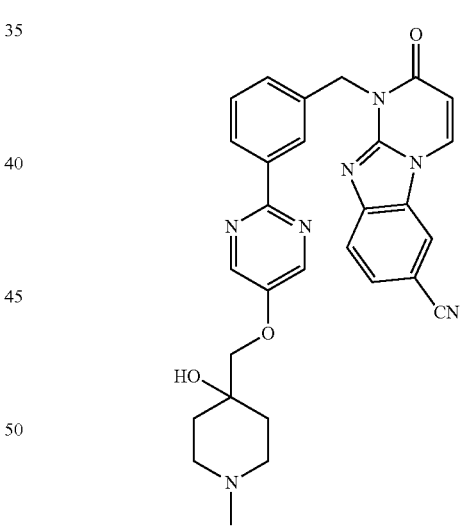

According to the method of compound 1 by replacing compound 1L with compound 34F, and the mixture purified by high performance liquid preparative chromatography separation (formic acid system) was concentrated, and saturated sodium bicarbonate aqueous solution (30 mL) was added thereto, and the pH value of the mixture was adjusted to 10 with 2 mol/L sodium hydroxide aqueous solution, then the mixture was extracted with dichloromethane (20 mL×3 times), and the combined organic phase was concentrated under reduced pressure to obtain compound 34. Water (30 mL) and acetonitrile (6 mL) were added to the residue, then the hydrochloric acid aqueous solution (1 mol/L, 1 mL) was added thereto and stirred at 25° C. for 0.5 hours, the mixture was freeze-dried to obtain the hydrochloride of compound 34. ¹H NMR (400 MHz, DMSO-$d_6$) δ=10.33 (br s, 1H), 8.95 (d, J=7.8 Hz, 1H), 8.70-8.64 (m, 2H), 8.59 (s, 1H), 8.37 (s, 1H), 8.20 (d, J=7.6 Hz, 1H), 7.81-7.72 (m, 2H), 7.55-7.50 (m, 1H), 7.48-7.42 (m, 1H), 6.46 (d, J=7.6 Hz, 1H), 5.47 (s, 2H), 4.07 (s, 2H), 3.35-3.29 (m, 2H), 3.22-3.10 (m, 2H), 2.76 (d, J=4.9 Hz, 3H), 1.99 (dt, J=4.3, 13.8 Hz, 2H), 1.83 (m, 2H); LCMS (ESI) m/z: 522.2 [M+1].

Embodiment 35

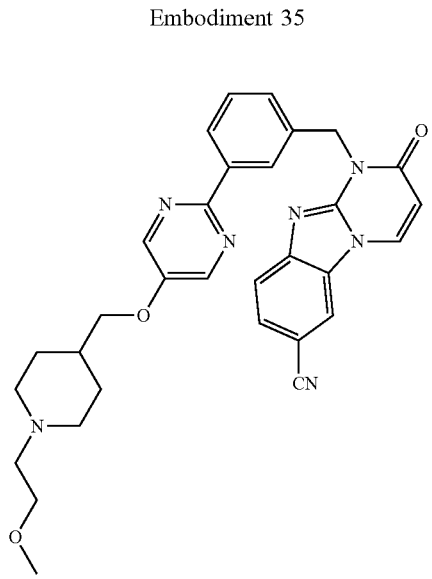

The hydrochloride of compound 35 was prepared according to the method of compound 30 by replacing the compound 2-bromoethanol with 1-bromo-2-methoxyethane. ¹H NMR (400 MHz, CD₃OD) δ=8.74 (d, J=7.8 Hz, 1H), 8.58-8.49 (m, 2H), 8.39 (s, 1H), 8.30 (d, J=0.9 Hz, 1H), 8.23 (d, J=7.8 Hz, 1H), 7.78-7.74 (m, 1H), 7.73-7.69 (m, 1H), 7.61 (d, J=7.8 Hz, 1H), 7.45 (t, J=7.7 Hz, 1H), 6.38 (d, J=7.8 Hz, 1H), 5.58 (s, 2H), 4.16-4.07 (m, 2H), 3.79-3.75 (m, 2H), 3.70 (br d, J=12.5 Hz, 2H), 3.44 (s, 3H), 3.38-3.36 (m, 2H), 3.14-3.05 (m, 2H), 2.29-2.11 (m, 3H), 1.88-1.66 (m, 2H); LCMS (ESI) m/z: 550.2 [M+1].

Embodiment 36

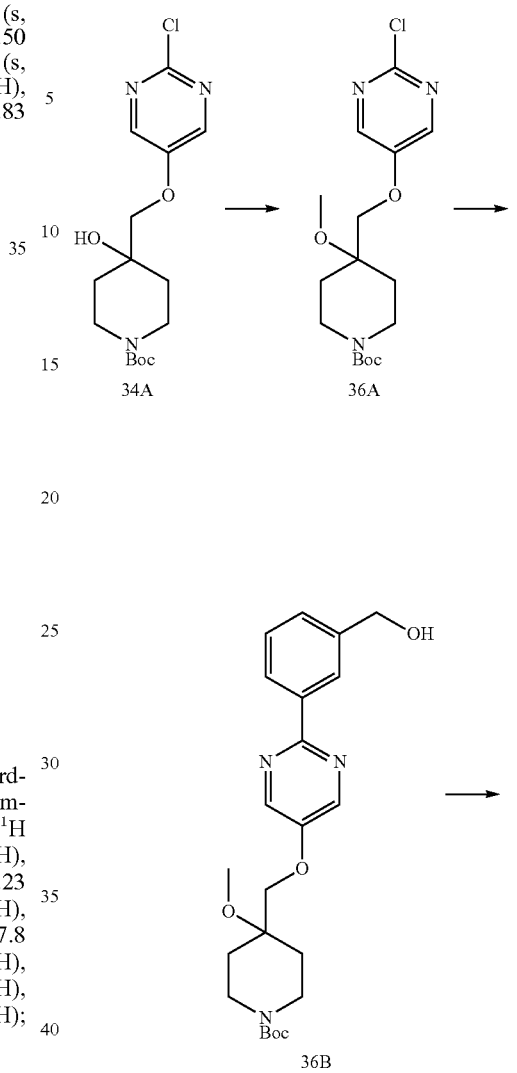

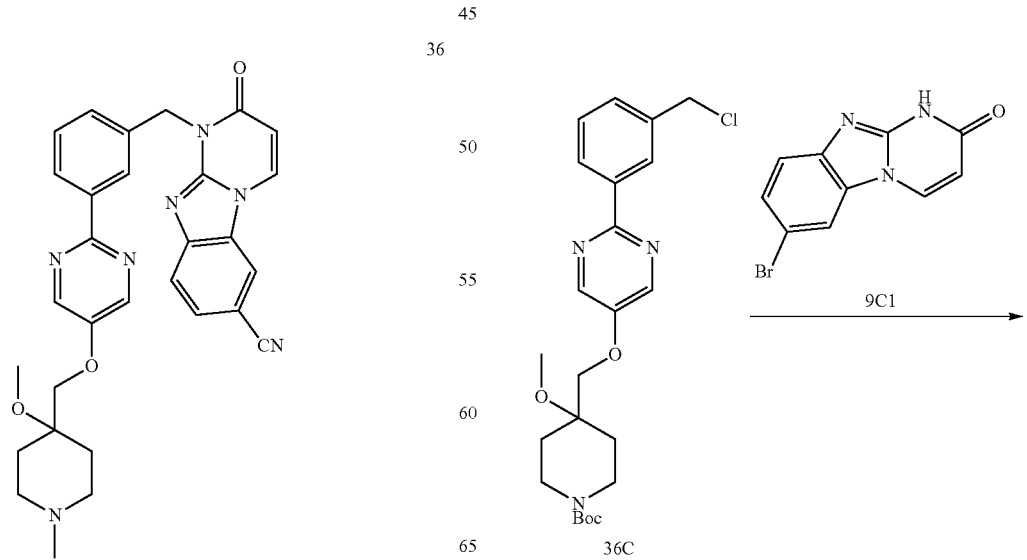

-continued

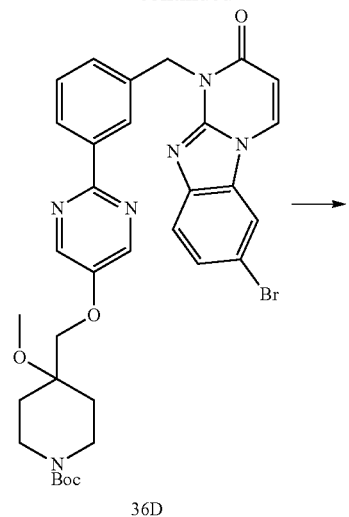

36D

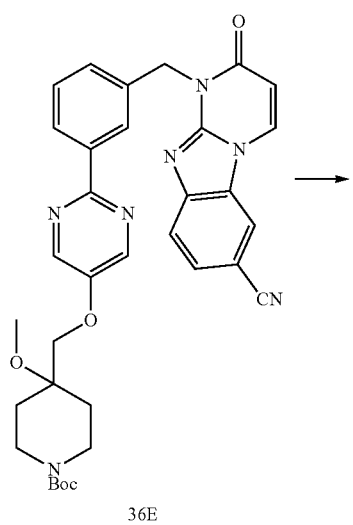

36E

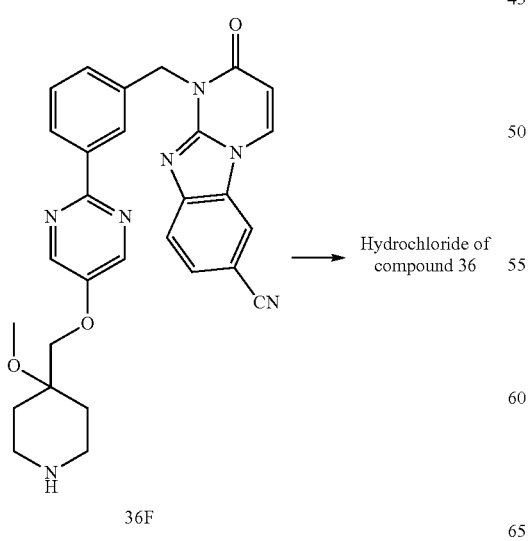

36F

Compound 36A:

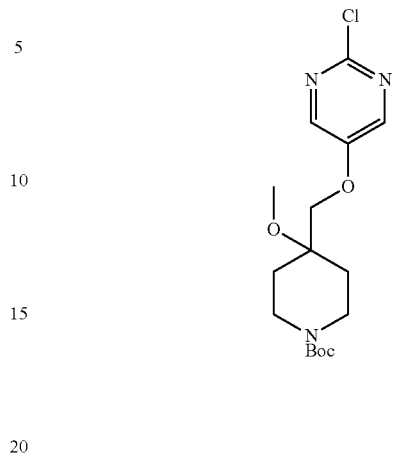

Sodium hydride (465 mg, 11.63 mmol, 60% purity) was added to a solution of compound 34A (3 g, 22.98 mmol) in tetrahydrofuran (20 mL). The mixture was stirred at 0° C. for 1 hour, methyl iodide (3.30 g, 23.27 mmol) was added thereto, and the mixture was stirred at 25° C. for 16 hours. Water (50 mL) was added to the reaction mixture and then extracted with ethyl acetate (300 mL×2 times), the combined organic phase was dried over sodium sulfate, filtered and concentrated, the residue was purified by silica gel column (petroleum ether:ethyl acetate=3:1 with 10% dichloromethane) to obtain the compound 36A. $^1$H NMR (400 MHz, CDCl$_3$) δ=8.33 (s, 2H), 3.96 (s, 2H), 3.94-3.78 (m, 2H), 3.30 (s, 3H), 3.12 (s, 2H), 1.92 (d, J=12.5 Hz, 2H), 1.65-1.52 (m, 2H), 1.47 (s, 9H); LCMS (ESI) m/z: 358.1 [M+1].

Compound 36B:

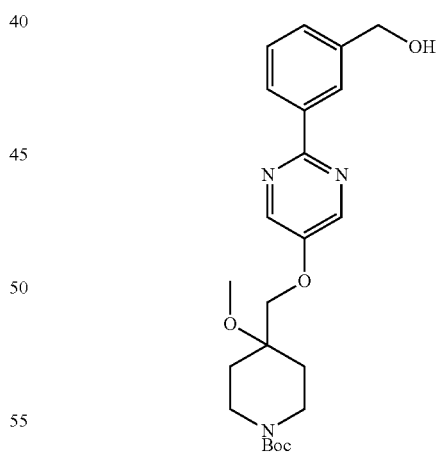

Compound 36B was prepared according to the method of compound 1H by replacing compound 1H with compound 36A. $^1$H NMR (400 MHz, CDCl$_3$) δ=8.50 (s, 2H), 8.35 (s, 1H), 8.28 (dt, J=1.7, 4.5 Hz, 1H), 7.48 (d, J=5.1 Hz, 2H), 4.80 (s, 2H), 4.01 (s, 2H), 3.96-3.78 (m, 2H), 3.39-3.31 (m, 3H), 3.25-3.01 (m, 2H), 1.99-1.86 (m, 2H), 1.72-1.56 (m, 2H), 1.48 (s, 9H); LCMS (ESI) m/z: 430.2 [M+1].

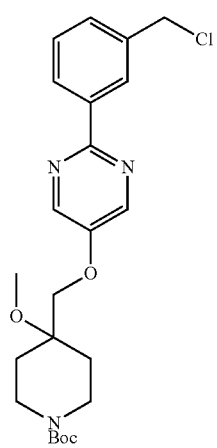 [SMILES: COC1(COc2cnc(-c3cccc(CCl)c3)nc2)CCN(C(=O)OC(C)(C)C)CC1]

Compound 36C:

Compound 36C was prepared according to the method of compound 6E by replacing compound 1I with compound 36B. $^1$H NMR (400 MHz, CDCl$_3$) δ=8.51 (s, 2H), 8.42-8.38 (m, 1H), 8.35-8.28 (m, 1H), 7.51-7.47 (m, 2H), 4.69 (s, 2H), 4.02 (s, 2H), 3.97-3.80 (m, 2H), 3.34 (s, 3H), 3.22-3.06 (m, 2H), 1.95 (d, J=12.6 Hz, 2H), 1.65-1.58 (m, 2H), 1.48 (s, 9H); LCMS (ESI) m/z: 448.2 [M+1].

Compound 36D:

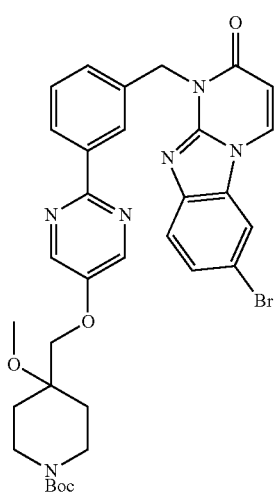 [SMILES: COC1(COc2cnc(-c3cccc(Cn4c(=O)ccn5c6cc(Br)ccc6nc45)c3)nc2)CCN(C(=O)OC(C)(C)C)CC1]

Compound 36D was prepared according to the method of compound 6F by replacing compound 6D with compound 9C1 and replacing the compound 6E with compound 36C. $^1$H NMR (400 MHz, CDCl$_3$) δ=8.58 (s, 1H), 8.49-8.45 (m, 2H), 8.24 (d, J=7.8 Hz, 1H), 7.97 (d, J=7.8 Hz, 1H), 7.66-7.61 (m, 2H), 7.57 (d, J=8.6 Hz, 1H), 7.48-7.37 (m, 2H), 6.22 (d, J=7.8 Hz, 1H), 5.57 (s, 2H), 3.99 (s, 2H), 3.95-3.79 (m, 2H), 3.32 (s, 3H), 3.13 (d, J=5.3 Hz, 2H), 1.93 (d, J=13.1 Hz, 2H), 1.66-1.54 (m, 2H), 1.45 (s, 9H); LCMS (ESI) m/z: 675.2 [M+1].

Compound 36E:

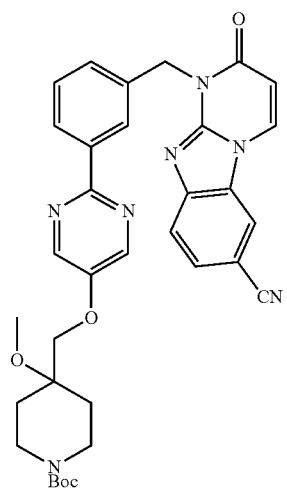 [SMILES: COC1(COc2cnc(-c3cccc(Cn4c(=O)ccn5c6cc(C#N)ccc6nc45)c3)nc2)CCN(C(=O)OC(C)(C)C)CC1]

Compound 36E was prepared according to the method of compound 6I by replacing compound 6H with compound 36D. $^1$H NMR (400 MHz, CDCl$_3$) δ=8.60 (s, 1H), 8.49 (s, 2H), 8.27 (d, J=7.7 Hz, 1H), 8.06 (d, J=7.7 Hz, 1H), 7.85-7.78 (m, 2H), 7.66 (t, J=6.5 Hz, 2H), 7.42 (t, J=7.8 Hz, 1H), 6.34 (d, J=7.7 Hz, 1H), 5.60 (s, 2H), 4.01 (s, 2H), 3.97-3.82 (m, 2H), 3.33 (s, 3H), 3.24-3.07 (m, 2H), 2.00-1.89 (m, 2H), 1.67-1.62 (m, 1H), 1.59-1.55 (m, 1H), 1.48 (s, 9H); LCMS (ESI) m/z: 622.4 [M+1].

Compound 36F:

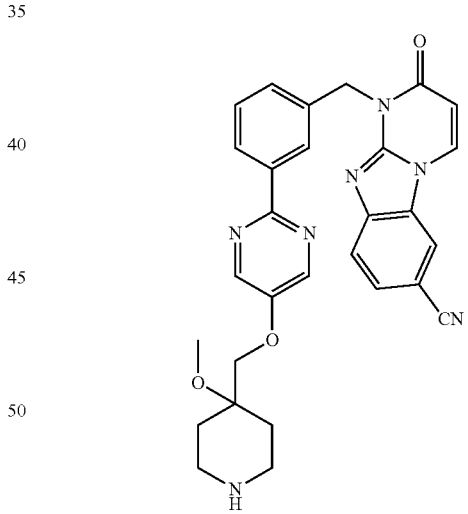

Compound 36F was prepared according to the method of compound 5J by replacing compound 5I with compound 36E. $^1$H NMR (400 MHz, DMSO-d$_6$) δ=8.91 (d, J=7.8 Hz, 1H), 8.69-8.65 (m, 2H), 8.56 (s, 1H), 8.36 (s, 1H), 8.19 (d, J=7.7 Hz, 1H), 7.79-7.74 (m, 1H), 7.79-7.72 (m, 1H), 7.52 (s, 1H), 7.48-7.41 (m, 1H), 6.46 (d, J=7.8 Hz, 1H), 5.46 (s, 2H), 4.15 (s, 2H), 3.17 (s, 3H), 2.84-2.74 (m, 4H), 1.77 (d, J=13.2 Hz, 2H), 1.63-1.49 (m, 2H); LCMS (ESI) m/z: 522.2 [M+1].

Hydrochloride of Compound 36:

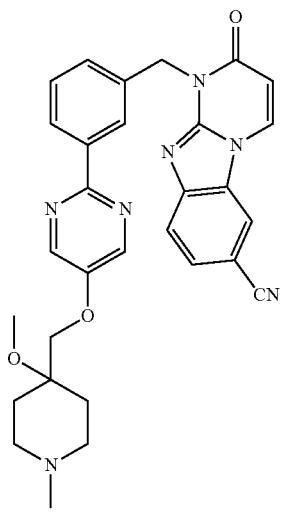

36

According to the method of compound 1 by replacing compound 1L with compound 36F, and the mixture purified by high performance liquid preparative chromatography separation (formic acid system) was concentrated, saturated sodium bicarbonate aqueous solution (30 mL) was added thereto, and the pH value of the mixture was adjusted to 10 with 2 mol/L sodium hydroxide aqueous solution, then the mixture was extracted with dichloromethane (20 mL×3 times), and the combined organic phase was concentrated under reduced pressure to obtain compound 36. Water (30 mL) and acetonitrile (10 mL) were added to compound 36, then hydrochloric acid aqueous solution (1 mol/L, 0.2 mL) was added thereto and stirred at 25° C. for 0.5 hours, the mixture was freeze-dried to obtain the hydrochloride of compound 36. $^1$H NMR (400 MHz, DMSO-$d_6$) δ=9.71 (s, 1H), 8.92 (d, J=7.8 Hz, 1H), 8.71-8.63 (m, 2H), 8.57 (s, 1H), 8.39-8.33 (m, 1H), 8.19 (d, J=7.7 Hz, 1H), 7.77-7.73 (m, 2H), 7.55-7.48 (m, 1H), 7.46-7.41 (m, 1H), 6.46 (d, J=7.8 Hz, 1H), 5.52-5.38 (m, 2H), 4.21 (s, 2H), 3.24-3.19 (m, 5H), 3.06-3.02 (m, 2H), 2.81-2.78 (m, 3H), 2.10 (d, J=13.8 Hz, 2H), 1.88-1.78 (m, 2H); LCMS (ESI) m/z: 536.1 [M+1].

Embodiment 37

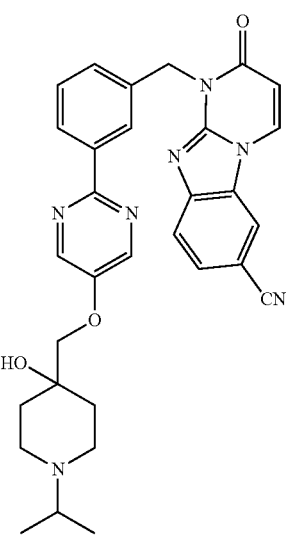

37

Hydrochloride of compound 37 was prepared according to the method of compound 30 by replacing compound 2-bromoethanol with 2-iodopropane, replacing trifluoroacetate of compound 24C with compound 34F, and replacing the purification method with high performance liquid preparative chromatography (formic acid system). $^1$H NMR (400 MHz, DMSO-$d_6$) δ=8.91 (d, J=7.8 Hz, 1H), 8.63 (s, 2H), 8.56 (s, 1H), 8.36 (s, 1H), 8.19 (d, J=7.8 Hz, 1H), 7.80-7.72 (m, 2H), 7.53-7.48 (m, 1H), 7.46-7.40 (m, 1H), 6.46 (d, J=7.8 Hz, 1H), 5.46 (s, 2H), 4.56 (s, 1H), 3.96 (s, 2H), 2.71-2.63 (m, 1H), 2.46 (m, 4H), 1.69-1.60 (m, 2H), 1.60-1.52 (m, 2H), 0.97 (d, J=6.5 Hz, 6H); LCMS (ESI) m/z: 550.2 [M+1].

Embodiment 38

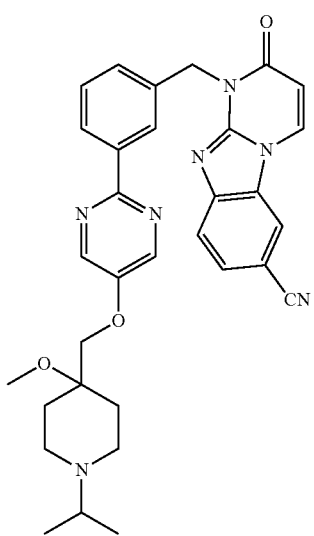

38

Hydrochloride of compound 38 was prepared according to the method of compound 30 by replacing compound 2-bromoethanol with 2-iodopropane, replacing trifluoroacetate of compound 24C with compound 36F, and replacing the purification method with high performance liquid preparative chromatography (formic acid system). $^1$H NMR (400 MHz, DMSO-$d_6$) δ=9.38-9.23 (m, 1H), 8.92 (d, J=7.8 Hz, 1H), 8.67 (s, 2H), 8.57 (s, 1H), 8.36 (s, 1H), 8.20 (d, J=7.7 Hz, 1H), 7.78-7.74 (m, 2H), 7.52 (d, J=7.6 Hz, 1H), 7.47-7.40 (m, 1H), 6.46 (d, J=7.8 Hz, 1H), 5.46 (s, 2H), 4.21 (s, 2H), 3.44-3.41 (m, 2H), 3.22 (s, 3H), 3.06-2.95 (m, 2H), 2.17-2.07 (m, 2H), 1.93-1.86 (m, 3H), 1.32-1.26 (d, J=6.4 Hz, 6H); LCMS (ESI) m/z: 564.2 [M+1].

Embodiment 39

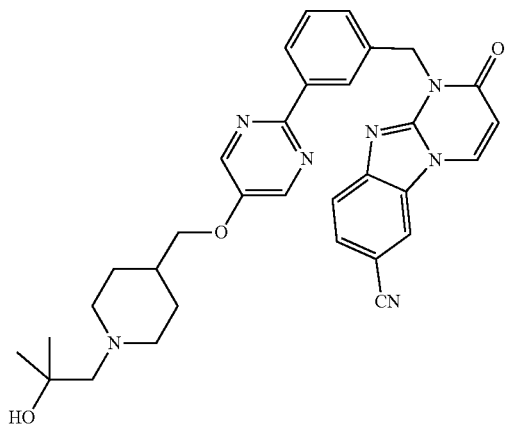

Potassium carbonate (90 mg, 651.21 µmol) was added to a mixture of trifluoroacetate of compound 24C (150 mg, 305.16 µmol, trifluoroacetate) and 2,2-dimethyloxirane (812 mg, 11.26 mmol) in DMF (2 mL). The reaction mixture was stirred at 80° C. for 2 hours, then cooled to room temperature and filtered, the filter cake was collected and concentrated to dryness to obtain compound 39. Water (10 mL) and acetonitrile (5 mL) and hydrochloric acid aqueous solution (1 mol/1, 0.1 mL) were sequentially added to compound 39 and stirred at 25° C. for 30 minutes, the mixture was concentrated under reduced pressure to obtain the hydrochloride of compound 39. $^1$H NMR (400 MHz, DMSO-d$_6$) δ=9.08 (br s, 1H), 8.94 (d, J=7.8 Hz, 1H), 8.70-8.61 (m, 2H), 8.59 (s, 1H), 8.35 (s, 1H), 8.20 (d, J=7.8 Hz, 1H), 7.82-7.73 (m, 2H), 7.57-7.49 (m, 1H), 7.49-7.41 (m, 1H), 6.46 (d, J=7.8 Hz, 1H), 5.47 (s, 2H), 4.21-4.05 (m, 2H), 3.63 (br s, 2H), 3.35-3.24 (m, 2H), 3.07 (br d, J=4.3 Hz, 2H), 2.08 (br s, 1H), 1.97-1.76 (m, 4H), 1.27 (s, 6H); LCMS (ESI) m/z: 564.3 [M+1].

Embodiment 40

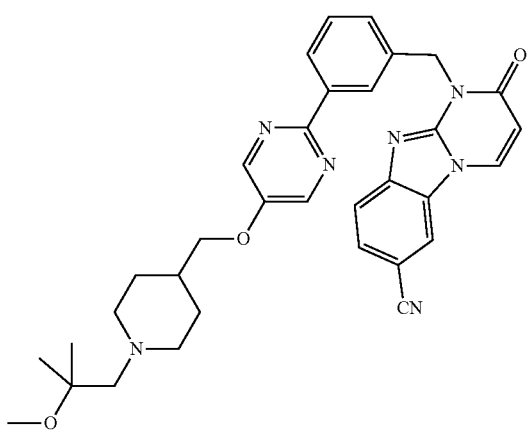

Hydrochloride of compound 40 was prepared according to the method of compound 30, by replacing the compound 2-bromoethanol with methyl iodide, and replacing trifluoroacetate of compound 24C with compound 39. $^1$H NMR (400 MHz, DMSO-d$_6$) δ=8.94 (br d, J=7.8 Hz, 1H), 8.66 (br s, 2H), 8.58 (br s, 1H), 8.35 (br s, 1H), 8.20 (br d, J=6.6 Hz, 1H), 7.77 (br s, 2H), 7.62-7.34 (m, 2H), 6.46 (br d, J=7.6 Hz, 1H), 5.47 (br s, 2H), 4.17 (br s, 2H), 3.95-3.49 (m, 2H), 3.22 (br d, J=18.8 Hz, 4H), 2.51-2.30 (m, 3H), 2.12 (br s, 1H), 1.95-1.81 (m, 4H), 1.34 (br s, 6H); LCMS (ESI) m/z: 578.2 [M+1].

Embodiment 41

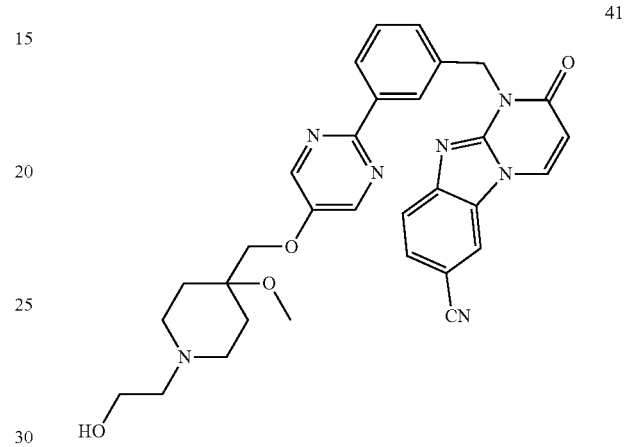

Hydrochloride of compound 41 was prepared according to the method of compound 30 by replacing compound 24C with compound 36F, and replacing the purification method with high performance liquid preparative chromatography (formic acid system). $^1$H NMR (400 MHz, DMSO-d$_6$) δ=9.72-9.41 (m, 1H), 8.98-8.88 (m, 1H), 8.76-8.64 (m, 2H), 8.57 (br d, J=2.8 Hz, 1H), 8.36 (br s, 1H), 8.25-8.15 (m, 1H), 7.86-7.72 (m, 2H), 7.58-7.40 (m, 2H), 6.53-6.40 (m, 1H), 5.46 (s, 2H), 5.40-5.16 (m, 1H), 4.24-4.12 (m, 4H), 3.74 (br s, 4H), 3.08-2.94 (m, 4H), 2.12-1.94 (m, 4H); LCMS (ESI) m/z: 566.3 [M+1].

Embodiment 42

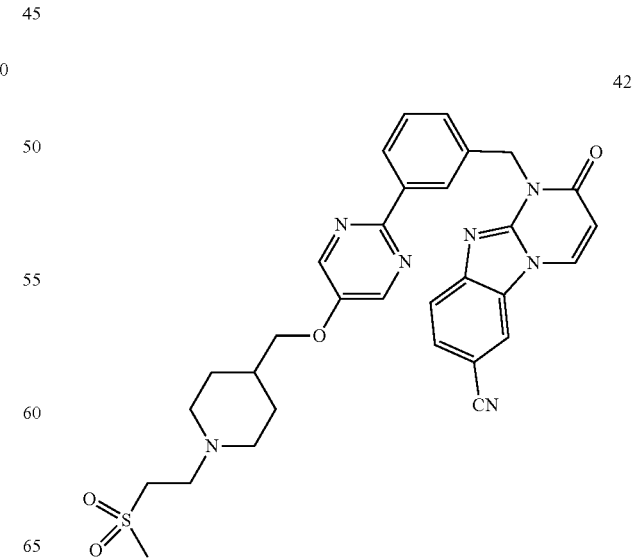

Hydrochloride of compound 42 was prepared according to the method of compound 30 by replacing compound 2-bromoethanol with 1-bromo-2-(methylsulfonyl)ethane. $^1$H NMR (400 MHz, DMSO-d$_6$) δ=10.80 (br s, 1H), 8.94 (d, J=7.8 Hz, 1H), 8.71-8.62 (m, 2H), 8.58 (s, 1H), 8.36 (s, 1H), 8.20 (d, J=7.8 Hz, 1H), 7.80-7.71 (m, 2H), 7.57-7.49 (m, 1H), 7.49-7.40 (m, 1H), 6.46 (d, J=7.8 Hz, 1H), 5.47 (s, 2H), 4.09 (br d, J=6.0 Hz, 2H), 3.85-3.72 (m, 2H), 3.59 (br d, J=11.9 Hz, 2H), 3.53-3.46 (m, 2H), 3.13 (s, 3H), 3.10-2.94 (m, 2H), 2.16-1.92 (m, 3H), 1.81-1.59 (m, 2H); LCMS (ESI) m/z: 598.3 [M+1].

Embodiment 43

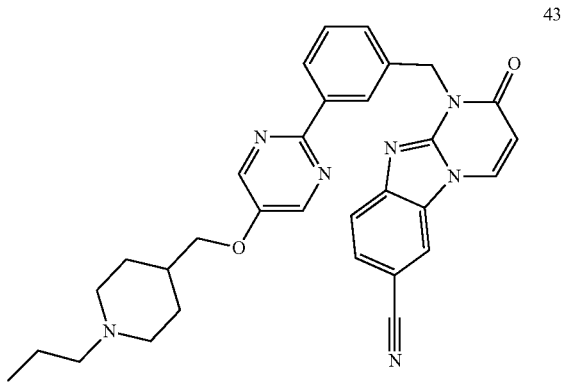 [SMILES: CCCN1CCC(COc2cnc(-c3cccc(Cn4c(=O)ccn5c6cc(C#N)ccc6nc45)c3)nc2)CC1]

43

Hydrochloride of compound 43 was prepared according to the method of compound 30 by replacing 2-bromoethanol with 1-bromopropane, and replacing the purification method with high performance liquid preparative chromatography (formic acid system). $^1$H NMR (400 MHz, DMSO-d$_6$) δ=9.58-9.32 (m, 1H), 8.93 (d, J=7.8 Hz, 1H), 8.64 (s, 2H), 8.60-8.55 (m, 1H), 8.35 (s, 1H), 8.24-8.16 (m, 1H), 7.81-7.73 (m, 2H), 7.56-7.49 (m, 1H), 7.48-7.39 (m, 1H), 6.47 (d, J=7.7 Hz, 1H), 5.49-5.44 (m, 2H), 4.10 (d, J=6.0 Hz, 2H), 3.64-3.48 (m, 2H), 3.05-2.80 (m, 4H), 1.99 (br d, J=14.3 Hz, 2H), 1.75-1.65 (m, 3H), 1.62-1.56 (m, 2H), 0.92-0.89 (m, 3H); LCMS (ESI) m/z: 534.2 [M+1].

Embodiment 44

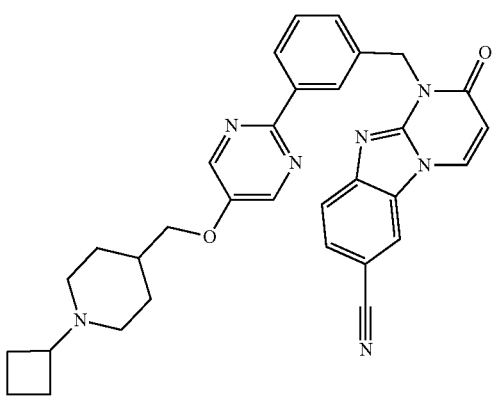

45

Hydrochloride of compound 44 was prepared according to the method of compound 30 by replacing 2-bromoethanol with 1-iodo-2-methylpropane, and replacing the purification method with high performance liquid preparative chromatography (formic acid system). $^1$H NMR (400 MHz, DMSO-d$_6$) δ=8.93 (d, J=7.7 Hz, 1H), 8.68-8.63 (m, 2H), 8.58 (s, 1H), 8.38-8.33 (m, 1H), 8.20 (d, J=7.5 Hz, 1H), 7.78-7.74 (m, 2H), 7.56-7.49 (m, 1H), 7.48-7.39 (m, 1H), 6.47 (d, J=7.7 Hz, 1H), 5.46 (s, 2H), 4.15-4.05 (m, 2H), 3.69-3.45 (m, 2H), 2.92-2.87 (m, 2H), 2.11-2.04 (m, 2H), 1.98-1.92 (m, 2H), 1.71-1.63 (m, 2H), 1.20-1.11 (m, 2H), 0.97 (d, J=6.6 Hz, 6H); LCMS (ESI) m/z: 548.3 [M+1].

Embodiment 45

45

Hydrochloride of compound 45 was prepared according to the method of compound 30 by replacing 2-bromoethanol with bromocyclobutane, and replacing the purification method with high performance liquid preparative chromatography (formic acid system). $^1$H NMR (400 MHz, DMSO-d$_6$) δ=10.22-9.62 (m, 1H), 9.01-8.90 (m, 1H), 8.68-8.63 (m, 2H), 8.58 (s, 1H), 8.35 (s, 1H), 8.20 (br d, J=7.3 Hz, 1H), 7.80-7.73 (m, 2H), 7.52 (br d, J=7.5 Hz, 1H), 7.48-7.40 (m, 1H), 6.46 (d, J=7.6 Hz, 1H), 5.46 (s, 2H), 4.10 (br d, J=5.1 Hz, 2H), 3.63-3.51 (m, 2H), 2.98-2.93 (m, 1H), 2.80-2.73 (m, 2H), 2.31-2.23 (m, 2H), 2.22-2.14 (m, 2H), 2.04-1.97 (m, 2H), 1.67-1.60 (m, 2H), 1.16-1.10 (m, 3H); LCMS (ESI) m/z: 546.3 [M+1].

Embodiment 46

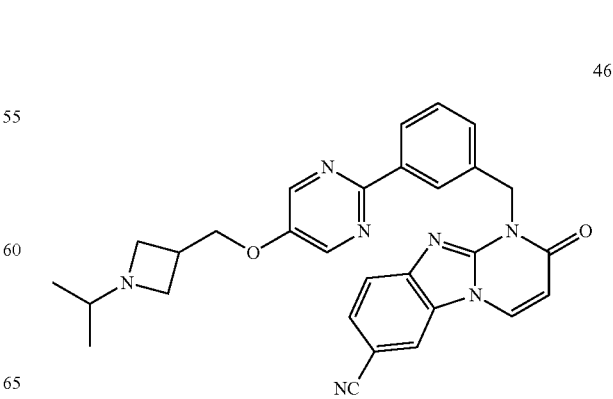

46

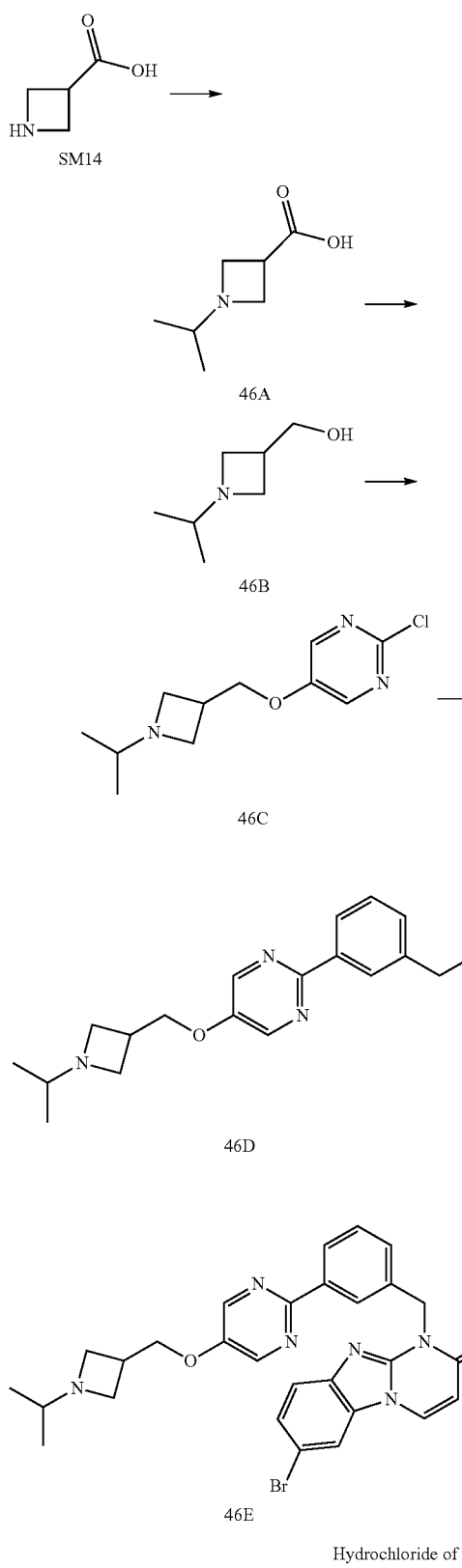

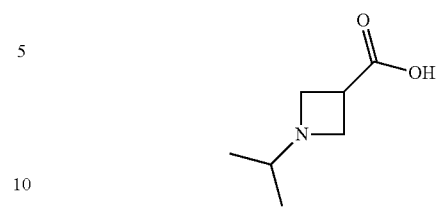

Compound 46A:

Wet palladium on carbon (720 mg, 10% content, containing 50% water)) was added to a solution of N-azacyclobutane-3-carboxylic acid (SM14, 3.6 g, 35.61 mmol) in methanol (72 mL) and acetone (14.35 mL, 195.25 mmol). The mixture was replaced with nitrogen for 3 times and with hydrogen for 3 times, then stirred at 20° C. for 8 hours under a hydrogen (15 Psi) atmosphere, filtered and the filtrate was concentrated to obtain the compound 46A. $^1$H NMR (400 MHz, DMSO-d$_6$) δ=3.50-3.41 (m, 2H), 3.29-3.21 (m, 2H), 3.09-2.97 (m, 1H), 2.43 (td, J=6.2, 12.4 Hz, 1H), 0.87 (d, J=6.2 Hz, 6H).

Compound 46B:

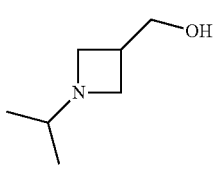

Lithium aluminum hydride (2.68 g, 70.72 mmol) was slowly added in batches to a solution of compound 46A (5.1 g, 35.62 mmol) in tetrahydrofuran (100 mL) at 0° C., and then stirred at 25° C. for 16 hours. Water (2.68 mL), 15% sodium hydroxide aqueous solution (2.68 mL) and water (8.1 mL) were sequentially added to the reaction mixture, then the mixture was stirred at 25° C. for 10 minutes, filtered and the filter cake was washed with a mixed solvent of dichloromethane:methanol=10:1 (50 mL×2 times), the filtrate was collected and dried over anhydrous sodium sulfate, filtered and concentrated to obtain the compound 46B. $^1$H NMR (400 MHz, CDCl$_3$) δ=3.75 (d, J=5.7 Hz, 2H), 3.29 (t, J=7.6 Hz, 2H), 2.99 (t, J=6.2 Hz, 2H), 2.61-2.48 (m, 1H), 2.34-2.19 (m, 1H), 0.91 (d, J=6.2 Hz, 6H).

Compound 46C:

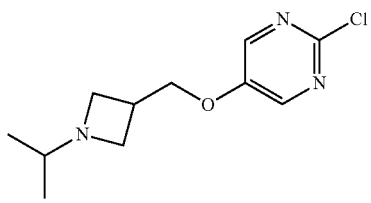 [SMILES: CC(C)N1CC(COc2cnc(Cl)nc2)C1]

Diisopropyl azodicarboxylate (10.24 g, 50.64 mmol) was added dropwise to a solution of 2-chloro-5-hydroxypyrimidine (3.3 g, 25.28 mmol), compound 46B (3.59 g, 27.81 mmol), triphenylphosphine (13.26 g, 50.56 mmol) and triethylamine (7.70 G, 76.05 mmol) in tetrahydrofuran (70 mL), after the addition, the temperature was raised to 25° C. and stirred at 25° C. for 4 hours. Water (50 mL) was added to the reaction mixture and the mixture was extracted with ethyl acetate (50 mL×2 times), the organic phase was combined and dried over anhydrous sodium sulfate, then filtered and concentrated, the residue was purified by column chromatography (petroleum ether:ethyl acetate=1:1 to pure dichloromethane and then to dichloromethane:methanol=10:1 with 1% ammonia water) to obtain the compound 46C. $^1$H NMR (400 MHz, CDCl$_3$) δ=8.28 (s, 2H), 4.26-4.14 (m, 2H), 3.39 (t, J=7.7 Hz, 2H), 3.10-3.03 (m, 2H), 2.90-2.80 (m, 1H), 2.33 (spt, J=6.2 Hz, 1H), 0.93 (d, J=6.3 Hz, 6H).

Compound 46D:

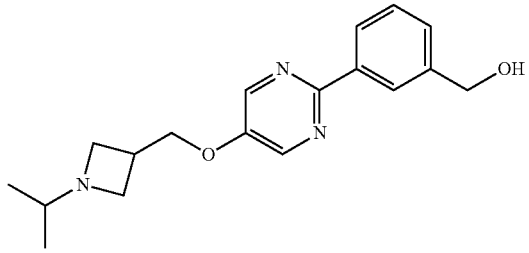 [SMILES: CC(C)N1CC(COc2cnc(-c3cccc(CO)c3)nc2)C1]

Compound 46D was prepared according to the method of compound 1I by replacing compound 1H with compound 46C. $^1$H NMR (400 MHz, CDCl$_3$) δ=8.44 (s, 2H), 8.34 (s, 1H), 8.26 (br s, 1H), 7.46 (br d, J=4.4 Hz, 2H), 4.78 (s, 2H), 4.21 (br d, J=6.6 Hz, 2H), 3.39 (br t, J=7.5 Hz, 2H), 3.05 (br t, J=6.5 Hz, 2H), 2.93-2.80 (m, 1H), 2.34 (td, J=6.1, 12.2 Hz, 1H), 0.94 (br d, J=6.1 Hz, 6H).

Compound 46E:

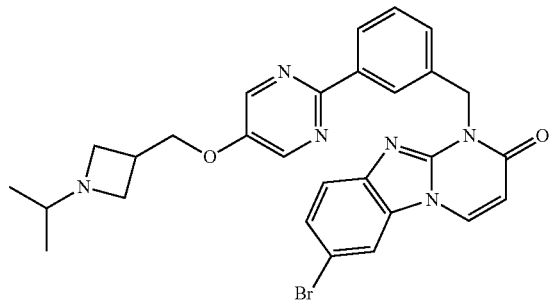 [SMILES: CC(C)N1CC(COc2cnc(-c3cccc(Cn4c(=O)ccn5c6cc(Br)ccc6nc45)c3)nc2)C1]

Diisopropyl azodicarboxylate (123 mg, 608.28 μmol) was added to a solution of compound 9C1 (80 mg, 302.94 mmol), compound 46D (105 mg, 335.04 μmol) and triphenylphosphonium (160 mg, 610.02 μmol) in DMF (10 mL) under the protection of nitrogen at 0° C., after the addition, the mixture was stirred at 20° C. for 2 hours. The reaction mixture was filtered, and the filtrate was concentrated. Brine (40 mL) was added to the residue and the mixture was extracted with dichloromethane:methanol=10:1 (20 mL×2 times), the organic phases were combined and dried over anhydrous sodium sulfate, then filtered and concentrated, the residue was purified by preparative plate (dichloromethane:methanol=10:1 with 1% ammonia water) to obtain the compound 46C. LCMS (ESI) m/z: 559.1 [M+1].

Hydrochloride of Compound 46:

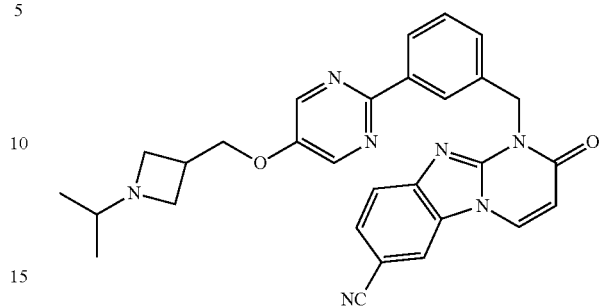

Compound 46E (70 mg, 125.12 mmol) and zinc cyanide (75 mg, 638.71 μmol) were added to DMF (10 mL), then zinc powder (17 mg, 259.98 μmol), dppf (27 mg, 48.70 μmol) and Pd$_2$(dba)$_3$ (22 mg, 24.02 μmol) were added thereto. The reaction system was stirred at 100° C. for 16 hours. The reaction system was cooled to room temperature and diluted with dichloromethane (10 mL) and then filtered, the filtrate was concentrated and purified by column chromatography (petroleum ether:ethyl acetate=5:1 to petroleum ether:ethyl acetate=1:1 to dichloromethane:methanol=8:1 with 1% ammonia water), the obtained product was purified by high performance liquid chromatography (hydrochloric acid system). The pH value of the obtained product was adjusted to 8 with saturated sodium bicarbonate aqueous solution, and then extracted with dichloromethane (40 mL×1 time) and dichloromethane:methanol=10:1 (40 mL×1 time), and the organic phases were combined and dried over anhydrous sodium sulfate, then filtered and concentrated to obtain compound 46. Ethanol (4 mL), acetonitrile (5 mL), water (20 mL), and 0.1 mol/L hydrochloric acid aqueous solution (0.1 mL) were added to compound 46, the mixture was freeze-dried to obtain the hydrochloride of compound 46. $^1$H NMR (400 MHz, DMSO-d$_6$) δ=11.35-10.84 (m, 1H), 8.94 (d, J=7.8 Hz, 1H), 8.68 (d, J=13.0 Hz, 2H), 8.58 (s, 1H), 8.37 (s, 1H), 8.20 (d, J=7.8 Hz, 1H), 7.82-7.71 (m, 2H), 7.55-7.48 (m, 1H), 7.48-7.39 (m, 1H), 6.46 (d, J=7.8 Hz, 1H), 5.46 (s, 2H), 4.61-4.44 (m, 1H), 4.42-4.26 (m, 1H), 4.22-4.02 (m, 2H), 4.00-3.81 (m, 2H), 3.43 (s, 1H), 3.24-2.97 (m, 1H), 1.16 (d, J=6.1 Hz, 6H). LCMS (ESI) m/z: 506.4 [M+1].

Embodiment 47

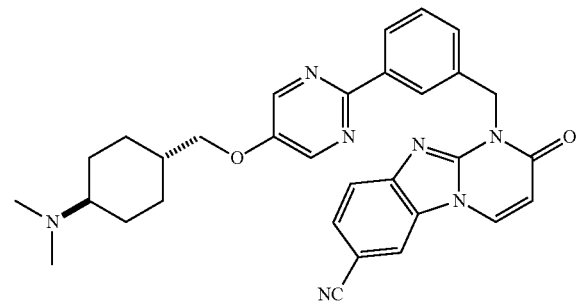

215

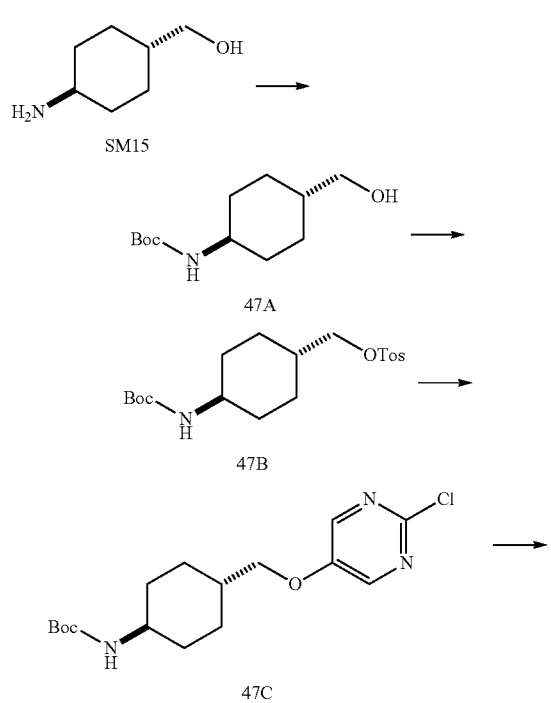

216

-continued

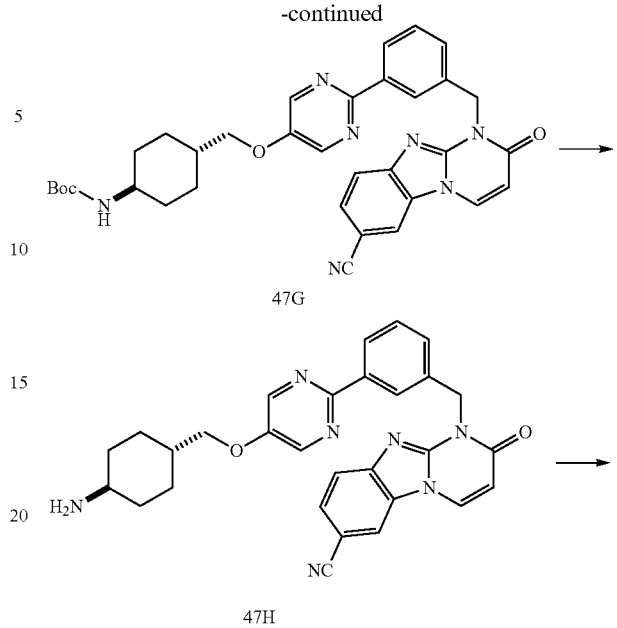

Hydrochloride of compound 47

Compound 47A:

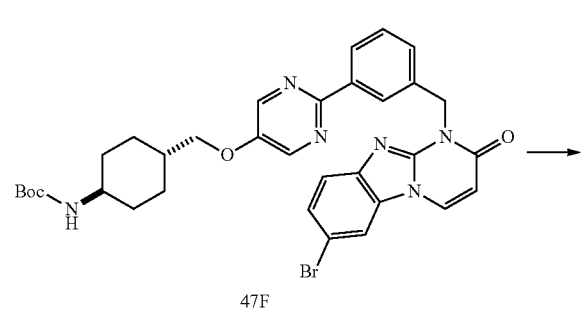

Boc₂O (405.33 mg, 1.86 mmol) was added to a solution of trans (4-aminocyclohexyl) methanol (200 mg, 1.55 mmol) in tetrahydrofuran (5 mL), and the reaction mixture was stirred at 20° C. for 2 hours, water (10 mL) was added to the reaction mixture, the mixture was extracted with ethyl acetate (20 mL×2 times), the organic phase was combined and washed with water (30 mL×1 time) and brine (40 mL×1 time), and then dried over anhydrous sodium sulfate, concentrated, the residue was slurried with n-hexane (2 mL) at 20° C. for 30 minutes and then filtered, the filter cake was dried in vacuum to obtain the compound 47A. $^1$H NMR (400 MHz, CDCl$_3$) δ=4.46-4.31 (m, 1H), 3.47 (t, J=6.0 Hz, 2H), 3.43-3.33 (m, 1H), 2.11-2.00 (m, 2H), 1.88-1.79 (m, 2H), 1.45 (s, 9H), 1.27 (t, J=5.6 Hz, 1H), 1.18-0.97 (m, 4H).

Compound 47B:

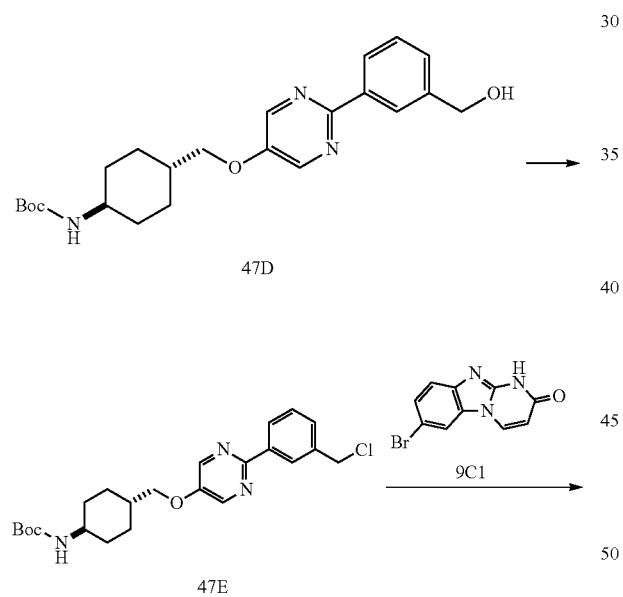

Compound 47B was prepared according to the method of compound 28A by replacing compound 6-hydroxy-2-azaspiro[3.3]heptane-2-carboxylic acid tert-butyl ester with compound 47A. $^1$H NMR (400 MHz, CDCl$_3$) δ=7.79 (s, 1H), 7.77 (s, 1H), 7.36 (s, 1H), 7.34 (s, 1H), 4.35 (br s, 1H), 3.82 (d, J=6.5 Hz, 2H), 3.39-3.22 (m, 1H), 2.46 (s, 3H), 2.05-1.96 (m, 2H), 1.81-1.71 (m, 2H), 1.67-1.59 (m, 1H), 1.43 (s, 9H), 1.12-1.03 (m, 2H), 1.02-0.92 (m, 2H).

Compound 47C:

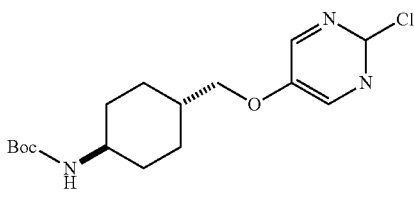 [SMILES: CC(C)(C)OC(=O)N[C@H]1CC[C@H](COC2=CNC(Cl)N=C2)CC1]

Compound 47C was prepared according to the method of compound 1H by replacing compound 1G with compound 47B. $^1$H NMR (400 MHz, CDCl$_3$) δ=8.27 (s, 2H), 4.41 (br s, 1H), 3.85 (d, J=6.4 Hz, 2H), 3.50-3.36 (m, 1H), 2.10 (br d, J=10.0 Hz, 2H), 1.97-1.88 (m, 2H), 1.85-1.73 (m, 1H), 1.46 (s, 9H), 1.23-1.09 (m, 4H).

Compound 47D:

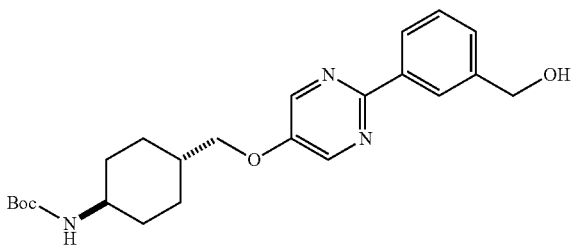 [SMILES: CC(C)(C)OC(=O)N[C@H]1CC[C@H](COc2cnc(-c3cccc(CO)c3)nc2)CC1]

Compound 47D was prepared according to the method of compound 1I by replacing compound 1H with compound 47C, and replacing the purification method with silica gel preparative plate separation (petroleum ether:ethyl acetate=1:1). $^1$H NMR (400 MHz, CDCl$_3$) δ=8.45 (s, 2H), 8.34 (s, 1H), 8.30-8.25 (m, 1H), 7.50-7.45 (m, 2H), 4.80 (s, 2H), 4.42 (br d, J=5.4 Hz, 1H), 3.91 (d, J=6.4 Hz, 2H), 3.50 (s, 1H), 3.45 (br d, J=4.9 Hz, 1H), 2.11 (br d, J=10.3 Hz, 2H), 2.02-1.93 (m, 2H), 1.87-1.76 (m, 1H), 1.46 (s, 9H), 1.29-1.13 (m, 4H). LCMS (ESI) m/z: 414.3 [M+1].

Compound 47E:

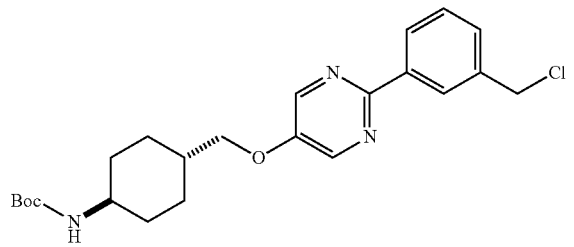

Compound 47E was prepared according to the method of compound 6E by replacing compound 1I with compound 47D. $^1$H NMR (400 MHz, CDCl$_3$) δ=8.45 (s, 2H), 8.39 (s, 1H), 8.32 (ddd, J=1.8, 3.8, 5.2 Hz, 1H), 7.50-7.46 (m, 2H), 4.69 (s, 2H), 4.42 (br d, J=4.8 Hz, 1H), 3.92 (d, J=6.4 Hz, 2H), 3.45 (br d, J=1.1 Hz, 1H), 2.16-2.07 (m, 2H), 2.03-1.93 (m, 2H), 1.87-1.76 (m, 1H), 1.46 (s, 9H), 1.24-1.14 (m, 4H). LCMS (ESI) m/z: 432.2 [M+1].

Compound 47F:

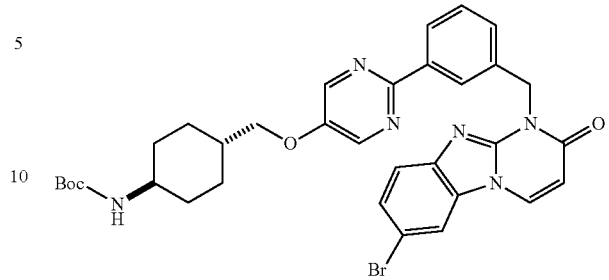

Compound 47F was prepared according to the method of compound 6F by replacing compound 6D with compound 9C1 and replacing the compound 6E with compound 47E. $^1$H NMR (400 MHz, CDCl$_3$) δ=8.58 (s, 1H), 8.42 (s, 2H), 8.25 (d, J=7.9 Hz, 1H), 7.99 (d, J=7.8 Hz, 1H), 7.67-7.58 (m, 3H), 7.48 (dd, J=1.7, 8.6 Hz, 1H), 7.41 (t, J=7.7 Hz, 1H), 6.25 (d, J=7.9 Hz, 1H), 5.58 (s, 2H), 4.42 (br dd, J=1.1, 4.3 Hz, 1H), 3.89 (d, J=6.4 Hz, 2H), 3.44 (br dd, J=5.0, 7.6 Hz, 1H), 2.11 (br d, J=9.5 Hz, 2H), 2.01-1.93 (m, 2H), 1.87-1.73 (m, 1H), 1.46 (s, 9H), 1.27-1.10 (m, 4H). LCMS (ESI) m/z: 659.0 [M+1].

Compound 47G:

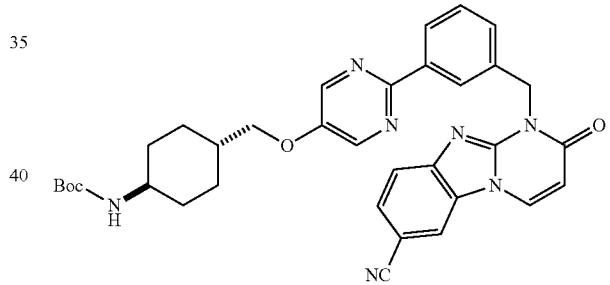

Compound 47F (200 mg, 303.23 μmol) and zinc cyanide (178 mg, 1.52 mmol) were added to DMF (5 mL), then zinc powder (40 mg, 612.52 μmol), dppf (67 mg, 121.29 μmol) and Pd$_2$(dba)$_3$ (56 mg, 61.25 μmol) were added thereto. The reaction system was stirred at 90 to 100° C. for 12 hours. The reaction system was cooled to room temperature and diluted with dichloromethane (10 mL) and then filtered, the filtrate was concentrated and purified by column chromatography (dichloromethane:methanol=1:0 to 100:1) to obtain the compound 47G. $^1$H NMR (400 MHz, CDCl$_3$) δ=8.60 (s, 1H), 8.43 (s, 2H), 8.26 (d, J=8.0 Hz, 1H), 8.09-8.02 (m, 1H), 7.84-7.77 (m, 2H), 7.66 (dd, J=1.4, 8.4 Hz, 2H), 7.42 (t, J=7.8 Hz, 1H), 6.34 (d, J=7.8 Hz, 1H), 5.60 (s, 2H), 4.41 (br dd, J=3.5, 5.5 Hz, 1H), 3.90 (d, J=6.4 Hz, 2H), 3.54-3.37 (m, 1H), 2.11 (br d, J=9.4 Hz, 2H), 2.01-1.93 (m, 2H), 1.85-1.75 (m, 1H), 1.46 (s, 9H), 1.24-1.10 (m, 4H). LCMS (ESI) m/z: 606.3 [M+1].

Trifluoroacetate of Compound 47H:

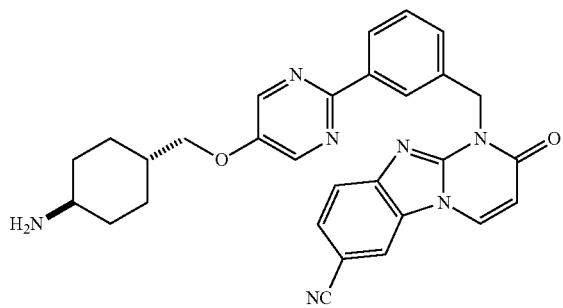

Trifluoroacetic acid (0.8 mL) was added to the solution of compound 47G (115 mg, 1.52 mmol) in dichloromethane (5 mL), the mixture was stirred at 25° C. for 1 hour and then concentrated under reduced pressure to dryness to obtain the trifluoroacetate of compound 47H. LCMS (ESI) m/z: 506.2 [M+1].

Hydrochloride of Compound 47:

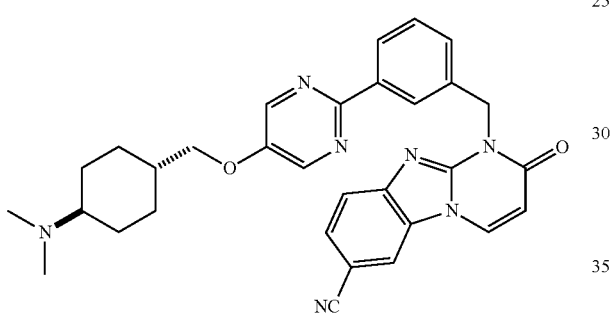

According to the preparation method of the hydrochloride salt of compound 24 by replacing trifluoroacetate of compound 24C with trifluoroacetate of compound 47H and replacing the acetaldehyde aqueous solution with formaldehyde aqueous solution, the mixture separated by high performance liquid preparative chromatography (formic acid system) was concentrated, saturated sodium bicarbonate aqueous solution (30 mL) was added thereto, the pH value of the mixture was adjusted to 10 with 2 mol/L sodium hydroxide aqueous solution, and the mixture was extracted with dichloromethane (20 mL×3 times), the organic phase was combined and concentrated under reduced pressure to obtain compound 47. Water (20 mL) and acetonitrile (10 mL) were added to compound 47, then hydrochloric acid aqueous solution (0.1 mol/1, 1.12 mL) was added thereto, the mixture was evaporated to remove the organic solvent and then freeze-dried to obtain the hydrochloride of compound 47. $^1$H NMR (400 MHz, CD$_3$OD) δ=8.63 (d, J=7.8 Hz, 1H), 8.39 (s, 2H), 8.28 (s, 1H), 8.19 (s, 1H), 8.12 (br d, J=7.8 Hz, 1H), 7.68-7.63 (m, 1H), 7.62-7.57 (m, 1H), 7.49 (br d, J=7.8 Hz, 1H), 7.33 (t, J=7.8 Hz, 1H), 6.26 (d, J=7.8 Hz, 1H), 5.47 (s, 2H), 3.92 (d, J=6.1 Hz, 2H), 2.77 (s, 6H), 2.10-1.99 (m, 4H), 1.59-1.46 (m, 3H), 1.26-1.14 (m, 3H); LCMS (ESI) m/z: 534.3 [M+1].

Embodiment 48

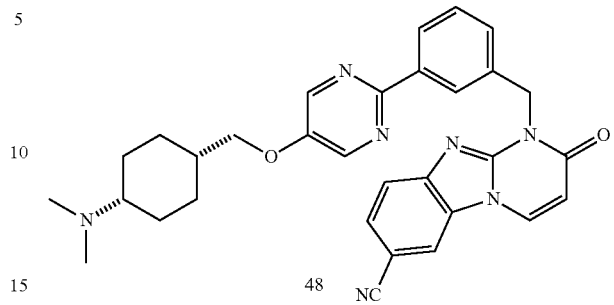

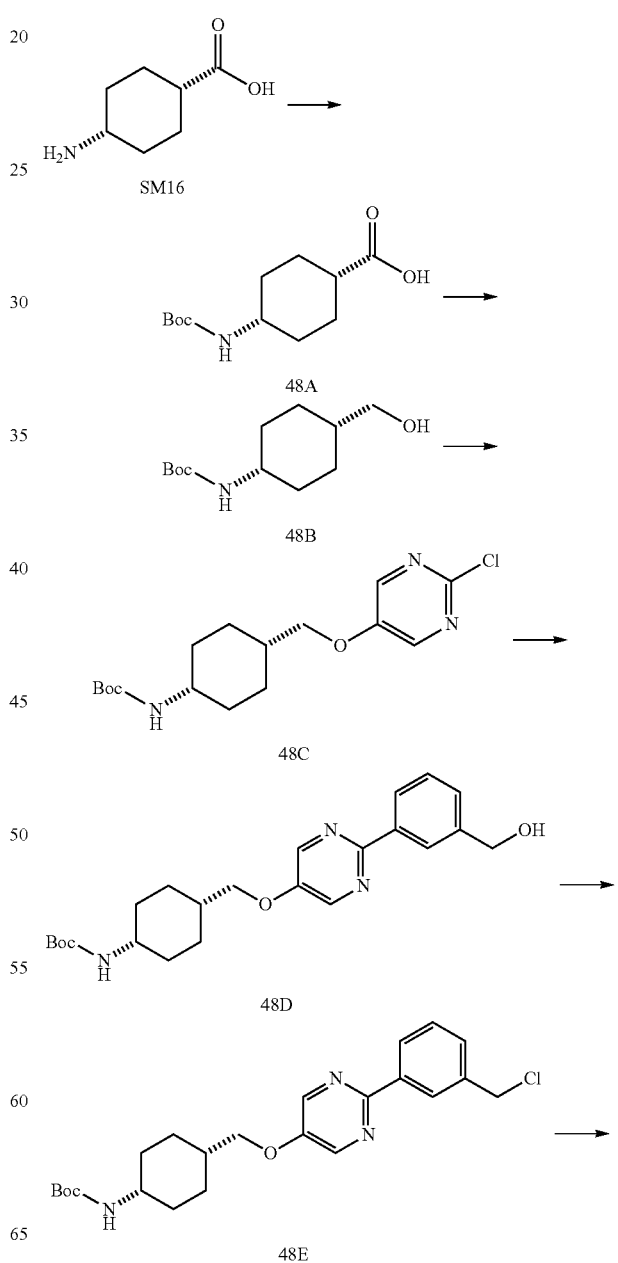

221

-continued

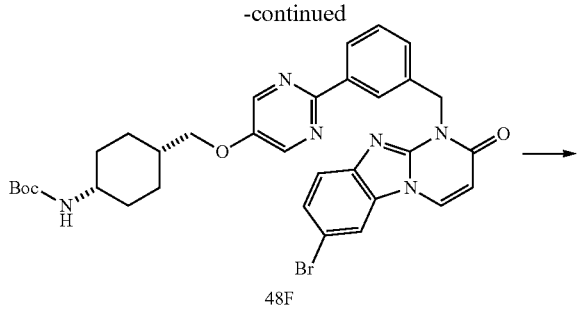
48F

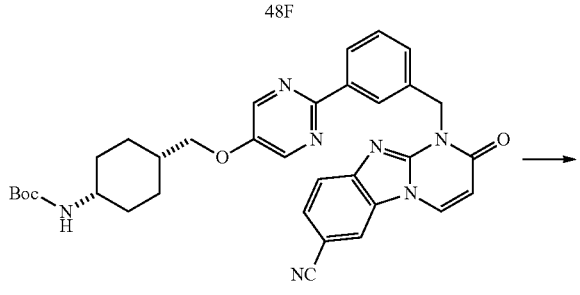
48G

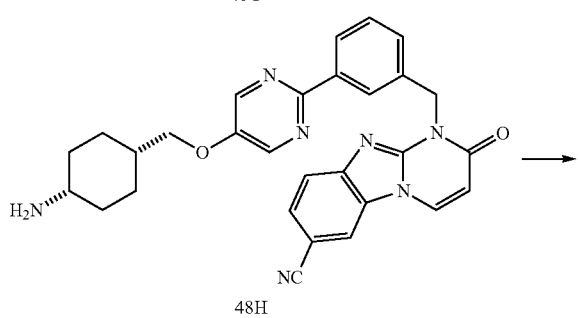
48H

Hydrochloride of compound 48

Compound 48A:

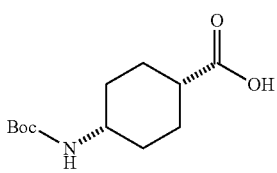

1 mol/L sodium hydroxide aqueous solution (19.52 mL) was added to a solution of cis-4-aminocyclohexanoic acid (1.30 g, 9.08 mmol) in 1,4-dioxane (20 mL), the mixture was cooled to 0° C., Boc$_2$O (2.28 g, 10.44 mmol) was dissolved in 1,4-dioxane (20 mL) and then added to the reaction mixture at 0° C., the reaction mixture was stirred at 0-25° C. for 4 hours, hydrochloric acid aqueous solution (1 mol/L, 50 mL) was added thereto and extracted with dichloromethane: methanol=10:1 (200 mL×5 times), the organic phase was combined and dried over anhydrous sodium sulfate then filtered, and the filtrate was evaporated and concentrated to dryness to obtain the compound 48A. $^1$H NMR (400 MHz, CDCl$_3$) δ=4.65 (br s, 1H), 3.63 (br s, 1H), 2.51 (br s, 1H), 1.96-1.83 (m, 2H), 1.79-1.52 (m, 6H), 1.45 (s, 9H).

222

Compound 48B:

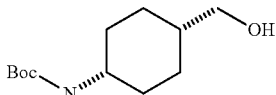

Borane-dimethyl sulfide solution (10 mol/L, 6.17 mL) was added dropwise to a solution of compound 48A (5.00 g, 20.55 mmol) in tetrahydrofuran (50 mL) at 0° C., after the addition, the reaction mixture was stirred at 10° C. for 16 hours, then methanol (40 mL) was added thereto at 20° C. to quench the reaction, and then the reaction mixture was evaporated and concentrated to dryness to obtain the compound 48B. $^1$H NMR (400 MHz, CDCl$_3$) δ=4.65 (br s, 1H), 3.75 (br t, J=6.5 Hz, 2H), 3.63 (br d, J=6.2 Hz, 1H), 3.51 (br s, 1H), 1.60 (br s, 9H), 1.45 (s, 9H).

Compound 48C:

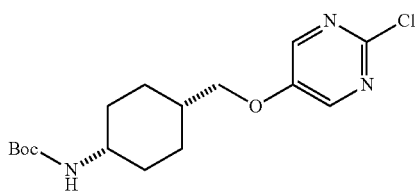

Compound 48C was prepared according to the method of compound 46C by replacing compound 46B with compound 48B. $^1$H NMR (400 MHz, CDCl$_3$) δ=8.33 (s, 2H), 4.74-4.58 (m, 1H), 4.14 (q, J=7.1 Hz, 1H), 3.92 (d, J=6.5 Hz, 1H), 3.53 (d, J=6.3 Hz, 1H), 1.78-1.63 (m, 9H), 1.47 (d, J=2.4 Hz, 9H).

Compound 48D:

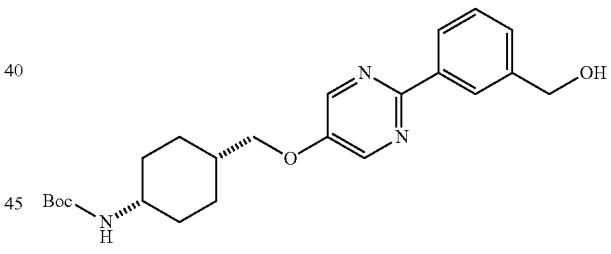

Compound 48C (5.5 g, 16.09 mmol) and 3-hydroxymethyl phenylboronic acid (2.47 g, 16.25 mmol) were dissolved in 55 mL of dioxane and 12 mL of water, and sodium carbonate (5.12 g, 48.27 mmol) and Pd(dppf)Cl$_2$·CH$_2$Cl$_2$ (1.31 g, 1.61 mmol) were added thereto. The mixture was stirred and the reaction was carried out for 1 hour under the protection of nitrogen at 90° C., then the mixture was cooled down to room temperature and then filtered, the filtrate was evaporated to remove the organic solvent. 50 mL of water was added to the residue, and then the mixture was extracted three times with 80 mL of dichloromethane. The organic phase was combined and evaporated, the residue was purified by silica gel column chromatography (petroleum ether: ethyl acetate=1:0 to 3:1) and then purified by high performance liquid chromatography (formic acid system) to obtain the compound 48D. $^1$H NMR (400 MHz, CDCl$_3$) δ=8.38 (s, 2H), 8.26 (s, 1H), 8.22-8.16 (m, 1H), 7.66 (s, 1H), 7.28 (br d, J=7.5 Hz, 1H), 4.71-4.68 (m, 2H), 4.60 (br d, J=17.6 Hz, 1H), 3.88 (d, J=6.6 Hz, 2H), 3.73 (br s, 1H), 2.05 (br s, 1H), 1.93-1.85 (m, 1H), 1.73-1.67 (m, 6H), 1.39 (s, 9H).

Compound 48E:

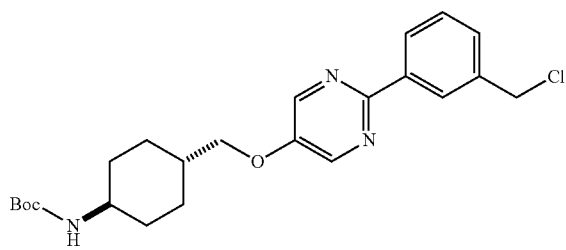

Compound 48E was prepared according to the method of compound 6E by replacing compound 1I with compound 48D. $^1$H NMR (400 MHz, CDCl$_3$) δ=8.73 (s, 2H), 8.45 (s, 1H), 8.32 (br d, J=6.8 Hz, 1H), 7.58-7.51 (m, 1H), 6.81 (br d, J=5.3 Hz, 1H), 4.94 (s, 2H), 4.12 (br d, J=7.0 Hz, 2H), 3.59 (br s, 1H), 1.95 (br s, 1H), 1.69-1.55 (m, 8H), 1.45 (s, 9H).

Compound 48F:

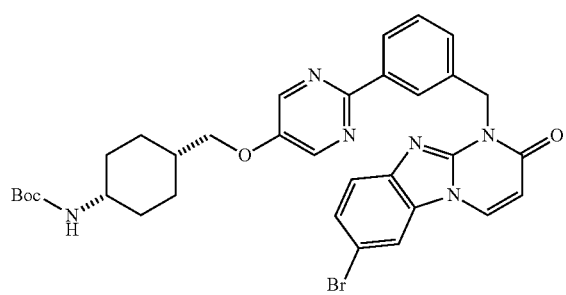

Compound 48F was prepared according to the method of compound 6F by replacing compound 6D with compound 9C1 and replacing the compound 6E with compound 48E. $^1$H NMR (400 MHz, CDCl$_3$) δ=8.90 (d, J=7.9 Hz, 1H), 8.64 (s, 2H), 8.36-8.30 (m, 2H), 8.20 (d, J=7.8 Hz, 1H), 7.61-7.56 (m, 1H), 7.53-7.40 (m, 2H), 6.72 (br d, J=6.3 Hz, 1H), 6.37 (d, J=7.8 Hz, 1H), 5.44 (s, 2H), 4.04 (d, J=7.0 Hz, 2H), 3.53 (br s, 1H), 1.88 (br s, 1H), 1.65-1.45 (m, 8H), 1.39 (s, 9H). LCMS (ESI) m/z: 661.3 [M+3].

Compound 48G:

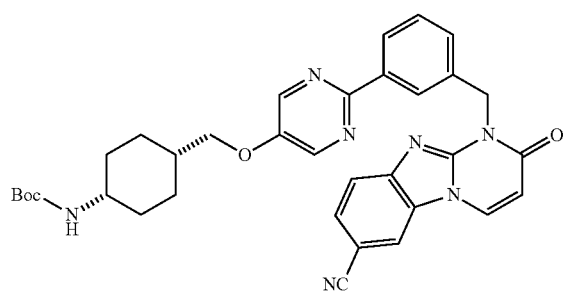

Compound 48G was prepared according to the method of compound 6I by replacing compound 6H with compound 48F. $^1$H NMR (400 MHz, DMSO-d$_6$) δ=8.93 (d, J=7.9 Hz, 1H), 8.64 (s, 2H), 8.60-8.54 (m, 1H), 8.36 (s, 1H), 8.20 (d, J=7.9 Hz, 1H), 7.96 (s, 1H), 7.80-7.75 (m, 2H), 7.52 (br d, J=7.9 Hz, 1H), 6.72 (br d, J=7.1 Hz, 1H), 6.47 (d, J=7.8 Hz, 1H), 5.47 (s, 2H), 4.07-4.02 (m, 2H), 3.53 (br s, 1H), 1.88 (br s, 1H), 1.64-1.47 (m, 9H), 1.39 (s, 9H). LCMS (ESI) m/z: 606.4 [M+1].

Trifluoroacetate of Compound 48H:

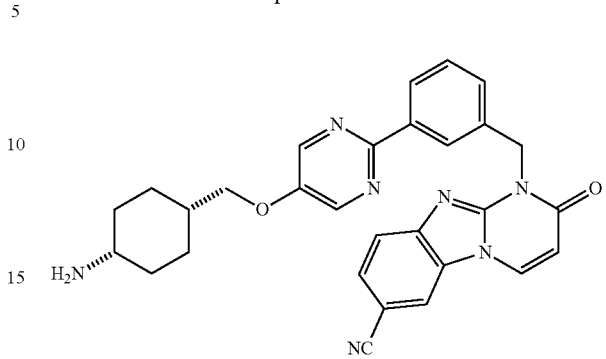

Trifluoroacetic acid (0.6 mL) was added to a solution of compound 48G (200 mg, 330.20 μmol) in dichloromethane (1.4 mL), the mixture was stirred at 25° C. for 0.5 hours, and then concentrated under reduced pressure to dryness to obtain the trifluoroacetate of compound 48H. LCMS (ESI) m/z: 506.4 [M+1].

Hydrochloride of Compound 48:

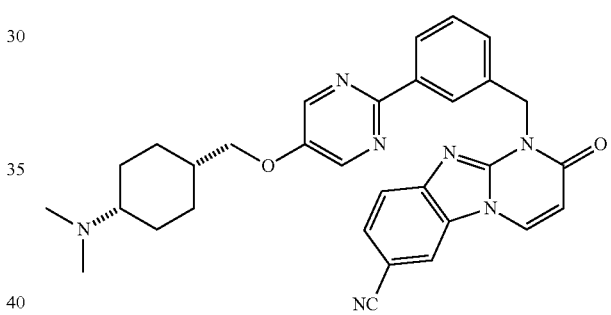

According to the method of the hydrochloride of compound 24, by replacing the trifluoroacetate of compound 24C with trifluoroacetate of compound 48H, replacing the acetaldehyde aqueous solution with formaldehyde aqueous solution, and replacing the high performance liquid chromatography (formic acid system) with preparative plate separation (dichloromethane:methanol=10:1), water (10 mL) and acetonitrile (6 mL) were added to the obtained compound 48, and then hydrochloric acid aqueous solution (1 mol/1, 28 μL) was added thereto, the mixture was evaporated to remove the organic solvent and then freeze-dried to obtain the hydrochloride of compound 48. $^1$H NMR (400 MHz, DMSO-d$_6$) δ=9.89 (br s, 1H), 8.99 (d, J=7.9 Hz, 1H), 8.72 (s, 2H), 8.64 (s, 1H), 8.41 (s, 1H), 8.26 (d, J=7.8 Hz, 1H), 7.87-7.78 (m, 2H), 7.62-7.55 (m, 1H), 7.54-7.44 (m, 1H), 6.53 (d, J=7.8 Hz, 1H), 5.53 (s, 2H), 4.26 (d, J=7.5 Hz, 2H), 2.78 (d, J=5.0 Hz, 6H), 2.20 (br s, 1H), 2.11-1.99 (m, 1H), 1.97-1.83 (m, 4H), 1.79-1.63 (m, 4H); LCMS (ESI) m/z: 534.4 [M+1].

In Vitro Activity Test

Biochemical Experiment

Experimental Objectives:

To detect the inhibitory effect of the compounds on c-Met enzyme activity.

Experimental Materials:

The c-Met Kinase Enzyme System was purchased from Promega. Envision multi-label analyzer (PerkinElmer).

Experimental Method:

The kinase buffer in the kit was used to dilute the enzyme, substrate, ATP and inhibitor.

The compound to be tested was diluted 5-fold to the eighth concentration with a discharge gun, i.e., from 50 µM to 0.65 nM, with a final DMSO concentration of 5%, and double duplicate wells experiment was set. 1 µL of each concentration gradient of the inhibitor, 2 µL of c-Met enzyme (4 ng), 2 µL of a mixture of the substrate and ATP (10 µM ATP, 0.2 µg/µL poly $E_4Y_1$) were added to the microplate, and the final concentration gradient of the compound of 10 µM was diluted to 0.13 nM. The reaction system was placed at 30° C. and the reaction was carried out for 60 minutes. When the reaction was completed, 5 µL of ADP-Glo reagent was added to each well and the reaction was carried out at 30° C. for another 40 minutes, when the reaction was completed, 10 µL of kinase detection reagent was added to each well, then the reaction was carried out at 30° C. for still another 30 minutes, chemiluminescence was read by the PerkinElmer Envision multi-label analyzer with an integration time of 0.5 seconds.

Data Analysis:

Using the equation (Sample-Min)/(Max-Min)*100% to convert the original data to the inhibition rate, the $IC_{50}$ value can be obtained by curve fitting with four parameters (obtained by log(inhibitor) vs. response in GraphPad Prism—Variable slope mode). Table 1 shows the enzymatic inhibitory activity of the compounds of the present disclosure on c-Met.

EBC-1 Cell Proliferation Experiment:

Experimental Materials:

MEM medium, fetal bovine serum, penicillin/streptomycin antibiotics were purchased from Wisent. EBC-1 cell line was purchased from Nanjing COBIO Bioscience Co., LTD. Envision multi-label analyzer (PerkinElmer).

Experimental Method:

EBC-1 cells were seeded in a white 96-well plate, 80 µmL cell suspension per well, which contained 3000 EBC-1 cells. The cell plate was placed in a carbon dioxide incubator for overnight culture.

The compound to be tested was diluted 5-fold to the eighth concentration with a discharge gun, i.e., from 2 mM to 26 nM, and double duplicate wells experiment was set. 78 µL of the medium was added to the middle plate, then 2 µL per well of gradient diluted compound was transferred to the corresponding position on the middle plate, then mixed well and 20 µL per well was transferred to the cell plate. The cell plate was cultured in a carbon dioxide incubator for 3 days. Another cell plate was prepared and the signal values were read on the day of dosing as Max values to be used in the data analysis. 25 µL of Promega CellTiter-Glo was added to each well of this cell plate, and incubated at room temperature for 10 minutes to stabilize the luminescence signal. Readings were taken using a PerkinElmer Envision multi-label analyzer.

25 µL of Promega CellTiter-Glo reagent was added to each well of this cell plate, and incubated at room temperature for 10 minutes to stabilize the luminescence signal. Readings were taken using a PerkinElmer Envision multi-label analyzer.

Data Analysis:

Using the equation (Sample-Min)/(Max-Min)*100% to convert the original data to the inhibition rate, the $IC_{50}$ value can be obtained by curve fitting with four parameters (obtained by "log(inhibitor) vs. response in GraphPad Prism—Variable slope mode). Table 1 shows the inhibitory activity of the compounds of the present disclosure on the proliferation of EBV-1 cells.

Hs746T Cell Proliferation Experiment:

Experimental Materials:

DMEM medium was purchased from Gibco, and fetal bovine serum was purchased from Hyclone. Hs746T cell line was purchased from ATCC. Envision multi-label analyzer (PerkinElmer).

Experimental Method:

Hs746T cells were seeded in a 384-well plate, 50 µL of cell suspension per well, which contained 1500 Hs746T cells. The cell plate was placed in a carbon dioxide incubator for overnight culture.

The compounds to be tested were 3-fold diluted into 9 concentrations with Tecan, double-duplicate well experiment was set, and the final compound concentrations added to the 384-well cell plate were 1000 nM to 0.15 nM. The cell plate was cultured in a carbon dioxide incubator for 4 days.

After 4 days, 25 µL of Promega CellTiter-Glo reagent was added to each well of this cell plate, and incubated at room temperature for 10 minutes to stabilize the luminescence signal. Readings were taken using a PerkinElmer Envision multi-label analyzer.

Data Analysis:

The action curves of the compounds were automatically fitted using Xlfit software and the values of $IC_{50}$ were calculated, High control was the values of DMSO-treated wells and Low control was the values of cell-free medium wells. Table 1 shows the inhibitory activity of the compounds of the present disclosure on the proliferation of Hs746T cells.

TABLE 1

$IC_{50}$ data of the compounds of the present disclosure inhibiting c-Met enzyme and anti-proliferative activity on EBC-1 cells and Hs746T cells

| Compound | c-Met enzyme $IC_{50}$ (nM) | EBC-1 cell proliferation activity $IC_{50}$ (nM) | Hs746T cell proliferation activity $IC_{50}$ (nM) |
| --- | --- | --- | --- |
| Formate of compound 1 | 42 | 133 | — |
| Formate of compound 2 | 10 | 5.79 | — |
| Formate of compound 3 | 16 | 32.8 | — |
| Formate of compound 4 | 167 | — | — |
| Formate of compound 5 | 131 | 585 | — |
| Hydrochloride of compound 6 | 24.9 | 62.8 | — |
| Hydrochloride of compound 8 | 21.5 | 36 | — |
| Hydrochloride of compound 9 | 21.8 | 31.8 | — |
| Hydrochloride of compound 10 | 15.7 | 31.6 | — |
| Hydrochloride of compound 11 | 3.26 | 6.99 | — |
| Hydrochloride of compound 12 | 5.06 | 6.66 | — |
| Hydrochloride of compound 13 | 42 | 133 | — |
| Hydrochloride of compound 14-1 | 16.2 | 14 | — |
| Hydrochloride of compound 15-1 | — | 309 | — |

TABLE 1-continued

IC$_{50}$ data of the compounds of the present disclosure inhibiting c-Met enzyme and anti-proliferative activity on EBC-1 cells and Hs746T cells

| Compound | c-Met enzyme IC$_{50}$ (nM) | EBC-1 cell proliferation activity IC$_{50}$ (nM) | Hs746T cell proliferation activity IC$_{50}$ (nM) |
|---|---|---|---|
| Hydrochloride of compound 15-2 | — | 401 | — |
| Hydrochloride of compound 16 | 45 | 135 | — |
| Hydrochloride of compound 17-2 | — | 15.6 | — |
| Hydrochloride of compound 18-1 | — | 402 | — |
| Hydrochloride of compound 19 | 13.4 | 14.12 | — |
| Hydrochloride of compound 20 | 26 | — | — |
| Hydrochloride of compound 21-1 | — | 33 | — |
| Hydrochloride of compound 21-2 | — | 213.7 | — |
| Hydrochloride of compound 22-1 | 76 | 74 | — |
| Hydrochloride of compound 22-2 | 11 | 10.86 | — |
| Hydrochloride of compound 23 | 6.46 | 16.77 | — |
| Hydrochloride of compound 24 | 2.03 | 4.26 | — |
| Hydrochloride of compound 25 | 2.75 | 1.87 | 2.2 |
| Hydrochloride of compound 26 | 3.12 | 16.2 | — |
| Hydrochloride of compound 27 | 17.7 | 38 | — |
| Hydrochloride of compound 28 | 58 | 66 | — |
| Hydrochloride of compound 29 | 6.31 | 10.35 | — |
| Hydrochloride of compound 30 | 7.48 | 7.09 | 2.0 |
| Compound 31 | — | 492.7 | — |
| Hydrochloride of compound 32 | — | 816.3 | — |
| Hydrochloride of compound 33 | — | 898.7 | — |
| Hydrochloride of compound 34 | 2.82 | 4.91 | 2.6 |
| Hydrochloride of compound 35 | 11.6 | 5.8 | — |
| Hydrochloride of compound 36 | 7.38 | 6.13 | 2.7 |
| Hydrochloride of compound 37 | 4.26 | 4.91 | 2.5 |
| Hydrochloride of compound 38 | 7.65 | 8.51 | 3.2 |
| Hydrochloride of compound 39 | 5.51 | 4.81 | 1.5 |
| Hydrochloride of compound 41 | 6.63 | 5.08 | 2.3 |
| Hydrochloride of compound 42 | 15.24 | — | — |
| Hydrochloride of compound 43 | — | 7.32 | — |
| Hydrochloride of compound 44 | — | 6.83 | — |
| Hydrochloride of compound 45 | — | 19.3 | — |
| Hydrochloride of compound 46 | — | 12.15 | — |

Note:
"—" means not tested

Conclusion: The compound of the present disclosure has strong inhibitory activity on c-Met enzyme, and also has strong anti-proliferative activity on EBC-1 cells and Hs746T cells.

In Vivo Drug Efficacy Experiment of Human Lung Cancer EBC-1 Xenograft Tumor in Nude Mice:

BALB/c nude mice, female, 6-8 weeks old, weighing about 18-20 grams, animals were raised in SPF-class animal rooms in IVC (independent air supply system, constant temperature and humidity) cages (3 per cage). All cages, bedding and water were disinfected before use. All animals had free access to standard certified commercial laboratory diets. A total of 36 mice purchased from Shanghai Lingchang Biotechnology Co., Ltd. were used for research. Each animal was inoculated with 0.1 mL (5×10$^6$ cells) of EBC-1 cells on the right back, when the average tumor volume reached 243 mm$^3$, the animals were randomly grouped and the administration was started. The test compound was orally administered daily, the dose of hydrochloride of compound 24 was 10 mg/kg, the two doses of hydrochloride of compound 25 were 10 mg/kg and 20 mg/kg, respectively, and the dose of hydrochloride of compound 29 was 10 mg/kg. The tumor diameter was measured with vernier calipers twice a week. The calculation formula of tumor volume was: V=0.5a×b$^2$, a and b represented the long diameter and short diameter of the tumor, respectively. The anti-tumor efficacy of the compound was evaluated by TGI (%) or the relative tumor proliferation rate T/C (%). Relative tumor proliferation rate T/C (%)=$T_{RTV}/C_{RTV}$×100% ($T_{RTV}$: average RTV in the treatment group; $C_{RTV}$: average RTV in the negative control group). The relative tumor volume (RTV) was calculated according to the results of tumor measurement, the calculation formula was RTV=$V_t/V_0$, wherein $V_0$ was the tumor volume measured at the time of the grouping administration (i.e. D0), $V_t$ was the tumor volume at a certain measurement, and $T_{RTV}$ and $C_{RTV}$ were taken on the same day. TGI (%) reflected the tumor growth inhibition rate. TGI (%)=[(1−(average tumor volume of a certain treatment group after administration−average tumor volume of the treatment group at the beginning of administration))/(average tumor volume of the solvent control group after the administration−average tumor volume of the solvent control group at the beginning of the administration)]×100%. Statistical analysis was performed based on RTV data at the end of the experiment, and SPSS software was used for analysis. The comparison between two groups was analyzed by T test, and the comparison between three or more groups was analyzed by one-way ANOVA, if the variance was uniform (the F value is not significantly different), the analysis was performed by Tukey's method, if the variance was not uniform (there is a significant difference in the F value), and the Games-Howell method was used to test. p<0.05 was considered a significant difference appeared.

This experiment evaluated the efficacy of the compound in the human lung cancer EBC-1 xenograft tumor model, the drug was stopped after 15 days of administration and observation was continued from that on to the 25th day, the average tumor volume of the blank group as the reference was 2034 mm$^3$, the average tumors volume of the hydrochloride of compound 24 (10 mg/kg), hydrochloride of compound 25 (10 mg/kg), hydrochloride of compound 25 (20 mg/kg), and hydrochloride of compound 29 (10 mg/kg) were 257 mm$^3$, 83 mm$^3$, 4 mm$^3$, and 337 mm$^3$, respectively, $T_{RTV}/C_{RTV}$ was 13.7%, 4.3%, 0.2%, and 16.2%, and TGI was 99.3%, 108.9%, 113.4%, and 94.8%, respectively, P values were 0.001, 0.002, 0.001 and 0.002, respectively. The compound of the present disclosure has a significant inhibitory effect on the growth of human lung cancer EBC-1 xenograft tumor in nude mice.

TABLE 2

Tumor volume at different time points in each group

| After administration Number of days | Blank group | Hydrochloride of compound 24 10 mg/kg | Hydrochloride of compound 25 10 mg/kg | Hydrochloride of compound 25 20 mg/kg | Hydrochloride of compound 29 10 mg/kg |
|---|---|---|---|---|---|
| 0 | 243 ± 15 | 244 ± 23 | 243 ± 21 | 244 ± 22 | 243 ± 17 |
| 4 | 328 ± 23 | 270 ± 22 | 247 ± 20 | 174 ± 12 | 299 ± 13 |
| 7 | 427 ± 26 | 224 ± 16 | 162 ± 13 | 100 ± 8 | 318 ± 21 |
| 11 | 531 ± 33 | 142 ± 24 | 67 ± 9 | 32 ± 3 | 294 ± 27 |
| 14 | 768 ± 65 | 120 ± 25 | 46 ± 5 | 12 ± 3 | 205 ± 37 |
| 18 | 1110 ± 103 | 123 ± 31 | 34 ± 4 | 4 ± 0 | 218 ± 50 |
| 21 | 1531 ± 162 | 164 ± 45 | 44 ± 6 | 4 ± 0 | 243 ± 56 |
| 25 | 2034 ± 214 | 257 ± 72 | 83 ± 11 | 4 ± 0 | 337 ± 83 |
| 27 | Euthanasia | 366 ± 92 | 120 ± 25 | 2 ± 1 | 412 ± 100 |

Note:
[a]Mean ± standard error, n = 6 (6 per group)

In Vivo Drug Efficacy Experiment of Human Gastric Cancer Hs746T Xenograft Tumor in Nude Mice:

BALB/c nude mice, female, 6-8 weeks old, weighing about 18-22 grams, animals were raised in SPF-class animal rooms in IVC (independent air supply system, constant temperature and humidity) cages (3 per cage). All cages, bedding and water were disinfected before use. All animals had free access to standard certified commercial laboratory diets. 0.2 mL (5×10$^6$ cells) of Hs746T cell suspension (with matrix gel, volume ratio 1:1) was subcutaneously inoculated on the right back of each mouse, and a total of 55 mice were inoculated. When the average tumor volume reached 160 mm$^3$, a random stratified grouping method was adopted according to the tumor volume and animal body weight to start grouping administration. The test compound was orally administered daily, the two doses of hydrochloride of compound 25 were 3 mg/kg and 6 mg/kg, respectively, and the dose of hydrochloride of compound 39 was 3 mg/kg. The tumor diameter was measured with vernier calipers twice a week. The calculation formula of tumor volume was: V=0.5a×b$^2$, a and b represented the long diameter and short diameter of the tumor, respectively. The anti-tumor efficacy of the compound was evaluated by TGI (%) or the relative tumor proliferation rate T/C (%). Relative tumor proliferation rate T/C (%)=$T_{RTV}/C_{RTV}$×100% ($T_{RTV}$: average RTV in the treatment group; $C_{RTV}$: average RTV in the negative control group). The relative tumor volume (RTV) was calculated according to the results of tumor measurement, the calculation formula was RTV=$V_t/V_0$, wherein $V_0$ was the tumor volume measured at the time of the grouping administration (i.e. D0), $V_t$ was the tumor volume of the mice at a certain measurement, and $T_{RTV}$ and $C_{RTV}$ were taken on the same day. TGI (%) reflected the tumor growth inhibition rate. TGI (%)=[(1−(average tumor volume of a certain treatment group after administration−average tumor volume of the treatment group at the beginning of administration))/(average tumor volume of the solvent control group after the administration−average tumor volume of the solvent control group at the beginning of the administration)]×100%. Statistical analysis was performed based on the tumor volume (RTV) on the 20th day, and SPSS software was used for analysis. The comparison between two groups was analyzed by T test, and the comparison between three or more groups was analyzed by one-way ANOVA, if the variance was uniform (the F value is not significantly different), the analysis was performed by Tukey's method, if the variance was not uniform (there is a significant difference in the F value), and the Games-Howell method was used to test. p<0.05 was considered a significant difference appeared.

This experiment evaluated the in vivo efficacy of the compound in the human gastric cancer Hs746T xenograft tumor model, drug was stopped after 20 days of the administration, the average tumor volume of the blank group as the reference was 2301 mm$^3$, the average tumors volume of the hydrochloride of compound 25 (3 mg/kg), hydrochloride of compound 25 (6 mg/kg), and hydrochloride of compound 39 (3 mg/kg) were 234 mm$^3$, 17 mm$^3$, and 16 mm$^3$, respectively, $T_{RTV}/C_{RTV}$ were 10.2%, 0.7%, and 0.7%, and TGI were 96.6%, 106.7% and 106.7%, respectively, P values were all below 0.001. The compound of the present disclosure has a significant inhibitory effect on the growth of human gastric cancer Hs746T xenograft tumor in nude mice.

TABLE 3

Tumor volume at different time points in each group

| After administration Number of days | Blank group | Hydrochloride of compound 25 3 mg/kg | Hydrochloride of compound 25 6 mg/kg | Hydrochloride of compound 39 3 mg/kg |
|---|---|---|---|---|
| 0 | 160 ± 5 | 160 ± 7 | 160 ± 7 | 160 ± 6 |
| 2 | 180 ± 6 | 179 ± 8 | 146 ± 6 | 159 ± 8 |
| 5 | 225 ± 7 | 173 ± 12 | 118 ± 6 | 125 ± 4 |
| 9 | 415 ± 22 | 151 ± 7 | 89 ± 9 | 92 ± 3 |
| 12 | 766 ± 56 | 144 ± 6 | 83 ± 9 | 82 ± 5 |
| 16 | 1443 ± 70 | 139 ± 20 | 55 ± 6 | 59 ± 7 |

TABLE 3-continued

Tumor volume at different time points in each group

| After administration Number of days | Blank group | Tumor volume (mm³)[a] Hydrochloride of compound 25 3 mg/kg | Hydrochloride of compound 25 6 mg/kg | Hydrochloride of compound 39 3 mg/kg |
|---|---|---|---|---|
| 19 | 2033 ± 107 | 221 ± 49 | 30 ± 4 | 26 ± 4 |
| 20 | 2301 ± 152 | 234 ± 79 | 17 ± 4 | 16 ± 3 |

Note:
[a]Mean ± standard error, n = 6 (6 per group)

Study on the Pharmacokinetics of Single Intravenous and Oral Administration in Mice and Dogs The objective of this experiment was to study the pharmacokinetics (PK) of the test compound in different species after a single intravenous and a single oral administration.

Sample Collection and Preparation:

After intravenous injection or oral administration, animal blood samples were collected and the actual blood collection time was recorded. Immediately after collection, blood samples were transferred to labeled centrifuge tubes containing K2-EDTA and subsequently centrifuged and processed to obtain plasma. Plasma was transferred to pre-cooled centrifuge tubes, snap-frozen in dry ice and stored in an ultra-low temperature refrigerator at −70±10° C. until LC-MS was performed.

Pharmacokinetic Data Analysis:

Plasma drug concentration data of the compounds were processed using pharmacokinetic software with a non-compartmental model. The peak concentration ($C_{max}$) and time to peak ($T_{max}$), as well as the quantifiable end time, were obtained directly from the blood concentration-time diagram. The log-linear trapezoidal method was used to calculate the following pharmacokinetic parameters: half-life ($T_{1/2}$), apparent volume of distribution ($V_{dss}$) and clearance rate (Cl), and the area under the time-plasma concentration curve from 0 points to the end time ($AUC_{0\text{-}last}$), the initial concentration ($C_0$).

Experimental Results:

See Table 3 and Table 4.

Experimental Conclusion:

The compound of the present disclosure has better oral absorption in mice, a lower clearance rate, longer half-life and better bioavailability; the compound has better oral absorption in dogs, longer half-life and higher bioavailability.

TABLE 4

The pharmacokinetic parameters of a single intravenous and oral administration of the compound of the present disclosure in mice

| | PK parameters in mice | | Hydrochloride of compound 25 | Hydrochloride of compound 39 |
|---|---|---|---|---|
| PK | Intravenous injection | Dose (mg/kg/day) | 1 | 1 |
| | | Clearance rate (mL/kg/min) | 14.7 | 15.8 |
| | | Apparent volume of distribution (L/kg) | 5.41 | 7.27 |
| | | Exposure AUC (nmol · hour) | 2079 | 1805 |
| | | Half-life ($T_{1/2}$) (hours) | 4.51 | 6.73 |
| | Oral administration | Dose (mg/kg/day) | 10 | 10 |
| | | Maximum blood concentration (nmol) | 541 | 1070 |
| | | Peak time (hours) | 2.33 | 4 |
| | | Exposure $AUC_{0\text{-}last}$ (nmol · hour): | 5559 | 14863 |
| | | Oral bioavailability (%) | 27 | 82.3 |

TABLE 5

The pharmacokinetic parameters of a single intravenous and oral administration of the compound of the present disclosure in dogs

| | PK parameters in dogs | | Hydrochloride of compound 25 | Hydrochloride of compound 39 |
|---|---|---|---|---|
| PK | Intravenous injection | Dose (mg/kg/day) | 1 | 1 |
| | | Clearance rate (mL/kg/min) | 24.2 | 18.7 |

TABLE 5-continued

The pharmacokinetic parameters of a single intravenous and oral administration of the compound of the present disclosure in dogs

| PK parameters in dogs | | Hydrochloride of compound 25 | Hydrochloride of compound 39 |
|---|---|---|---|
| | Apparent volume of distribution (L/kg) | 14.4 | 14.6 |
| | Exposure AUC (nmol · hour) | 1227 | 1340 |
| | Half-life ($T_{1/2}$) (hours) | 7.87 | 9.47 |
| Oral administration | Dose (mg/kg/day) | 5 | 5 |
| | Maximum blood concentration (nmol) | 246 | 451 |
| | Peak time (hours) | 4 | 5 |
| | Exposure $AUC_{0\text{-}last}$ (nmol · hour): | 3540 | 4741 |
| | bioavailability (%) | 57.7 | 70.6 |

What is claimed is:

1. A compound represented by formula (I), (I-D), (I-E) or (I-F) a pharmaceutically acceptable salt thereof,

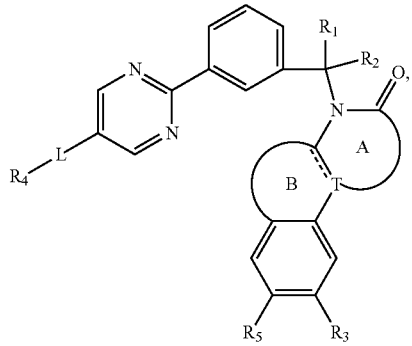

(I)

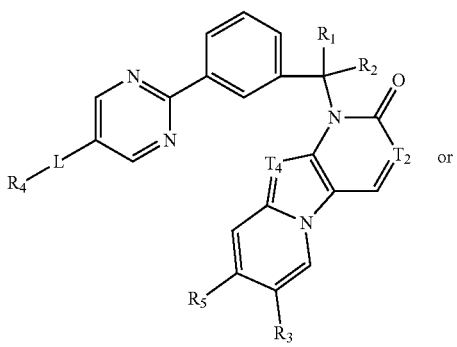

(I-D)

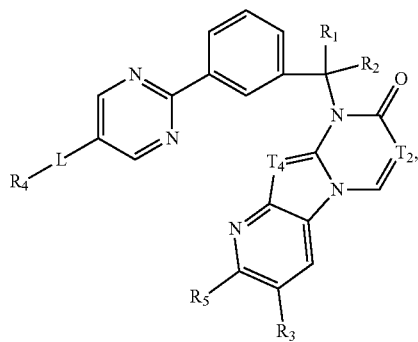

(I-E)

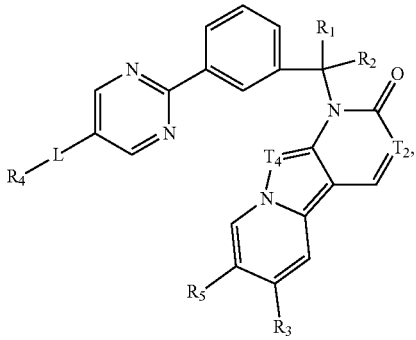

(I-F)

wherein, --- is — or =;
when --- is =, T is C;
the structural moiety

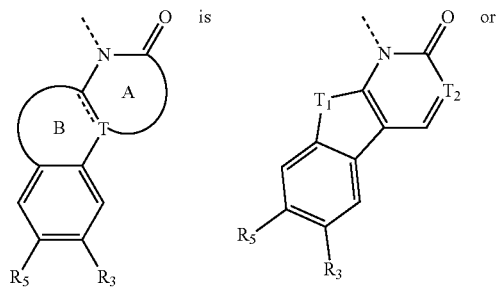

-continued

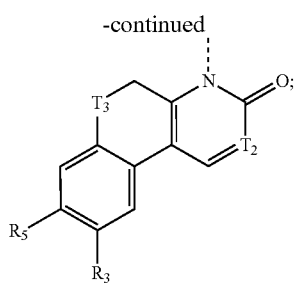

when ⸺ is —, T is N;
the structural moiety

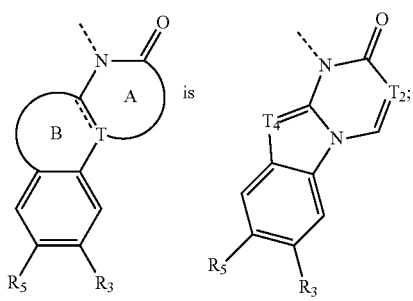

T is

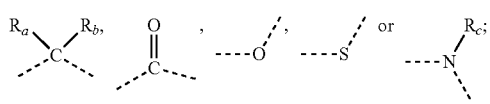

each of $R_a$ and $R_b$ is independently H, F or —CH$_3$;
each of $R_c$ is independently H or —CH$_3$;
each of $T_2$ is independently N or CR$_d$;
each of $R_d$ is independently H or F;
$T_3$ is —CH$_2$— or

each of $T_4$ is independently N or CR$_e$;
$R_e$ is H, F, Cl or —CH$_3$;
each of $R_1$ and $R_2$ is independently H, —CH$_3$, —CF$_3$, —CH$_2$CH$_3$, —CH$_2$CH$_2$CH$_3$ or —CH$_2$(CH$_3$)$_2$;
each of $R_3$ and $R_5$ is independently H, F, Cl, —CN, —OH or C$_{1-3}$ alkoxyl;
L is

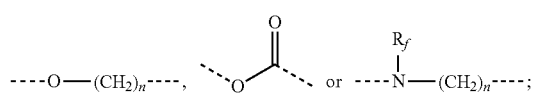

$R_f$ is H, —CH$_3$ or —CH$_2$CH$_3$;
n is 0, 1 or 2;
$R_4$ is 6-12 membered heterocycloalkyl optionally substituted by 1, 2 or 3 $R_g$, azetidinyl optionally substituted by 1, 2 or 3 $R_g$ or cyclohexyl optionally substituted by 1, 2 or 3 $R_g$;

each of $R_g$ is independently H, F, Cl, —OH, —CN, C$_{1-3}$ alkoxy, C$_{1-3}$ alkylamino, C$_{3-4}$ cycloalkyl, 4-6 membered heterocycloalkyl or C$_{1-5}$ alkyl optionally substituted by 1, 2 or 3 substituents independently selected from F, Cl, —OH, —CN,

C$_{1-3}$ alkylamino and —OCH$_3$;
the 6-12 membered heterocycloalkyl and the 4-6 membered heterocycloalkyl respectively comprise 1, 2, 3 or 4 heteroatoms independently selected from N, —O— and —S—.

2. The compound as defined in claim 1, the pharmaceutically acceptable salt thereof, wherein the compound has a structure represented by formula (I-A), (I-B), (I-C) or (I-E):

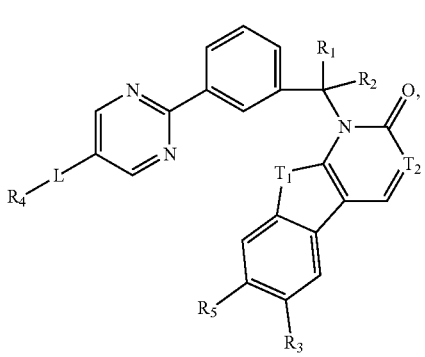
(I-A)

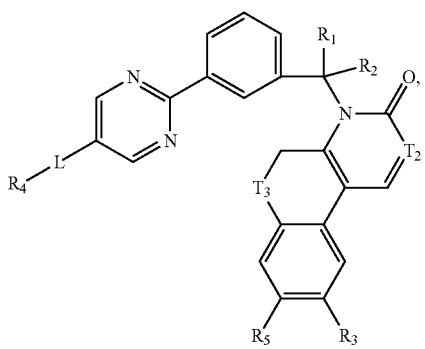
(I-B)

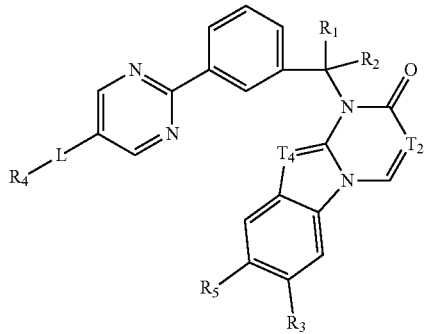
(I-C)

or

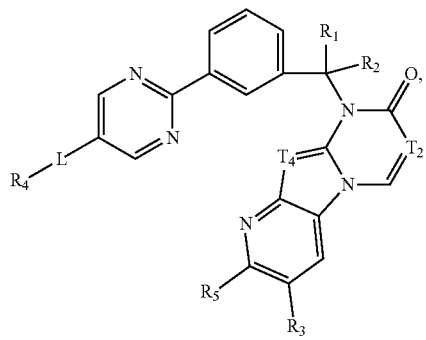
(I-E)
wherein, $T_1$, $T_2$, $T_3$, $T_4$, $R_1$, $R_2$, $R_3$, $R_4$, $R_5$ and L are as defined in claim 1.
3. The compound as defined in claim 2, the pharmaceutically acceptable salt thereof, wherein the compound has a structure represented by formula (I-A1) to (I-A5), (I-B1), (I-C1), (I-C2) or (I-E1):
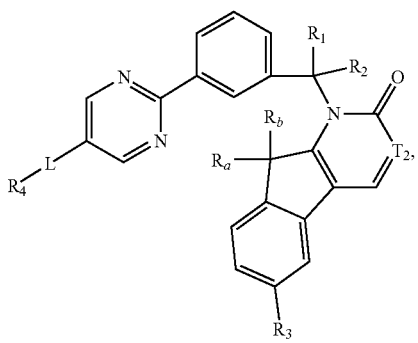
(I-A1)
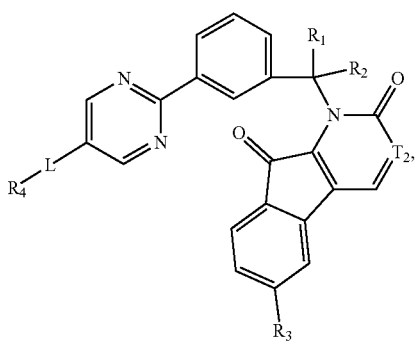
(I-A2)
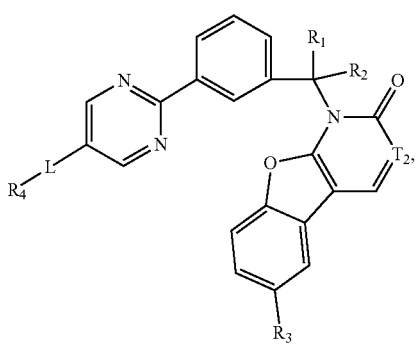
(I-A3)
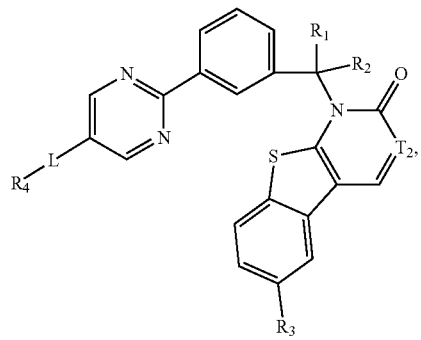
(I-A4)
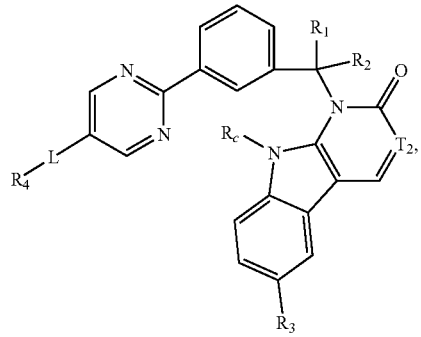
(I-A5)
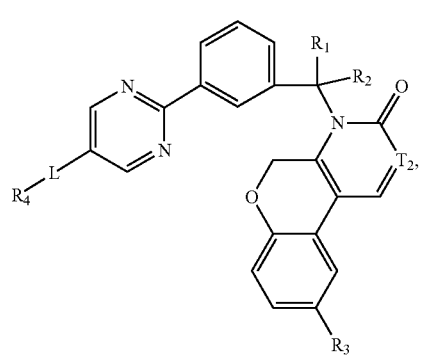
(I-B1)
(I-C1)

-continued (I-C2)

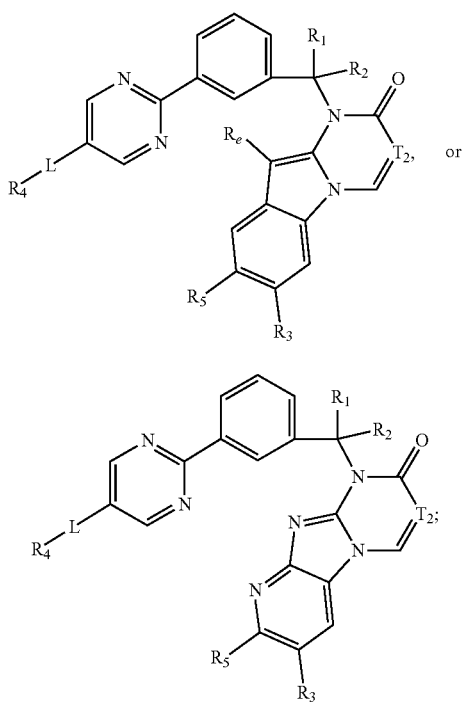

(I-E1)

wherein, $T_2$, $R_1$, $R_2$, $R_3$, $R_4$, $R_5$, L, $R_a$, $R_b$, $R_c$ and $R_e$ are as defined in claim 1.

4. The compound as defined in claim 1, the pharmaceutically acceptable salt thereof, wherein the compound has a structure represented by formula (I-D) or (I-F), (I-D)

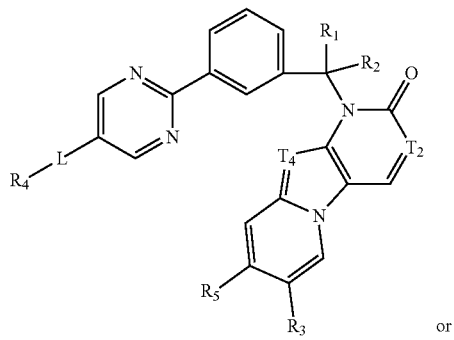

or (I-F)

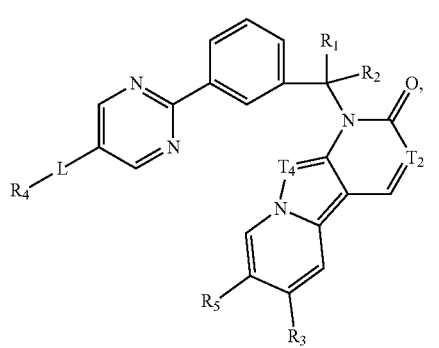

wherein, each of $T_2$ is independently N or $CR_d$;

each of $R_d$ is independently H or F;
each of $T_4$ is independently N or $CR_e$;
$R_e$ is H, F, Cl or —$CH_3$;
each of $R_1$ and $R_2$ is independently H, —$CH_3$, —$CF_3$, —$CH_2CH_3$, —$CH_2CH_2CH_3$ or —$CH_2(CH_3)_2$;
each of $R_3$ and $R_5$ is independently H, F, Cl, —CN, —OH or $C_{1-3}$ alkoxyl;
L is ----O—$(CH_2)_n$----,  or ----N—$(CH_2)_n$----;

$R_f$ is H, —$CH_3$ or —$CH_2CH_3$;
n is 0, 1 or 2;
$R_4$ is 6-12 membered heterocycloalkyl optionally substituted by 1, 2 or 3 $R_g$, azetidinyl optionally substituted by 1, 2 or 3 $R_g$ or cyclohexyl optionally substituted by 1, 2 or 3 $R_g$;
each of $R_g$ is independently H, F, Cl, —OH, —CN, $C_{1-3}$ alkoxy, $C_{1-3}$ alkylamino, $C_{3-4}$ cycloalkyl, 4-6 membered heterocycloalkyl or $C_{1-5}$ alkyl optionally substituted by 1, 2 or 3 substituents independently selected from F, Cl, —OH, —CN,

$C_{1-3}$ alkylamino and —$OCH_3$;
the 6-12 membered heterocycloalkyl and the 4-6 membered heterocycloalkyl respectively comprise 1, 2, 3 or 4 heteroatoms independently selected from N, —O— and —S—.

5. The compound as defined in claim 1, the pharmaceutically acceptable salt thereof, wherein L is

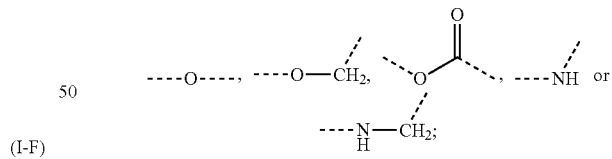

or, each of $R_g$ is H, F, Cl, —OH, —CN,

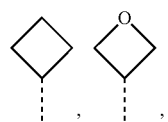

—$CH_3$, —$CH_2CH_3$, —$CH_2CH_2CH_3$, —$CH(CH_3)_2$, —$CH_2CH(CH_3)_2$, —$OCH_3$, —$OCH_2CH_3$, —$N(CH_3)_2$, —$CF_3$, —$CH_2CF_3$, —$CH_2CH_2CF_3$, —$CH_2OH$, —$CH_2CH_2OH$, —$CH_2CH_2OCH_3$, —$CH_2CH_2N(CH_3)_2$,

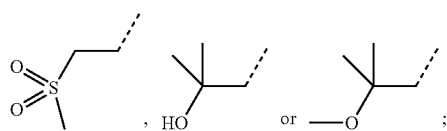

or, R₄ is 6-10 membered heterocycloalkyl optionally substituted by 1, 2 or 3 R_g, azetidinyl optionally substituted by 1, 2 or 3 R_g or cyclohexyl optionally substituted by 1, 2 or 3 R_g;

or, each of R₃ and R₅ is independently H, F, Cl, —CN, —OH or —OCH₃.

6. The compound as defined in claim 1, the pharmaceutically acceptable salt thereof, or the isomer thereof, wherein R₄ is

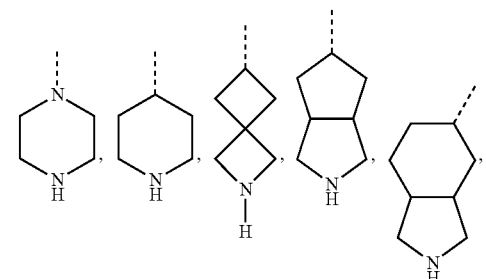

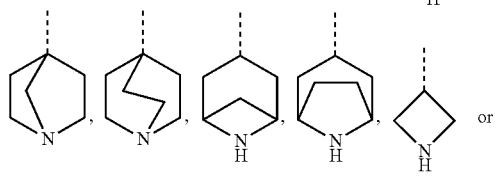

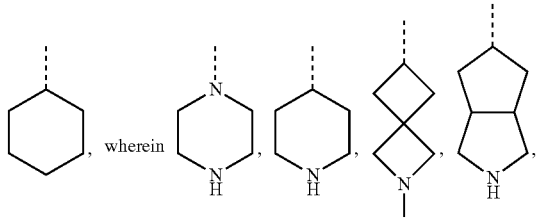

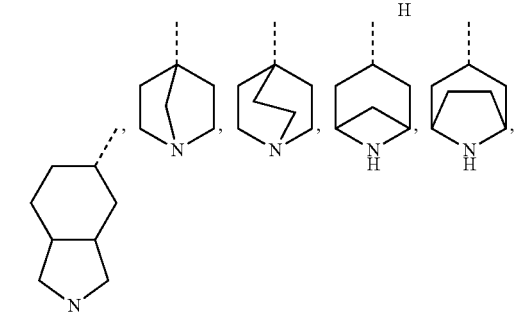

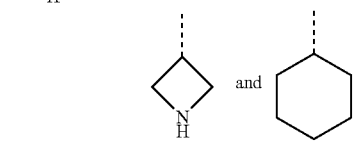

are optionally substituted by 1, 2 or 3 R_g.

7. The compound as defined in claim 6, the pharmaceutically acceptable salt thereof, wherein R₄ is

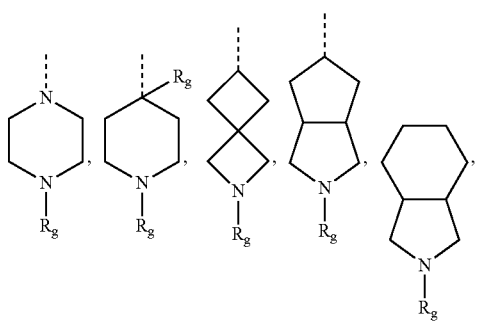

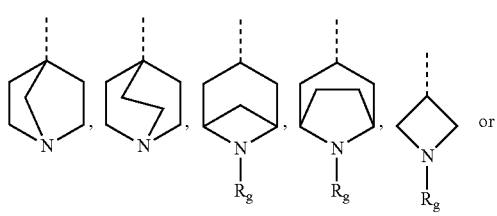

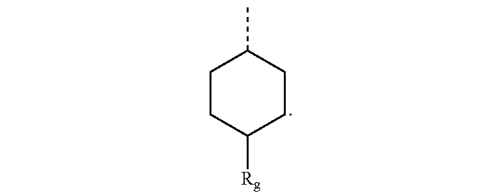

8. The compound as defined in claim 7, the pharmaceutically acceptable salt thereof, wherein R₄ is

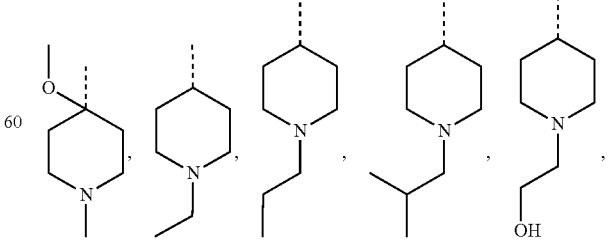

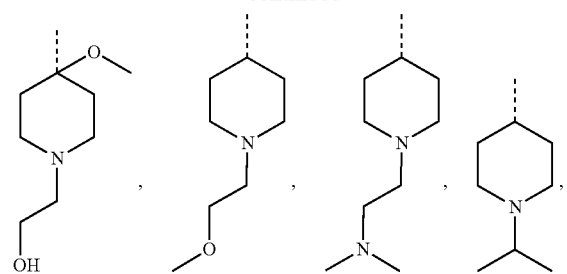
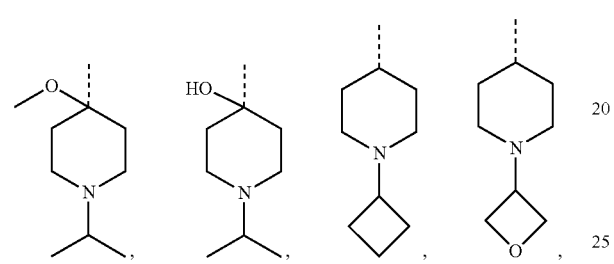
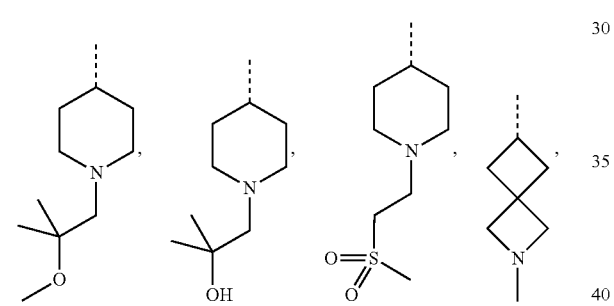
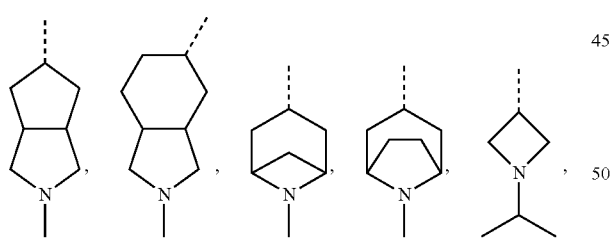
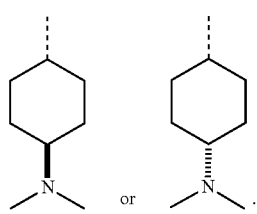
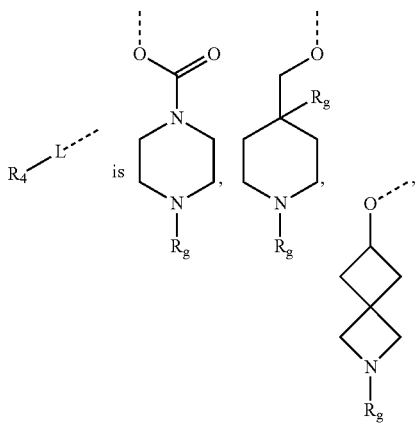
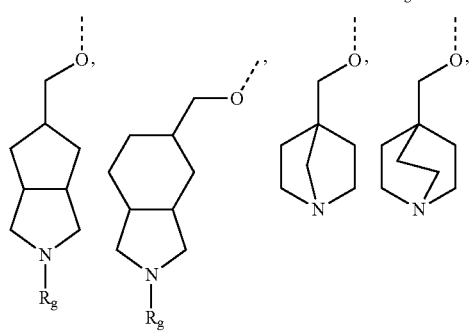
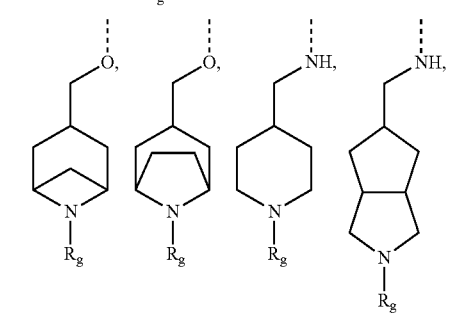
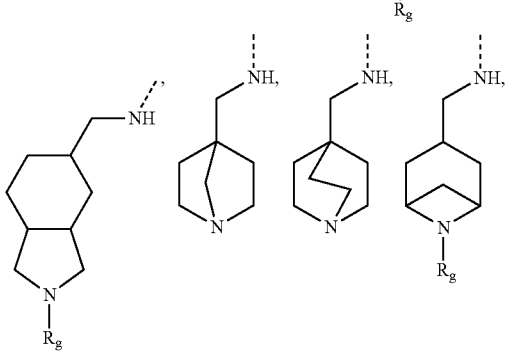
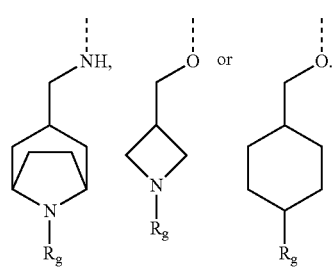
9. The compound as defined in claim 1, the pharmaceutically acceptable salt thereof, wherein the structural moiety
10. The compound as defined in claim 9, the pharmaceutically acceptable salt thereof, wherein the structural moiety -continued
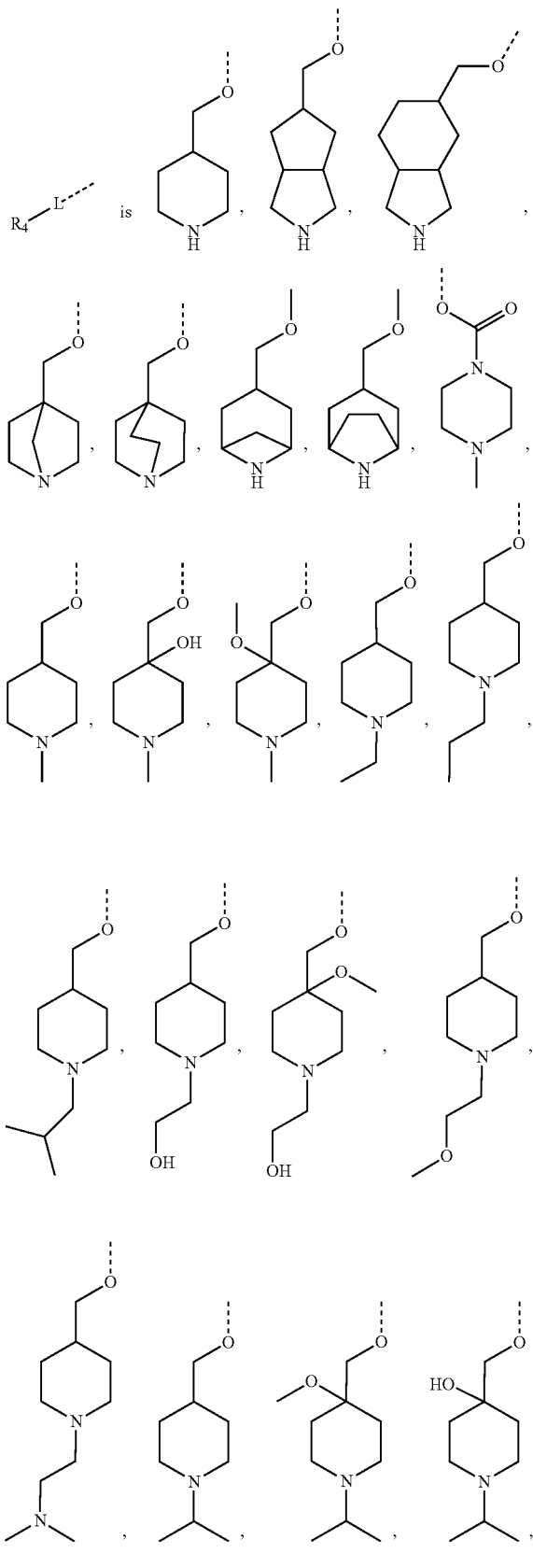
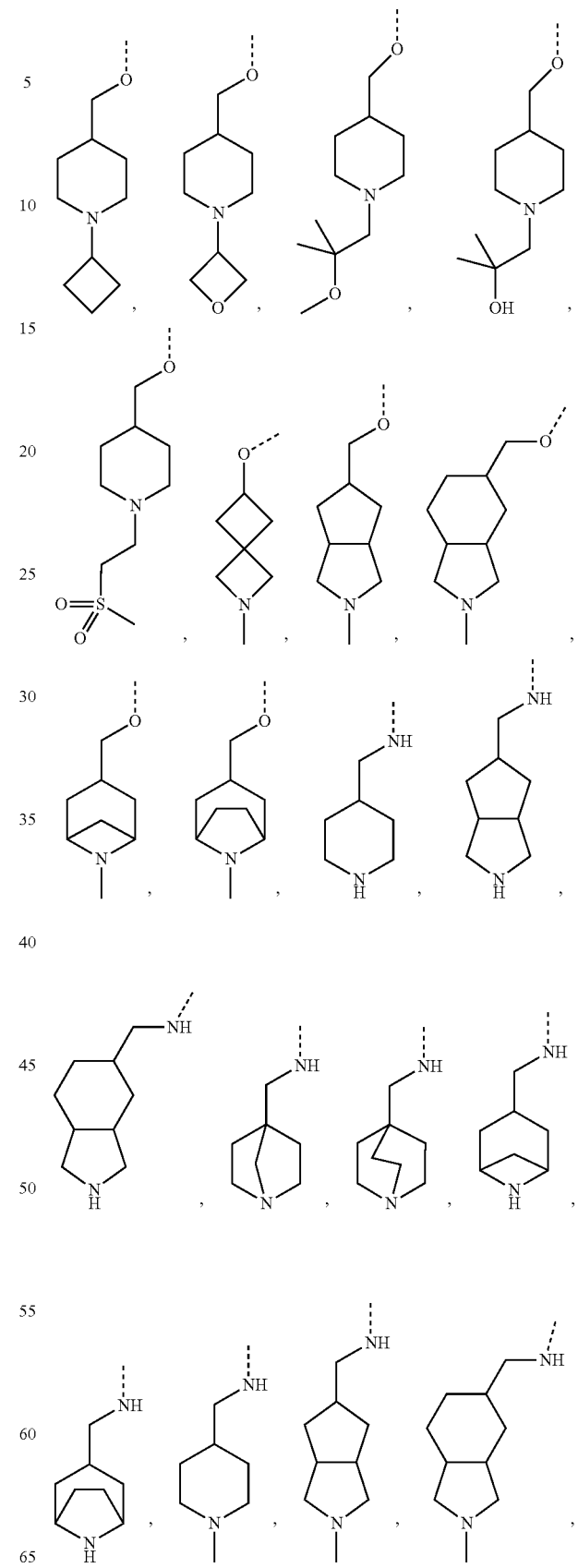

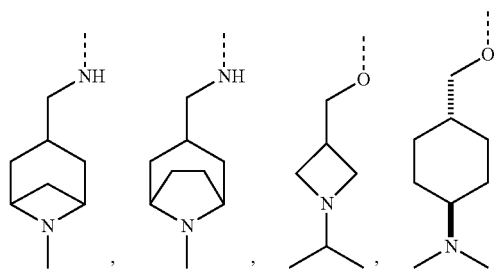
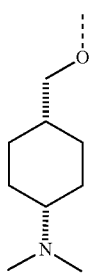
11. The compound as defined in claim 1, the pharmaceutically acceptable salt thereof, wherein the compound has a structure represented by formula (I-A6) to (I-A11), (I-B2), (I-C4) to (I-C6), (I-E2), (I-D2) or (I-F2):
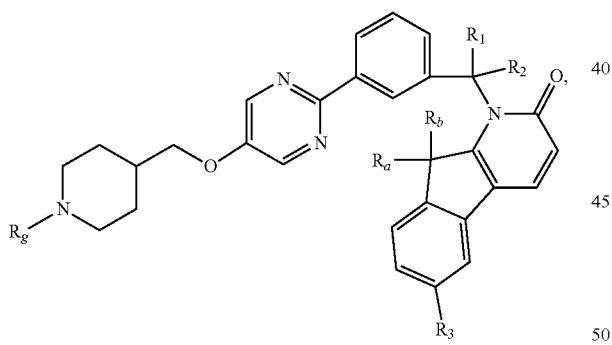
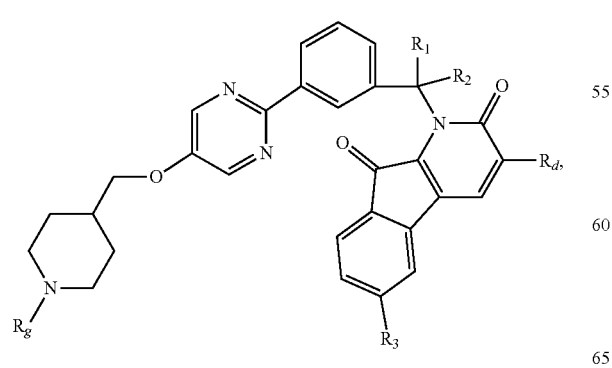
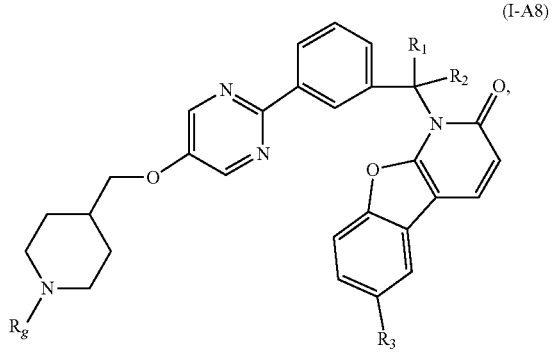
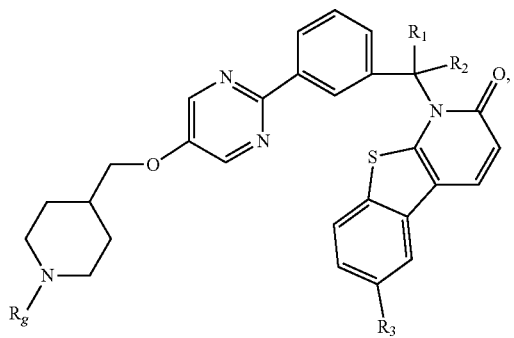
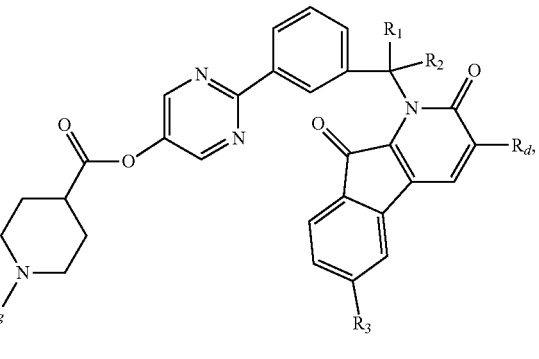

(I-B2)
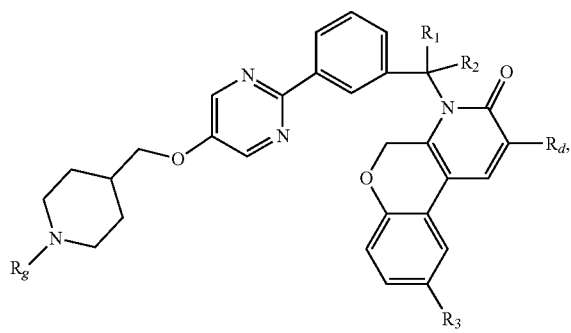
(I-C4)
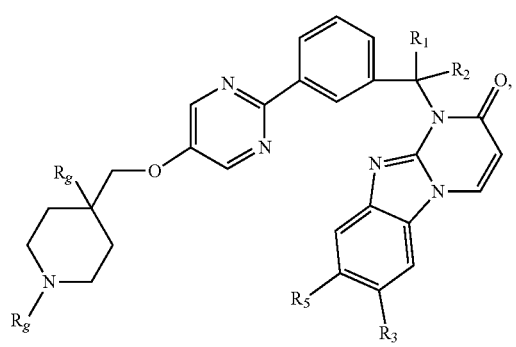
(I-C5)
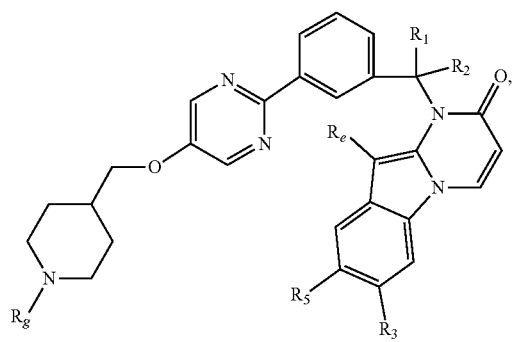
(I-C6)
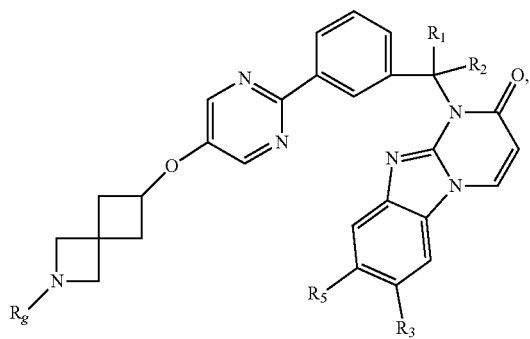
(I-E2)
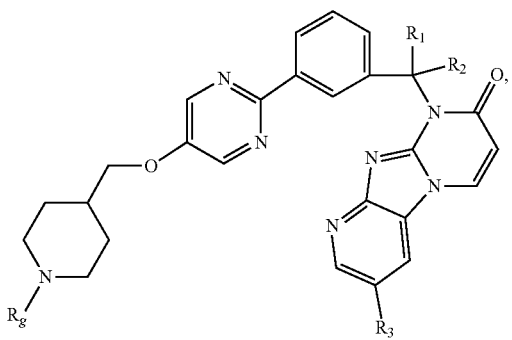
(I-D2)
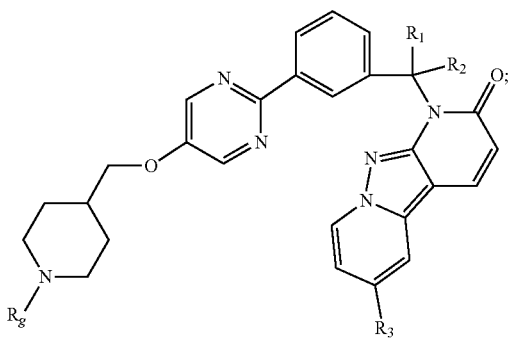
or
(I-F2)
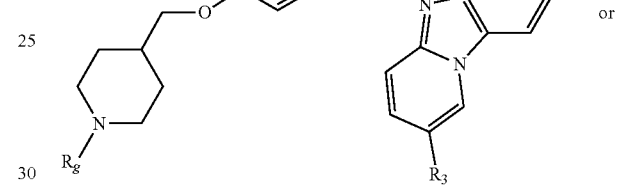
wherein, $R_1$, $R_2$, $R_3$, $R_5$, $R_a$, $R_b$, $R_c$, $R_d$, $R_e$ and $R_g$ are as defined in claim 1.
12. The compound as defined in claim 1, the pharmaceutically acceptable salt thereof, wherein the structural moiety
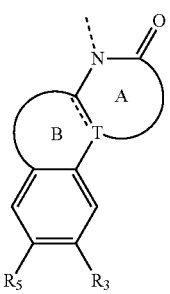 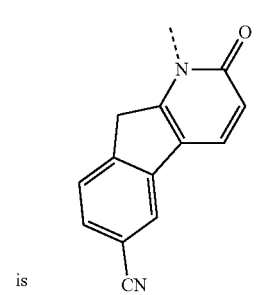
is

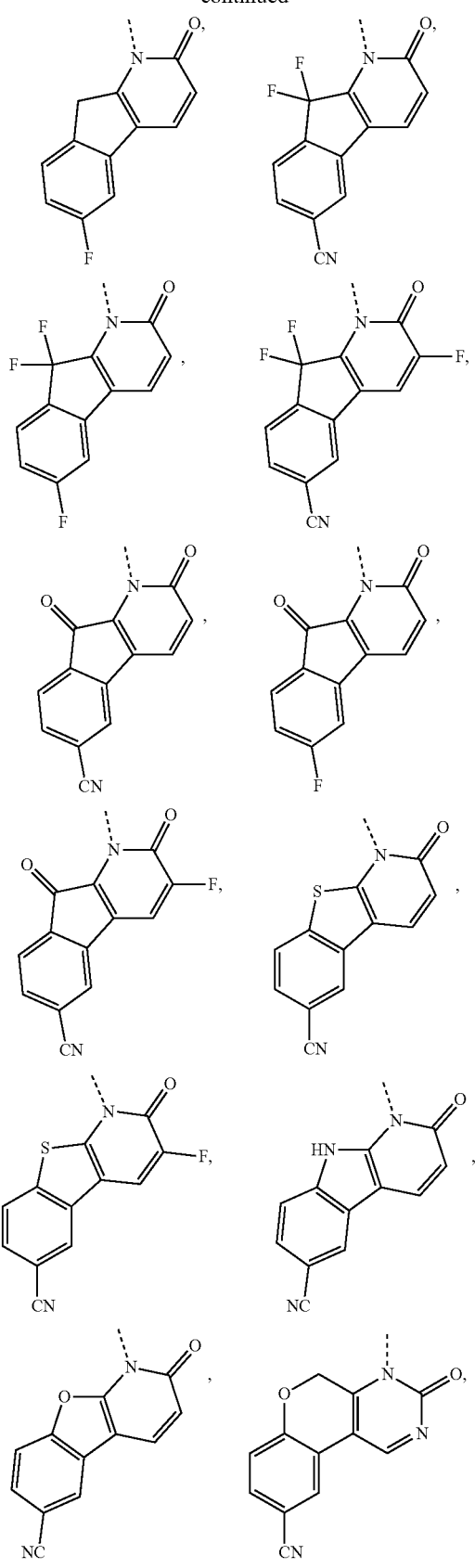
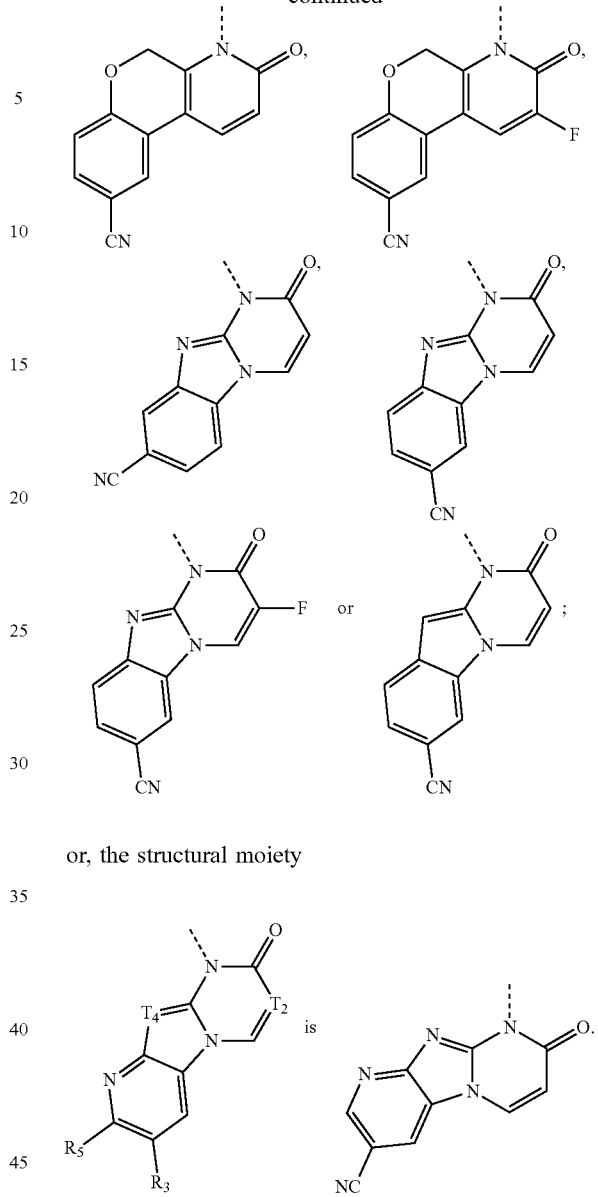
or, the structural moiety
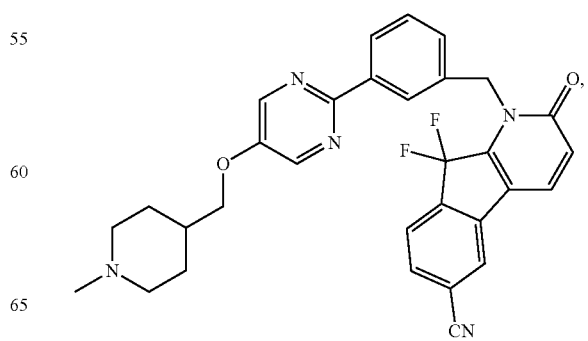
13. The compound as defined in claim 1, the pharmaceutically acceptable salt thereof,
wherein the compound is selected from the following formula:

253
-continued
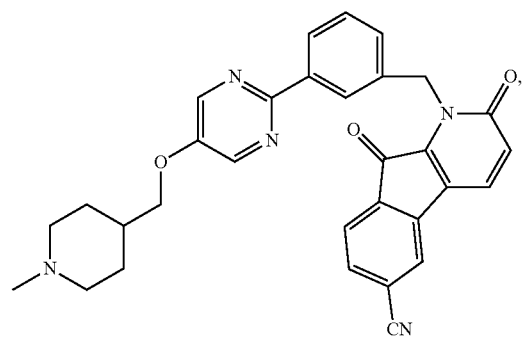
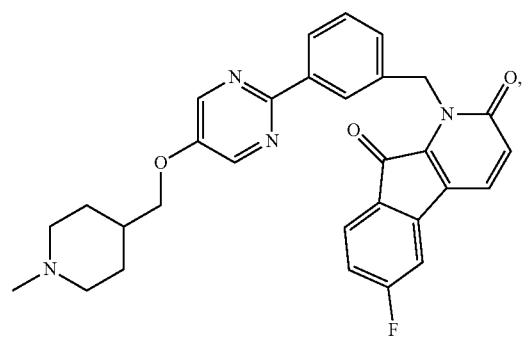
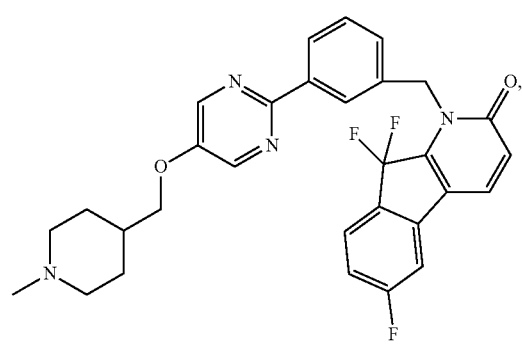
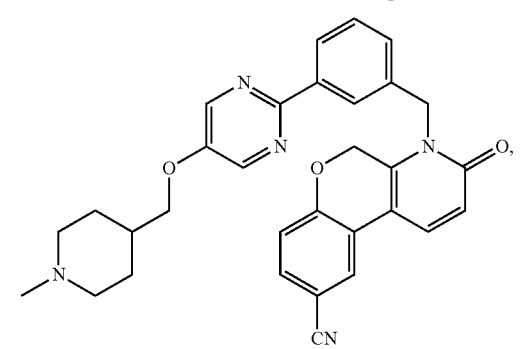
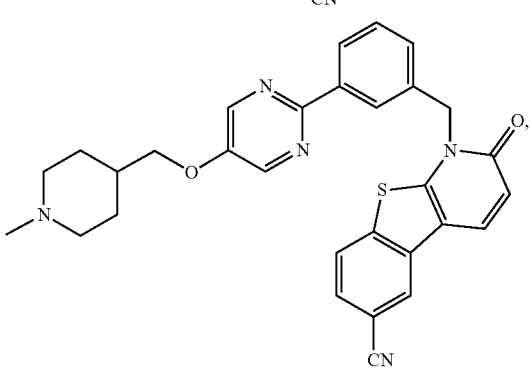
254
-continued
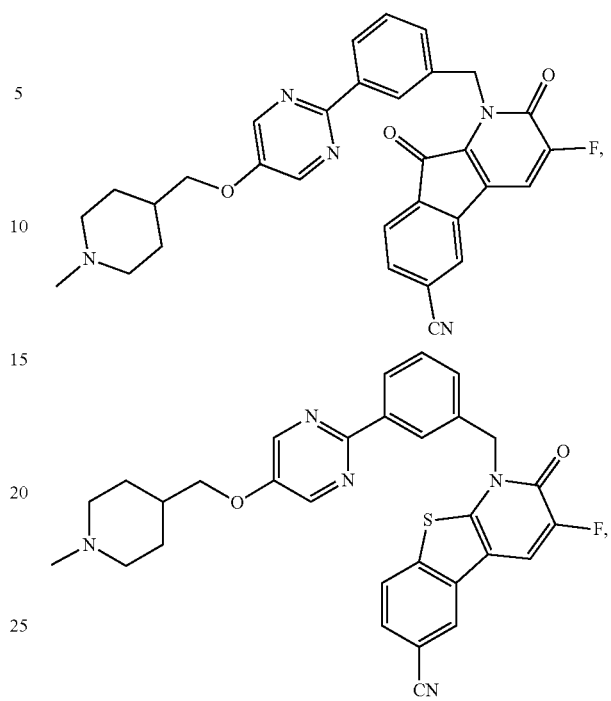
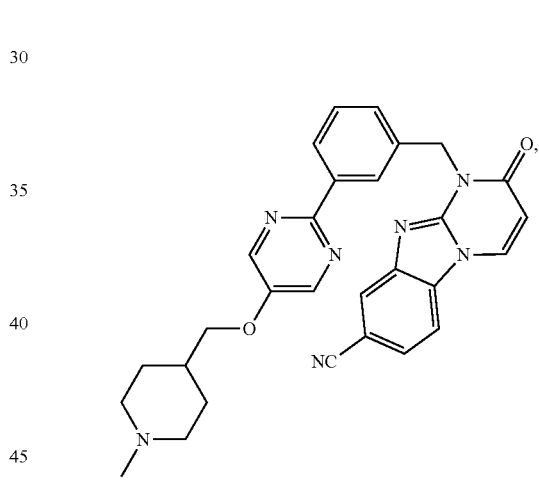
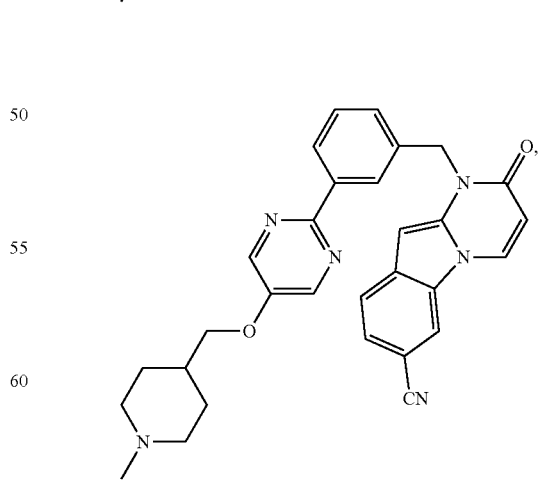

255
-continued
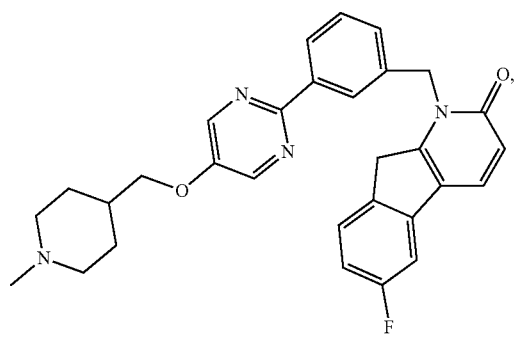
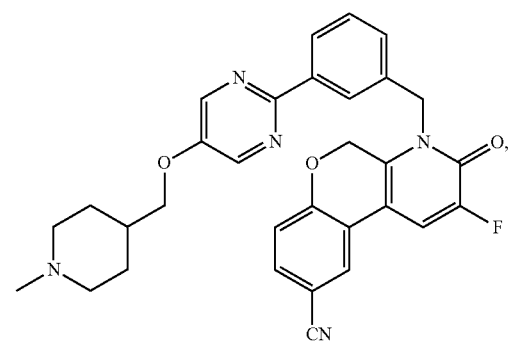
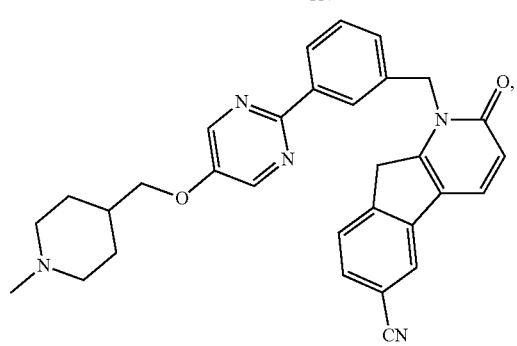
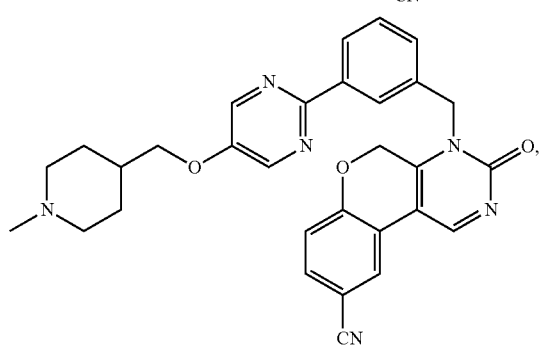
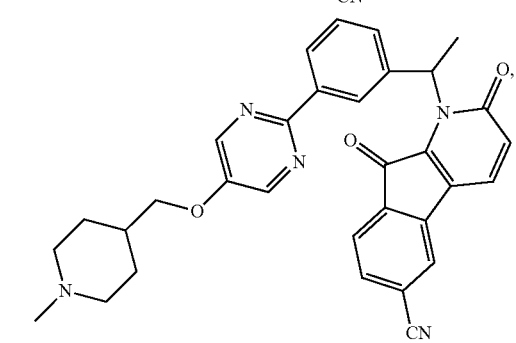
256
-continued
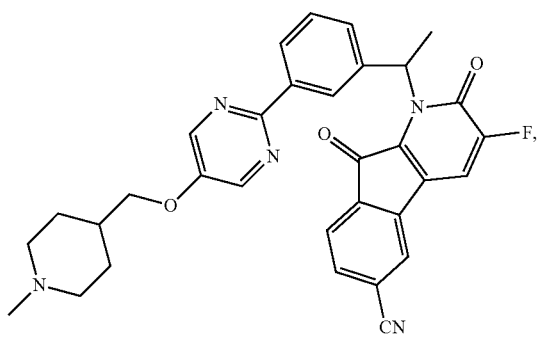
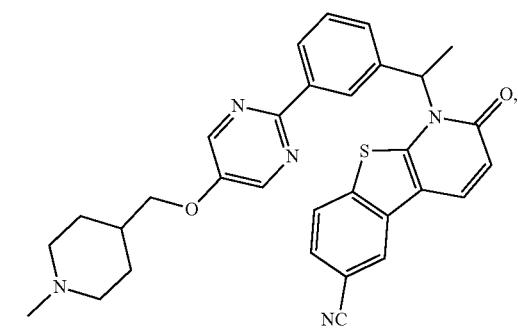
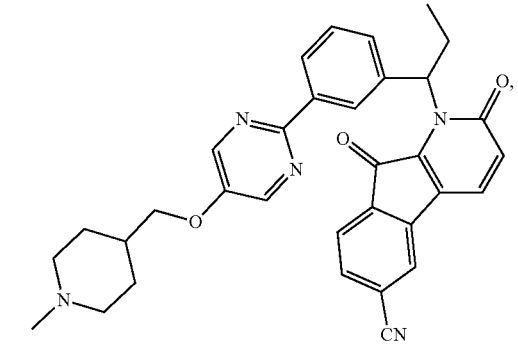
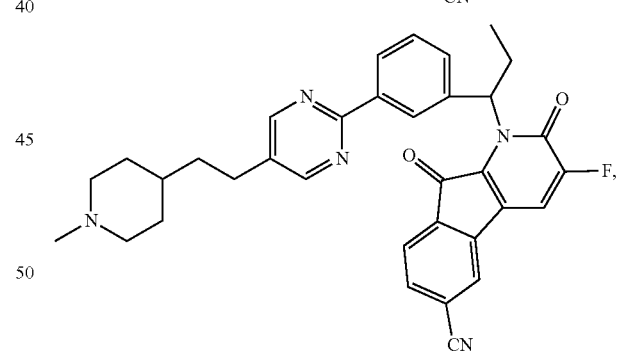
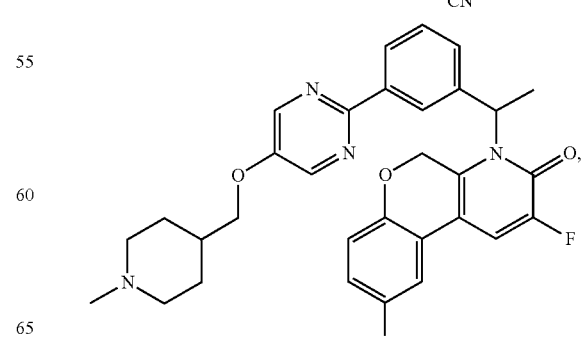

257
-continued
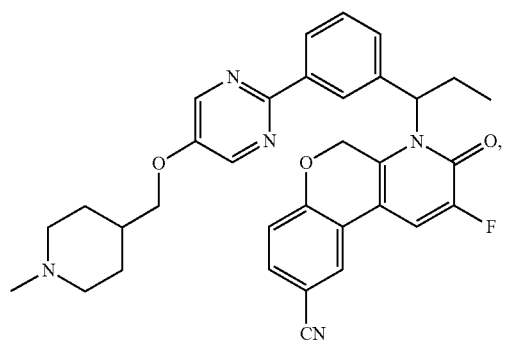
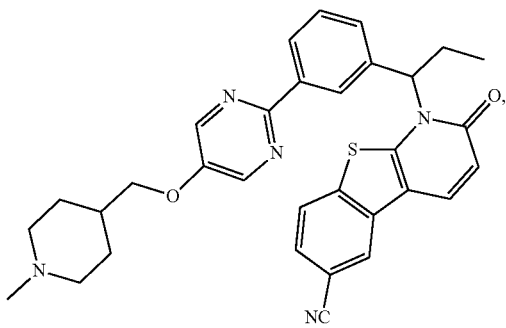
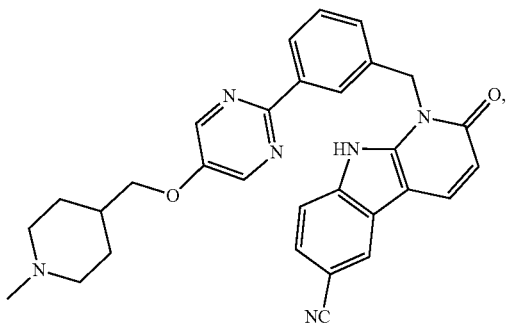
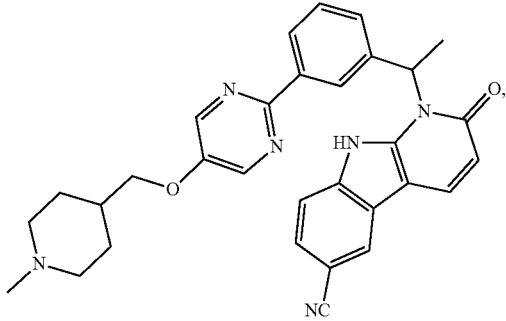
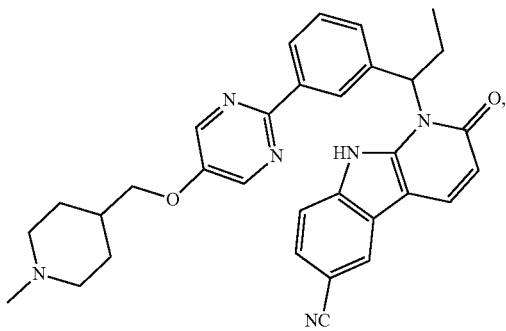
258
-continued
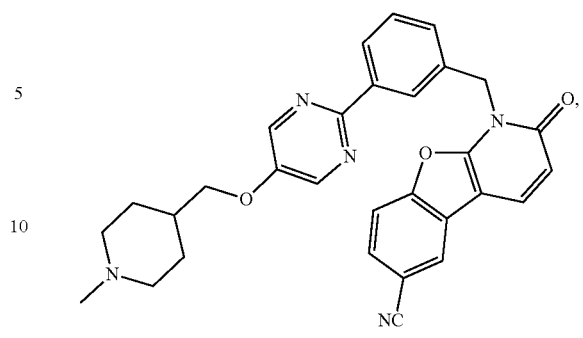
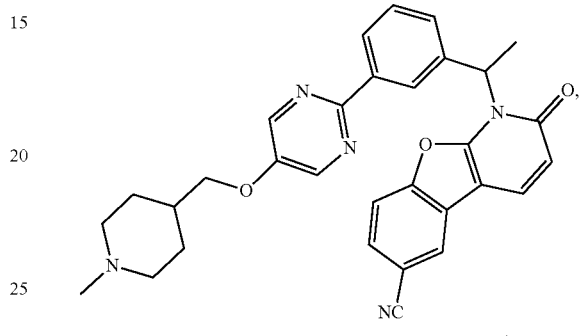
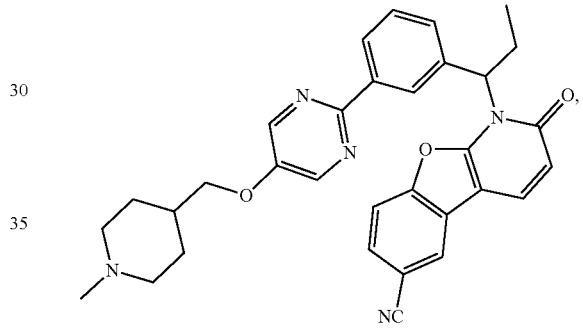
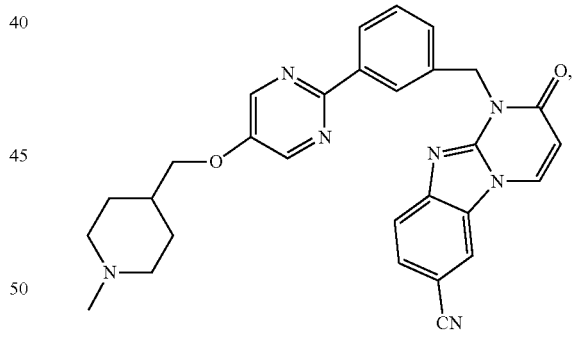
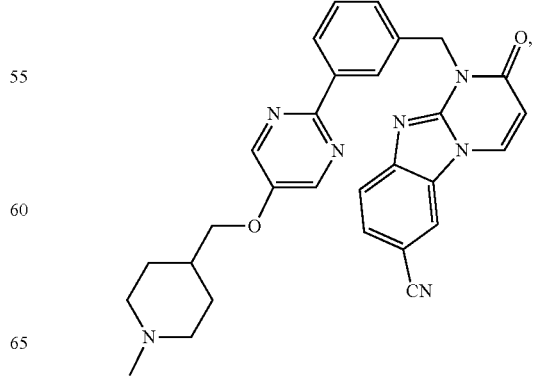

259
-continued
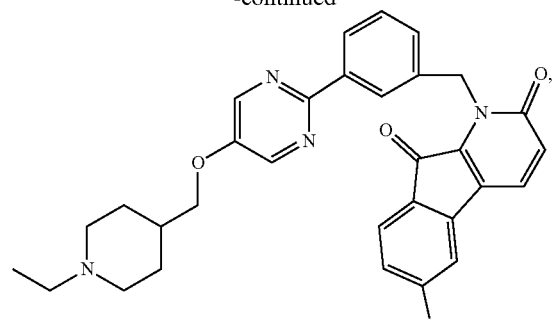
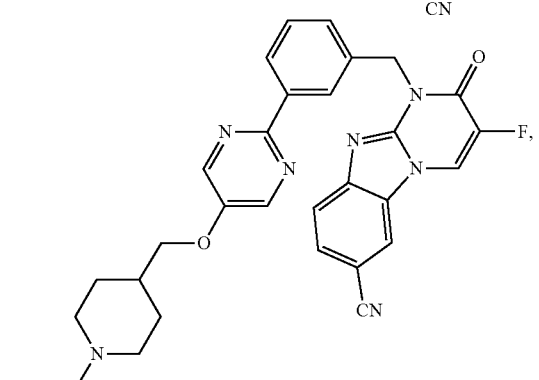
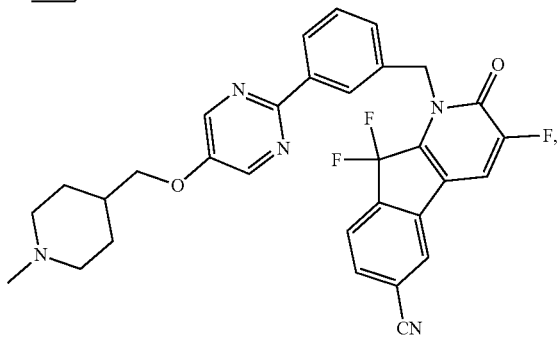
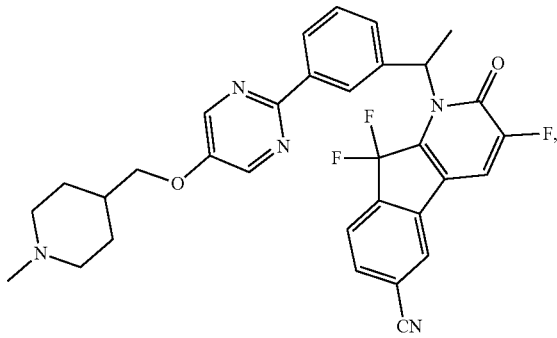
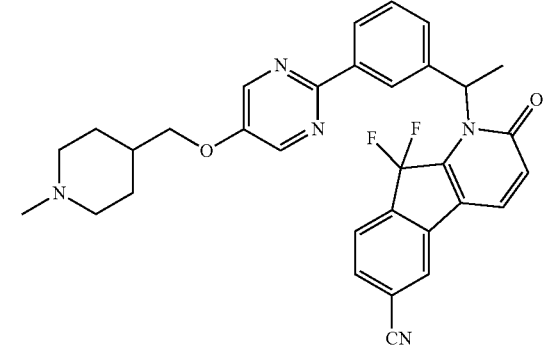
260
-continued
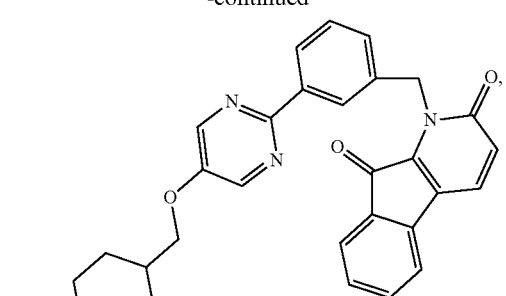
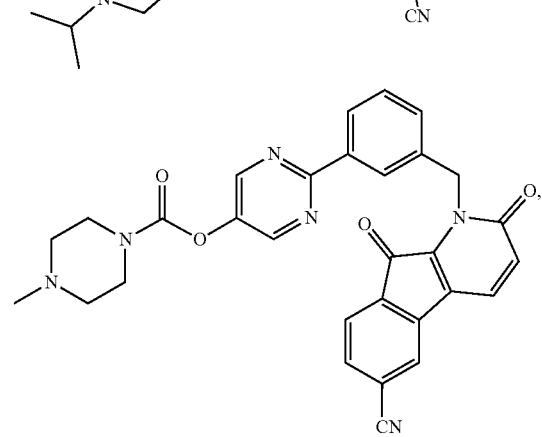
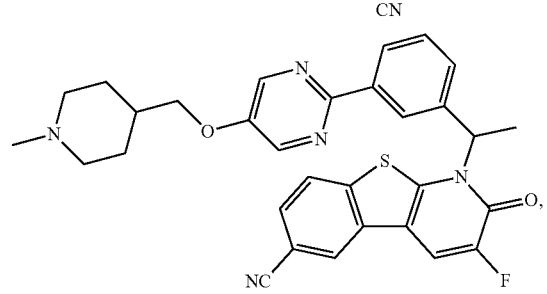
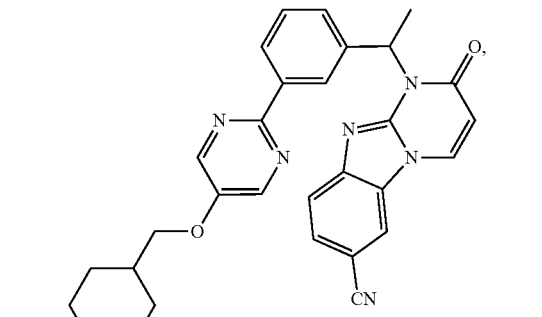
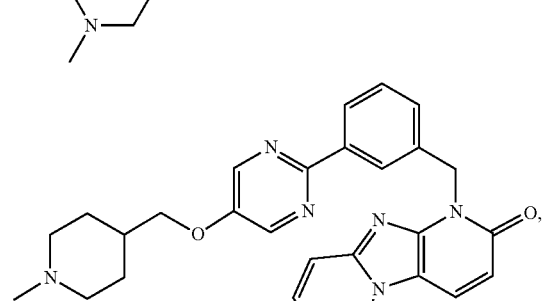

261
-continued
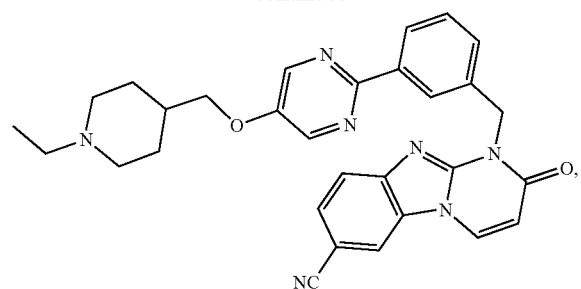
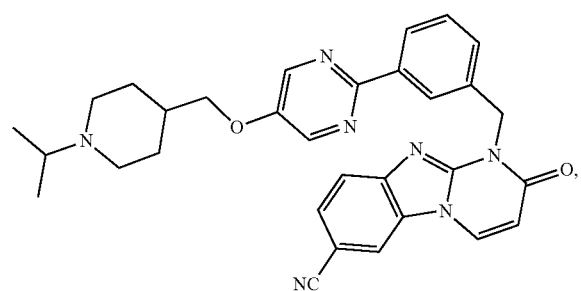
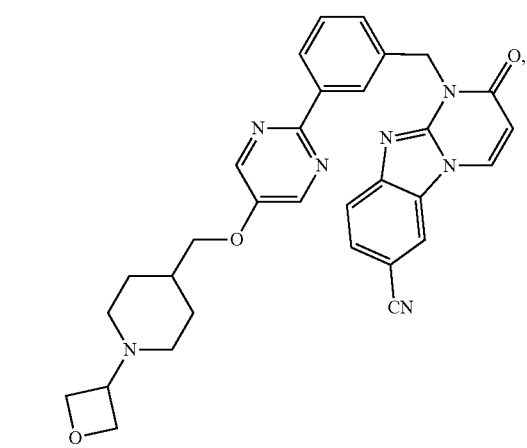
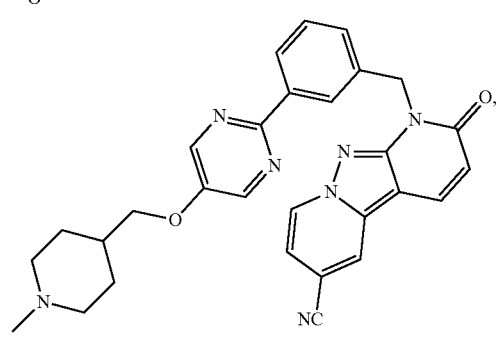
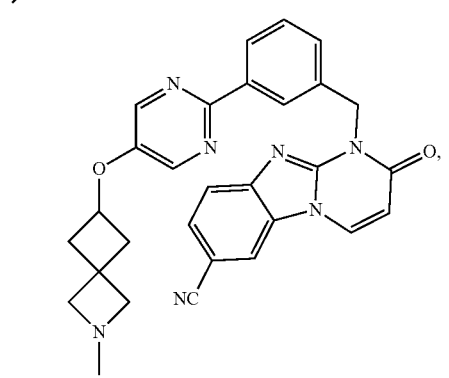
262
-continued
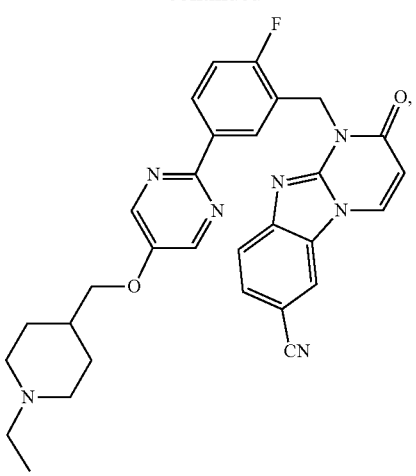
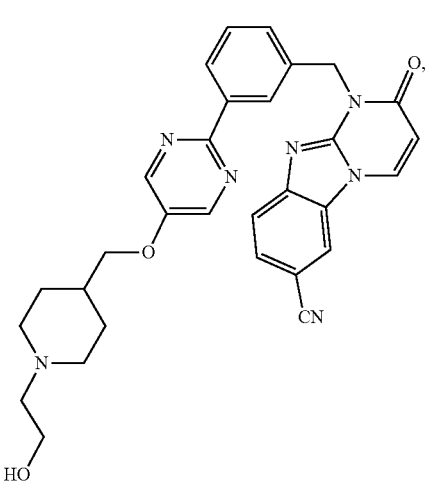
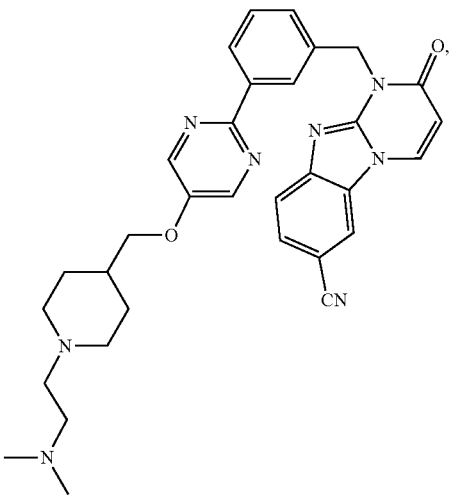

263
-continued
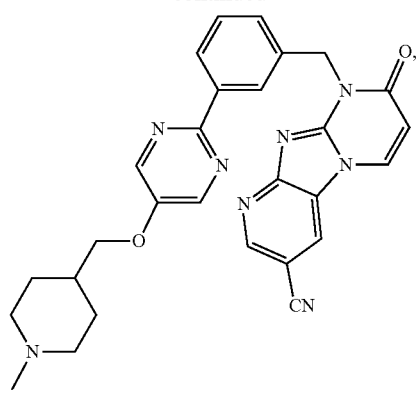
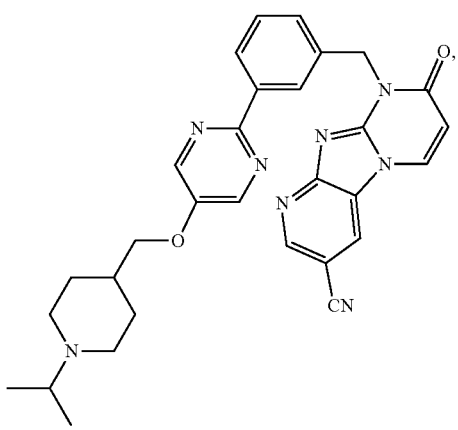
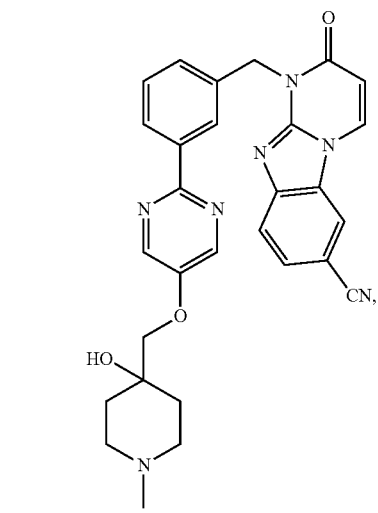
264
-continued
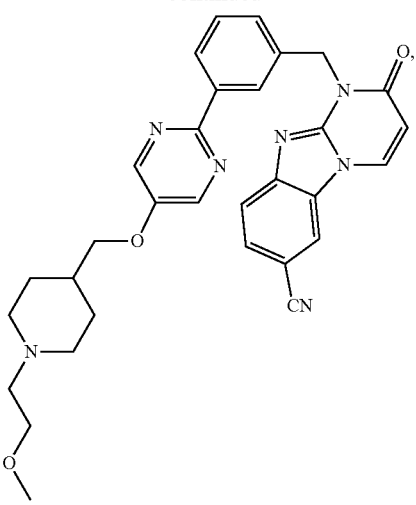
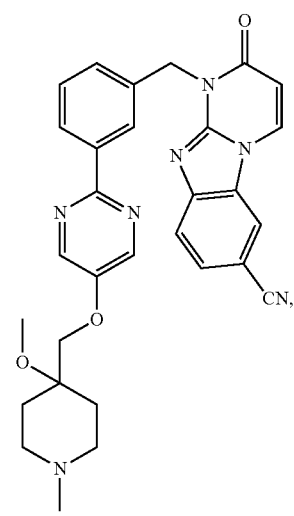
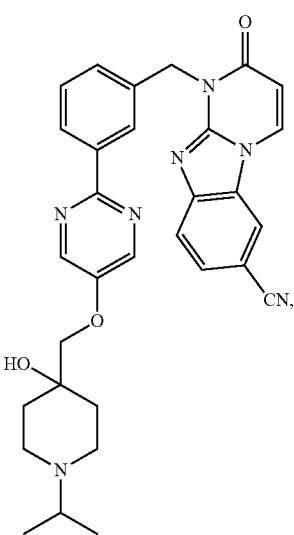

265
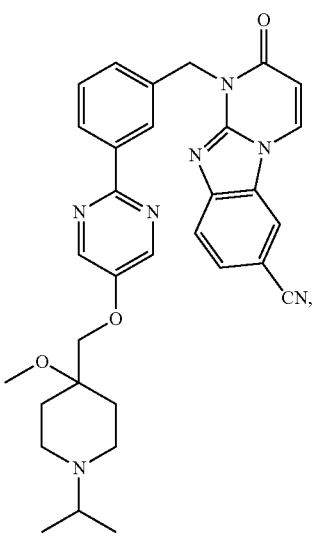
266
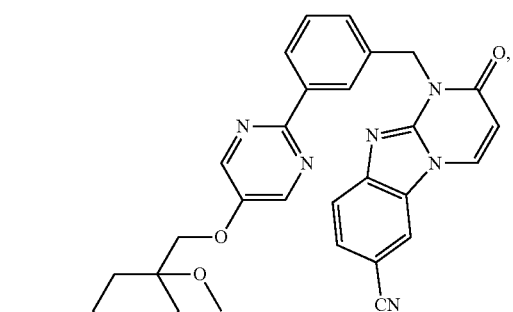
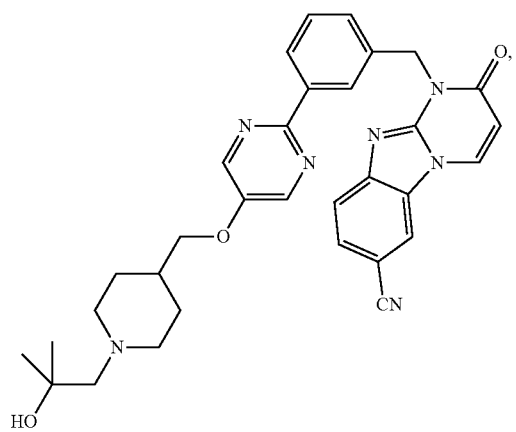
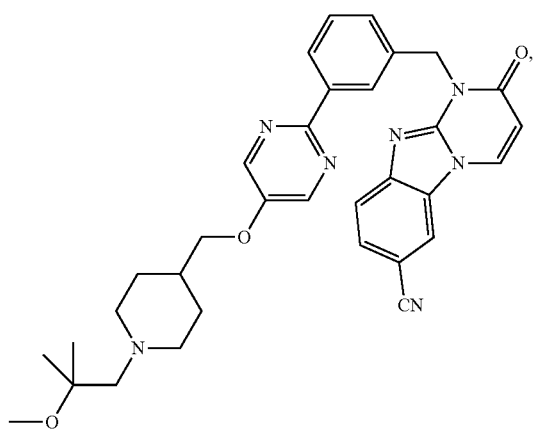
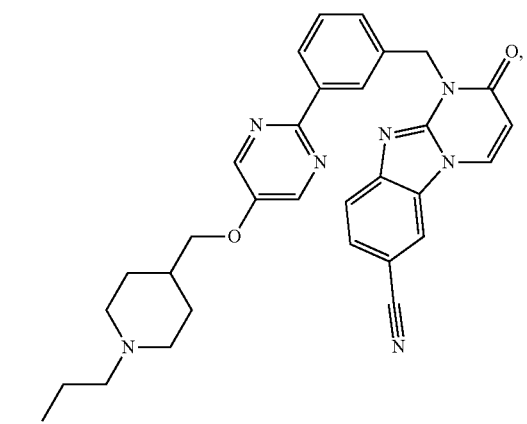

267
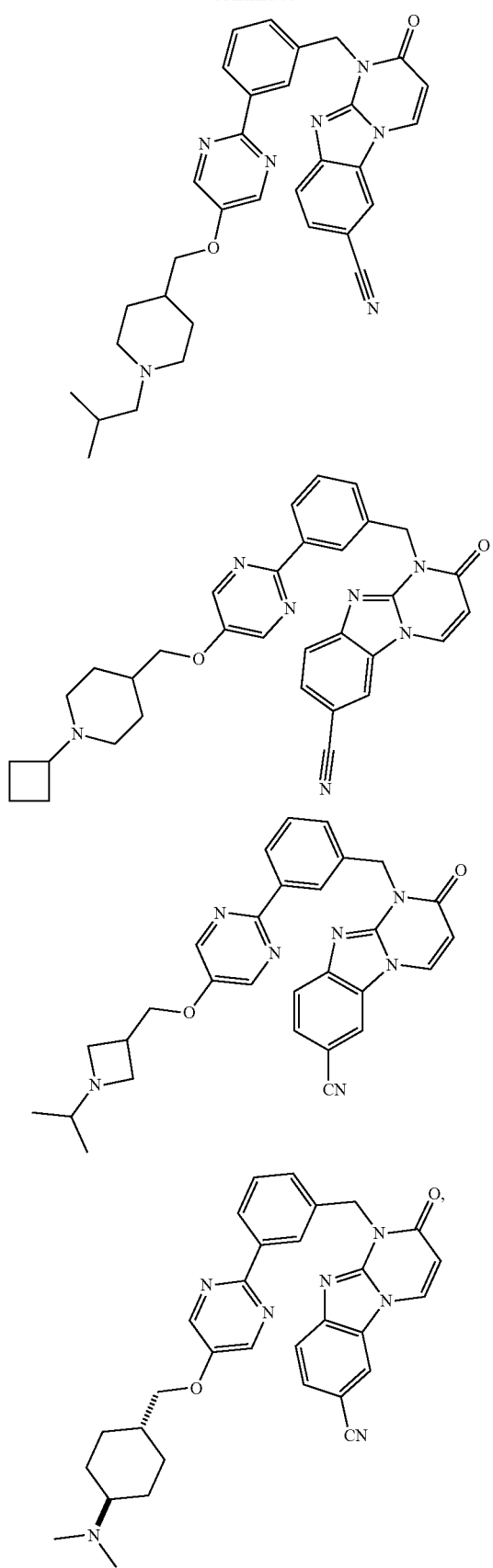
268
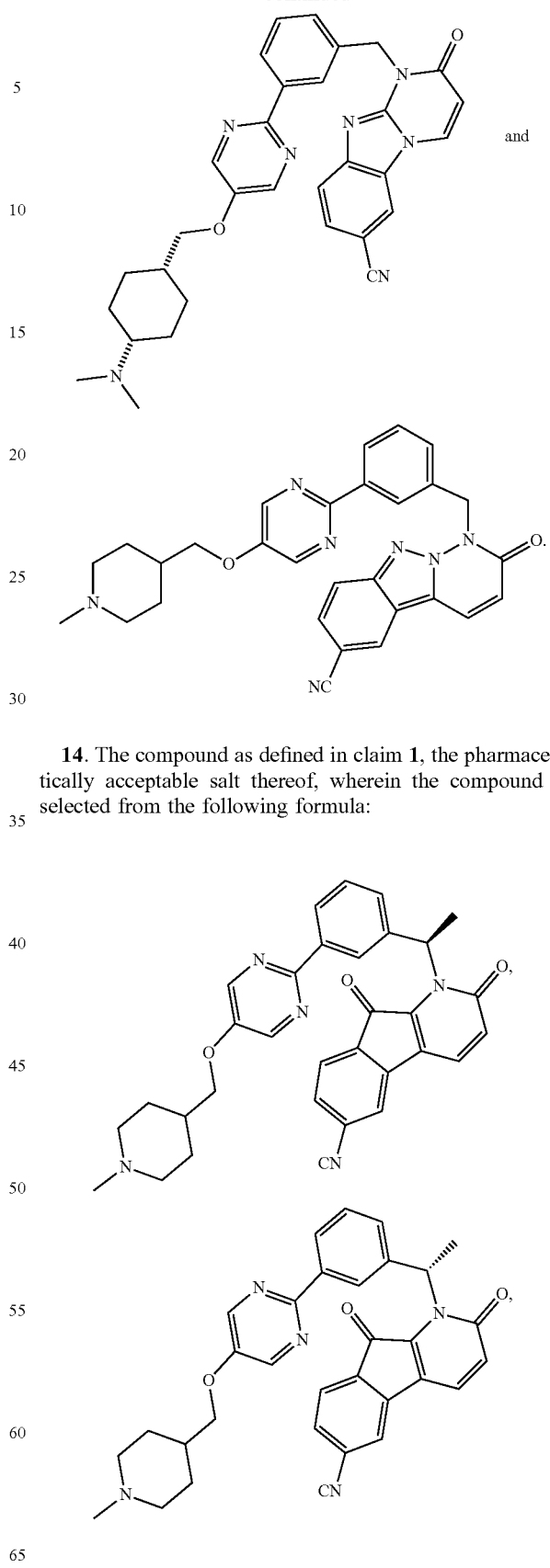
14. The compound as defined in claim 1, the pharmaceutically acceptable salt thereof, wherein the compound is selected from the following formula:

269
-continued
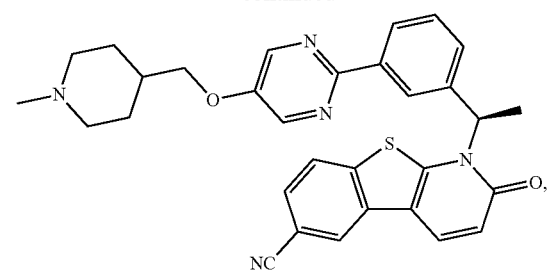
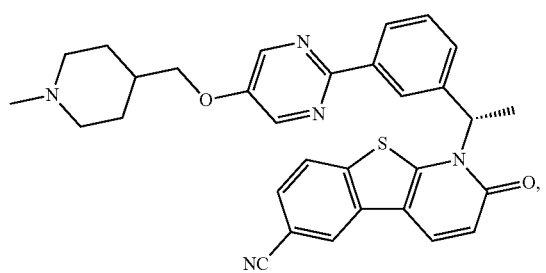
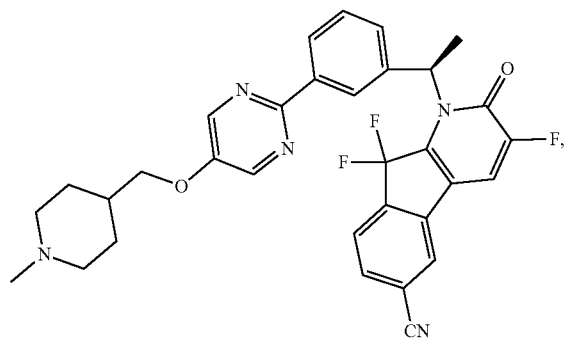
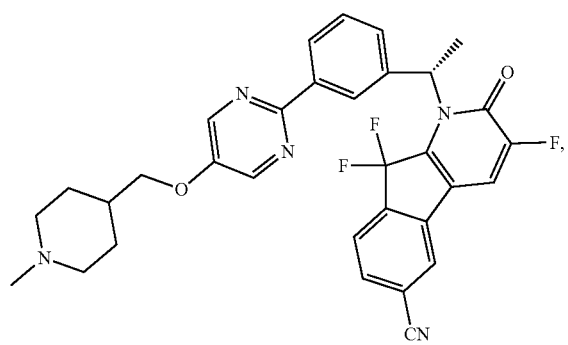
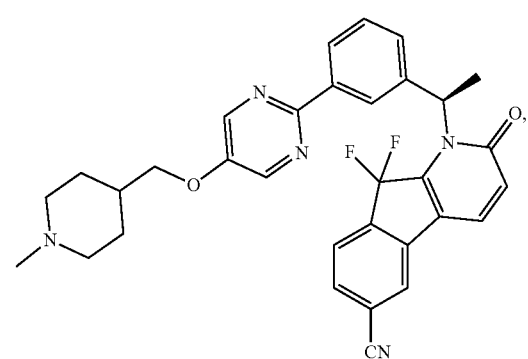
270
-continued
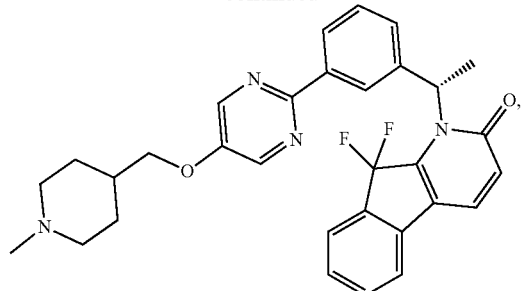
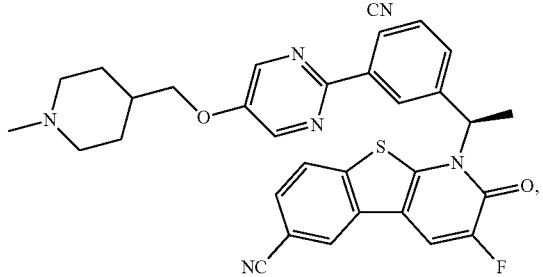
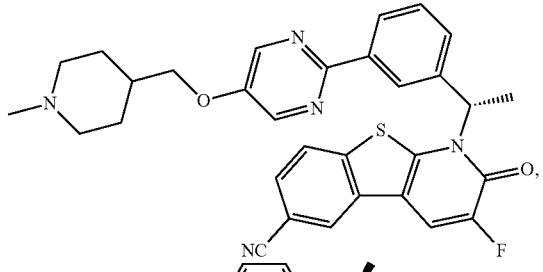
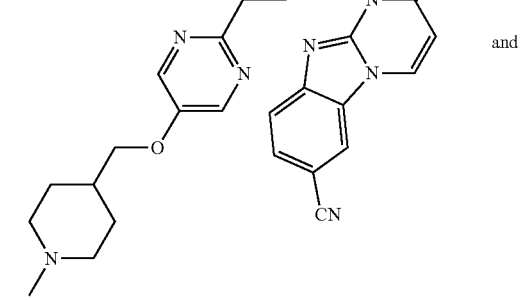
and
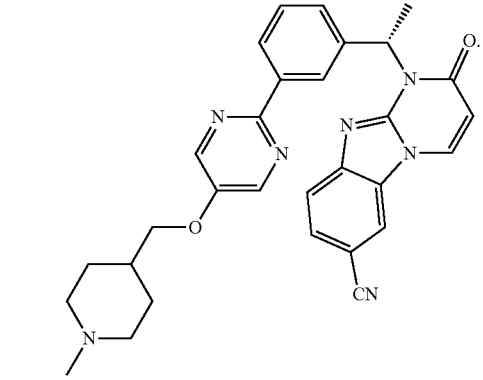
15. The compound as defined in claim 1, the pharmaceutically acceptable salt thereof, wherein the pharmaceutically acceptable salt is formate or hydrochloride.

16. A pharmaceutical composition, containing a therapeutically effective amount of the compound as defined in claim 1, the pharmaceutically acceptable salt and a pharmaceutically acceptable carrier.

17. A method for modulating c-Met in a subject in need thereof, comprising administering an effective amount of the compound as defined in claim 1, the pharmaceutically acceptable salt to the subject.

* * * * *